(12) United States Patent
Schreiber et al.

(10) Patent No.: US 7,186,709 B2
(45) Date of Patent: Mar. 6, 2007

(54) DIHYDROPYRANCARBOXAMIDES AND USES THEREOF

(75) Inventors: Stuart L. Schreiber, Boston, MA (US); Robert A. Stavenger, Blue Bell, PA (US); Timothy J. Mitchison, Brookline, MA (US); Zoltan Maliga, East Brunswick, NJ (US)

(73) Assignee: President and Fellows of Harvard College, Cambridge, MA (US)

(*) Notice: Subject to any disclaimer, the term of this patent is extended or adjusted under 35 U.S.C. 154(b) by 7 days.

(21) Appl. No.: 10/649,532

(22) Filed: Aug. 27, 2003

(65) Prior Publication Data

US 2004/0059138 A1 Mar. 25, 2004

Related U.S. Application Data

(60) Provisional application No. 60/406,140, filed on Aug. 27, 2002.

(51) Int. Cl.
*A61K 31/351* (2006.01)
*A61K 31/436* (2006.01)
*A61K 31/4375* (2006.01)
*C07D 405/06* (2006.01)
*C07D 405/08* (2006.01)

(52) U.S. Cl. ............ 514/183; 514/294; 514/336; 514/414; 540/480; 548/468; 546/282.1; 549/419

(58) Field of Classification Search ............ 514/183, 514/294, 336, 414, 459; 540/480; 548/468; 546/96, 282.1; 549/419
See application file for complete search history.

(56) References Cited

OTHER PUBLICATIONS

Akiyama et al., "Genistein, a Specific Inhibitor of Tyrosine-specific Protein Kinases" *J. Biol. Chem.*, (1987) 262:5592-5595.
Amara et al., "A versatile synthetic dimerizer for the regulation of protein-protein interactions" *Proc. Natl. Acad. Sci. USA*, (1997) 94:10618-10623.
Annis et al., "Stereochemistry as a Diversity Element: Solid-Phase Synthesis of Cyclic RGD Peptide Derivatives by Asymmetric Catalysis" *Angew. Chem. Int. Ed. Engl.*, (1998) 37:1907-1909.
Blackwell et al., "A one-bead, one-stock solution approach to chemical genetics: part 1" *Chem. Biol.*, (2001) 1167-1182.
Blackwell et al., "Decoding Products of Diversity Pathways from Stock Solutions Derived from Single Polymeric Macrobeads" *Angew. Chem. Int. Ed. Engl.*, (2001) 40(18):3421-3425.
Clemons et al., "A one-bead, one-stock solution approach to chemical genetics: Part 2" *Chem. Biol.*, (2001) 8:1183-1195.
Coste et al., "PyBOP: a new peptide coupling reagent devoid of toxic by-product" *Tetrahedron lett.*, (1990) 31:205-208.
Cramer et al., "Actin-dependent motile forces and cell motility" *Curr. Opin. Cell. Biol.*, (1994) 6(1):82-86.
Czarnik et al., "Encoding methods for combinatorial chemistry" *Current Opinion in Chemical Biology*, (1997) 1:60.

Dolle et al., "A Statistical-Based Approach to Assessing the Fidelity of Combinatorial Libraries Encoded with Electrophoric Molecular Tags, Development and Application of Tag Decode-Assisted Single Bead LC/MS Analysis" *J. Comb. Chem.*, (2000) 2:716-731.
Evans et al., "Chiral $C_2$-Summetric $Cu^{II}$ Complexes as Catalysts for Enantioselective Hetero-Diels-Alder Reactions" *Angew. Chem. Int. Ed. Engl.*, (1998) 37:3372-3375.
Evans et al., "An Improved Procedure for the Preparation of 2,2-Bis[2[4(S)-*tert*-butyl-1,3-oxazolinyl]]propane ](S,S)-*tert*-Butylbis (oxazoline)] and Derived Copper (II) Complexes" *J. Org. Chem.*, (1998) 63:4541-4544.
Evans et al., "Enantioselective Synthesis of Dihydropyrans, Catalysis of Hetero Diels—Alder Reactions by Bis (oxazoline) Copper(II) Complexes" *J. Am. Chem. Soc.*, (2000) 122:1635-1649.
Fitch et al., "High-Resolution $^1$H NMR in Solid-Phase Organic Synthesis" *J. Org. Chem.*, (1994) 59:7955-7956.
Hanessian et al., "Stereocontrolled solution and solid phase enolate alkylations and hydroxylations—generation of three and four contiguous stereogenic carbon atoms in acyclic systems" *Tetrahedron Lett.*, (1999) 40:4631.
Hergenrother et al., "Small-Molecule Microarrays: Covalent Attachment and Screening of Alcohol-Containing Small Molecules on Glass Slides" *J. Am. Chem. Soc.*, (2000) 122:7849-7850.
Holt et al., "Design, Synthesis and Kinetic Evaluation of High-Affinity FKBP Ligands and the X-ray Crystal Structures of Their Complexes with FKBP12" *J. Am. Chem. Soc.*, (1993) 115:9925-9938.
Hukreide et al., "Radiation hybrid mapping of the zebrafish genome" *Proc. Natl. Acad. Sci.*, (1999) 96:9745-9750.
Johnson et al., "Chiral Bis(oxazoline) Copper(II) Complexes: Versatile Catalysts for Enantioselective Cycloaddition, Aldol, Michael, and Carbonyl Ene Reactions" *Acc. Chem. Res.*, (2000) 33:325-335.
Jorgensen et al., "Catalytic Asymmetric Addition Reactions of Carbonyls. A Common Catalytic Approach" *Acc. Chem. Res.*, (1999) 32:605-613 D.

(Continued)

*Primary Examiner*—Taofiq Solola
(74) *Attorney, Agent, or Firm*—Brenda Herschbach Jarrell; Nadege M. Lagneau; Choate Hall and Stewart LLP

(57) ABSTRACT

The present invention provides novel dihydropyrancarboxamide compounds of formula (I):

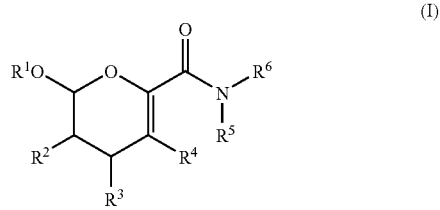

and collections of these compounds, and provides methods for the synthesis of these compounds; wherein $R^1$–$R^6$ are as defined herein. Additionally, the present invention provides pharmaceutical compositions and methods for treating disorders such as proliferative diseases, and cancer, to name a few.

22 Claims, 40 Drawing Sheets

OTHER PUBLICATIONS

Keifer et al., "Influence of Resin Structure, Tether Length, and Solvent upon the High-Resolution $^1$H NMR Spectra of Solid-Phase-Synthesis Resins" *J. Org. Chem.*, (1996) 61:1558-1559.

Keifer et al., "A Comparison of NMR Spectra Obtained for Solid-Phase-Synthesis Resins Using Conventional High-resolution, Magic-Angle-Spinning, and High-Resolution Magic-Angle-Spinning Probes" *Magn. Reson., Series A*, (1996) 119:65-75.

Leconte et al., "Solid-Phase Synthesis of Dihydropyrans by Eu(fod)$_3$-Catalysed [4+2] Heterocycloaddition of Vinyl Ethers with Benzylidenepyruvic Acid Esters. Comparison with Conventional Homogeneous Liquid Phase Conditions" *Eur. J. Org. Chem.*, (2000) 639-643.

Lee et al., "A Strategy for Macrocyclic Ring Closure and Functionalization Aimed toward Split-Pool Syntheses" *J. Am. Chem. Soc.*, (1999) 121:10648-10649.

Macbeath et al., "Printing Small Molecules as Microarrays and Detecting Protein-Ligand Interactions en Masse" *J. Am. Chem. Soc.*, (1999) 121:7967-7968.

Maliga et al., "Evidence that Monstrol Is an Allosteric Inhibitor of the Mitotic Kinesin Eg5" *Chem. Biol.*, (2002) 9:989-996.

Mayer et al., "Small Molecule Inhibitor of Mitotic Spindle Bipolarity Identified in a Phenotype-Based Screen" *Science*, (1999) 286:971-974.

Mitchison et al., Towards a pharmacological genetics *Chem. Biol.*, (1994) 1:3-6.

Nakatsuka et al., "Total Synthesis of FK506 and an FKBP Probe Reagent, ($C_8C_9$-$^{13}C_2$)-FK506" *J. Am. Chem. Soc.*, (1990) 112:5583.

Nestler et al., "A General Method for Molecular Tagging of Encoded Combinatorial Chemistry Libraries" *J. Org. Chem.*, (1994) 59:4723-4724.

Newman et al., "The influence of natural products upon drug discovery" *Nat. Prod. Rep.*, (2000) 17:215-234.

Ohlmeyer et al., "Complex synthetic chemical libraries indexed with molecular tags" *Proc. Natl. Acad. Sic. USA*, (1993) 90:10922-10926.

Pace et al., "How to measure and predict the molar absorption coefficient of a protein" *Protein science*, (1995) 4(11):2411-2423.

Pangborn et al., "Safe and Convenient Procedure for Solvent Purification" *Organometallics*, (1996) 15:1518-1520.

Panek et al., "Asymmetric Crotylation Reactions of Solid Support: Synthesis of Stereochemically Well-Defined Polypropionate-Like Subunits" *J. Am. Chem. Soc.*, (1997) 119:12022-12023.

Paterson et al., "A Combinatorial Approach to Polyketide-Type Libraries by Iterative Asymmetric Aldol Reactions Performed on Solid Support" *Angew. Chem. Int. Ed. Engl.*, (2000) 39:3315-3319.

Reggelin et al., "Toward Polyketide Libraries—II: Synthesis of Chiral Aracemic Di and Triketides on a Solid Support" *Tetrahedron Lett*, (1998) 39:4801-4804.

Schreiber et al., "Using the Principles of Organic Chemistry to Explore Cell Biology" *Chem. Eng. New*, (1992) Oct. 26, 22-32.

Schreiber et al., "Chemical Genetics Resulting from a Passion for Synthetic Organic Chemistry" *Bioorg. Med. Chem.*, (1998) 6:1127-1152.

Schreiber et al., "Target-Oriented and Diversity-Oriented Organic Synthesis in Drug Discovery" Di*Science*, (2000) 287:1964-1969.

Spring et al., "Towards Diversity-Oriented, Stereoselective Syntheses of Biraryl- or Bis(aryl)metal-Containing Medium Rings" *J. Am. Chem. Soc.*,(2000) 122:5656-5657.

Stavenger et al.,"Asymmetric Catalysis in Diversity-Oriented Organic Synthesis: Enantioselective Synthesis of 4320 Encoded and Spatially Segregated Dihydropyrancarboxamides" *Angew. Chem. Int. Ed. Engl.*, (2001) 40(18):3417-3421.

Sternson et al., "Split-Pool Synthesis of 1,3-Dioxanes Leading to Arrayed Stock Solutions of Single Compounds Sufficient for Multiple Phenotypic and Protein-Binding Assays" *J. Am. Chem. Soc.*, (2001) 123:1740-1747.

Stockwell et al., "High-throughput screening of small molecules in miniaturized mammalian cell-based assays involving post-translational modifications" *Chem. Biol.*, (1999) 6:71-83.

Sugimura et al., "A New Synthetic Method for α-Oxo-β,γ-unsaturated Esters" *Bull. Chem. Soc. Jpn..*, (1992) 65:3209-3211.

Tallarico et al., "An Alkylsilyl-Tethered, High-Capacity Solid Support Amenable to Diversity-Oriented Synthesis for One-Bead, One-Stock Solution Chemical Genetics"0 *J. Comb. Chem.*, (2001) 3:312-318.

Tan et al., "Stereoselective Synthesis of over Two Million Compounds Having Structural Features Both Reminiscent of Natural Products and Compatible with Miniaturized Cell-Based Assays" *J. Am. Chem. Soc.*, (1998) 120:8565-8566.

Tan et al., "Synthesis and Preliminary Evaulation of a Library of Polycyclic Small Molecules for Use in Chemical Genetic Assays" *J. Am. Chem. Soc.*, (1999) 121:9073-9087.

Thorhauge et al., "Highly Enantioselective Catalytic Hetero-Diels-Alder Reaction with Inverse Electron Demand" *Angew. Chem. Int. Ed. Engl.*, (1998) 37:2404-2406.

Tietze et al., "Solid-Phase Three-Component Domino Reactions: Combinatorial Approach to Substituted 3,4-Hihyrdo-2*H*-pyrans" *Synlett*, (1996) 1043-1044.

Woehlke et al., "Microtubule Interaction Site of the Kinesin Motor" *Cell*, (1997) 90:207-216.

Zou et al., "Solid Phase Asymmetric Synthesis of Isoxazolines" *J. Comb. Chem.*, (1999) 2:6-7.

↑ 10%FBS ↖ 200mM genestein

Screen of RAS-384 for
Inhibitors of BrdU Incorporation
5 pinnings/cmpd (250-500nL; 25-50uM)
16-hr incubation with 1%FBS
Probed with 1:1000 α-BrdU
5-min exposure Inhibition of BrdU Incorporation Suppression of Genistein Antiproliferative Effects

DIHYDROPYRANCARBOXAMIDES AND USES THEREOF

PRIORITY INFORMATION

The present application claims priority under 35 U.S.C. § 119 to U.S. provisional application No. 60/406,140, filed Aug. 27, 2002, entitled "Dihydropyrancarboxamides and Uses Thereof", the entire contents of which are hereby incorporated by reference.

GOVERNMENT SUPPORT

This invention was made in part with a grant from the National Institute of General Medical Sciences (Grant Number: GM-52067). Therefore, the government has certain rights in the invention.

BACKGROUND OF THE INVENTION

The identification of small organic molecules that affect specific biological functions is an endeavor that impacts both biology and medicine. Such molecules are useful as therapeutic agents and as probes of biological function. In but one example from the emerging field of chemical genetics, in which small molecules are used to alter the function of biological molecules to which they bind, small molecules have helped elucidate signal transduction pathways by acting as chemical protein knockouts. (Schreiber et al., *J. Am. Chem. Soc.*, 1990, 112, 5583; Mitchison, *Chem. and Biol.*, 1994, 1, 3). Of course, small molecules that interact with particular biological targets and affect specific biological functions, may also serve as candidates for the development of therapeutics. One important class of small molecules are natural products, which are small molecules obtained from nature. Natural products have played an important role in the development of biology and medicine, serving as pharmaceutical leads, drugs (Newman et al., *Nat. Prod. Rep.* 2000, 17, 215–234), and powerful reagents for studying cell biology (Schreiber, S. L. *Chem. and Eng. News* 1992 (October 26), 22–32). More generally, any organic compounds, whether naturally-occurring, reminiscent of natural products or artificially created (e.g., via chemical synthesis or semi-synthesis), are also of interest since they may serve as candidates for the development of therapeutics.

Because it is difficult to predict which small molecules will interact with a biological target, and it is often difficult to obtain or effiently synthesize small molecules found in nature, intense efforts have been directed toward the generation of large numbers, or libraries, of small organic compounds, often "natural product-like" libraries. These libraries can be tested in sensitive assays for a particular biological activity, such as binding to a target of interest.

Clearly, it would be desirable to develop compounds with a desired biological activity. Additionally, it would be desirable to identify novel compounds capable of acting as probes of biological function.

SUMMARY OF THE INVENTION

In one aspect of the invention, novel compounds having the structure (I) are provided:

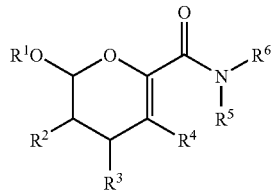

(I)

wherein $R^1$–$R^4$ are each independently hydrogen or an aliphatic, heteroaliphatic, aryl, heteroaryl, alkylaryl or alkylheteroaryl moiety;

$R^5$ and $R^6$ are each independently hydrogen or an aliphatic, heteroaliphatic, aryl, heteroaryl, alkylaryl, or alkylheteroaryl moiety, and wherein $R^5$ and $R^6$, taken together, may form a cyclic aliphatic, heteroaliphatic, aliphatic (aryl), heteroaliphatic(aryl), aliphatic(heteroaryl) or heteroaliphatic(heteroaryl) moiety, or an aryl or heteroaryl moiety;

wherein each of the foregoing aliphatic and heteroaliphatic moieties may be substituted or unsubstituted, cyclic or acyclic, saturated or unsaturated or linear or branched; and each of the foregoing aryl, heteroaryl, alkylaryl or alkylheteroaryl moieties may be substituted or unsubstituted; and pharmaceutically acceptable derivatives thereof.

In certain embodiments, compounds having the structure (II) are provided:

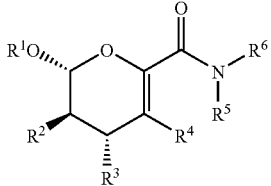

(II)

or enantiomer thereof;

wherein $R^1$–$R^4$ are each independently hydrogen or an aliphatic, heteroaliphatic, aryl, heteroaryl, alkylaryl or alkylheteroaryl moiety;

$R^5$ and $R^6$ are each independently hydrogen or an aliphatic, heteroaliphatic, aryl, heteroaryl, alkylaryl, or alkylheteroaryl moiety, and wherein $R^5$ and $R^6$, taken together, may form a cyclic aliphatic, heteroaliphatic, aliphatic (aryl), heteroaliphatic(aryl), aliphatic(heteroaryl) or heteroaliphatic(heteroaryl) moiety, or an aryl or heteroaryl moiety;

wherein each of the foregoing aliphatic and heteroaliphatic moieties may be substituted or unsubstituted, cyclic or acyclic, saturated or unsaturated or linear or branched; and each of the foregoing aryl, heteroaryl, alkylaryl or alkylheteroaryl moieties may be substituted or unsubstituted; and pharmaceutically acceptable derivatives thereof.

In yet other embodiments, a collection of compounds comprising two or more of the compounds of structures (I) or (II) is provided. In certain embodiments, the collection is provided in array format. In yet other embodiments, the collection is provided in array format on a glass slide. In still other embodiments, the collection comprises at least 100 compounds. In yet other embodiments, the collection comprises at least 1,000 compounds. In still further embodiments, the collection comprises at least 2,000 compounds. In yet other embodiments, the collection comprises at least 10,000 compounds.

In another aspect of the invention, a method for the synthesis of the core structure (III) is provided, one method comprising steps of:

providing a vinyl ether having the structure:

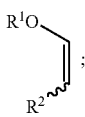

providing an unsaturated ketoester having the structure:

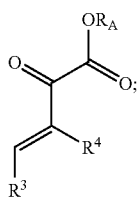

subjecting the vinyl ether and the unsaturated ketoester to suitable conditions to generate a scaffold having the core structure:

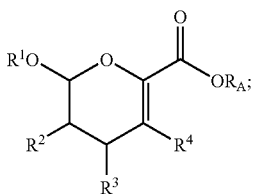

wherein $R^1$ and $R^2$ are each independently hydrogen or an aliphatic, heteroaliphatic, aryl, heteroaryl, alkylaryl or alkylheteroaryl moiety; wherein one of $R^1$ or $R^2$ is attached to a solid support;

$R^3$ and $R^4$ are each independently hydrogen or an aliphatic, heteroaliphatic, aryl, heteroaryl, alkylaryl or alkylheteroaryl moiety;

$R_A$ is hydrogen or is an aliphatic, heteroaliphatic, aryl, heteroaryl, alkylaryl, or alkylheteroaryl moiety;

wherein each of the foregoing aliphatic and heteroaliphatic moieties may be substituted or unsubstituted, cyclic or acyclic, saturated or unsaturated or linear or branched; and each of the foregoing aryl, heteroaryl, alkylaryl or alkylheteroaryl moieties may be substituted or unsubstituted.

In certain embodiments, the method further comprises cleaving the core structure (III) from the solid support to which it is attached.

In certain embodiments, the method further comprises subjecting the core structure (III) to one or more diversification reactions to generate one or more compounds having the structure (I):

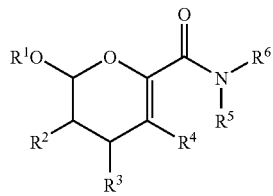

wherein $R^1$ and $R^6$ are as defined above.

In certain embodiments, the method further comprises cleaving the core structure (I) from the solid support to which it is attached.

In yet another aspect of the invention, pharmaceutical compositions are provided comprising any one of the compounds described above and herein; and a pharmaceutically acceptable carrier or diluent.

In still another aspect of the invention, methods of treating a variety of disorders are provided comprising administering a therapeutically effective compound or composition thereof to a subject in need thereof. In certain other embodiments, the inventive compounds are utilized to treat proliferative disorders, including, but not limited to cancer.

In yet another aspect of the present invention, methods of screening compounds for identifying those inventive compounds that exhibit a biological activity of interest are provided.

DEFINITIONS

This invention provides a new family of compounds with a range of biological properties. Compounds of this invention have biological activities relevant for the treatment of diseases including proliferative diseases such as cancer. Compounds of this invention include those specifically set forth above and described herein, and are illustrated in part by the various classes, subgenera and species disclosed elsewhere herein.

It will be appreciated by one of ordinary skill in the art that asymmetric centers may exist in the compounds of the present invention. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, a mixtures of stereoisomers or diastereomers are provided.

Additionally, the present invention provides pharmaceutically acceptable derivatives of the inventive compounds, and methods of treating a subject using these compounds, pharmaceutical compositions thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail below.

Certain compounds of the present invention, and definitions of specific functional groups are also described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, may utilize a variety of protecting groups. By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

It will be appreciated that the compounds described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position unless otherwise indicated. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of proliferative disorders, cancer, and wound healing, to name a few. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched), branched, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes both straight, branched and cyclic alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups.

In certain embodiments, the alkyl, alkenyl and alkynyl groups employed in the invention contain 1–20 aliphatic carbon atoms. In certain other embodiments, the alkyl, alkenyl, and alkynyl groups employed in the invention contain 1–10 aliphatic carbon atoms. In still other embodiments, the alkyl, alkenyl, and alkynyl groups employed in the invention contain 1–6 aliphatic carbon atoms. In yet other embodiments, the alkyl, alkenyl, and alkynyl groups employed in the invention contain 1–4 aliphatic carbon atoms. Illustrative aliphatic groups thus include, but are not limited to, for example, methyl, ethyl, n-propyl, isopropyl, cyclopropyl, —$CH_2$-cyclopropyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alkoxy", or "thioalkyl" as used herein refers to an alkyl group, as previously defined, attached to the parent molecular moiety through an oxygen atom or through a sulfur atom. In certain embodiments, the alkyl group contains 1–20 alipahtic carbon atoms. In certain other embodiments, the alkyl group contains 1–10 aliphatic carbon atoms. In still other embodiments, the alkyl group contains 1–6 aliphatic carbon atoms. In yet other embodiments, the alkyl group contains 1–4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. In certain embodiments, the alkyl group contains 1–20 aliphatic carbon atoms. In certain other embodiments, the alkyl group contains 1–10 aliphatic carbon atoms. In still other embodiments, the alkyl group contains 1–6 aliphatic carbon atoms. In yet other embodiments, the alkyl group contains 1–4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples which are described herein.

In general, the terms "aryl" and "heteroaryl", as used herein, refer to stable monoor polycyclic, heterocyclic, polycyclic, and polyheterocyclic unsaturated moieties having preferably 3–14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a monoor bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one, two or three of the hydrogen atoms thereon independently with any one or more of the following moieties including, but not limited to: aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCON(R$_x$)$_2$; —N(R$_x$)$_2$; —S(O)$_2$R$_x$; wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples which are described herein.

The term "heteroaliphatic", as used herein, refers to aliphatic moieties which contain one or more oxygen, sulfur, nitrogen, phosphorous or silicon atoms, e.g., in place of carbon atoms. Heteroaliphatic moieties may be branched, unbranched or cyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; OH; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$ R$_x$; wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples which are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a nonaromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples which are described herein.

The term "solid support", as used herein, refers to a material having a rigid or semi-rigid surface. Such materials will preferably take the form of small beads, pellets, disks, chips, dishes, multi-well plates, glass slides, wafers, or the like, although other forms may be used. In some embodiments, at least one surface of the substrate will be substantially flat. The term "surface" refers to any generally two-dimensional structure on a solid substrate and may have steps, ridges, kinks, terraces, and the like without ceasing to be a surface.

The term "polymeric support", as used herein, refers to a soluble or insoluble polymer to which an amino acid or other chemical moiety can be covalently bonded by reaction with a functional group of the polymeric support. Many suitable polymeric supports are known, and include soluble polymers such as polyethylene glycols or polyvinyl alcohols, as well as insoluble polymers such as polystyrene resins. A suitable polymeric support includes functional groups such as those described below. A polymeric support is termed "soluble" if a polymer, or a polymer-supported compound, is soluble under the conditions employed. However, in general, a soluble polymer can be rendered insoluble under defined conditions. Accordingly, a polymeric support can be soluble under certain conditions and insoluble under other conditions.

The term "linker", as used herein, refers to a chemical moiety utilized to attach a compound of interest to a solid support to facilitate synthesis of inventive compounds. Exemplary linkers are described in Example 2, as described herein. It will be appreciated that other linkers (including silicon-based linkers and other linkers) that are known in the art can also be employed for the synthesis of the compounds of the invention.

BRIEF DESCRIPTION OF THE DRAWING

FIG. 18 depicts exemplary raw data from protein-binding experiments described in Example 3.

FIG. 19 depicts exemplary raw data from BrdU Cytoblot (cell-based assay) experiments described in Example 3.

FIG. 20 depicts results of an exemplary genistein suppressor assay, as described in Example 3.

DETAILED DESCRIPTION OF CERTAIN EMBODIMENTS OF THE INVENTION

Figure 1:
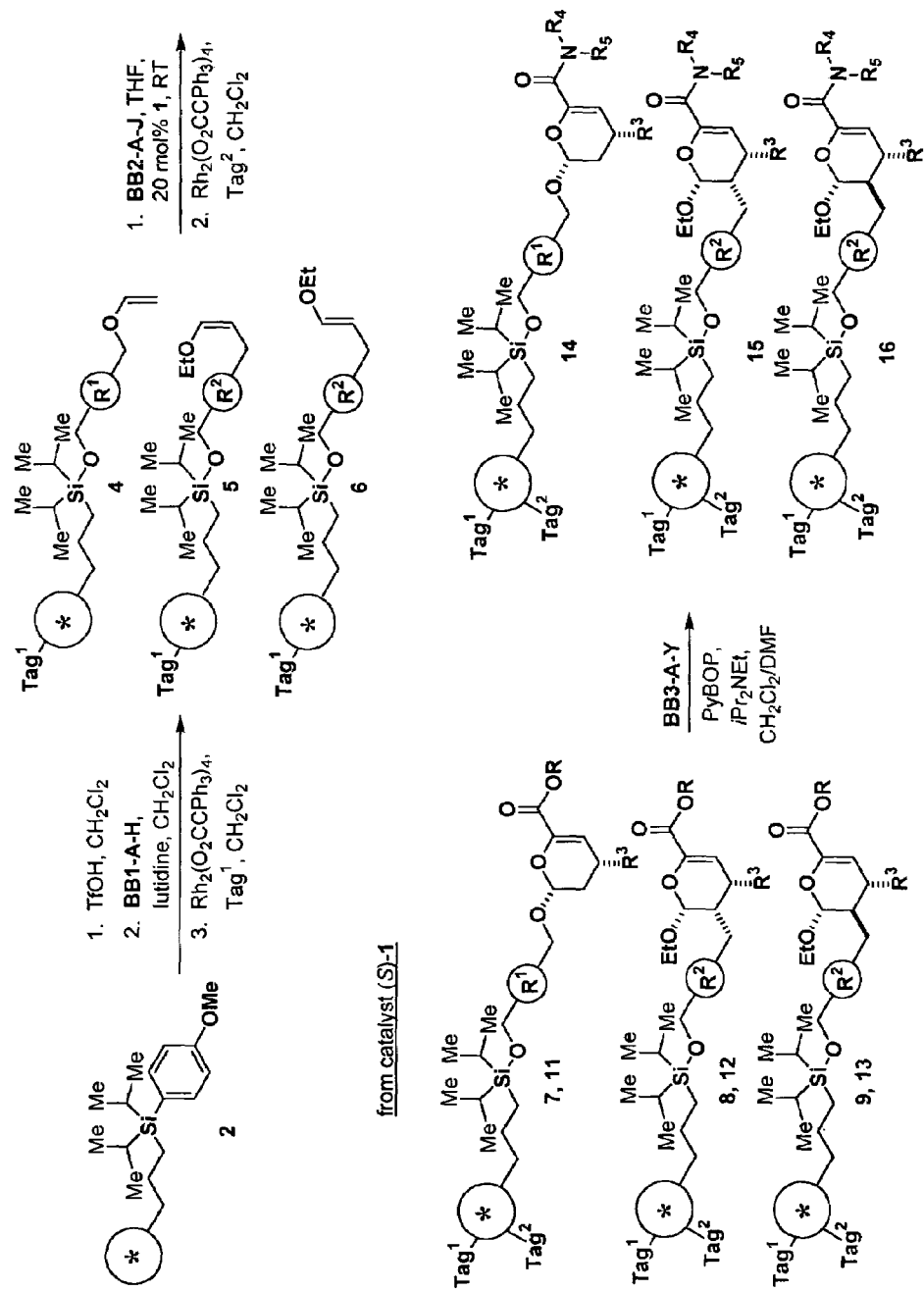
FIG. 1 depicts an exemplary synthesis of the inventive dihydropyrancarboxamides.

As discussed above, there remains a need for the development of novel therapeutic agents and agents capable of elucidating biological functions. In one aspect, the present invention provides novel compounds of general formula (I), and methods for the synthesis thereof, which compounds are useful, for example, as DNA synthase inhibitors and Eg5 inhibitors, and thus are useful for the treatment of, for example, proliferative diseases and cancer. In certain embodiments, the inventive compounds are additionally useful as tools to probe biological function.

GENERAL DESCRIPTION OF COMPOUNDS OF THE INVENTION

As detailed above, in one aspect of the invention, novel dihydropyrancarboxamides having the following structure (I) are provided:

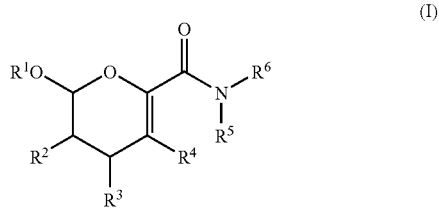

wherein $R^1$–$R^4$ are each independently hydrogen or an aliphatic, heteroaliphatic, aryl, heteroaryl, aliphatic(aryl), heteroaliphatic(aryl), aliphatic(heteroaryl) or heteroaliphatic (heteroaryl) moiety;

$R^5$ and $R^6$ are each independently hydrogen or an aliphatic, heteroaliphatic, aryl, heteroaryl, alkylaryl, or alkylheteroaryl moiety, and wherein $R^5$ and $R^6$, taken together, may form a cyclic aliphatic, heteroaliphatic, aliphatic (aryl), heteroaliphatic(aryl), aliphatic(heteroaryl) or heteroaliphatic(heteroaryl) moiety, or an aryl or heteroaryl moiety;

wherein each of the foregoing aliphatic and heteroaliphatic moieties may be substituted or unsubstituted, cyclic or acyclic, saturated or unsaturated or linear or branched; and each of the foregoing aryl, heteroaryl, aliphatic(aryl), heteroaliphatic(aryl), aliphatic(heteroaryl) or heteroaliphatic(heteroaryl) moieties may be substituted or unsubstituted; and pharmaceutically acceptable derivatives thereof.

In one exemplary subset of the invention, compounds having the following structure (II) are provided:

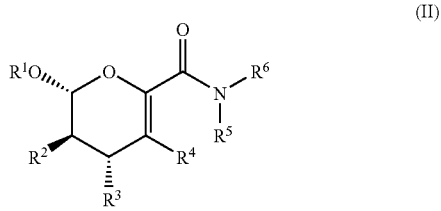

(II)

wherein $R^1$–$R^4$ are each independently hydrogen or an aliphatic, heteroaliphatic, aryl, heteroaryl, aliphatic(aryl), heteroaliphatic(aryl), aliphatic(heteroaryl) or heteroaliphatic (heteroaryl) moiety;

$R^5$ and $R^6$ are each independently hydrogen or an aliphatic, heteroaliphatic, aryl, heteroaryl, alkylaryl, or alkylheteroaryl moiety, and wherein $R^5$ and $R^6$, taken together, may form a cyclic aliphatic, heteroaliphatic, aliphatic (aryl), heteroaliphatic(aryl), aliphatic(heteroaryl) or heteroaliphatic(heteroaryl) moiety, or an aryl or heteroaryl moiety;

wherein each of the foregoing aliphatic and heteroaliphatic moieties may be substituted or unsubstituted, cyclic or acyclic, saturated or unsaturated or linear or branched; and each of the foregoing aryl, heteroaryl, aliphatic(aryl), heteroaliphatic(aryl), aliphatic(heteroaryl) or heteroaliphatic(heteroaryl) moieties may be substituted or unsubstituted; and pharmaceutically acceptable derivatives thereof.

In still other subsets of the invention, compounds are provided in which the conjugated carboxylate ($R^4$) is functionalized. In still other subsets of the invention, compounds are provided in which the carbonyl is functionalized. In still other subsets of the invention, compounds are provided in which $R^1$ is a solid support linked through a silyl linker as described in Examples 1 and 2 herein. In still other subsets of the invention, compounds are provided in which $R^2$ is a solid support linked through a silyl linker as described in Examples 1 and 2 herein. In further subsets of the invention, compounds having functionalization at two or more of these sites are provided. In still other subsets of the invention, compounds having functionalization at each of these sites are provided. In certain other subsets of the invention, compounds are provided as described using the reagents detailed in Example 1.

In another embodiment of the invention, the inventive compounds are provided as a collection and thus may be provided as a collection of two or more of any of the compounds as detailed above or as described herein. In certain embodiments, the collection is provided in array format. In certain other embodiments, the collection is provided in array format on a glass slide. In still other embodiments, the collection comprises at least 100 compounds. In yet other embodiments, the collection comprises at least 1,000, 2,000 or 10,000 compounds.

2) Featured Classes of Compounds

In certain embodiments, the present invention defines certain classes of compounds which are of special interest.

For example, one class of compounds of special interest includes those compounds of the invention as described above and in certain subclasses herein, in which $R^1$ is hydrogen, Z or an alkyl, heteroalkyl, aryl or heteroaryl moiety substituted with Z, wherein Z is hydrogen, —$(CH_2)_q$OR$^Z$, —$(CH_2)_q$SR$^Z$, —$(CH_2)_q$N(R$^Z$)$_2$, —(C=O)R$^Z$, —(C=O)N(R$^Z$)$_2$, or an aliphatic, heteroaliphatic, aryl, heteroaryl, -(aliphatic)aryl, -(aliphatic)heteroaryl, -(heteroaliphatic)aryl, or -(heteroaliphatic)heteroaryl moiety, wherein q is 0–4, and wherein each occurrence of R$^Z$ is independently hydrogen, a protecting group, a solid support unit, or an aliphatic, heteroaliphatic, aryl, heteroaryl, -(aliphatic)aryl, -(aliphatic)heteroaryl, -(heteroaliphatic)aryl, or -(heteroaliphatic)heteroaryl moiety; wherein each of the foregoing alkyl or heteroalkyl moieties may be substituted or unsubstituted, linear or branched, cyclic or acyclic, saturated or unsaturated; and wherein each of the foregoing aryl, heteroaryl, -(alkyl)aryl, -(alkyl)heteroaryl, -(heteroalkyl) aryl, or -(heteroalkyl)heteroaryl moieties may be substituted or unsubstituted.

Another class of compounds of special interest includes those compounds of the invention as described above and in certain subclasses herein, in which $R^2$ is hydrogen, Z or an alkyl, heteroalkyl, aryl or heteroaryl moiety substituted with Z, wherein Z is hydrogen, —$(CH_2)_q$OR$^Z$, —$(CH_2)_q$SR$^Z$, —$(CH_2)_q$N(R$^Z$)$_2$, —(C=O)R$^Z$, —(C=O)N(R$^Z$)$_2$, or an aliphatic, heteroaliphatic, aryl, heteroaryl, -(aliphatic)aryl, -(aliphatic)heteroaryl, -(heteroaliphatic)aryl, or -(heteroaliphatic)heteroaryl moiety, wherein q is 0–4, and wherein each occurrence of R$^Z$ is independently hydrogen, a protecting group, a solid support unit, or an aliphatic, heteroaliphatic, aryl, heteroaryl, -(aliphatic)aryl, -(aliphatic) heteroaryl, -(heteroaliphatic)aryl, or -(heteroaliphatic)heteroaryl moiety; wherein each of the foregoing alkyl or heteroalkyl moieties may be substituted or unsubstituted, linear or branched, cyclic or acyclic, saturated or unsaturated; and wherein each of the foregoing aryl, heteroaryl, -(alkyl)aryl, -(alkyl)heteroaryl, -(heteroalkyl)aryl, or -(heteroalkyl)heteroaryl moieties may be substituted or unsubstituted.

Another class of compounds of special interest includes those compounds of the invention as described above and in certain subclasses herein, in which $R^3$ is an alkyl, heteroalkyl, aryl, heteroaryl, -(alkyl)aryl, -(alkyl)heteroaryl, -(heteroalkyl)aryl, or -(heteroalkyl)heteroaryl moiety; wherein each of the foregoing alkyl or heteroalkyl moieties may be substituted or unsubstituted, linear or branched, cyclic or acyclic, saturated or unsaturated; and wherein each of the foregoing aryl, heteroaryl, -(alkyl)aryl, -(alkyl)heteroaryl, -(heteroalkyl)aryl, or -(heteroalkyl)heteroaryl moieties may be substituted or unsubstituted.

Another class of compounds of special interest includes those compounds of the invention as described above and in certain subclasses herein, in which $R^4$ is hydrogen or an alkyl, heteroalkyl, aryl, heteroaryl, -(alkyl)aryl, -(alkyl)heteroaryl, -(heteroalkyl)aryl, or -(heteroalkyl)heteroaryl moiety; wherein each of the foregoing alkyl or heteroalkyl moieties may be substituted or unsubstituted, linear or branched, cyclic or acyclic, saturated or unsaturated; and wherein each of the foregoing aryl, heteroaryl, -(alkyl)aryl, -(alkyl)heteroaryl, -(heteroalkyl)aryl, or -(heteroalkyl)heteroaryl moieties may be substituted or unsubstituted.

Another class of compounds of special interest includes those compounds of the invention as described above and in certain subclasses herein, in which $R^5$ and $R^6$ are each independently hydrogen or an alkyl, heteroalkyl, aryl, heteroaryl, -(alkyl)aryl, -(alkyl)heteroaryl, -(heteroalkyl)aryl, or -(heteroalkyl)heteroaryl moiety; or wherein $R^5$ and $R^6$, taken together, form a substituted or unsubstituted, saturated or unsaturated cyclic moiety comprising 5–12 carbon atoms, 0–5 oxygen atoms, 0–5 sulfur atoms and 1–5 nitrogen atoms; and wherein each of the foregoing alkyl or heteroalkyl moieties may be substituted or unsubstituted, linear or branched, cyclic or acyclic, saturated or unsaturated; and wherein each of the foregoing aryl, heteroaryl, -(alkyl)aryl, -(alkyl)heteroaryl, -(heteroalkyl)aryl, or -(heteroalkyl)heteroaryl moieties may be substituted or unsubstituted.

The following compounds are illustrative of certain of the compounds described generally and in classes and subclasses herein:

A number of important subclasses of each of the foregoing classes deserve separate mention; these subclasses include subclasses of each of the foregoing classes in which:

i) compounds of the invention as described above and herein wherein $R^1$ is hydrogen, lower alkyl, a substituted or unsubstituted phenyl or -(lower alkyl)phenyl moiety, —$(CH_2)_n OR^z$, —$[(CH_2)_n O]_m R^z$, or —$(CH_2)_n$—Ar—$(CH_2)_m OR^z$; wherein n and m are each independently integers from 1–6, Ar represents a substituted or unsubstituted aryl or heteroaryl moiety, and $R^z$ is independently hydrogen, a protecting group, a solid support unit, or an aliphatic, heteroaliphatic, aryl, heteroaryl, -(aliphatic)aryl, -(aliphatic)heteroaryl, -(heteroaliphatic)aryl, or -(heteroaliphatic)heteroaryl moiety; wherein each of the foregoing alkyl or heteroalkyl moieties may be substituted or unsubstituted, linear or branched, cyclic or acyclic, saturated or unsaturated; and wherein each of the foregoing aryl, heteroaryl, -(alkyl)aryl, -(alkyl)heteroaryl, -(heteroalkyl)aryl, or -(heteroalkyl)heteroaryl moieties may be substituted or unsubstituted;

ii) compounds of the invention as described above and herein wherein $R^1$ is attached to a solid support;

iii) compounds of the invention as described above and herein wherein $R^1$ is —$(CH_2)_n OR^z$, —$[(CH_2)_n O]_m R^z$, or —$(CH_2)_n$—Ar—$(CH_2)_m OR^z$; wherein n and m are each independently integers from 1–6, Ar represents a substituted or unsubstituted aryl or heteroaryl moiety, and $R^z$ is hydrogen, a protecting group or a solid support unit;

iv) compounds of the invention as described above and herein wherein $R^1$ is —$(CH_2)_n OR^z$, —$[(CH_2)_n O]_m R^z$, or —$(CH_2)_n$—Ar—$(CH_2)_m OR^z$; wherein n and m are each independently integers from 1–6, Ar represents a substituted or unsubstituted aryl or heteroaryl moiety, and $R^z$ is a solid support unit linked to O through a silyl linker;

v) compounds of the invention as described above and herein wherein $R^1$ is hydrogen, or lower alkyl;

vi) compounds of the invention as described above and herein wherein $R^1$ is ethyl;

vii) compounds of the invention as described above and herein wherein $R^1$ is hydrogen, ethyl, or has one of the structures:

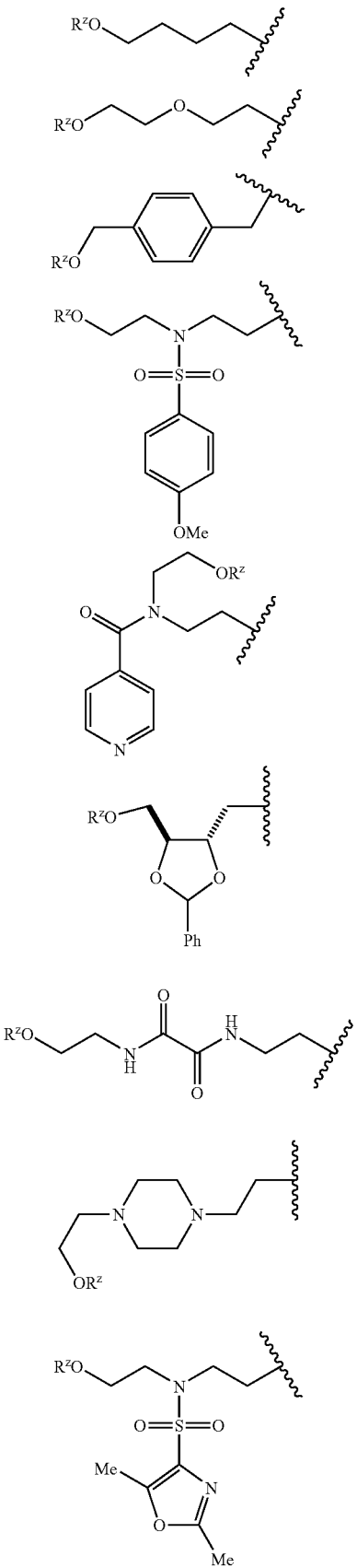

-continued

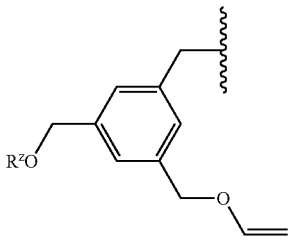

wherein $R^z$ is hydrogen, a protecting group or a solid support unit;

viii) compounds of the invention as described above and herein wherein $R^1$ is hydrogen, ethyl, or has one of the structures:

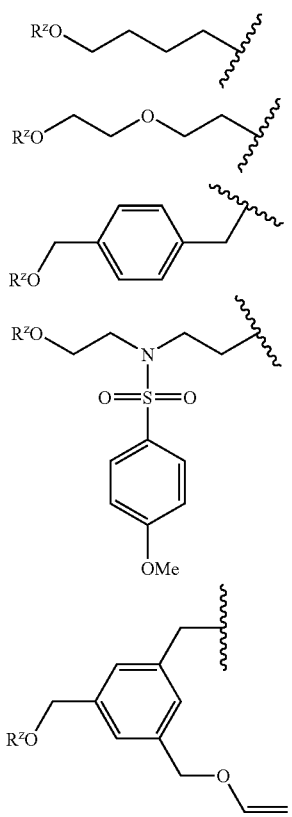

wherein $R^z$ is hydrogen, a protecting group or a solid support unit;

ix) compounds of the invention as described above and herein wherein $R^2$ is hydrogen, lower alkyl, a substituted or unsubstituted phenyl or -(lower alkyl)phenyl moiety, —$(CH_2)_nOR^z$, —$[(CH_2)_nO]_mR^z$, —$(CH_2)_n$—Ar—$(CH_2)_m$OR$^z$; wherein n and m are each independently integers from 1–6, Ar represents a substituted or unsubstituted aryl or heteroaryl moiety, and $R^z$ is independently hydrogen, a protecting group, a solid support unit, or an aliphatic, heteroaliphatic, aryl, heteroaryl, -(aliphatic)aryl, -(aliphatic)heteroaryl, -(heteroaliphatic)aryl, or -(heteroaliphatic)heteroaryl moiety; wherein each of the foregoing alkyl or heteroalkyl moieties may be substituted or unsubstituted, linear or branched, cyclic or acyclic, saturated or unsaturated; and wherein each of the foregoing aryl, heteroaryl, -(alkyl)aryl, -(alkyl)heteroaryl, -(heteroalkyl)aryl, or -(heteroalkyl)heteroaryl moieties may be substituted or unsubstituted;

x) compounds of the invention as described above and herein wherein $R^2$ is attached to a solid support;

xi) compounds of the invention as described above and herein wherein $R^2$ is —$(CH_2)_nOR^z$, $[(CH_2)_nO]_mR^z$, or —$(CH_2)_n$—Ar—$(CH_2)_m$OR$^z$; wherein n and m are each independently integers from 1–6, Ar represents a substituted or unsubstituted aryl or heteroaryl moiety, and $R^z$ is hydrogen, a protecting group or a solid support unit;

xii) compounds of the invention as described above and herein wherein $R^2$ is —$(CH_2)_nOR^z$, —$[(CH_2)_nO]_mR^z$, or —$(CH_2)_n$—Ar—$(CH_2)_m$OR$^z$; wherein n and m are each independently integers from 1–6, Ar represents a substituted or unsubstituted aryl or heteroaryl moiety, and $R^z$ is a solid support unit linked to O through a silyl linker;

xiii) compounds of the invention as described above and herein wherein $R^2$ is hydrogen or lower alkyl;

xiv) compounds of the invention as described above and herein wherein $R^2$ is hydrogen, methyl or ethyl;

xv) compounds of the invention as described above and herein wherein $R^2$ is ethyl;

xvi) compounds as described above and herein wherein $R^2$ is hydrogen or has one of the structures:

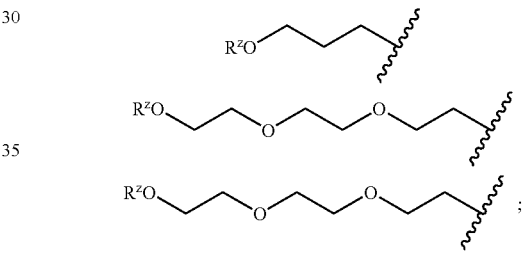

wherein $R^z$ is hydrogen, a protecting group or a solid support unit;

xvii) compounds of the invention as described above and herein wherein $R^3$ is substituted or unsubstituted, cyclic or acyclic, linear or branched, saturated or unsaturated alkyl or heteroalkyl, or substituted or unsubstituted aryl, heteroaryl, -(alkyl)aryl, -(alkyl)heteroaryl, -(heteroalkyl)aryl, or -(heteroalkyl)heteroaryl;

xviii) compounds as described above and herein wherein $R^3$ has one of the structures:

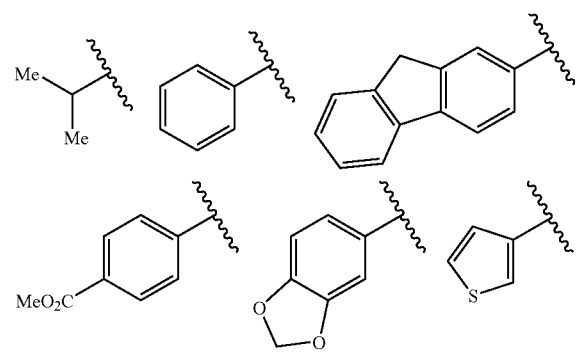

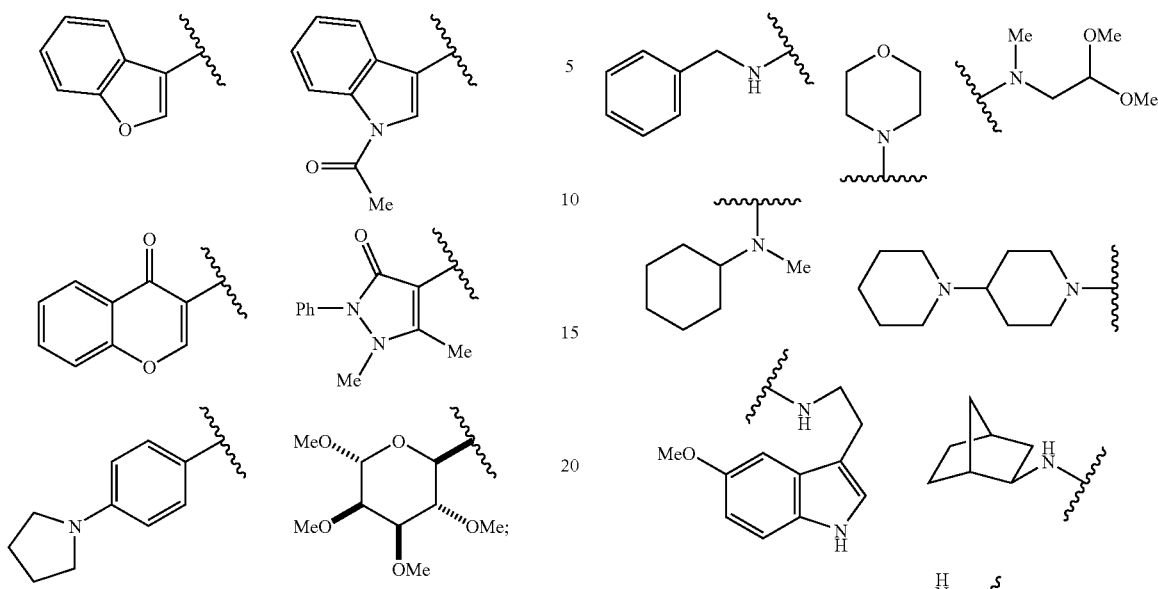
xix) compounds as described above and herein wherein R³ has one of the structures:
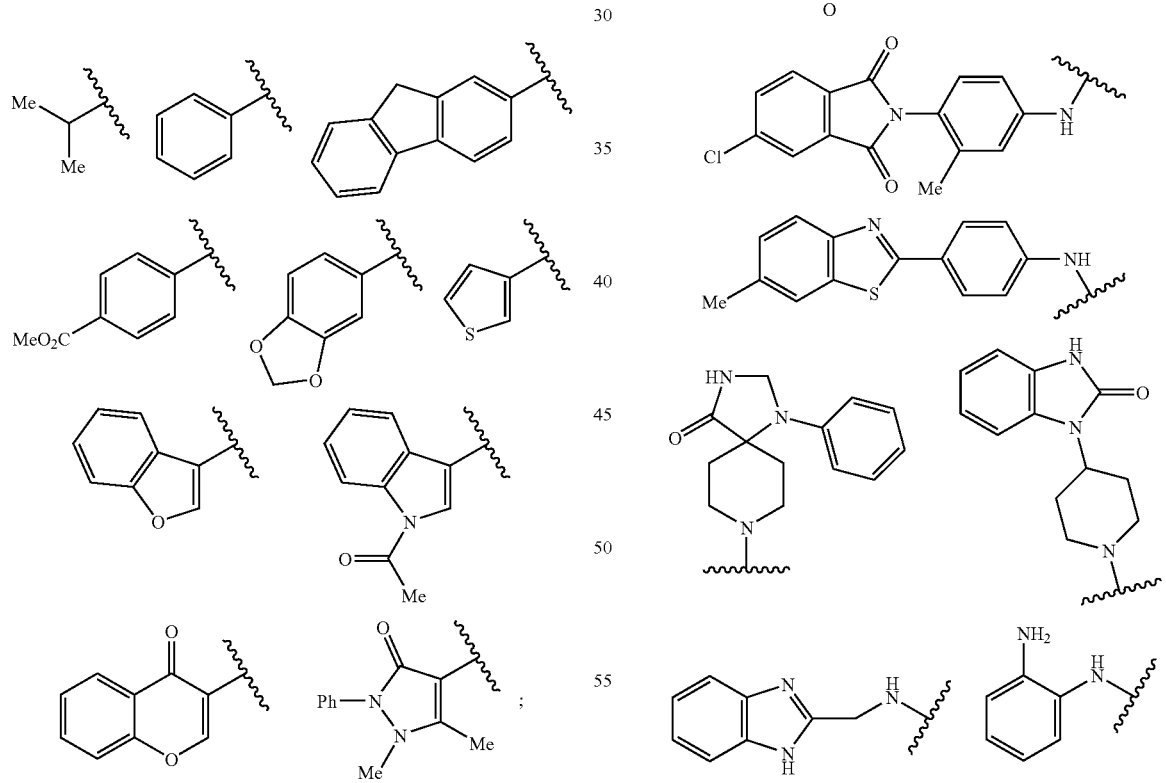
xx) compounds as described above and herein wherein R⁴ is hydrogen, alkyl, or heteroalkyl;
xxi) compounds as described above and herein wherein R⁴ is hydrogen; and
xxii) compounds as described above and herein wherein —NR⁵R⁶ has one of the structures:

-continued

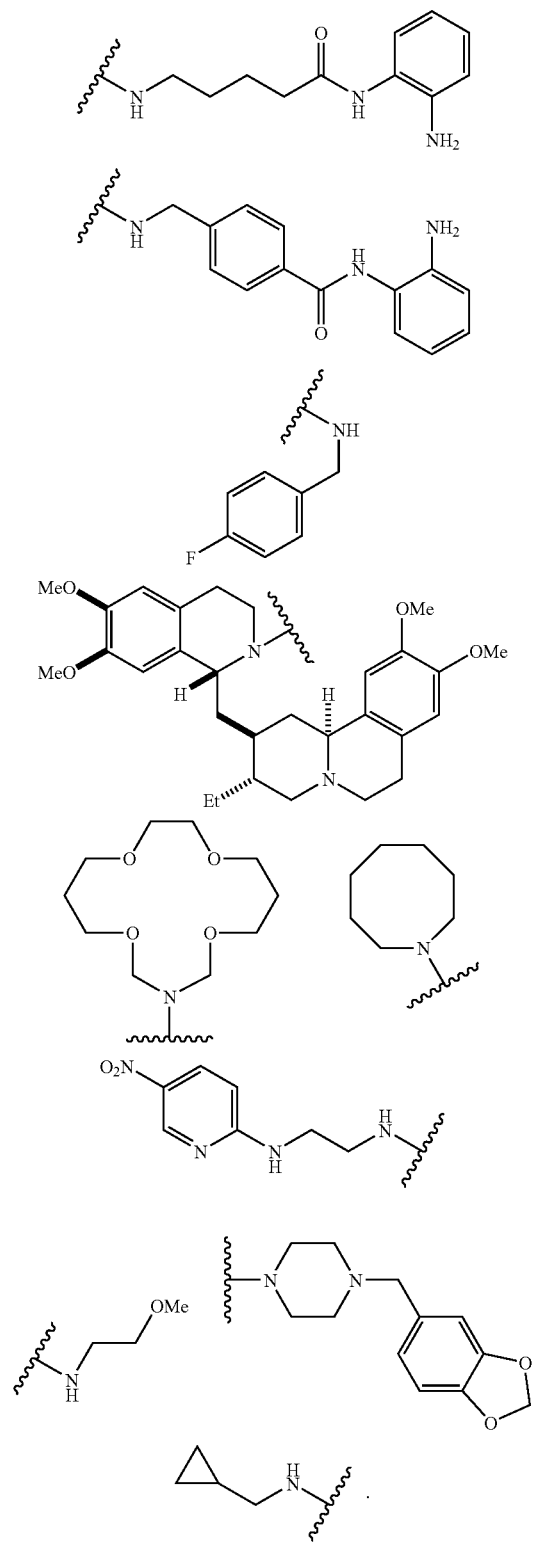

I) Compounds of the Formula:

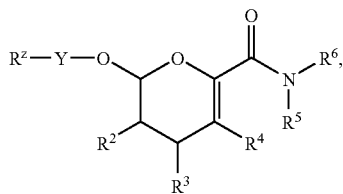

wherein $R^2$, $R^3$, $R^4$, $R^5$, $R^6$ and $R^Z$ are as described in classes and subclasses herein; and Y is a substituted or unsubstituted, cyclic or acyclic, linear or branched, saturated or unsaturated aliphatic or heteroaliphatic moiety, or a substituted or unsubstituted aryl, heteroaryl, -(aliphatic)aryl, -(aliphatic)heteroaryl, -(heteroaliphatic)aryl, or -(heteroaliphatic)heteroaryl moiety; wherein each of the foregoing alkyl or heteroalkyl moieties may be substituted or unsubstituted, linear or branched, cyclic or acyclic, saturated or unsaturated; and wherein each of the foregoing aryl, heteroaryl, (aliphatic)aryl, -(aliphatic)heteroaryl, -(heteroaliphatic)aryl, or -(heteroaliphatic)heteroaryl moieties may be substituted or unsubstituted.

In certain exemplary embodiments, Y is an alkyl, heteroalkyl, aryl, heteroaryl, -(alkyl)aryl, -(alkyl)heteroaryl, -(heteroalkyl)aryl, or -(heteroalkyl)heteroaryl moiety; $R^Z$ is hydrogen, a protecting group or a solid support unit; $R^2$, $R^3$ and $R^4$ are each independently hydrogen or an alkyl, heteroalkyl, aryl, heteroaryl, -(alkyl)aryl, -(alkyl)heteroaryl, -(heteroalkyl)aryl, or -(heteroalkyl)heteroaryl moiety; and $R^5$ and $R^6$ are each independently hydrogen or an alkyl, heteroalkyl, aryl, heteroaryl, -(alkyl)aryl, -(alkyl)heteroaryl, -(heteroalkyl)aryl, or -(heteroalkyl)heteroaryl moiety; or wherein $R^5$ and $R^6$, taken together, form a substituted or unsubstituted, saturated or unsaturated cyclic moiety comprising 5–12 carbon atoms, 0–5 oxygen atoms, 0–5 sulfur atoms and 1–5 nitrogen atoms; and wherein each of the foregoing alkyl or heteroalkyl moieties may be substituted or unsubstituted, linear or branched, cyclic or acyclic, saturated or unsaturated; and wherein each of the foregoing aryl, heteroaryl, -(alkyl)aryl, -(alkyl)heteroaryl, -(heteroalkyl)aryl, or -(heteroalkyl)heteroaryl moieties may be substituted or unsubstituted.

In certain embodiments, $R^Z$—Y— together represents a moiety having the structure:

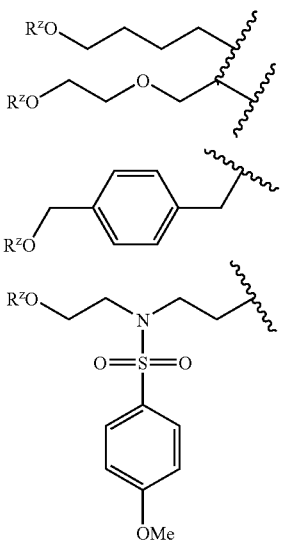

As the reader will appreciate, compounds of particular interest include, among others, those which share the attributes of one or more of the foregoing subclasses. Some of those subclasses are illustrated by the following sorts of compounds:

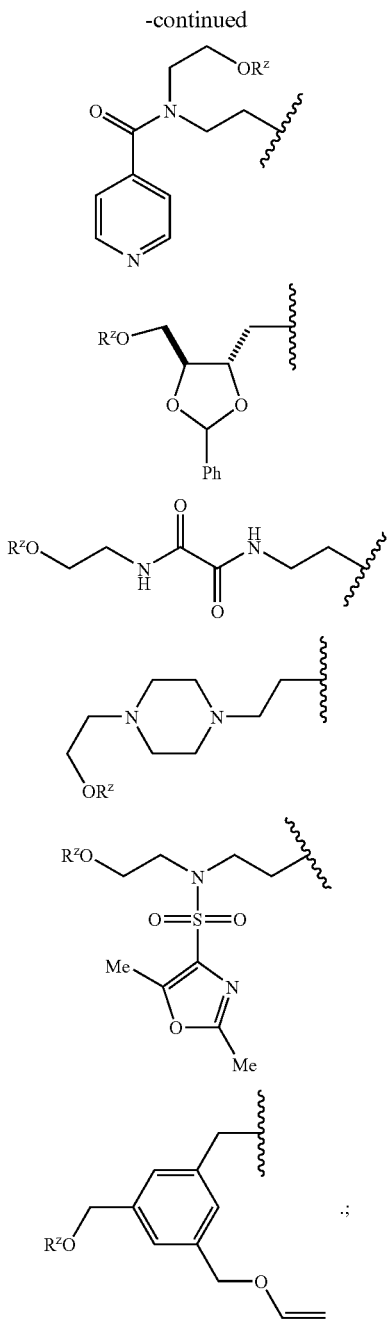

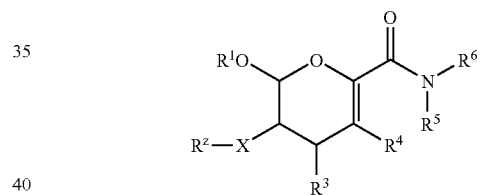

wherein $R^z$ is hydrogen, a protecting group or a solid support unit.

In certain exemplary embodiments, $R^z$—Y— together represents a moiety having the structure:

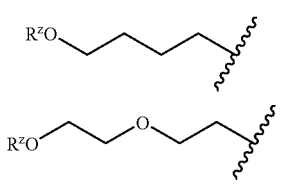

wherein $R^z$ is hydrogen, a protecting group or a solid support unit.

II) Compounds of the Formula:

wherein $R^1$, $R^3$, $R^4$, $R^5$, $R^6$ and $R^Z$ are as described in classes and subclasses herein; and X is a substituted or unsubstituted, cyclic or acyclic, linear or branched, saturated or unsaturated aliphatic or heteroaliphatic moiety, or a substituted or unsubstituted aryl, heteroaryl, -(aliphatic)aryl, -(aliphatic)heteroaryl, -(heteroaliphatic)aryl, or -(heteroaliphatic)heteroaryl moiety; wherein each of the foregoing alkyl or heteroalkyl moieties may be substituted or unsubstituted, linear or branched, cyclic or acyclic, saturated or unsaturated; and wherein each of the foregoing aryl, heteroaryl, (aliphatic)aryl, -(aliphatic)heteroaryl, -(heteroaliphatic)aryl, or -(heteroaliphatic)heteroaryl moieties may be substituted or unsubstituted.

In certain exemplary embodiments, X is an alkyl, heteroalkyl, aryl, heteroaryl, -(alkyl)aryl, -(alkyl)heteroaryl, -(heteroalkyl)aryl, or -(heteroalkyl)heteroaryl moiety; $R^Z$ is hydrogen, a protecting group or a solid support unit; $R^2$, $R^3$ and $R^4$ are each independently hydrogen or an alkyl, heteroalkyl, aryl, heteroaryl, -(alkyl)aryl, -(alkyl)heteroaryl, -(heteroalkyl)aryl, or -(heteroalkyl)heteroaryl moiety; and $R^5$ and $R^6$ are each independently hydrogen or an alkyl, heteroalkyl, aryl, heteroaryl, -(alkyl)aryl, -(alkyl)heteroaryl, -(heteroalkyl)aryl, or -(heteroalkyl)heteroaryl moiety; or wherein $R^5$ and $R^6$, taken together, form a substituted or unsubstituted, saturated or unsaturated cyclic moiety comprising 5–12 carbon atoms, 0–5 oxygen atoms, 0–5 sulfur atoms and 1–5 nitrogen atoms; and wherein each of the foregoing alkyl or heteroalkyl moieties may be substituted or unsubstituted, linear or branched, cyclic or acyclic, saturated or unsaturated; and wherein each of the foregoing aryl, heteroaryl, -(alkyl)aryl, -(alkyl)heteroaryl, -(heteroalkyl)aryl, or -(heteroalkyl)heteroaryl moieties may be substituted or unsubstituted.

In certain embodiments, $R^z$—X— together represents a moiety having the structure:

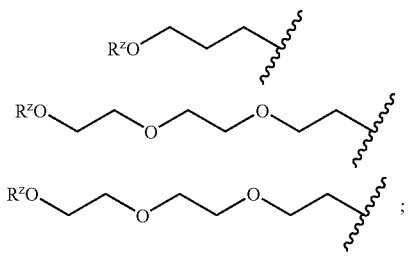

wherein $R^z$ is hydrogen, a protecting group or a solid support unit.

III) Compounds of the Formula:

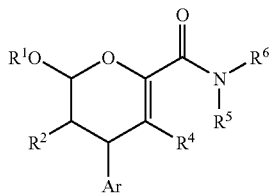

wherein $R^1$, $R^2$, $R^4$, $R^5$ and $R^6$ are as described in classes and subclasses herein; and Ar is a substituted or unsubstitued aryl or heteroaryl moiety.

In certain exemplary embodiments, $R^1$ and $R^2$ are each independently hydrogen, Z or an alkyl, heteroalkyl, aryl or heteroaryl moiety substituted with Z, wherein Z is hydrogen, —$(CH_2)_qOR^Z$, —$(CH_2)_qSR^Z$, $(CH_2)_qN(R^Z)_2$, —$(C=O)R^Z$, —$(C=O)N(R^Z)_2$, or an aliphatic, heteroaliphatic, aryl, heteroaryl, -(aliphatic)aryl, -(aliphatic)heteroaryl, -(heteroaliphatic)aryl, or -(heteroaliphatic)heteroaryl moiety, wherein q is 0–4, and wherein each occurrence of $R^Z$ is independently hydrogen, a protecting group, a solid support unit, or an aliphatic, heteroaliphatic, aryl, heteroaryl, -(aliphatic)aryl, -(aliphatic)heteroaryl, -(heteroaliphatic)aryl, or -(heteroaliphatic)heteroaryl moiety; $R^4$ is hydrogen or an alkyl, heteroalkyl, aryl, heteroaryl, -(alkyl)aryl, -(alkyl)heteroaryl, -(heteroalkyl)aryl, or -(heteroalkyl)heteroaryl moiety; and $R^5$ and $R^6$ are each independently hydrogen or an alkyl, heteroalkyl, aryl, heteroaryl, -(alkyl)aryl, -(alkyl)heteroaryl, -(heteroalkyl)aryl, or -(heteroalkyl)heteroaryl moiety; or wherein $R^5$ and $R^6$, taken together, form a substituted or unsubstituted, saturated or unsaturated cyclic moiety comprising 5–12 carbon atoms, 0–5 oxygen atoms, 0–5 sulfur atoms and 1–5 nitrogen atoms; and wherein each of the foregoing aliphatic, heteroaliphatic, alkyl or heteroalkyl moieties may be substituted or unsubstituted, linear or branched, cyclic or acyclic, saturated or unsaturated; and wherein each of the foregoing aryl, heteroaryl, -(alkyl)aryl, -(alkyl)heteroaryl, -(heteroalkyl)aryl, -(heteroalkyl)het-
eroaryl, -(aliphatic)aryl, -(aliphatic)heteroaryl, -(heteroaliphatic)aryl, or -(heteroaliphatic)heteroaryl moieties may be substituted or unsubstituted.

In certain exemplary embodiments, Ar is a moiety having the structure:

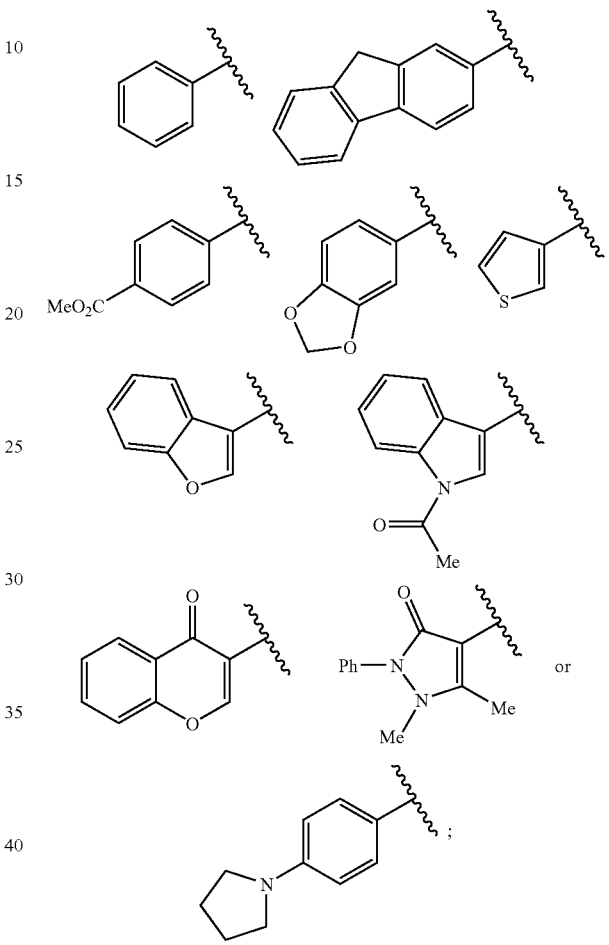

which may further be substituted with one or more occurrences of any substitutents described in the Definitions above.

In certain other exemplary embodiments, Ar is a moiety having the structure:

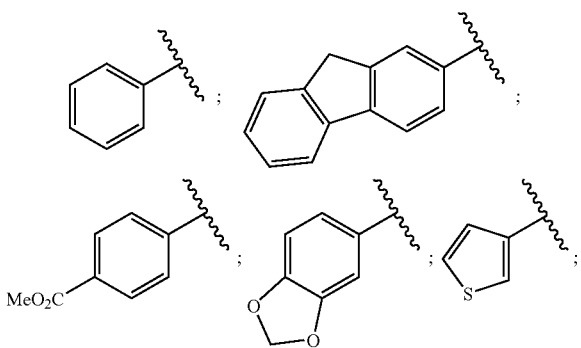

-continued

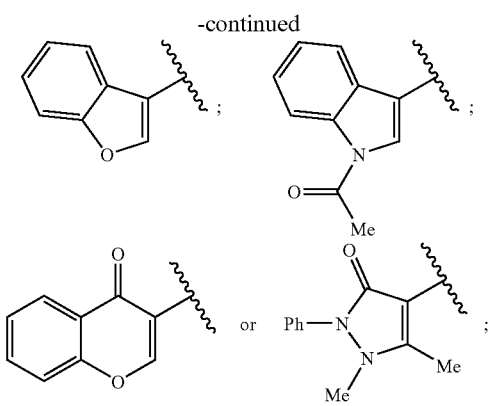

which may further be substituted with one or more occurrences of any substitutents described in the Definitions above.

IV) Compounds of the Formula:

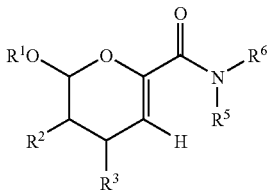

wherein $R^1$, $R^2$, $R^3$, $R^5$ and $R^6$ are as described in classes and subclasses herein.

In certain exemplary embodiments, $R^1$ and $R^2$ are each independently hydrogen, Z or an alkyl, heteroalkyl, aryl or heteroaryl moiety substituted with Z, wherein Z is hydrogen, $-(CH_2)_qOR^Z$, $-(CH_2)_qSR^Z$, $(CH_2)_qN(R^Z)_2$, $-(C=O)R^Z$, $-(C=O)N(R^Z)_2$, or an aliphatic, heteroaliphatic, aryl, heteroaryl, -(aliphatic)aryl, -(aliphatic)heteroaryl, -(heteroaliphatic)aryl, or -(heteroaliphatic)heteroaryl moiety, wherein q is 0–4, and wherein each occurrence of $R^Z$ is independently hydrogen, a protecting group, a solid support unit, or an aliphatic, heteroaliphatic, aryl, heteroaryl, -(aliphatic)aryl, -(aliphatic)heteroaryl, -(heteroaliphatic)aryl, or -(heteroaliphatic)heteroaryl moiety; $R^3$ is hydrogen or an alkyl, heteroalkyl, aryl, heteroaryl, -(alkyl)aryl, -(alkyl)heteroaryl, -(heteroalkyl)aryl, or -(heteroalkyl)heteroaryl moiety; $R^5$ and $R^6$ are each independently hydrogen or an alkyl, heteroalkyl, aryl, heteroaryl, -(alkyl)aryl, -(alkyl)heteroaryl, -(heteroalkyl)aryl, or -(heteroalkyl)heteroaryl moiety; or wherein $R^5$ and $R^6$, taken together, form a substituted or unsubstituted, saturated or unsaturated cyclic moiety comprising 5–12 carbon atoms, 0–5 oxygen atoms, 0–5 sulfur atoms and 1–5 nitrogen atoms; and wherein each of the foregoing aliphatic, heteroaliphatic, alkyl or heteroalkyl moieties may be substituted or unsubstituted, linear or branched, cyclic or acyclic, saturated or unsaturated; and wherein each of the foregoing aryl, heteroaryl, -(alkyl)aryl, -(alkyl)heteroaryl, -(heteroalkyl)aryl, -(heteroalkyl)heteroaryl, -(aliphatic)aryl, -(aliphatic)heteroaryl, -(heteroaliphatic)aryl, or -(heteroaliphatic)heteroaryl moieties may be substituted or unsubstituted.

It will be appreciated that some of the foregoing classes and subclasses of compounds can exist in various isomeric forms. The invention encompasses the compounds as individual isomers substantially free of other isomers and alternatively, as mixtures of various isomers, e.g., racemic mixtures of stereoisomers. Additionally, when $R^1$, $R^2$, $R^3$, $R^4$, $R^5$ and/or $R^6$ comprise a double bond, the invention encompasses both (Z) and (E) double bond isomers unless otherwise specifically designated. The invention also encompasses tautomers of specific compounds as described above. In addition to the above-mentioned compounds per se, this invention also encompasses pharmaceutically acceptable derivatives of these compounds and compositions comprising one or more compounds of the invention and one or more pharmaceutically acceptable excipients or additives.

Synthetic Methodology

In yet another aspect of the present invention, novel methods for the synthesis of the novel dihydropyrancarboxamides as described herein are provided.

According to the present invention, any available techniques can be used to make or prepare the inventive dihydropyrancarboxamides or compositions including them. For example, combinatorial techniques, parallel synthesis and/or solid phase synthetic methods such as those discussed in detail below may be used. Alternatively, the inventive compounds may be prepared using any of a variety of solution phase synthetic methods known in the art (e.g., one compounds at a time).

Figure 2:
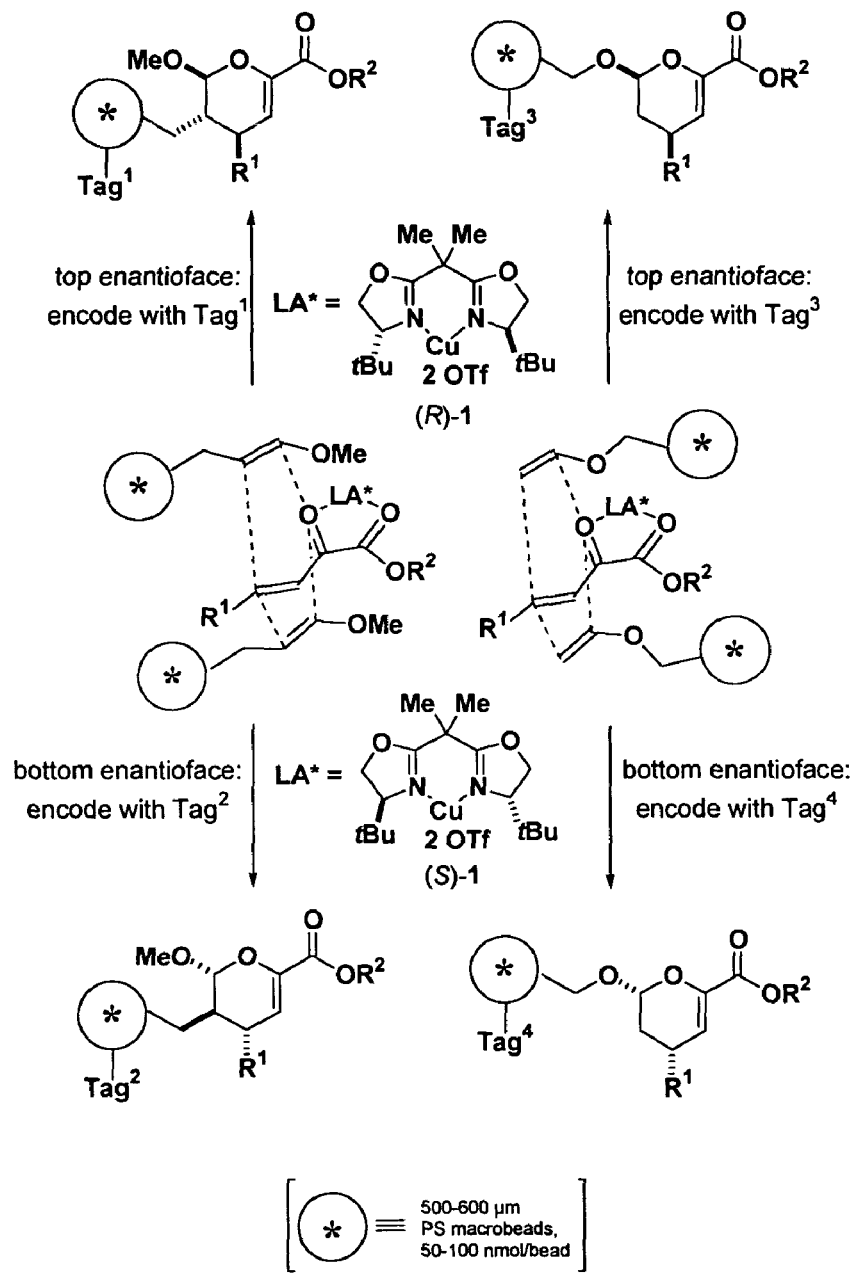
FIG. 2 depicts an exemplary encoded split-pool synthesis of dihydropyrancarboxamides, with the (S)-1 catalyst. The corresponding opposite enantiomers of compounds 7–15 are obtained when the (R)-1 catalyst is used. Encircled $R^1$ and $R^2$ symbols represent elements found in building blocks BB1-A-H in FIG. 3. PyBOP=benzotriazol-1yloxytripyrrolidinophosphonium hexafluorophosphate, DMF=N,N-dimethylformamide, THF=tetrahydrofuran.

In certain exemplary embodiments, the method takes advantage of efficient catalytic asymmetric heterocycloaddition reactions as depicted in FIG. 2 (see, a) D. A. Evans, J. S. Johnson, E. J. Olhava, *J. Am. Chem. Soc.* 2000, 122, 1635–1649; b) D. A. Evans, E. J. Olhava, J. S. Johnson, J. M. Janey, *Angew. Chem.* 1998, 110, 3554–3557; *Angew. Chem. Int. Ed.* 1998, 37, 3372–3375; c) J. Thorhauge, M. Johannsen, K. A. Jorgensen, *Angew. Chem.* 1998, 110, 2543–2546; *Angew. Chem. Int. Ed.* 1998, 37, 2404–2406; d) H. E. Balckwell, L. Pérez, R. A. Stavenger, J. A. Tallarico, E. Cope Eatough, M. A. Foley, S. L. Schreiber, *Chem. Biol.* 2001, 1167–1182; e) P. A. Clemmons, A. N. Koehler, B. K. Wagner, T. G. Sprigings, D. R. Spring, R. W. King, S. L. Schreiber, M. A. Foley, *Chem. Biol.* 2001, 1183–1195; and f) R. A. Stavenger, S. L. Schreiber, *Angew. Chem. Int. Ed.* 2001, 40(18), 3417–3421). In certain embodiments, following the heterocycloaddition reaction, as depicted in FIG. 2, a variety of diversity generating reactions may be performed to complete the synthesis of each member of the library of compounds.

In certain exemplary embodiments, according to the method of the present invention, a core structure can be provided, wherein the core structure is synthesized by the method comprising:

providing a vinyl ether having the structure:

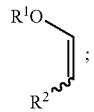

providing an unsaturated ketoester having the structure:

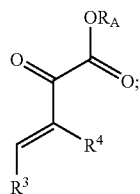

subjecting the vinyl ether and the unsaturated ketoester to suitable conditions to generate a scaffold having the core structure:

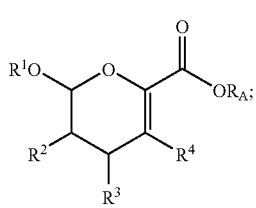

(III)

wherein $R^1$ and $R^2$ are each independently hydrogen or an aliphatic, heteroaliphatic, aryl, heteroaryl, alkylaryl or alkylheteroaryl moiety; wherein one of $R^1$ or $R^2$ is attached to a solid support;

$R^3$ and $R^4$ are each independently hydrogen or an aliphatic, heteroaliphatic, aryl, heteroaryl, alkylaryl or alkylheteroaryl moiety;

$R_A$ is hydrogen or is an aliphatic, heteroaliphatic, aryl, heteroaryl, alkylaryl, or alkylheteroaryl moiety;

wherein each of the foregoing aliphatic and heteroaliphatic moieties may be substituted or unsubstituted, cyclic or acyclic, saturated or unsaturated or linear or branched; and each of the foregoing aryl, heteroaryl, alkylaryl or alkylheteroaryl moieties may be substituted or unsubstituted.

In certain embodiments, $R^1$ or $R^2$ is attached to a solid support via a silyl linker.

It will be appreciated that the synthetic methods, as described herein, may utilize a variety of protecting groups (e.g. O, S, or N protecting groups) to temporarily block a particular functional group so that a reaction can be carried out selectively at another reactive site in a multifunctional compound. One of ordinary skill in the art will recognize that, in addition to the specific protecting groups described in the Examples herein, a variety of well-known protecting groups in the art of organic synthesis can also be utilized as detailed in Greene and Wuts, *Protective Groups in Organic Synthesis*, Third Edition, John Wiley & Sons, New York: 1999, the entire contents of which are hereby incorporated by reference.

Once the core structure is prepared, as detailed above, one or more compounds can be synthesized via combinatorial techniques, or by synthesizing one compound at a time, by diversifying at particular functional groups. Thus, in another embodiment, the method further comprises functionalizing the core structure (III) at one or more sites to generate compounds having the structures (Ia):

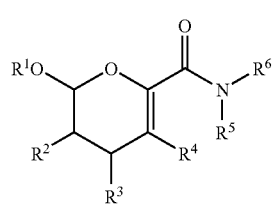

(Ia)

wherein $R^1$–$R^6$ are as defined in classes and subclasses herein; and one of $R^1$ or $R^2$ is attached to a solid support.

In certain embodiments, the method further comprises functionalizing the core structure (III) at one or more sites to generate compounds having the structures (IIa):

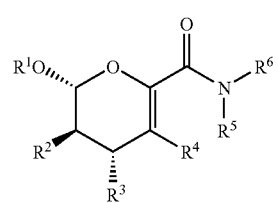

(IIa)

and/or enantiomer thereof;

wherein $R^1$–$R^6$ are as defined in classes and subclasses herein; and one of $R^1$ or $R^2$ is attached to a solid support.

In certain embodiments, the carboxylic ester moiety can be converted, among others, to an acid halide, amide, anhydride, diketone, imide or nitrile moiety; the conjugated carboxyl moiety can be functionalized via conjugate addition and can be diversified using oxygen, sulfur, nitrogen or carbon nucleophiles, to name a few. In addition, where the substitutents $R_A$, $R^1$, $R^2$, $R^3$, $R^4$, $R^5$ and/or $R^6$ comprise an aryl or heteroaryl group, such aryl or heteroaryl group may be further diversified by introducing additional functionalities according to methods known in the art.

In certain embodiments, the method further comprises cleaving the core structure (III) from the solid support to which it is attached either before or after chemical derivatization.

In certain exemplary embodiments, the carboxylic ester —$CO_2R_A$ can be derivatized to form the corresponding amido compound having the structure (Ia):

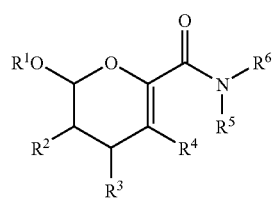

(Ia)

wherein $R^1$ and $R^2$ are each independently hydrogen or an aliphatic, heteroaliphatic, aryl, heteroaryl, alkylaryl or alkylheteroaryl moiety; wherein one of $R^1$ or $R^2$ is attached to a solid support;

$R^3$ and $R^4$ are each independently hydrogen or an aliphatic, heteroaliphatic, aryl, heteroaryl, alkylaryl or alkylheteroaryl moiety;

R[5] and R[6] are each independently hydrogen or an aliphatic, heteroaliphatic, aryl, heteroaryl, alkylaryl, or alkylheteroaryl moiety, and wherein R[5] and R[6], taken together, may form a cyclic aliphatic, heteroaliphatic, aliphatic (aryl), heteroaliphatic(aryl), aliphatic(heteroaryl) or heteroaliphatic(heteroaryl) moiety, or an aryl or heteroaryl moiety;

wherein each of the foregoing aliphatic and heteroaliphatic moieties may be substituted or unsubstituted, cyclic or acyclic, saturated or unsaturated or linear or branched; and each of the foregoing aryl, heteroaryl, alkylaryl or alkylheteroaryl moieties may be substituted or unsubstituted.

In certain exemplary embodiments, synthetic transformation of the carboxylic moiety —CO$_2$R$_A$ is achieved by conversion of the ester moiety to the corresponding carboxylic acid, followed reaction with a suitable amine under conditions suitable to effect amide formation. Examples of amines suitable for practicing the invention include, but are not limited to:

-continued

BB3-R
BB3-S
BB3-T
BB3-U
BB3-V
BB3-W
BB3-X
BB3-Y

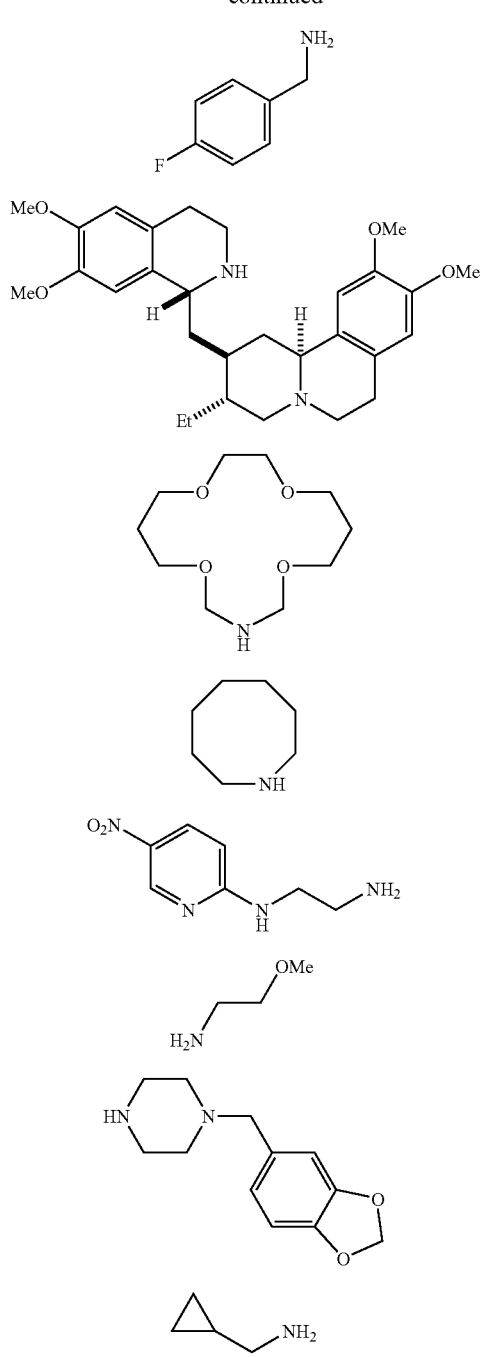

In certain exemplary embodiments, conjugated carboxylate functionalization is achieved using furfuryl mercaptan, 3-(trifluoromethyl)benzyl mercaptan, 3-methyl-1-buranethiol, 4-methoxy-alpha-toluenethiol, benzyl mercaptan, 2-(tert butyldimethylsiloxy)ethylmercaptan, cyclopentanethiol, or a skip codol. In certain embodiments, amine (nitrogen functionalization) is achieved using benzoyl chloride, benzyl isocyanate, ethyl isocyanate, thiophene-2-carbonyl chloride, 3-(methylthio)propionaldehyde, undecanal, cyclopropanecarboxaldehyde, or a skip codon. In certain embodiments, ketone functionalization is achieved using p-toluenesulfonhydrazide, dansyl hydrazine, methoxyamine hydrochloride, o-Benzylhydroxylamine hydrochloride, Carboxymethoxylamine hemihydrochloride, p-Methoxybenzensulfonylhydrazide, 4-Nitrophenylhydrazine or a skip codon.

Although certain exemplary diversification reactions and reagents are described in more detail herein, it will be appreciated that the present invention is intended to encompass equivalent diversification reactions within the arsenal of synthetic organic chemistry that can be utilized to diversify the inventive scaffold as described herein (See, generally, March, Advanced Organic Chemistry, John Wiley & Sons, 1992; and "Comprehensive Organic Transformations, a guide to functional group preparations", Richard C. Larock, VCH publishers, 1999; the entire contents of which are incorporated herein by reference). For example, although certain reagents for amide formation are described in the examples (e.g., 2-methoxy-ethylamine), it will be appreciated that other derivatives can be utilized (e.g., 2-ethoxyethylamine, 2-propoxyethylamine, etc.), including, but not limited to, homologues and other similarly substituted moieties. These additional examples are not intended to limit the scope of the invention; rather they are provided to exemplify the broad utility of the inventive scaffold in the employment of a variety of diversification reactions and reagents.

In certain embodiments, the method further comprises cleaving the structure (Ia) from the solid support to which it is attached to give a compound having the structure (I):

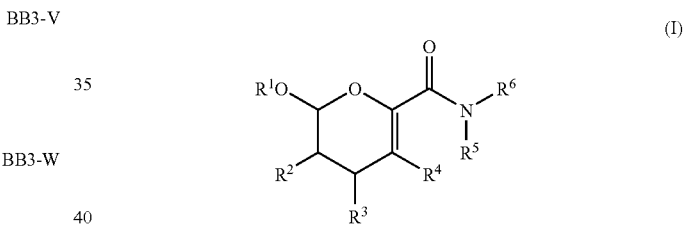

(I)

wherein $R^1$–$R^4$ are each independently hydrogen or an aliphatic, heteroaliphatic, aryl, heteroaryl, alkylaryl or alkylheteroaryl moiety;

$R^5$ and $R^6$ are each independently hydrogen or an aliphatic, heteroaliphatic, aryl, heteroaryl, alkylaryl, or alkylheteroaryl moiety, and wherein $R^5$ and $R^6$, taken together, may form a cyclic aliphatic, heteroaliphatic, aliphatic (aryl), heteroaliphatic(aryl), aliphatic(heteroaryl) or heteroaliphatic(heteroaryl) moiety, or an aryl or heteroaryl moiety;

wherein each of the foregoing aliphatic and heteroaliphatic moieties may be substituted or unsubstituted, cyclic or acyclic, saturated or unsaturated or linear or branched; and each of the foregoing aryl, heteroaryl, alkylaryl or alkylheteroaryl moieties may be substituted or unsubstituted.

In one exemplary embodiment, as depicted in FIG. 1, and as described in Example 1, a library was synthesized on 500–600 μm high capacity polystyrene beads functionalized with a trialkylsilyl linker (See also, Scheme 1) (P. A. Clemmons, A. N. Koehler, B. K. Wagner, T. G., Sprigings, D. R. Spring, R. W. King, S. L. Schreiber, M. A. Foley, Chem. Biol. 2001, 1183–1195; see also Example 2, herein).

Scheme 1

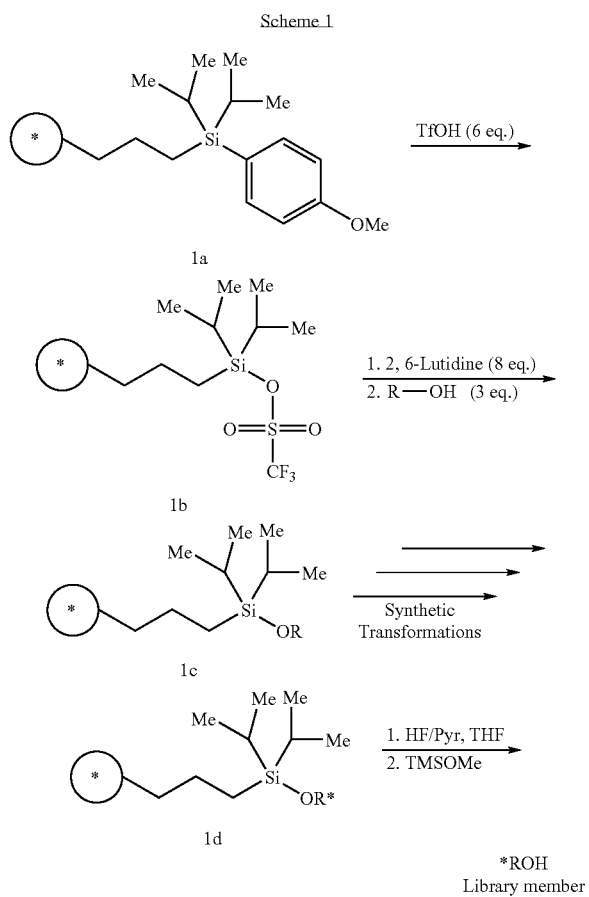

*ROH Library member

Figure 3:
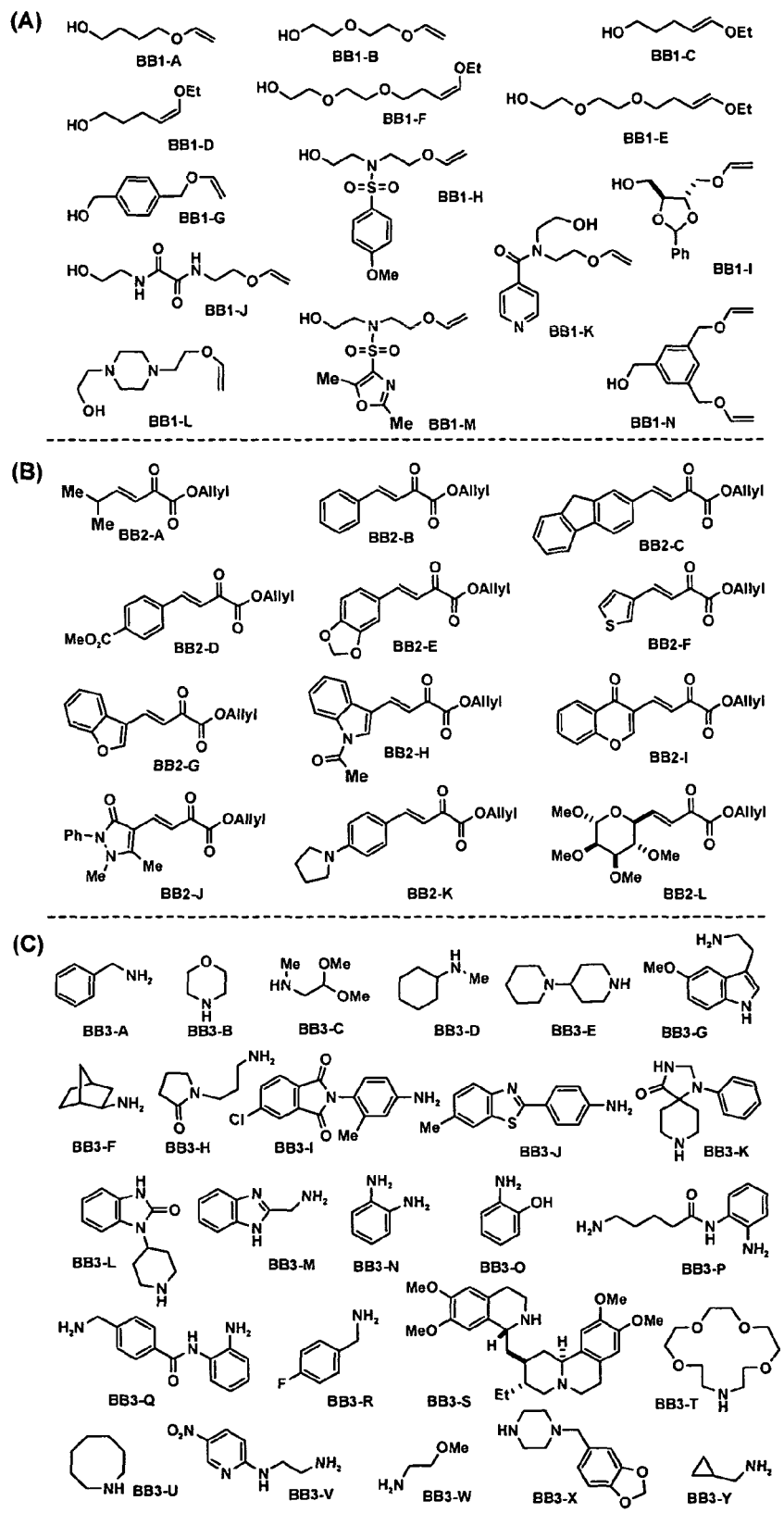
FIG. 3 depicts building blocks for the inventive dihydropyrancarboxamide libraries.

For example, as depicted in Scheme 1, disoprolyalkylsilyl-functionalized resin 1a can be activated by treatment with excess triflic acid to form 1b. Alcohol compound ROH can then be trapped onto the activated resin in the presence of excess 2,6-lutidine to generate the corresponding silyl ether 1c. After subjecting —R to suitable reaction conditions to effect the desired synthetic transformations, the substrate may be cleaved from the solid support 1d by reaction with HF, followed by quenching of excess HF with methoxytrimethylsilane (TMSOMe), to give the desired library members. In certain embodiments, for the library synthesis, building blocks can be selected that reacted in good yield and, as a group, possess diverse physical characteristics. Exemplary building blocks suitable for practicing the invention are depicted in FIG. 3. One of ordinary skill in the art will appreciate that other building blocks may be used.

In but one exemplary embodiment, the library was prepared as a triplicate copy (3 bead per library member), arrayed in 384-well plates, and detached from the solid-support with HF-pyridine. Evaporation of the cleavage cocktail and resuspension in DMF or DMSO afforded 4320 stock solutions for biological screening.

Research Uses

According to the present invention, the inventive compounds may be assayed in any of the available assays known in the art for identifying compounds having a biological activity of interest. For example, the assay may be cellular or non-cellular, in vivo or in vitro, etc. Any assay format may be used to screen the inventive compounds (e.g., formats amenable to high-throughput screening). Examples of biological activity include, but are not limited to, binding activity or biological activity against target molecules (e.g., inhibitors of target enzymes, competitors for binding of a natural ligand to its receptor, agonists or antagonists for receptor-mediated intracellular processes, to name a few), toxicity evaluation or bioavailability assessment, etc.

In certain exemplary embodiments, compounds of this invention were assayed for their ability to:
inhibit DNA synthesis (e.g., DNA replication);
exhibit genistein suppressor activity;
exhibit Eg5 inhibitory activity;

Thus, in one aspect, compounds of this invention which are of particular interest include those which:
inhibit DNA synthesis (e.g., DNA replication);
have genistein suppressor activity;
exhibit Eg5 inhibitory activity;
exhibit cytotoxic or growth inhibitory effect on cancer cell lines maintained in vitro or in animal studies using a scientifically acceptable cancer cell xenograft model;
exhibit a therapeutic profile (e.g., optimum safety and curative effect) that is comparable or superior to existing chemotherapeutic agents.

As discussed above, the compounds of the invention may be assayed for any of a variety of biological activities (e.g., in high-throughput screening assays). For example, the library members may be arrayed according to the method described in patent application Ser. No.: 09/567,910, filed May 10, 2000, which is incorporated herein by reference in its entirety, and screened for detecting binding and/or activation events occurring between members in the inventive library and biological macromolecules of interest (e.g., for identifying small molecule partners (library members) for biological macromolecules of interest). The partners may be compounds that bind to particular macromolecules of interest and are capable of activating or inhibiting the biological macromolecules of interest. As discussed above, in one aspect, the present invention provides methods, referred to herein as "small molecule printing", for the generation of high density arrays and the resulting compositions. According to the method of the present invention, a collection of chemical compounds, or one type of compound, can be "printed" onto a support to generate extremely high density arrays. In certain embodiments, one or more library members may be arrayed by (1) providing a solid support, wherein the solid support is functionalized with a desired chemical moiety capable of interacting with a desired chemical compound to form an attachment; (2) providing one or more solutions of the library members to be attached to the solid support; and (3) delivering the one or more solutions of the library members to the solid support, whereby an array of compounds is generated and the array has a density of at least 1000 spots per $cm^2$. In certain exemplary embodiments, a silylation reaction can be employed to attach the library members to a glass slide.

In certain embodiments, plain glass slides are derivatized to yield surfaces that are densely functionalized with silyl halides. Compounds containing hydroxyl groups (e.g., library members) can then be provided and contacted with the functionalized glass surface. The hydroxyl containing compounds readily attach to the surface through the silicon-oxygen bond formed by nucleophilic substitution on the silyl halide. In a preferred embodiment, the silyl halide is silyl chloride, bromide, or iodide. In other preferred embodiments, leaving groups on the silicon such as mesylate and tosylate are used rather than halides. Preferably, the hydroxyl groups of the compounds to be attached are unhindered (e.g., primary alcohols). See, for example, Hergenrother et al., *J. Am. Chem. Soc.*, 122:7849–7850, 2000, which is incorporated herein by reference in its entirety.

In certain embodiments, assaying the library members may be accomplished by (1) arraying the library members, as described above, with a density of at least 1000 spots per $cm^2$; (2) contacting the array with one or more types of biological macromolecules of interest; and (3) determining the interaction of specific small molecule-biological macromolecule partners.

It will also be appreciated that the arrays of compounds may be utilized in a variety of ways to enable detection of interactions between library members and biological macromolecules. In one particularly preferred embodiment, an array of different types of chemical compounds attached to the surface is utilized and is contacted by one or a few types of biological macromolecules to determine which compounds are capable of interacting with the specific biological macromolecule(s). As one of ordinary skill in the art will realize, if more than one type of compound is utilized, it is desirable to utilize a method for encoding each of the specific compounds so that a compound having a specific interaction can be identified. Specific encoding techniques have been recently reviewed and these techniques, as well as other equivalent or improved techniques, can be utilized in the present invention (see, Czarnik, A. W. *Current Opinion in Chemical Biology* 1997, 1, 60; which is incorporated herein by reference in its entirety). Alternatively the arrays of the present invention may comprise one type of chemical compound and a library of biological macromolecules may be contacted with this array to determine the ability of this one type of chemical compound to interact with a variety of biological macromolecules.

As one of ordinary skill in the art will realize, the biological macromolecule of interest may comprise any biomolecule. In preferred embodiments, the biological macromolecule of interest comprises a protein, and more preferably the array is contacted with a library of recombinant proteins of interest. In yet another preferred embodiment, the biological molecules of interest are provided in the form of cell lysates such as, for example, those of tumor-associated cells. As will be appreciated by one of ordinary skill in the art, these proteins may comprise purified proteins, pools of purified proteins, and complex mixtures such as cell lysates, and fractions thereof, to name a few. Examples of particularly preferred biological macromolecules to study include, but are not limited to those involved in signal transduction, dimerization, gene regulation, cell cycle and cell cycle checkpoints, and DNA damage checkpoints. Furthermore, the ability to construct libraries of expressed proteins from any organism or tissue of interest will lead to large arrays of recombinant proteins. The compounds of interest may be capable of either inactivating or activating the function of the particular biomolecule of interest.

In certain exemplary embodiments, the inventive library may be screened to identify those library members capable of exerting an effect on an intracellular biological or chemical process. For a detailed description of the screening method, see U.S. patent application Ser. No.: 09/361,576 and PCT Patent Application No.: US99/17046, each of which is incorporated herein by reference in its entirety. In one aspect, the method encompasses screening chemical compounds for their effects on chemical and/or biological systems by detecting the presence or amount of a component present or produced by the system, which component acts as a marker for the chemical or biological process of interest. Often, detection of the presence or amount of such a biological component will reveal a perturbation in an underlying biological process. For example, the biological component may be a component or product of a cell signaling pathway, so that detection of the component allows the identification of test compounds that perturb the pathway. In certain embodiments, whole cells may be arrayed on a suitable solid support and one or more library members may be contacted with the arrayed cells under conditions suitable for at least one of the test compounds to exert an effect on an intracellular biological or chemical process. A ligand may then be contacted with said cells in each reaction vessel under conditions suitable for said ligand to associate intracellularly with at least one biological component whose presence or amount is indicative of said biological or chemical process. Finally, the presence or amount of the ligand associated with said biological component may be measured with a suitable detection method. Preferably, the biological component is detected by means of its interaction with a binding partner ligand. Preferably, the binding is specific. In certain preferred embodiments, the binding partner ligand is an antibody. In certain embodiments, the library may be screened to identify compounds that effect changes in a variety of different cellular processes, including, for example, protein concentration, protein phosphorylation, methylation, acetylation, lipidation, isoprenylation, ubiquitination, second messenger concnetration, and the rate or extent of DNA synthesis.

In certain embodiments, compounds of the invention inhibit BrdU incorporation in cells. BrdU (5-bromodeoxyuridine) is a thymidine analog in which the methyl group at the 5-position is replaced with bromine (FIG. 2a). This analog is efficiently incorporated into DNA during DNA replication, and can be detected with an antibody raised specifically against this modified form. By detecting the incorporation of a natural nucleotide or non-natural nucleotide, it is possible to determine growth and viability of a cell or collection of cells. DNA synthesis in a cell is an indicator of growth and viability. Therefore, compounds which may affect cell growth, the cell cycle, and viability of cells may be assayed using BrdU as a signaling cellular component. In certain exemplary embodiments, inventive compounds are useful for the treatment of disorders associated with abnormal cell growth or cell proliferation (e.g., cancer).

In certain other embodiments, compounds of the invention exhibit Eg5 inhibitory activity. Eg5 is a kinesin-related motor essential for bipolar spindle formation in vivo. Mitotic kinesins are enzymes essential for assembly and function of the mitotic spindle, but are not generally part of other microtubule structures, such as nerve processes. Mitotic kinesins play essential roles during all phases of mitosis. These enzymes are "molecular motors" that translate energy released by hydrolysis of ATP into mechanical force which drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest. From both the biological and enzymatic perspectives, these enzymes are attractive targets for the discovery and development of novel anti-mitotic chemotherapeutics.

In yet other embodiments, compounds of the invention exhibit genistein suppressor activity. Genistein (4',5,7 trihydroxyisoflavone) is a broad-spectrum protein tyrosine kinase inhibitor that has been shown to have growth inhibitory effects against several cancers both in vitro and in vivo.

Pharmaceutical Compositions

In another aspect, this invention also provides pharmaceutical preparations comprising at least one of the compounds as described above and herein, optionally, though typically in combination with a pharmaceutically acceptable carrier. In certain embodiments, the compounds are capable of inhibiting the growth of or killing cancer cells. Thus, the present invention provides pharmaceutical compositions for treating cancer, preferably for preventing the recurrence of cancer, comprising a compound of the present invention disclosed herein, as an active ingredient, optionally, though typically in combination with a pharmaceutically acceptable carrier.

As detailed herein, several of the inventive compositions have been determined to have a wide range of biological activities (e.g., inhibition of Eg5 ATPase activity, FKBP12 binding, inhibition of DNA replication, genistein suppressor activity). Thus, in another aspect of the present invention, pharmaceutical compositions are provided, wherein these compositions include a compound that is useful in treating a "physiological condition," defined herein as any biological or biochemical process that affects the health of an individual, and a pharmaceutically acceptable carrier. It will be appreciated that the inventive pharmaceutical compositions encompasses each of those compounds identified that inhibit or activate any physiological process.

It will also be appreciated that certain of the compounds of the present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof, e.g., a prodrug.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutical Compositions

In yet another aspect, according to the methods of treatment of the present invention, physiological conditions are treated or prevented in a subject such as a human, lower mammal, or other organism, by administering to the patient a therapeutically effective amount of an inventive compound or pharmaceutical composition thereof, as described in detail above, in such amounts and for such time as is necessary to achieve the desired result. In certain embodiments of the present invention a "therapeutically effective amount" of an inventive compound or pharmaceutical composition is that amount effective for reducing the symptoms associated with the physiological condition. In other preferred embodiments, a "therapeutically effective amount" of an inventive compound or pharmaceutical composition is that amount effective for affecting the secretory pathway of a cell. Other "therapeutically effective amounts" include amounts effective for inhibiting the cell cycle, e.g., inhibiting the growth of cancer cells. Alternatively or additionally, a "therapeutically effective amount" is an amount that is effective for inhibiting or activating a physiological process of interest, wherein the physiological process is related to improving the health of the individual.

The compounds and compositions, according to the method of the present invention, may be administered using any amount and any route of administration effective for obtaining the physiological result. Thus, the expression "therapeutically effective amount," as used herein, refers to a nontoxic but sufficient amount of an inventive compound to provide the desired treatment. The exact amount required will vary from subject to subject, depending on the species, age, and general condition of the subject, the severity of the physiological condition (e.g., a proliferative disorder or cancer), the particular compound, its mode of administration, and the like. The compounds of the invention are preferably formulated in dosage unit form for ease of administration and uniformity of dosage. The expression "dosage unit form" as used herein refers to a physically discrete unit of compound appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see Goodman and Gilman's, "The Pharmacological Basis of Therapeutics", Tenth Edition, A. Gilman, J. Hardman and L. Limbird, eds., McGraw-Hill Press, 155–173, 2001, which is incorporated herein by reference in its entirety).

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the condition being treated. In certain embodiments, the compounds of the invention may be administered orally or parenterally at dosage levels of about 0.01 mg/kg to about 50 mg/kg and preferably from about 0.1 mg/kg to about 25 mg/kg, of patient body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The invention further encompasses compounds and pharmaceutical compositions employed in combination therapies, that is, the compounds and pharmaceutical compositions can be administered concurrently with, prior to, or subsequent to, one or more other desired therapeutics or medical procedures The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects.

For example, other compounds that may be used in combination with the compounds that can be provided using the structural information of the present invention. For example, if the inventive compound is a chemotherapeutic agent, a second or third chemotherapeutic agent, such as cisplatin, may be administered with the inventive compound to achieve the benefit of their combined effects. As but another example, if the compound were to treat or prevent a reproductive disorder, the inventive compound may be administered with a hormone, such as testosterone or estrogen. For a more comprehensive discussion regarding physiological conditions, symptoms and treatment, see The Merck Manual, Seventeenth Ed. 1999, the entire contents of which are hereby incorporated by reference.

In certain embodiments, the pharmaceutical compositions of the present invention may further comprise other therapeutically active ingredients (e.g., chemotherapeutic and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

In yet another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

Methods of Treatment

In another embodiment, the compounds of the present invention, e.g., compounds having cell cycle inhibitory activity or kinesin (e.g., Eg5) inhibitory activity, may be administered to a subject to treat or prevent cancer including, but are not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus, to name a few.

In another embodiment, the compounds of the present invention, e.g., inhibitors of Eg5, may be administered to a subject to prevent or treat a proliferative disorder. Such disorders may include, but are not limited to, disorders or prolactin production; infertility including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, fibrocystic breast disease, and galactorrhea; and disruptions of spermatogenesis, abnormal sperm physiology, cancer of the testis, cancer of the prostate, benign prostatic hyperplasia, prostatitis, carcinoma of the male breast, and gynecomastia.

As discussed above, the methods and compositions herein are not limited to cancer. Disease states which can be treated by the methods and compositions provided herein include, but are not limited to, cancer (further discussed below), restenosis, autoimmune disease, arthritis, graft rejection, inflammatory bowel disease, proliferation induced after medical procedures, including, but not limited to, surgery, angioplasty, and the like. It is appreciated that in some cases the cells may not be in a hyper or hypo proliferation state (abnormal state) and still require treatment. For example, during wound healing, the cells may be proliferating "normally", but proliferation enhancement may be desired. Similarly, as discussed above, in the agriculture arena, cells may be in a "normal" state, but proliferation modulation may be desired to enhance a crop by directly enhancing growth of a crop, or by inhibiting the growth of a plant or organism which adversely affects the crop. Thus, in one embodiment, the invention herein includes application to cells or individuals afflicted or impending affliction with any one of these disorders or states.

In certain embodiments, the compositions and methods provided herein are useful for the treatment of cancer including solid tumors such as skin, breast, brain, cervical carcinomas, testicular carcinomas, etc. More particularly, cancers that may be treated by the compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastom, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (rheningioma, meningiosarcoma, gliomatosis), brain (astrocytoma, medulloblastoma, glioma, ependymoma, germinoma [pinealoma, glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma], fallopian tubes (carcinoma); Hematoloaic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. The cancer can be solid tumors or metastatic. Thus, the term "cancerous cell" as provided herein, includes a cell afflicted by any one of the above identified conditions.

Those skilled in the art will appreciate that the invention is by no means limited to the treatment of the above disorders, but can be used to treat any disorder that may be identified by a practicing physician and which symptoms may be decreased by the compounds of the invention.

In another aspect, diagnostic assays are provided herein. In one embodiment, the cellular proliferation sequences are used in the diagnostic assays. This can be done on an individual gene or corresponding polypeptide level. In a preferred embodiment, the expression profiles are used, preferably in conjunction with high throughput screening techniques to allow monitoring for expression profile genes and/or corresponding polypeptides. In a preferred embodiment, in situ hybridization of labeled cellular proliferation nucleic acid probes to tissue arrays is done. For example, arrays of tissue samples, including cellular proliferation tissue in various states and or time points and/or normal tissue, are made. In situ hybridization as is known in the art can then be done. It is understood that conventional antibody and protein localization methods can also be used in diagnostic assays herein.

EQUIVALENTS

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional information, exemplification and guidance which can be adapted to the practice of this invention in its various embodiments and the equivalents thereof.

EXEMPLIFICATION

Example 1

Synthesis of Inventive Compounds

I. Description of Synthetic Methods

Small molecules have been used to explore many facets of biology for over a century. However, research in biology is not routinely performed using this approach, in the way that it is with biochemical, genetic, and increasingly, genomic approaches. Several problems limit the use of the former approach. Arguably, the primary one is the lack of routine access to structurally complex and diverse small molecules that can be used to modulate biological systems. There are examples of simple, achiral modulators of biological systems, notably "drug-like" molecules, though in these cases the smaller size and complexity of the species have more to do with delivery and pharmacokinetic parameters than with affinity and selectivity for a protein target. Without wishing to be bound to any particular theory, we propose that structurally complex and diverse collections of "natural product-like", rather than "drug-like" molecules will be better suited as biological probes. Diversity-oriented organic synthesis, especially when coupled with an economical and efficient technology platform, offers the means to change this situation, as it aims to synthesize complex and diverse small molecules efficiently (S. L. Schreiber, *Science* 2000, 287, 1964–1969). Diversity-oriented synthesis represents a versatile tool to chemical genetics, which aims to explore biology with small molecules in a systematic way (See for example, (a) T. J. Mitchison, *Chem. Biol.* 1994, 1, 3–6; (b) S. L. Schreiber, *Bioorg. Med. Chem.* 1998, 6, 1127–1152; (c) http://www-schreiber.chem.harvard.edu; and http://iccb.med.harvard.edu).

Though enantioselective catalysis is often used in target-oriented synthesis, it is still relatively under explored in diversity-oriented synthesis (See, for example, a) D. S. Tan, M. A. Foley, M. D. Shair, S. L. Schreiber, *J. Am. Chem. Soc.* 1998, 120, 8565–8566; b) D. S. Tan, M. A. Foley, B. R. Stockwell, M. D. Shair, S. L. Schreiber, *J. Am. Chem. Soc.* 1999, 121, 9073–9087; c) D. Lee, J. K. Sello, S. L. Schreiber, *J. Am. Chem. Soc.* 1999, 121, 10648–10649; d) D. R. Spring, S. Krishnan, S. L. Schreiber, *J. Am. Chem. Soc.* 2000, 122, 5656–5657; e) S. M. Sternson, J. B. Louca, J. C. Wong, S. L. Schreiber, *J. Am. Chem. Soc.* 2001, 123, 1740–1747).

For other approaches to asymmetric diversity synthesis, see: a) J. S. Panek, B. Zhu, *J. Am. Chem. Soc.* 1997, 119, 12022–12023; b) D. A. Annis, O. Helluin, E. N. Jacobsen, *Angew. Chem.* 1998, 110, 2010–2012; *Angew. Chem., Int. Ed. Engl.* 1998, 37, 1907–1909; c) M. Reggelin, V. Brenig, R. Welcker, *Tetrahedron Lett.* 1998, 39, 4801–4804; d) N. Zou, B. Jiang, *J. Comb. Chem.* 1999, 2, 6–7; e) S. Henessian, J. Ma, W. Wang, *Tetrahedron Lett.* 1999, 40, 4631; f) I. Paterson, M. Donghi, K. Gerlach, *Angew. Chem., Int. Ed.* 2000, 39, 3315–3319.

In certain embodiments, reactions catalyzed by bis(oxazoline)metal Lewis acid complexes were explored because of their high efficiency, selectivity, and broad substrate tolerance (See, a) J. S. Johnson, D. A. Evans, *Acc. Chem. Res.* 2000, 33, 325–335; b) K. A. Jorgensen, M. Johannsen, S. Yao, H. Audrain, J. Thorhauge, *Acc. Chem. Res.* 1999, 32, 605–613). In certain exemplary embodiments, inverse electron demand heterocycloadditions of vinyl ethers and β,χ-unsaturated ketoesters (FIG. 2) were investigated. See, a) D. A. Evans, J. S. Johnson, E. J. Olhava, *J. Am. Chem. Soc.* 2000, 122, 1635–1649; b) D. A. Evans, E. J. Olhava, J. S. Johnson, J. M. Janev, *Angew. Chem.* 1998, 110, 3554–3557; *Angew. Chem. Int. Ed.* 1998, 37, 3372–3375; c) J. Thorhauge, M. Johannsen, K. A. Jorgensen, *Angew. Chem.* 1998, 110, 2543–2546; *Angew. Chem. Int. Ed.* 1998, 37, 2404–2406.

An account of related cycloadditions on solid support has been described (S. Leconte, G. Dujardin, E. Brown, *Eur. J. Org. Chem.* 2000, 639–643. For a related heterocycloaddition on solid support see: F. Tietze, T. Hippe, A. Steinmetz, *Synlett* 1996, 1043–1044. For a report of an asymmetric cycloaddition with external control on a solid support, see reference 5d); however, the reported reactions were performed in the presence of achiral catalysts and with the heterodiene bound to the polystyrene (PS) solid support through the ester. In certain embodiments, this mode of cycloaddition was initially investigated and found to be highly selective when using the enantiomerically pure catalysts (S)- or (R)-1 [(a) D. A. Evans, J. S. Johnson, E. J. Olhava, *J. Am. Chem. Soc.* 2000, 122, 1635–1649; b) D. A. Evans, E. J. Olhava, J. S. Johnson, J. M. Janey, *Angew. Chem.* 1998, 110, 3554–3557; *Angew. Chem. Int. Ed.* 1998, 37, 3372–3375; c) J. Thorhauge, M. Johannsen, K. A. Jorgensen, *Angew. Chem.* 1998, 110, 2543–2546; *Angew. Chem. Int. Ed.* 1998, 37, 2404–2406].

In certain exemplary embodiments, support-bound vinyl ethers were used, that were linked to the macrobead through either carbon or oxygen. This approach was found to be more effective with regard to effective functionalization of the cycloadduct.

Descrived herein is an application of this asymmetric cycloaddition reaction to the synthesis of dihydropyrancarboxamides on high capacity, 500–600 μm PS macrobeads in a one bead-one stock solution technology platform. The diversity pathway explored resulted in the highly diastereo- and enantioselective synthesis of 4320 encoded small molecules [See (a) M. H. J. Ohlmeyer, R. N. Swanson, L. W. Dillard, J. C. Reader, G. Asouline, R. Kobayashi, M. Wigler, W. C. Still, *Proc. Natl. Acad Sci. U.S.A.* 1993, 90, 10922–10926; (b) H. P. Nestler, P. A. Bartlett, W. C. Still *J. Org. Chem.* 1994, 59, 4723–4724; and (c) H. E. Blackwell, L. Pérez, S. L. Schreiber, *Angew. Chem. Int. Ed.* 2001, 40(18), 3421–3425], which were arrayed as 5 mM stock solutions from individual beads, each containing predominantly a single dihydropyrancarboxamide. These stock solutions permit many phenotypic and proteomic assays to be performed. For a description of a fully automated procedure for deriving and arraying stock solutions from the dihydropyrancarboxamide-containing macrobead, see Paul A. Clemons et al., "A one-bead, one-stock solution approach to chemical genetics: Part 2"; *Chemistry & Biology*, 2001, 8:1183–1195.

Collections of vinyl ethers and unsaturated ketoesters were first synthesized and were used as candidate partners for the cycloaddition reaction. Depicted below are the vinyl ethers that were synthesized for the study:

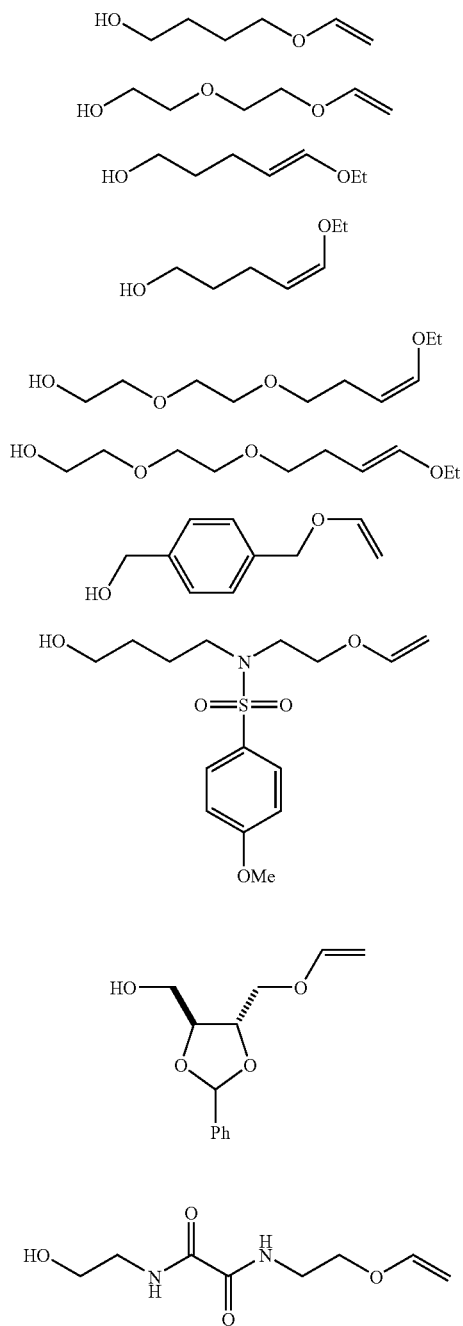

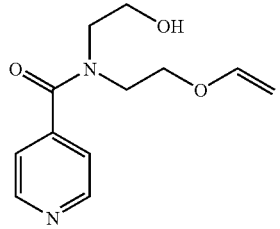

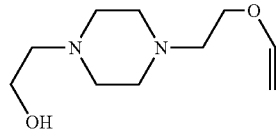

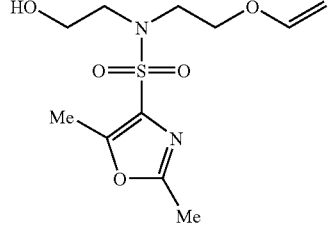

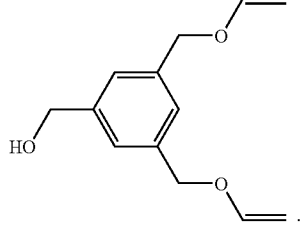

Depicted below are the unsaturated ketoesters that were synthesized for the study:

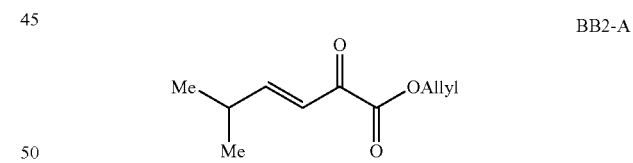

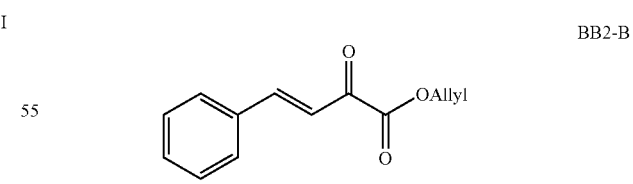

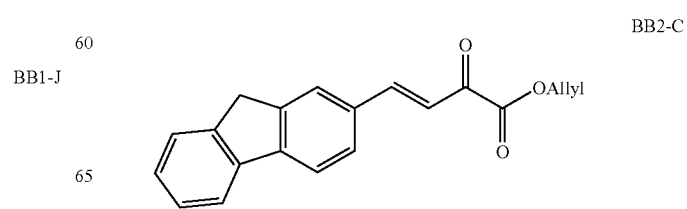

-continued

BB2-D
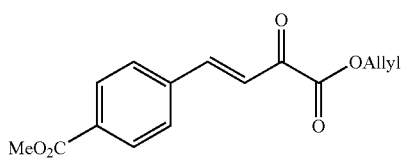

BB2-E
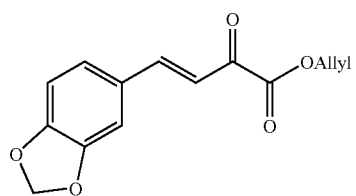

BB2-F
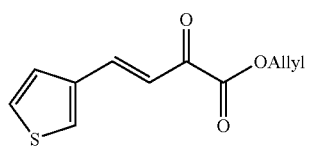

BB2-G
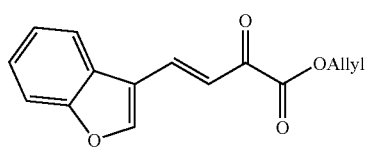

BB2-H
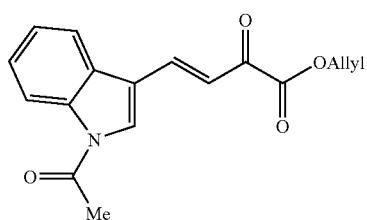

BB2-I
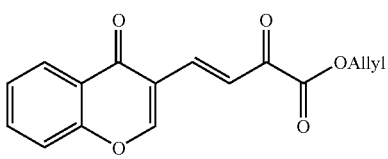

-continued

BB2-J
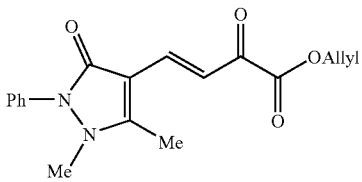

BB2-K
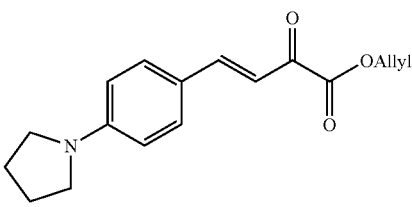

BB2-L
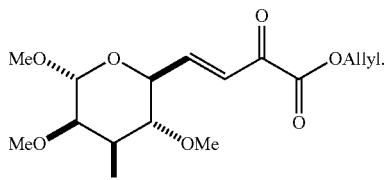

One of ordinary skill in the art will recognize that other vinyl ether and/or unsaturated ketoester building blocks may be used to practice the invention, leading to the preparation of dihydropyrancarboxamides other than those disclosed in the Exemplification herein, without departing from the scope of the invention.

In certain embodiments, each of the vinyl ethers BB1A-N was loaded onto pools of PS macrobeads via the in situ generated silyl triflate 3 as depicted in Scheme 2. The support-bound vinyl ethers were then treated with heterodienes (either BB2-B, R=phenyl or BB2-E, R=4-piperonyl) (3 equiv) in tetrahydrofuran (THF) in the presence of 20 mol % of the t-Bu BOX-Cu(OTf)$_2$ complex ((S)- or (R)-1) and 4 Å molecular sieves to provide support-bound cycloadducts (not shown) [Note: After surveying several loading/ligand/metal/solvent combinations, 20 mol % of 1 in THF was found to provide the best combination of kinetics and selectivity]. Both enantiomers of the ligand were used in separate reactions to obtain a duplicate result and to detect potential matched/mismatched pairs when chiral starting materials were used. After washing and drying steps, each of the cycloadducts was cleaved from the silyl ether linker with hydrogen fluoride-pyridine (HF-py) and analyzed for purity using $^1$H NMR spectroscopy and mass spectrometry (LC-MS).

Scheme 2

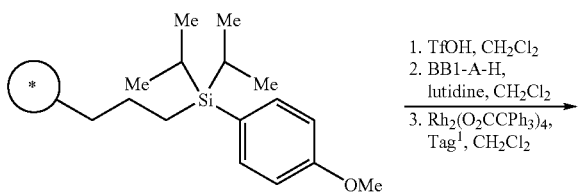

1. TfOH, CH$_2$Cl$_2$
2. BB1-A-H, lutidine, CH$_2$Cl$_2$
3. Rh$_2$(O$_2$CCPh$_3$)$_4$, Tag$^1$, CH$_2$Cl$_2$

2

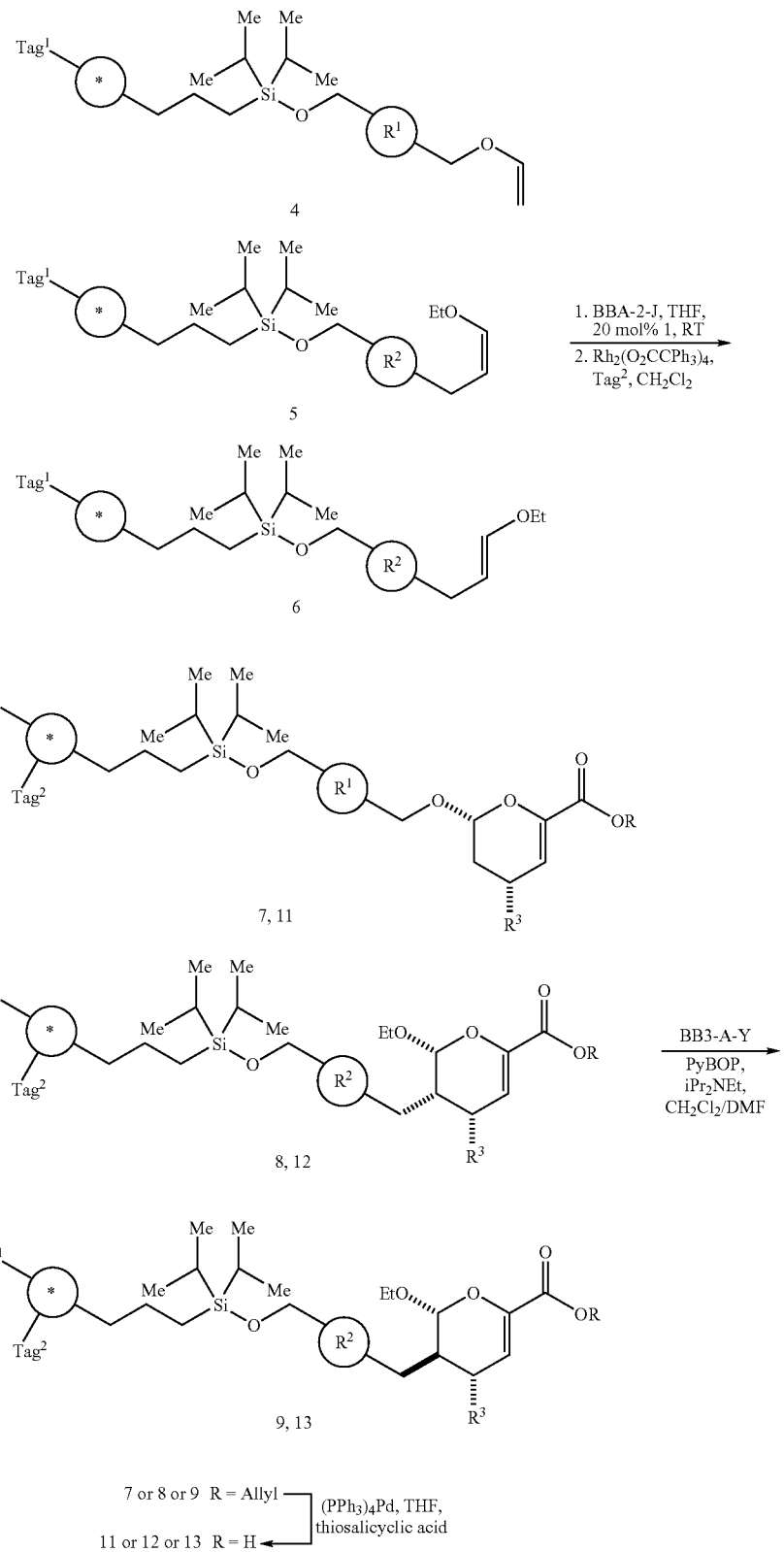

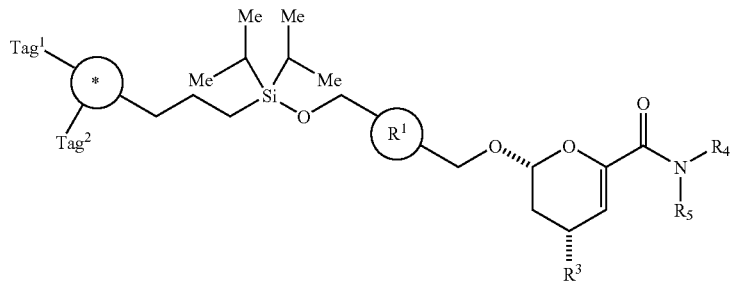

14

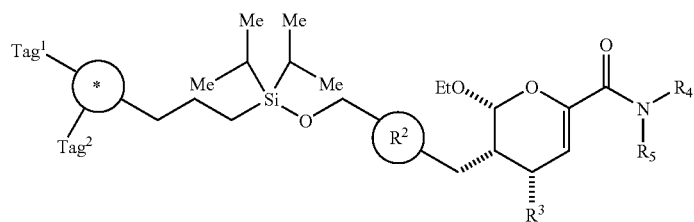

15

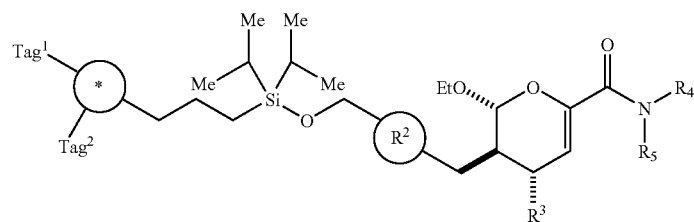

16

These studies showed that support-bound vinyl ethers with amino or amido functionality led to low conversion, and the support-bound form of bis(vinyl ether) BB1-N underwent a single, rather than the desired double, cycloaddition, even when a stoichiometric amount of the copper complex was used. The chiral vinyl ether derived from threitol (support-bound form of BB1-I) reacted efficiently with only the (S)-enantiomer of the catalyst, suggesting that double diastereoselection was taking place (see below). Upon treatment of the corresponding PS macrobeads with HF-py, the remaining vinyl ethers studied provided high purity cycloadducts 4–6 (Table 1). The ethenyl ethers BB1-A,B,G,H also yielded dihydropyrans 4 in high diastereo- and enantioselectivity (The configurations of the cycloadducts were assigned by analogy. See D. A. Evans, J. S. Johnson, E. J. Olhava, *J. Am. Chem. Soc*. 2000, 122, 1635-1649; and J. Thorhauge, M. Johannsen, K. A. Jorgensen, *Angew. Chem*. 1998, 110, 2543–2546; *Angew. Chem. Int. Ed*. 1998, 37, 2404–2406). Both configurations of substituted enol ethers BB1-C-F led to good to high diastereoselectivity of the tetrasubstituted dihydropyrans 5 and 6. Although previous results had shown high diastereoselectivity with cyclic vinyl ethers (See D. A. Evans, J. S. Johnson, E. J. Olhava, *J. Am. Chem. Soc*. 2000, 122, 1635–1649; and J. Thorhauge, M. Johannsen, K. A. Jorgensen, *Angew. Chem*. 1998, 110, 2543–2546; *Angew. Chem. Int. Ed*. 1998, 37, 2404–2406), we found that Z-configured enol ethers (BB1-D,F) provided only moderate diastereoselection, whereas the E-enol ethers (BB1-C,E) resulted in high levels of diastereoselection. Without wishing to be bound to any particular theory, we propose that the lower diastereoselectivity in the Z-enol ether cycloadditions may arise from an endo-exo switch in the transition structure for cycloaddition. It was thought unlikely that isomerization of the alkenyl ether and epimerization of the acetal center is/are responsible for the lower selectivity.

TABLE 1

Asymmetric cycloadditions of resin-bound vinyl ethers BB1.[i]

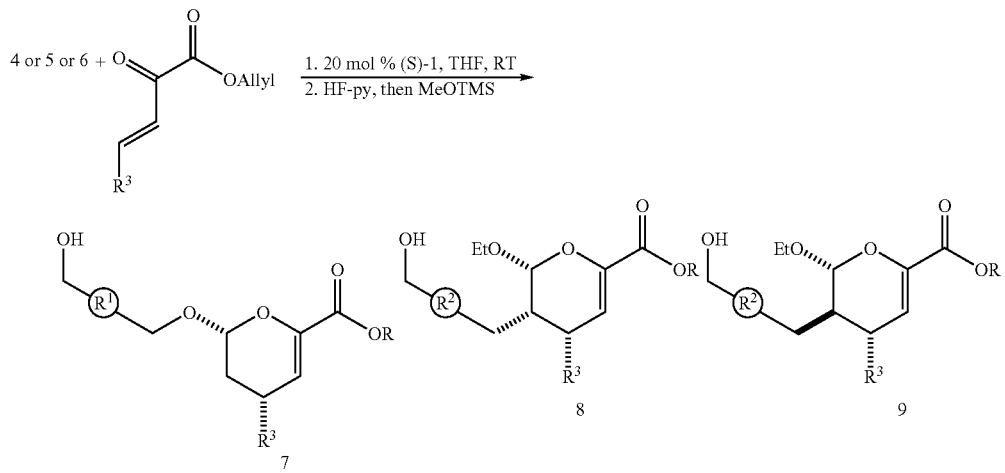

| BB1- | BB2- | product | purity, %[ii] | dr[iii] | er[iv] |
|---|---|---|---|---|---|
| A | E | 7-A-E | ≧95 | ≧15/1 | ≧49/1 |
| B | E | 7-B-E | ≧95 | ≧15/1 | ≧24/1 |
| C | B | 9-C-b | ≧95 | ≧20/1 | ≧49/1 |
| D | B | 8-D-B | ≧95 | ≧5/1 | ≧30/1 |
| E | B | 9-E-B | ≧95 | ≧20/1 | ≧49/1 |
| F | B | 8-D-B | ≧95 | ≧10/1 | ≧30/1 |
| G | E | 7-G-E | ≧95 | ≧30/1 | ≧49/1 |
| H | E | 7-G-E | ≧95 | ≧20/1 | ≧24/1 |

[i]Reactions were performed with 20 mol % of (S)-1 or (R)-1; the results presented are an average of the two runs.
[ii]Estimated based on $^1$H NMR analysis and HPLC-ESIMS.
[iii]Determined by $^1$H NMR analysis and/or CSP HPLC or CSP SFC.
[iv]Determined by CSP HPLC or CSP SFC.

We next turned our attention to the substitution on the heterodiene partner. In most instances, treatment of the support-bound vinyl ether BB1-H with a variety of heterodienes under the previous conditions again led to highly pure cycloadducts following HF-py cleavage from the PS macrobeads (Table 2), though again amine functionality (BB2-K) was incompatible. Similar to the case above with the threitol-derived vinyl ether, only the (S)-enantiomer of the catalyst efficiently provided cycloadduct with the mannose-derived heterodiene BB2-L. Overall, ten heterodienes (BB2-A-J) resulted in somewhat variable, but uniformly high diastereo- and enantioselectivities and high purities based on $^1$H NMR spectroscopy and LC-MS analyses. These building blocks were chosen for subsequent incorporation into the library synthesis.

TABLE 2

Asymmetric cycloadditions of resin-bound vinyl ether 4-H with heterodienes.[i]

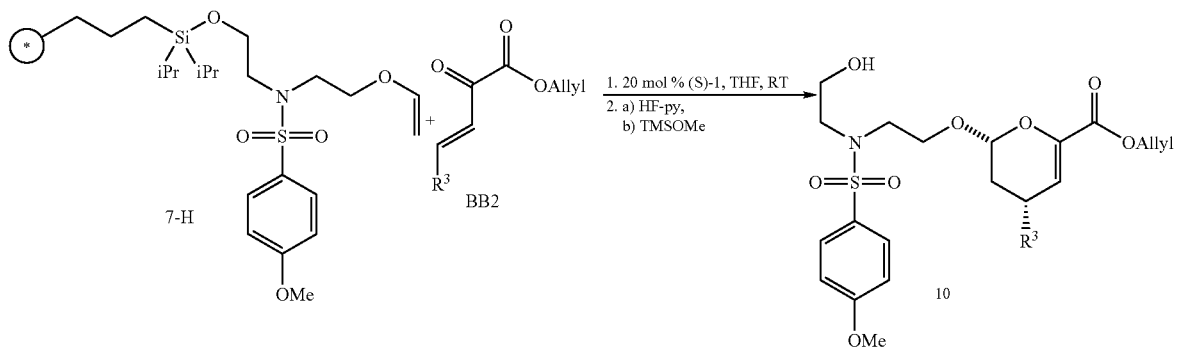

| BB2- | products | purity, %[ii] | dr[iii] | er[iv] |
|---|---|---|---|---|
| A | 10-H-A | ≧95 | ≧16/1 | ≧16/1 |
| B | 10-H-B | ≧95 | ≧20/1 | ≧24/1 |
| C | 10-H-C | ≧95 | ≧9/1 | ≧24/1 |
| D | 10-H-D | ≧95 | ≧9/1 | ≧9/1 |
| E | 10-H-E | ≧95 | ≧20/1 | ≧24/1 |
| F | 10-H-F | ≧95 | ≧25/1 | ≧24/1 |
| G | 10-H-G | ≧95 | ≧9/1 | ≧49/1 |
| H | 10-H-H | ≧95 | ≧15/1 | ≧24/1 |
| I | 10-H-I | ≧95 | ≧12/1 | ≧49/1 |
| J | 10-H-J | ≧95 | ≧9/1 | ≧49/1 |

[i]Reactions were performed with 20 mol % of (S)-1 or (R)-1; the results presented are an average of the two runs.
[ii]Estimated based on ¹H NMR analysis and HPLC-ESIMS.
[iii]Determined by ¹H NMR analysis and/or CSP HPLC or CSP SFC.
[iv]Determined by CSP HPLC or CSP SFC.

Further functionalization of the cycloadducts was then pursued. Conversion of the support-bound cycloadduct 7-H-E, upon treatment with (PPh₃)₄Pd and thiosalicylic acid, to the corresponding acid 11-H-E was achieved in high purity (Scheme 2). Treatment of the support-bound acid 11-H-E with 20 equiv of benzylamine, PyBOP, and diisopropylethylamine in 3:1 CH₂Cl₂:DMF led to the desired benzylamide. These conditions were applied to a diverse collection of amines and support-bound acid 11-H-E to select 25 amines for use in the library synthesis:

BB3-A
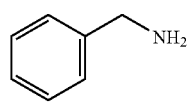

BB3-B
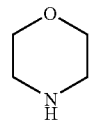

BB3-C
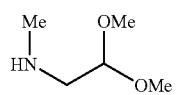

BB3-D
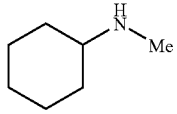

BB3-E
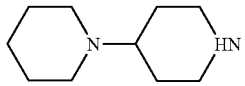

BB3-F
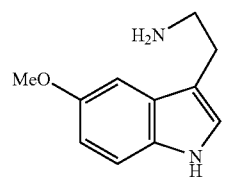

BB3-G
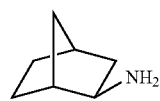

BB3-H
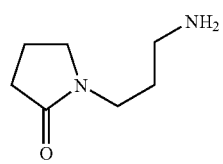

BB3-I
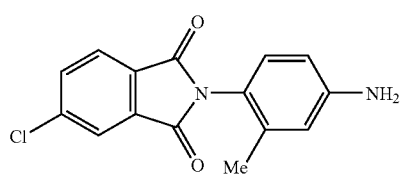

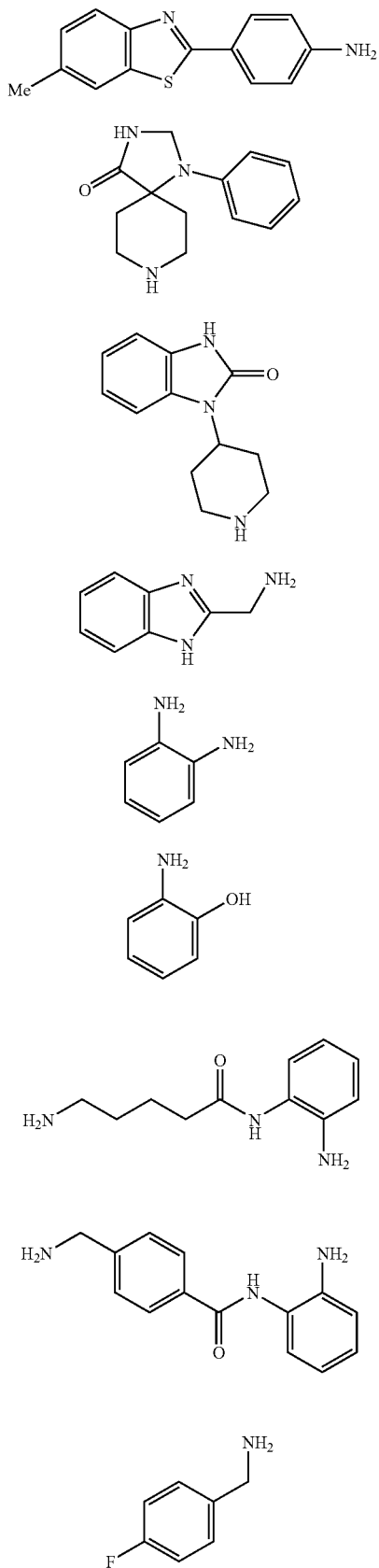
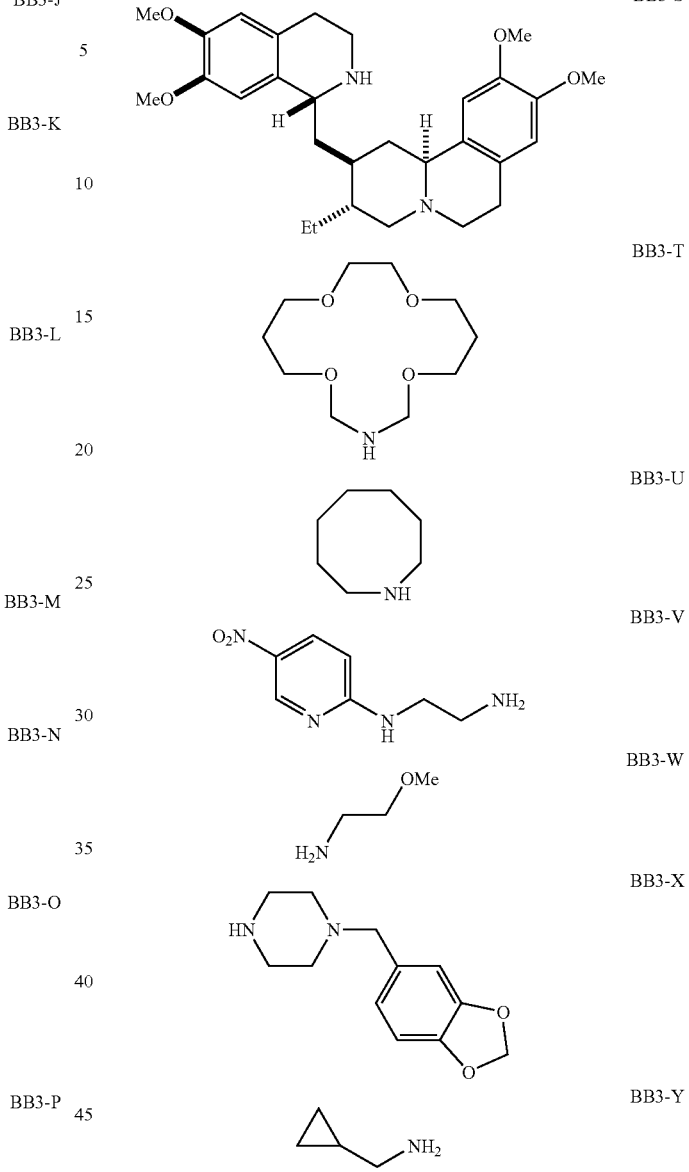

These pathway development studies were necessary to select the reactions and building blocks for a library realization that would result in single compound stock solutions from individual macrobeads. The library synthesis was initiated with sufficient PS macrobeads (13,000) to produce, on average, three beads containing each theoretical compound. The chosen vinyl ethers were attached to the supports, and following the initial cycloaddition step, the two enantiomeric sets of cycloadducts were not pooled. (Each set includes cycloadduct attached to either the C1 oxygen or C2 carbon of the dihydropyran ring.) Instead, the two sets were carried through the remaining steps in parallel in order to provide an independent means (when coupled to mass spectrometry) to assess the ability of tags to infer the absolute configuration of library members (See Scheme 3). The supports were not repooled following the amide coupling, thereby reducing the number of chemical encoding steps to which the macrobeads were subjected and simplifying the decoding of library members. In the end, 54 separate portions of macrobeads were produced (50 portions containing dihydropyrancarboxamides, 2 containing dihydropyrancarboxylic acids, and 2 containing dihydropyrancarboxylic esters), each containing, theoretically, three copies of 80 compounds for a total of 4320 distinct, spatially-segregated, and stereochemically-defined dihydropyran derivatives.

In order to analyze the purity of members of the library, two macrobeads from each of the above 54 pools were removed, arrayed, treated with HF-py, and fractions of the eluted products (10 μL of 5 mM stock solutions) were assayed by LC-MS (See H. E. Blackwell, L. Pérez, S. L. Schreiber, *Angew. Chem. Int. Ed.* 2001, 40(18), 3421–3425). In summary, 78 samples (72%) were ≧95% pure, 93 samples (86%) were ≧90% pure, 104 samples (96%) were ≧75% pure, and the remaining 4 samples were of roughly 50% purity. Direct structure determination by MS was successful in 83/108 cases (e.g., for 25 of the 108 samples, the molecular ion observed upon ionization corresponded to a fragment of the compound), and indirect structure inference by decoding of the chloroaromatic diazoketone tags (See for example, H. P. Nestler, P. A. Bartlett, W. C. Still *J. Org. Chem.* 1994, 59, 4723–4724; and H. E. Blackwell, L. Pérez, S. L. Schreiber, *Angew. Chem. Int. Ed.* 2001, 40(18), 3421–3425) was successful in 108/108 cases.

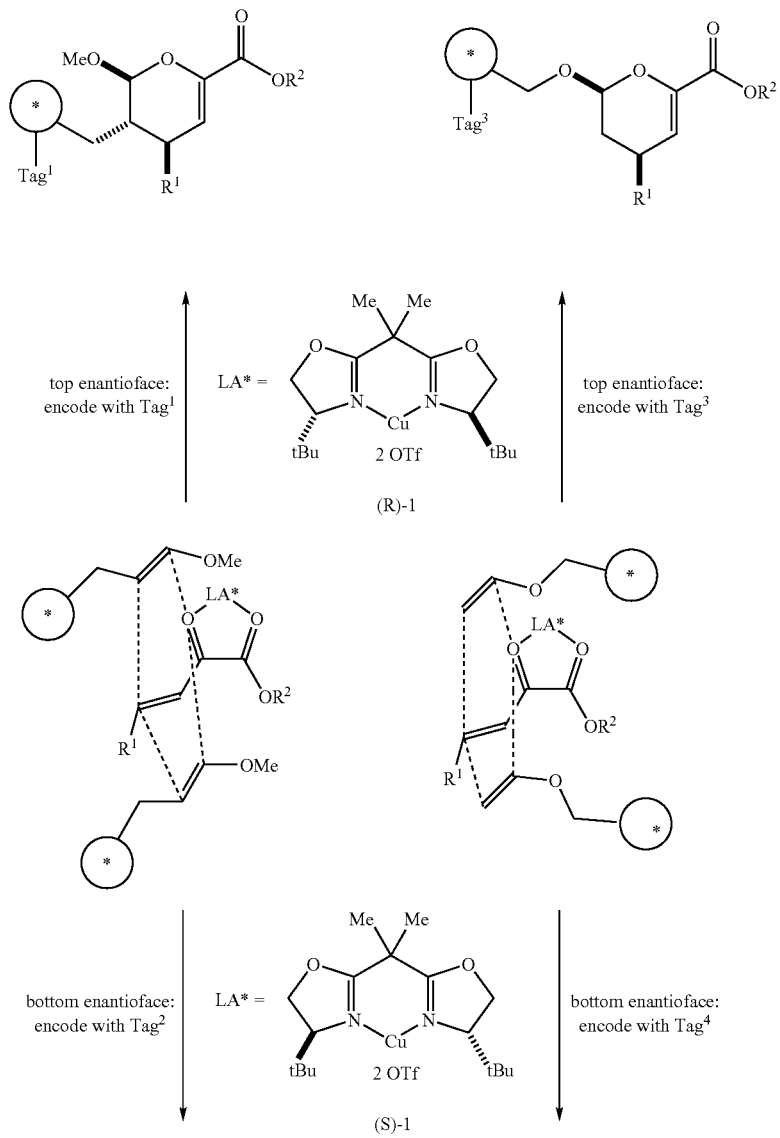

Scheme 3

-continued

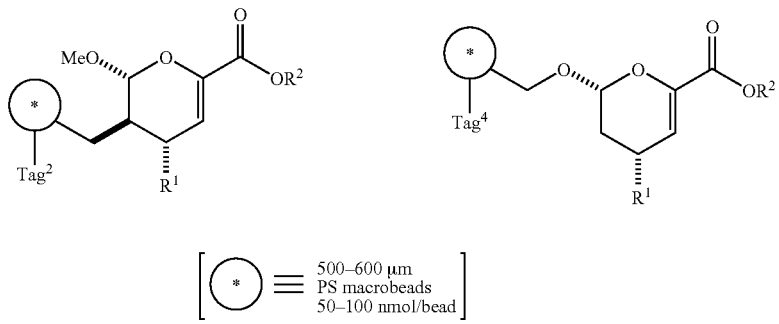

Although the Examples described herein disclose a synthesis of the inventive library using stereochemistry as a diversity element whereby only one of two potential diastereomers (for the unsubstituted vinyl ethers) was accessed, it is to be understood that other reagents (e.g., catalyst) and/or reaction conditions may be used that would allow access to the full set of diastereomers, without departing from the scope of the invention. For example, the present invention encompasses the use of catalyst systems with truly complete external control over enantioselectivity and diastereo-selectivity to allow access to stereoselective catalysis in diversity-oriented organic synthesis. In addition, in one aspect, the present invention discloses a novel approach whereby asymmetric heterocycloaddition reaction is applied to solid phase (To the best of our knowledge, this is the first report of the use of a sub-stoichiometric amount of chiral controller to perform a carbon-carbon bond forming reaction on solid phase). Additionally, in another aspect, the present invention describes the generation of spatiallysegregated stock solutions from individual macrobeads, which renders the inventive compounds amenable to both phenotypic and protein-binding assays. In addition, their common primary hydroxyl group ensures that every compound can be robotically arrayed onto a glass microscope slide for protein-binding assays [a] G. Macbeath, A. N. Koehler, S. L. Schreiber, J. Am. Chem. Soc. 1999, 121, 7967–7968; b) P. J. Hergenrother, K. M. Depew, S. L. Schreiber, J. Am. Chem. Soc. 2000, 122, 7849–7850]. Indeed, small molecule microarrays of the dihydropyrancarboxamides have already been manufactured and screened, leading to the discovery of a small molecule that binds to a protein of interest.

II. Experimental Protocol

General Methods. Reagents were obtained from commercial sources and used without purification. Reaction solvents (THF, DMF, $CH_2Cl_2$) were obtained from J. T. Baker (HPLC grade) and purified by passage through two solvent columns prior to use. The $CH_2Cl_2$ purification system was composed of one activated alumina (A-2) column and one supported copper redox catalyst (Q-5 reactant) column. The THF purification system was composed of two activated alumina (A-2) columns and the DMF purification system is composed of two activated molecular sieve columns. [See: A. B. Pangbom, M. A. Giardello, R. H. Grubbs, R. K. Rosen, F. J. Timmers, Organometallics 1996, 15, 1518–1520.] Triethylamine, diisopropylethylamine, and 2,6-lutidine were distilled from $CaH_2$. Brominated polystyrene resin (Br—PS, 2 meq/g) was obtained from Polymer Labs, and functionalized with the silicon-based linker according to the reported protocol (See J. A. Tallarico, K. M. Depew, H. E. Pelish, N. J. Westwood, C. W. Lindsley, M. D. Shair, S. L. Schreiber, M. A. Foley, J. Comb. Chem. 2001, 3, 312–318). 2,2'-Isopropylidenebis[(4S)-4-t-butyl-2-oxazoline] was purchased from Aldrich, while the enantiomer, 2,2'-Isopropylidenebis[(4R)-4-t-butyl-2-oxazoline] was prepared as previously described starting for (R)-t-leucine (See D. A. Evans, G. S. Peterson, J. S. Johnson, D. M. Barnes, K. R. Campos, K. A. Woerpel, J. Org. Chem. 1998, 63, 4541–4544). Flash chromatography was performed on E. Merck 60 230–400 mesh silica gel. TLC was performed on 0.25 mm E Merck silica gel $F_{254}$ plates and visualized by UV, cerium ammonium molybdate and/or $I_2$. NMR spectra were recorded on a Varian Mercury400 (400 MHz $^1H$, 100 MHz $^{13}C$), Varian Unity500 (500 MHz $^1H$) or Varian Unity600 (600 MHz $^1H$). Chemical shifts are quoted in ppm and reference to TMS or residual protonated solvent. Mass spectra were obtained on a Jeol AX-505H or SX-102A mass spectrometer.

Solid Phase Reactions. All solid phase reactions were conducted in oven dried glass vials under an atmosphere of dry Ar, with mixing provide by a VWR Vortex Genie-2 vortexer. Resin washings were performed in 2 mL fritted polypropylene Bio-Spin® chromatography columns (Bio-Rad) or 10 mL fritted polypropylene PD-10 columns (Pharmacia Biotech) with 360° rotation on a Barnstead-Thermolyne Labquake™ shaker. For cleavage reactions, resin samples were transferred to Eppendorf tubes and a cleavage cocktail comprising 85/10/5 THF/py/HF-py was added and the samples were vortexed for 1–2 h at rt. The samples were then treated with methoxytrimethylsilane and vortexed for an additional 30 min. The samples were then filtered through a pipette plugged with glass wool, the resin washed with additional THF and the filtrate concentrated.

(a) Synthesis of Vinyl Ethers (E)-5-Ethoxy-pent-4-en-1-ol

BB1-C

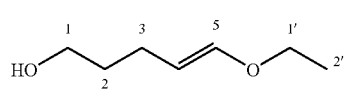

5-Ethoxy-pent-4-yn-l-ol (1.28 g, 10.0 mmol, 1.0 equiv) in THF (2 mL) was added to a suspension $LiAlH_4$ (0.80 g, 21 mmol, 2.1 equiv) in THF (20 mL) and the resulting solution was stirred at rt for 16 h. At this time 0.8 mL of $H_2O$ was added dropwise, followed by 0.8 mL of 15% NaOH, then 2.4 mL of $H_2O$. Eventually (30 min) white solids formed, the mixture was filtered and the solids were extensively washed with EtOAc. The filtrate and washings were combined, dried (Na₂SO₄), filtered, and the filtrate was concentrated to give and oil which was purified by column chromatography (6/1 hexanes/EtOAc) to give 1.14 g (88%) of the vinyl ether BB1-C as a clear colorless oil with better than 19/1 E/Z selectivity (¹H NMR):

¹H NMR (500 MHz) 6.24 (d, J=12.7, 1H, HC(5)); 4.76 (dt, J=12.7, 7.3, 1H, HC(4)); 3.69 (q, J=6.8, 2H, H₂C(1')); 3.65 (q, J=5.3, 2H, H₂C(1')); 2.01 (q, J=7.3, 2H, H₂C(3)); 1.60 (quint , J=7.3, 2H, H₂C(2)); 1.39 (t J=5.4, 1H, OH); 1.25 (t, J=6.8, 3H, H₃C(2')); ¹³C NMR (100 MHz) 146.12; 103.26; 64.56; 61.99; 33.46; 24.08; 14.85.

tert-Butyl-{2-[2-(2-chloro-ethoxy)-ethoxy]-ethoxy}-dimethyl-silane

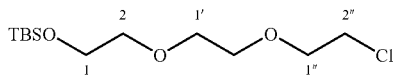

Triethylamine (9.2 mL, 66 mmol, 1.2 equiv), DMAP (0.67 g, 5.5 mmol, 0.1 equiv) and TBSCl (9.1 g, 60.5 mmol, 1.1 equiv) were dissolved in CH₂Cl₂ (60 mL). The 2-chloro (ethoxyethoxy)ethanol (8.0 mL, 55.0 mmol, 1.0 equiv) was added dropwise over 5 min, then the mixture was stirred at rt for 1.5 h. The reaction mixture was poured into H₂O and extracted with EtOAc, the combined organic layers were washed with brine, dried (MgSO₄), filtered and concentrated to give a cloudy oil which was passed through a short column of silica gel eluting with 9/1 hexane/EtOAc to give 14.8 g (96%) of the silyl ether as a clear, colorless oil:

¹H NMR (500 MHz) 3.74 (q, J=5.4, 4H, H₂C(1") and H₂C(2)); 3.64 (s, 4H, H₂C(1') and H₂C(2')); 3.60 (t, J=5.9, 2H, H₂CO); 3.54 (t, J=5.9, 2H, H₂CO)); 0.87 (s, 9H, H₃CCSi); 0.04 (s, 6H, H₃CSi) ¹³C NMR (100 MHz) 72.67; 71.31; 70.68; 70.66; 42.59; 25.86; 18.30; −5.34.

2-[2-(4-Ethoxy-but-3-ynyloxy)-ethoxy]-ethanol

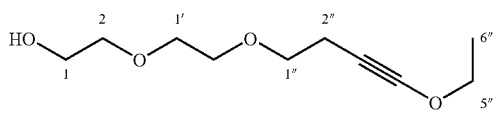

tert-Butyl-{2-[2-(2-chloro-ethoxy)-ethoxy]-ethoxy}-dimethyl-silane was converted to the corresponding iodide by refluxing with 5 equiv of NaI in 2-butanone for 6 h. This was then alkynylated and deprotected by the same process described above to provide E-5-Ethoxy-pent-4-en-1-ol: ¹H NMR (500 MHz) 4.02 (q, J=6.8, 2H, H₂C(5")); 3.74–3.70 (m, 2 H, HCO); 3.68–3.66 (m, 2H, HCO); 3.64–3.60 (m, 4H, HCO); 3.54 (t, J=7.3, 2H, H₂CO)); 2.49 (t, J=6.3, 1H, OH); 2.41 (t, J 7.3, 2H, H₂CO); 1.33 (t, J=7.3, 3H, H₃C(6")); ¹³C NMR (100 (M+NH₄); 186.

(Z)-5-Ethoxy-pent-4-en-1-ol

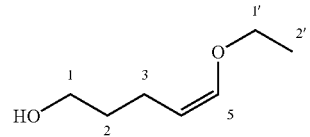

5-Ethoxy-pent-4-yn-1-ol (1.28 g, 10 mmol) and Lindlar catalyst (400 mg) were combined in EtOAc (20 mL) containing pyridine (1 mL). This mixture was hydrogenated at rt under 1 atm of H₂ for 16 h, then filtered through celite and poured into H₂O. The organic later was washed with sat. CuSO₄, H₂O and brine, then dried (Na₂SO₄), filtered, and the filtrate concentrated to give an oil which was purified by column chromatography (6/1 hexanes/EtOAc) to give 0.91 g (70%) of the vinyl ether BB1-D as a slightly yellow oil with better than 25/1 Z/E selectivity (¹H NMR): ¹H NMR (500 MHz) 6.01 (d, J=6.4, 1H, HC(5)); 4.36 (q, J=7.8, 1 H, HC(4)); 3.79 (q, J=7.3, 2H, H₂C(1')); 3.63 (t, J=6.3, 2H, H₂C(1); 2.17 (q, J=7.8, 2H H₂C(3)); 2.06 (br s, 1H, OH); 1.59 (quint, J=6.3, 2H, H₂C(2)); 1.25 (t, J=7.3, 3H, H₃C2')); ¹³C NMR (100 MHz) 145.20; 105.45; 67.55; 61.56; 31.83; 19.71; 15.18.

(E)-2-[2-(4-Ethoxy-but-3-enyloxy)-ethoxy]-ethanol

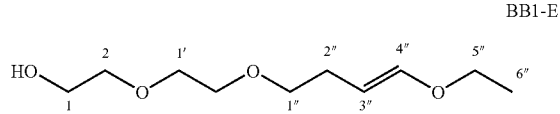

The procedure described above for the synthesis of BB1-C provided the Z-vinyl ether BB1-E: ¹H NMR (500 MHz) 6.29 (d, J=12.7, 1H, HC(4")); 4.73 (dt, J=12.2, 7.8, 1H, HC(3")); 3.76–3.64 (m, 6H, H₂CO); 3.62–3.59 (m, 4H, H₂CO); 3.44 (t, J=6.8, 2H, H₂C(1")); 2.21 (qd, J=7.3, 1.0, 2H, H₂C(2")); 1.25 (t, J=7.3, 3H, H₃C(6")); ¹³C NMR (100 MHz) 147.41; 99.52; 72.44; 71.97; 70.25; 70.05; 64.44; 61.59; 28.13; 14.60; MS (CI, NH₃) 222 (M+NH₄); 176.

(Z)-2-[2-(4-Ethoxy-but-3-enyloxy)-ethoxy]-ethanol

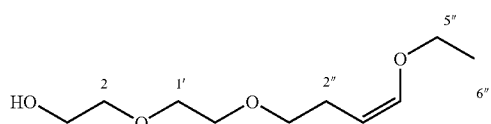

The procedure described above for the synthesis of BB1-D provided the Z-vinyl ether BB1-F: ¹H NMR (400 MHz) 5.99 (dt, J=6.3, 1.5, 1H, HC(4")); 4.36 (q, J=6.3, 1H, HC(3")); 3.77 (q, J=6.8, 2H, H₂C(5")); 3.74–3.70 (m, 2H, HCO); 3.68-3.66 (m, 2H, HCO); 3.62–3.58 (4H, m, H₂CO); 3.48 (t, J=7.3, 2H, H₂C(1")); 2.56 (br s, 1 H, OH) 2.37 (qd, J=6.8, 1.5, 2H, H₂C(2")); 1.23 (t, J=7.3, 3H, H₃C(6")); ¹³C NMR (100 MHz) 146.01; 102.19; 72.45; 71.00; 70.43; 69.95; 67.53; 61.77; 24.50; 15.21; MS (CI, NH$_3$) 222 (M+NH$_4$); 176; 159.

(4-Vinyloxymethyl-phenyl)-methanol

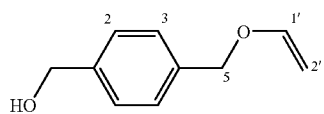

BB1-G

Benzene-1,4-dimethanol (2.76 g, 20.0 mmol, 1.0 equiv) and Hg(OAc)$_2$ (1 g, 3.0 mmol, 0.15 equiv) were heated to reflux in butyl vinyl ether (50 mL) for 30 min. The reaction mixture was cooled, poured into sat. NaHCO$_3$ and was extracted with EtOAc. The organic extracts were combined, washed with H$_2$O and brine, dried (Na$_2$SO$_4$), filtered and the filtrate concentrated to give a paste, which contained both mono- and bis-vinyl ethers and starting diol. Column chromatography (4/1 hexanes/EtOAc) provided 1.07 g (33%) of the mono-vinyl ether BB1-G as an oil which solidified on standing: $^1$H NMR (400 MHz) 7.39–7.34 (m, 4H, HAr); 6.65 (dd, J=14.6, 7.0, 1H, HC(1')); 4.76 (s, 2H, H$_2$C(5)); 4.70 (d, J=5.9, 2H, H$_2$COH)); 4.30 (dd, J=14.6, 2.2, 1H, HC(2')); 4.08 (dd, J=7.0, 2.2, 1H, HC(2')); 1.62 (t, J=5.9, 1H, OH); $^{13}$C NMR (100 MHz) 151.50; 140.57; 136.13; 127.70; 127.04; 87.39; 69.75; 64.83; MS (CI, NH$_3$)182 (M+NH$_4$); 138; 100.

tert-Butyl-(3-iodo-propoxy)-dimethyl-silane

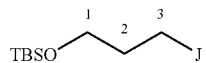

Triethylamine (8.5 mL, 61.0 mmol, 1.2 equiv), DMAP (0.610 g, 5.0 mmol, 0.1 equiv) and TBSCl (8.4 g, 55.5 mmol, 1.1 equiv) were dissolved in CH$_2$Cl$_2$ (50 mL). 3-Iodopropanol (9.4 g, 50.5 mmol, 1 equiv) was added and the mixture was allowed to stir at rt for 16 h. The cloudy mixture was then poured into H$_2$O and extracted with hexane. The combined organic layers were washed with H$_2$O, sat. CuSO$_4$, H$_2$O and brine, then dried (Na$_2$SO$_4$), filtered and the filtrate was concentrated to give an oil. The crude oil was purified by passed through a short plug of silica gel using 19/1 hexanes/EtOAc as eluent to give 13.9 g (92%) of the silyl ether as a clear, colorless oil: $^1$H NMR (500 MHz) 3.67 (t, J=5.9, 2H, H$_2$C(1)); 3.28 (t, J=6.8, 2H, H$_2$C(3)); 1.99 (quint, J=5.9, 2H, H$_2$C(2)); 0.89 (s, 9H, H$_3$CCSi); 0.07 (s, 6H, H$_3$CSi). $^{13}$C NMR (100 MHz) 62.33; 36.14; 25.90; 18.27; 3.68; –5.33.

5-Ethoxy-pent-4-yn-1-ol

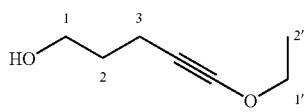

A solution of ethyl alkynyl ether (7.8 g of a 40% wt. soln. in hexanes, roughly 3.1 g alkynyl ether, 44 mmol, 1.2 equiv) in THF (80 mL) was cooled to –78° C. and nBuLi (16.1 mL of 2.5 M in hexane, 40.3 mmol, 1.1 equiv) was added over 5 min. This solution was allowed to stir for 20 min at –78° C., then HMPA (14.0 mL, 80.6 mmol, 2.2 equiv) was added and the solution was stirred for a further 20 min, then tert-butyl-(3-iodo-propoxy)-dimethyl-silane (11.0 g, 36.6 mmol, 1.0 equiv) was added over 1 min and the mixture was allowed to warm slowly to rt and stir overnight (16 h). The crude reaction mixture was poured into H$_2$O and extracted with hexane. The organic layers were combined, washed with brine, dried (Na$_2$SO$_4$), filtered and the filtrate was concentrated to give a dark oil which was immediately dissolved in THF (35 mL). TBAF (1.0 M in THF, 38 mL, 38 mmol, 1.04 equiv) was then added and the resulting solution was stirred at rt for 1 h, the then reaction mixture was poured into H$_2$O and extracted with EtOAc. The combined extracts were washed with H$_2$O and brine, dried (Na$_2$SO$_4$), filtered and the filtrate was concentrated to give a dark oil which was chromatographed (6/1 hexanes/EtOAc) to give 3.43 g (73%) of the alkynyl ether as a slightly yellow oil: $^1$H NMR (500 MHz) 4.02 (q, J=7.3, 2H, H$_2$C(2')); 3.73 (q, J=5.8, 2H, H$_2$C(1)); 2.24 (t, J=6.8, 2H, H$_2$C(3)); 1.70 (quint, J=6.8, 2H, H$_2$C(2)); 1.65 (t, J=5.9, 1H, OH); 1.33 (t, J=7.3, 3H, H$_3$C(2')); $^{13}$C NMR (100 MHz) 128.20; 89.55; 73.83; 61.67; 32.11; 14.22; 13.67.

N,N-Bis-(2-hydroxy-ethyl)-4-methoxy-benzene-sulfonamide

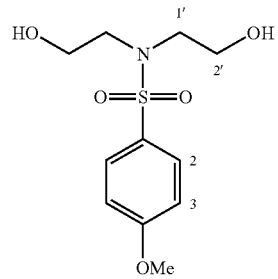

Diethanolamine (8.40 g, 80 mmol, 1.50 equiv) was dissolved in CH$_2$Cl$_2$ (30 mL) and pyridine (5.1 mL, 63.6 mmol, 1.2 equiv). A solution of 4-methoxybenzenesulfonyl chloride (10.9 g, 53 mmol, 1.0 equiv) n CH$_2$Cl$_2$ (30 mL) was added quickly and the resulting mixture was stirred at rt overnight, then poured into H$_2$O and extracted with EtOAc. The organic layers were washed with 1M HCl and brine, dried (MgSO$_4$), filtered, and the filtrate was concentrated to give an oil which was purified by column chromatography (95/5 CH$_2$Cl$_2$/MeOH) to give 12 g (83%) of the sulfonamide as an oil which crystallized on standing: $^1$H NMR (500 MHz) 7.75 (d, J=8.8, 2H, HAr); 6.99 (d, J=8.8, 2H, HAr); 3.87 (a, 3H, H$_3$CO); 3.86 (t, J=4.9, 4 H, H$_2$C(1'); 3.42 (br s, 2H, OH); 3.26 (t, J=4.9, 4H, H$_2$C(2')). $^{13}$C NMR (100 MHz) 163.05; 129.85; 129.37; 114.37; 62.25; 55.61; 52.90.

N-(2-Hydroxy-ethyl)-4-methoxy-N-(2-vinyloxy-ethyl)-benzenesulfonamide

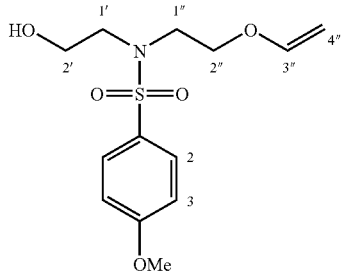
BB1-H

The general procedure above for the synthesis of monovinyl ether BB1-G provided 38% of the desired vinyl ether sulfonamide BB1-H: $^1$H NMR (500 MHz) 7.76 (d, J=8.8, 2H, HAr); 6.99 (d, J=8.8, 2H, HAr); 6.42 (dd, J=14.7, 6.8, 1H, HC(3″)); 4.23 (dd, J=14.6, 2.4, 1H, HC(4″)); 4.07 (dd, J=6.8, 2.4, 1H, HC(4″)); 3.93 (t, J=5.4, 2H, H$_2$C(2″)); 3.87 (s, 3H, H$_3$CO); 3.76 (q, J=5.4, 2H, H$_2$C(2′)); 3.42 (t, J=5.4, 2H, H$_2$C(1″)); 3.27 (t, J=5.4, 2H, H$_2$C(1′)); 2.75 (t, J=6.3, 1H, OH); $^{13}$C NMR (100 MHz) 163.00; 150.83; 130.12; 129.35; 114.31; 87.79; 67.48; 61.26; 55.58; 56.62; 48.87.

2-(Trimethylsilanyloxy)-acrylic acid allyl ester

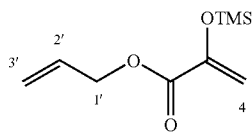

Triethylamine (33 mL, 235 mmol, 1.1 equiv) was added to a solution of TMSOTf (50 g, 225 mmol, 1.05 equiv) in benzene (225 mL) and the resulting solution was cooled to 0° C. Allyl pyruvate (27.4 g, 214 mmol, 1.0 equiv) was added over 30 min and the resulting two phase mixture was stirred at 0° C. for another 2 h, then poured into ice cold H$_2$O and extracted with hexane. The hexane extracts were washed with H$_2$O, sat. CuSO$_4$, H$_2$O and brine, then dried (Na$_2$SO$_4$), filtered, and the filtrate was concentrated to give 30.4 g (68%) of the silyl enol ether as a yellow oil which was used without further purification: $^1$H NMR (500 MHz) 5.86 (ddd, J=171, 10.7, 1.4, 1H, HC(2′)); 5.55 (d, J=1.0, 1H, HC(4)); 5.35 (dd, J=17.1, 1.3, 1H, HC(3′)); 5.26 (dd, J=10.7, 1.5, 1H, HC(3′)); 4.9 (d, J=1.0, 1H, HC(4)); 4.74–4.72 (m, 2H, H$_2$C(1′)); 0.06 (s, 9H, H$_3$CSi); $^{13}$C NMR (100 MHz) 164.01; 146.88; 131.79; 118.39; 104.24; 65.75; −0.08 MS (EI) 200 (M+); 185; 157; 141; 115.

(b) General Synthesis of β,γ-unsaturated ketoesters

See, for example, (a) H. Sugimura, K. Yoshida, *Bull. Chem. Soc. Jpn.* 1992, 65, 3209–3211. (b) D. A. Evans, J. S. Johnson, E. J. Olhava, *J. Am. Chem. Soc.* 2000, 122, 1635–1649. Borontrifluoride etherate (2.2 equiv) was added over 5 min to a solution of aldehyde (1.0 equiv) in CH$_2$Cl$_2$ (0.5 M) at −78° C. The resulting solution was stirred for 30 min, then 2-(Trimethylsilanyloxy)-acrylic acid allyl ester (1.1 equiv) was added dropwise over 5 min. The solution was allowed to stir at −78° C. for 10 min, then warmed slowly to rt and stirred overnight. The mixture was poured into sat. NaHCO$_3$ and extracted with EtOAc, the organic layers were combined, dried (Na$_2$SO$_4$), filtered and the filtrate concentrated to give an oil which was dissolved in benzene (0.2 M) and silica gel (1 g per mmol) added). This mixture was heated to reflux for 2–4 h, cooled, filtered, the filter pad washed with EtOAc and the combined filtrates were concentrated to give the crude unsatruated esters. Purification by column chromatography then provided the pure unsaturated esters.

5-Methyl-2-oxo-hex-3-enoic acid allyl ester

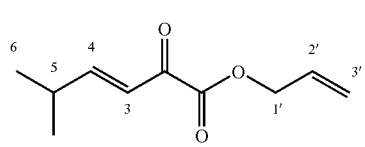
BB2-A $^1$H NMR (400 MHz) 7.14 (dd, J=15.6, 6.3, 1H, HC(4)); 6.60 (dd, J=15.6, 1.5, 1H, HC(3)); 5.98 (ddt, J=17.6, 10.7, 5.9, 1H, HC(2′)); 5.41 (d, J=17.1, 1H, HC(3′)); 5.31 (d, J=10.7, 1H, HC(3)); 4.76 (dt, J=5.6, 1.5, 2H, H$_2$C(1′)); 2.55 (m, 1H, HC(5)); 1.10 (d, J=6.8, 6H, H$_3$C(6)); $^{13}$C NMR (100 MHz) 183.22; 161.85; 160.67; 130.70; 122.25; 66.51; 31.76; 20.90; MS (EI) 182 (M+); 109; 97; 87.

2-Oxo-4-phenyl-but-3-enoic acid allyl ester

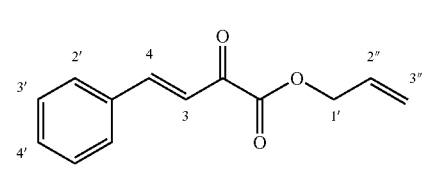
BB2-B $^1$H NMR (500 MHz) 7.87 (d J=16.1, 1H, HC(4)); 7.66 (d, J=8.3, 2H, HC(2′)); 7.45 (m, 3H, HAr); 7.36 (d, J=16.1, 1H, HC(3)); 6.02 (ddt, J=17.1, 10.8, 3.9, 1H, HC(2″)); 5.44 (dd, J=17.1, 1.5, 1H, HC(3″)); 5.35 (dd, J=10.7, 1.2, 1H, HC(3 ″)); 4.83 (d, J=5.9, 2H, H$_2$C(1″)); $^{13}$C NMR (100 MHz) 182.44; 161.72; 148.48; 133.86; 131.59; 130.78; 128.99; 128.95; 120.43; 119.83; 66.74; MS (EI) 216 (M+); 131; 103.

4-(9H-Fluoren-2-yl)-2-oxo-but-3-enoic acid allyl ester

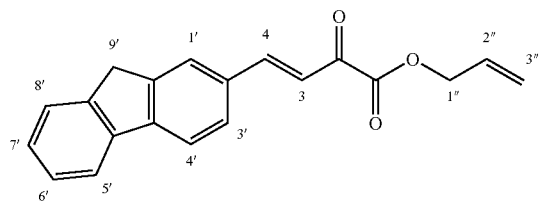
BB2-C $^1$H NMR (500 MHz) 7.96 (d, J=16.1, 1H, HC(4)); 7.82 (m, 2H, HC(1′ and 8′)); 7.67 (m, 1H, HAr); 7.59 (m, 1H, HAr); 7.43 (d, J=16.1, 1H, HC(3)); 7.44–7.35 (m, 3H, HAr); 6.05 (ddt, J=17.1, 10.3, 5.9, 1H, HC(2")); 5.46 (d, J=17.1, 1H, HC(3")); 5.36 (d, J=10.2, 1H, HC(3")); 4.84 (dt, J=5.9, 1.5, 2H, H₂C(1")); 3.95 (s, 2H, H₂C(9')); ¹³C NMR (100 MHz) 182.17; 161.85; 148.92; 145.40; 143.98; 143.76; 140.44; 132.36; 130.82; 128.63; 127.83; 127.00; 125.26; 125.10; 120.53; 120.23; 119.79; 119.38; 66.79; 36.75; MS (EI) 304 (M+); 220; 219; 191; 189.

4-(3-Allyloxycarbonyl-3-oxo-propenyl)-benzoic acid methyl ester

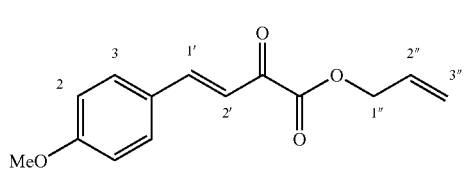

BB2-D

¹H NMR (500 MHz) 8.08 (d, J=8.8, 2H, HC(2)); 7.87 (d, J=16.1, 1H, HC(1')); 7.69 (d, J=8.3, 2H, HC(3)); 7.43 (d, J=16.1, 1H, HC(2')); 6.07 (ddt, J=17.1, 10.3 6.3, 1H, HC(2")); 5.44 (dd, J=17.1, 1.0, 1H, HC(3")); 5.35 (dd, J=10.7, 1.3, 1H, HC(3")); 4.82 (d, J=5.9, 2H, H₂C(1")); 3.94 (s, 3H, H₃CO₂)); ¹³C NMR (100 MHz) 182.03; 166.00; 161.31; 146.59; 137.86; 132.31; 130.61; 130.06; 128.66; 122.33; 119.97; 66.95; 52.36; MS (EI) 274 (M+); 243; 189.

4-Benzo[1,3]dioxol-5-yl-2-oxo-but-3-enoic acid allyl ester

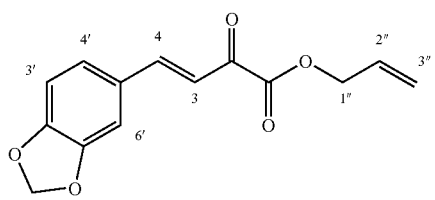

BB2-E

¹H NMR (500 MHz) 7.78 (d, 16.1, 1H, HC(4)); 7.14 (d, J=17.1, 1H, HC(3)); 6.85 (d, J=7.1, 1H, Har)); 7.14 (s, 1H, HC(6')); 7.13 (d, J=7.2, 1H, Har)); 6.04 (s, 2H, H₂CO₂); 6.01 (ddt, J=17.1, 10.7, 5.9, 1H, HC(2")); 5.43 (dd, J=17.1, 1.0, 1H, HC(3")); 5.33 (d, J=10.6, 1.0, 1H, HC(3")); 4.81 (dt, J=5.9, 1.5, 2H, H₂C(1")); ¹³C NMR (100 MHz) 182.01; 161.82; 150.83; 148.43; 148.22; 130.80; 128.42; 126.49; 119.77; 118.39; 108.68; 106.80; 101.79; 66.76; MS (EI) 260 (M+); 175.

2-Oxo-4-thiophen-3-yl-but-3-enoic acid allyl ester

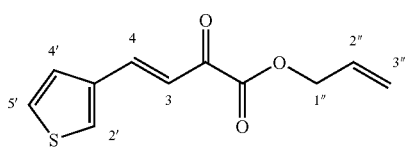

BB2-F

¹H NMR (500 MHz) 7.86 (d, J=16.1, 1H, HC(4)); 7.69 (m, 1H, HAr); 7.40 (m, 1H, HAr); 7.36 (s, 1H, HC(2')); 7.16 (d, J=16.1, 1H, HC(3); 6.04 (ddt, J=17.1, 10.7, 5.9, 1H, HC(2")); 5.44, (dd, J=17.1, 1.5, 1H, HC(3")); 5.34 (dd, J=10.6, 1.4, 1H, HC(3")); 4.8 (dt, J=6.3, 1.0, 2H, H₂C(1")); ¹³C NMR (100 MHz) 182.38; 161.56; 131.23; 130.66; 129.59; 127.64; 127.23; 125.07; 120.08; 119.62; 66.12; MS (EI) 222 (M+); 137; 109.

4-(Benzofuran-3-yl)-2-oxo-but-3-enoic acid allyl ester

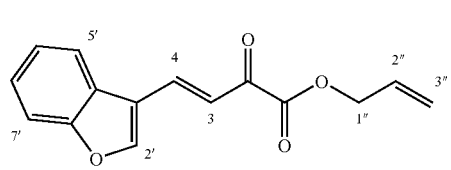

BB2-G

¹H NMR (500 MHz) 7.74 (d, J=15.6, 1H, HC(4)); 7.62 (d, J=7.3, 1H, HAr); 7.51 (d, J=8.3, 1H, HAr); 7.47 (d, J=15.6, 1H, HC(3)); 7.42 (td, J=7.3, 1.0, 1H, HAr); 7.28 (td, J=8.3, 1.0, 1H, HAr)); 7.14 (s, 1H, HC(2')); 6.03 (ddt, J=17.1, 10.3, 5.9, 1H, HC(2')); 5.45 (dd, J=17.1, 1.0, 1H, HC(3")); 5.36 (dd, J=10.2, 1.0, 1H, HC(3")); 4.83 (dt, J=5.9, 1.5, 2H, H₂C(1")); ¹³C NMR (100 MHz) 181.69; 161.26; 155.85; 152.04; 133.75; 130.73; 128.19; 127.49; 123.54; 122.07; 120.43; 119.87; 114.69; 111.55; 66.90; MS (EI) 256 (M+); 228; 213; 185; 129.

4-(1-Acetyl-1H-indol-3-yl)-2-oxo-but-3-enoic acid allyl ester

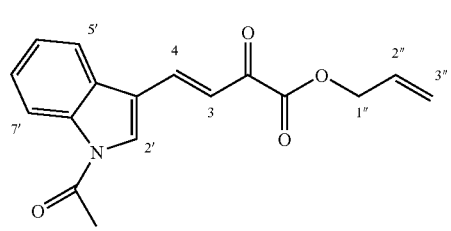

BB2-H

¹H NMR (500 MHz) 8.49 (d, J=7.8, 1H, HAr)); 8.03 (d, J=16.1, 1H, HC(4)); 7.91 (d, J=6.8, 1H, HAr); 7.86 (s, 1H, HC(2')); 7.53 (d, J=16.1, 1H, HC(3)); 7.48–7.40 (m, 2H, HAr); 6.21 (ddt, J=17.1, 10.7, 5.9, 1H, HC(2")); 5.46 (dd, J=17.1, 1.5, 1H, HC(3")); 5.36 (dd, J=10.7, 1.5, 1H, HC(3")); 4.84 (dt, J=5.9, 1.5, 2H, HC(1")); 2.71 (s, 3H, H₃CC(O)); ¹³C NMR (100 MHz) 181.88; 168.14; 161.75; 139.69; 136.63; 130.77; 130.14; 127.27; 126.35; 124.75; 120.23; 120.13; 119.85; 118.40; 116.87; 66.87; 24.01; MS (EI) 297 (M+); 212; 170.

2-Oxo-4-(4-oxo-4H-chromen-3-yl)-but-3-enoic acid allyl ester

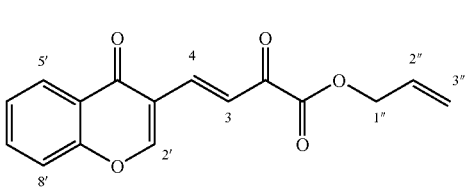

BB2-I

¹H NMR (500 MHz) 8.29 (dd, J=7.8, 1.5, 1H, HAr); 8.23 (t, J=8.8, 2H, HAr); 7.78 (m, 1H); 7.57 (d, J=15.1, 1H); 7.30 (m, 2H); 6.02 (ddt, J=17.1, 10.3, 6.3, 1H, HC(2")); 5.44 (dd, J=17.1, 1.0, 1H, HC(3")); 5.34 (dd, J=10.7, 1.5, 1H, HC(3")); 4.82 (dt, J=5.9, 1.4, 2H, H₂C(1")); ¹³C NMR (100 MHz) 183.08; 175.40; 161.39; 159.31; 155.23; 139.13; 130.72; 126.23; 126.06; 124.01; 123.84; 119.76; 118.99; 118.08; 66.76; MS (EI) 284 (M+); 256; 228; 199; 149.

4-(1,5-Dimethyl-3-oxo-2-phenyl-2,3-dihydro-1H-pyrazol-4-yl)-2-oxo-but-3-enoic acid allyl ester

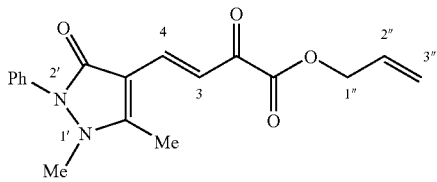

BB2-J

¹H NMR (500 MHz) 7.92 (d, J=15.1, 1H, HC(4)); 7.68 (d, J=15.1, 1H, HC(3)); 7.50 (t, J=7.3, 2H, HAr); 7.39 (t, J=6.3, 1H, HAr); 7.31 (d, J=8.3, 2H, HAr); 5.96 (ddt, J=17.6, 10.7, 2.9, 1H, HC(2")); 5.38 (dd, J=17.1, 1.5, 1H, HC(3")); 5.27 (dd, J=10.7, 1.5, 1H, HC(3")); 4.76 (d, J=3.0, 2H, H₂C(1")); 3.32 (s, 3H, H₃CN); 2.42 (s, 3H, H₃CC); ¹³C NMR (100 MHz) 182.87; 162.68; 162.09; 153.01; 137.21; 133.46; 130.97; 129.36; 128.20; 125.90; 119.34; 116.98; 103.62; 66.36; 34.46; 10.83; MS (EI) 326 (M+); 241.

(c) Building Block Testing

General procedure for test cycloadditions. Vinyl ether resin (prepared as described below) (5 mg, ~1.1 meq/g, ~0.005 mmol, 1 equiv), the appropriate heterodiene (0.015 mmol, 3 equiv) and 5 mg of activated powdered 4A molecular sieves were placed in a dry 4 mL vial, capped with septa and placed under Ar. THF (80 uL) was added, followed by a 0.05 M solution of the appropriate catalyst 1 solution (prepared as described below). The resulting mixture was vortexed gently for 16–24 h then filtered (powdered sieves pass through the filter, thus separating them from the resin beads) and washed with 4×1 mL×20 min THF, then 3×1 mL×15 min CH₂Cl₂ and dried briefly. The resin was then transferred to an Eppendorf tube and treated with cleavage cocktail as described above, after concentration the samples were analyzed by ¹H NMR, LCMS and CSP HPLC and/or CSP SFC.

(d) Vinyl Ether Testing.

(4R,6R)-4-Benzo[1,3]dioxol-5-yl-6-(4-hydroxy-butoxy)-5,6-dihydro-4H-pyran-2-carboxylic acid allyl ester

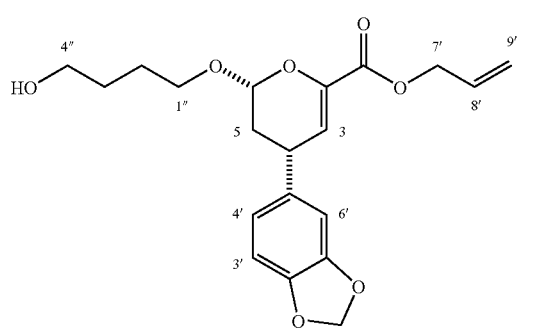

7-A-E

¹H NMR (600 MHz) 6.74–6.72 (m, 2H, HAr); 6.67 (dd, J=7.8, 1.5, 1H, HAr)); 6.14 (d, J=2.9, 1H, HC(3)); 5.96 (ddt, J=17.1, 10.7, 5.3, 1H, HC(8')); 5.93 (d, J=1.5, 2H, H₂CO₂)); 5.36 (dd, J=17.1, 1.5, 1H, HC(9')); 5.26 (dd, J=10.7, 1.5, 1H, HC(9')); 5.14 (dd, J=7.3, 2.0, 1H, HC(6)); 4.71 (ABX, J=14.3, 5.3, 2H, H₂C(7')); 4.01 (dt, J=9.8, 5.9, 1H, HC(1")); 3.70–3.60 (m, 4H, HC(4), HC(1"), H₂C(4")); 2.28 (ddd, J=13.2, 6.8, 1.5, 1H, HC(5)); 1.93 (dt, J=13.6, 7.8, 1H, HC(5)); 1.72–1.59 (m, 4H, H₂C(2"); H₂C(3")); MS (ESI) 400 (M+Na+1); 399 (M+Na); 387; 287; 261; HRMS (ESI) C₂₀H₂₄O₇—Na requires 399.1420; found 399.1432.

(4R,6R)-4-Benzo[1,3]dioxol-5-yl-6-[2-(2-hydroxy-ethoxy)-ethoxy]-5,6-dihydro-4H-pyran-2-carboxylic acid allyl ester

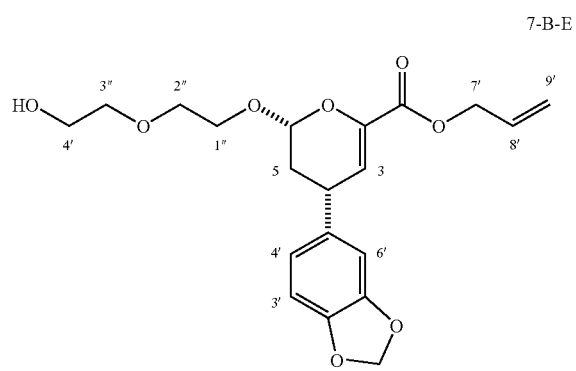

7-B-E

¹H NMR (600 MHz) 6.72–6.69 (m, 3H, HAr); 6.23 (d, J=4.3, 1H, HC(3)); 6.0-5.96 (m, 1H, HC(8')); 5.93 (d, J=5.4, 2H, H₂CO₂); 5.35 (dd, J=17.1, 1.0, 1H, HC(9')); 5.26 (dd, J=10.3, 1.0, 1H, HC(9')); 5.16 (d, J=2.4, 1H, HC(6)); 4.72 (ABX, J=18.6, 5.9, 5.9, 2H, H₂C(7')); 3.94 (ddd, J=14.1, 9.8, 6.8, 1H, HC(1")); 3.61–3.50 (m, 7H, HCO); 2.19)m, 1H, HC(5). Other low field signals obscurred by plasticizer.

(4R,6R)-4-Benzo[1,3]dioxol-5-yl-6-(4-hydroxymethyl-benzyloxy)-5,6-dihydro-4H-pyran-2-carboxylic acid allyl ester

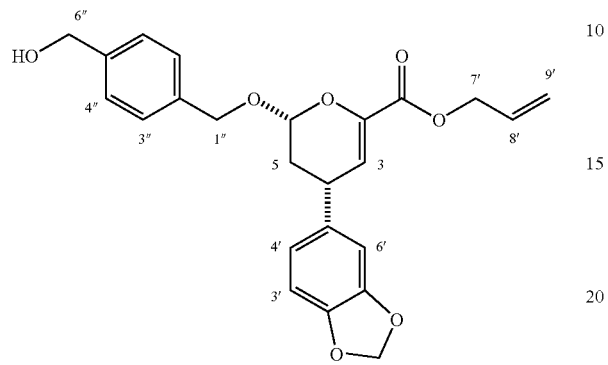

$^1$H NMR (600 MHz) 7.36–7.30 (m, 4H, HAr); 6.74–6.70 (m, 2H, HAr); 6.66 (dd, J=7.8, 1.5, 1H, HC(Ar)); 6.15 (d, J=2.9, 1H, HC(3)); 6.00–5.93 (m, 1H, HC(8')); 5.93 (s, 2H, H$_2$CO$_2$)); 5.37 (dd, J=17.1, 1.5, 1H, HC(9')); 5.27 (dd, J=10.7, 1.5, 1H, HC(9')); 5.20 (dd, J=7.3, 2.0, 1H, HC(6)); 4.96 (d, J=11.7, 1H, HC(1")); 4.78–4.68 (m, 5H, H$_2$C(6"); HC(1"); H$_2$C(7')); 3.62 (ddd, J=10.7, 8.3, 2.9, 1H, HC(4)); 2.29 (ddd, J=14.3, 6.8 1.5, 1H, HC(5)); 1.99 (dt, J=14.2, 7.8, 1H, HC(5)); MS (ESI) 447 (M+Na); 407; 363; 285; HRMS (ESI) C$_{24}$H$_{24}$O$_7$—Na requires 447.1420; found 447.1401.

(4R,5S,6R)-6-Ethoxy-5-(3-hydroxy-propyl)-4-phenyl-5,6-dihydro-4H-pyran-2-carboxylic acid allyl ester

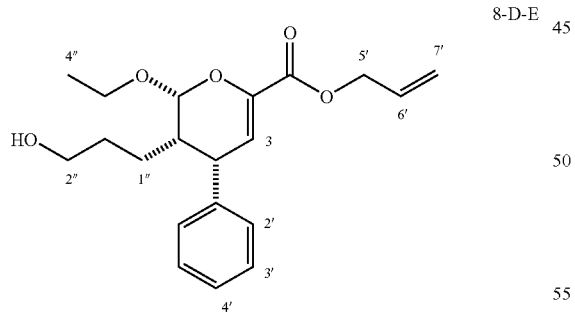

$^1$H NMR (600 MHz) 7.32–7.20 (m, 5H, HAr); 6.29 (d, J=3.9, 1H, HC(3)); 5.96 (ddt, J=17.1, 10.6, 5.9, 1H, HC(6')); 5.36 (dd, J=17.1, 1.5, 1H, HC(7')); 5.26 (dd, J=10.7, 1.5, 1H, HC(7')); 4.76–4.65 (m, 2H, H$_2$C(5')); 3.96 (dq, J=7.3, 7.1, 1H, HC(4")); 3.7–3.5 (m, 3H, HC(4") and H$_2$C(3")); 3.49 (t, J=6.3, 1H, HC(4)); 2.25–2.20 (m, 1H, HC(5); 1.60–1.22 (m, 4H, H$_2$C(1") and H$_2$C(2")); 1.19 (t, J=7.1, 3H, H$_3$C(5")); MS (ESI) 369 (M+Na); 357; 299; 280; 217; HRMS (ESI) C$_{20}$H$_{26}$O$_5$—Na requires 369.1678; found 369.1669.

(4R,5R,6R)-6-Ethoxy-5-(3-hydroxy-propyl)-4-phenyl-5,6-dihydro-4H-pyran-2-carboxylic acid allyl ester

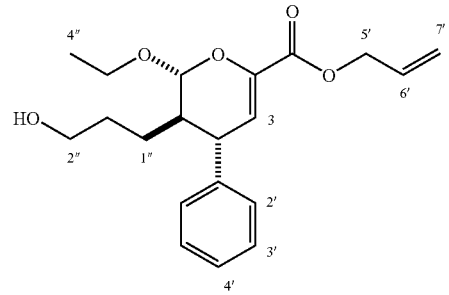

$^1$H NMR (600 MHz) 7.31–7.20 (m, 5H, HAr); 6.16 (d, J=3.4, 1H, HC(3)); 5.95 (ddt, J=17.1, 10.7, 5.9, 1H, HC(6')); 5.35 (dd, J=17.1, 1.5, 1H, HC(7')); 5.25 (dd, J=10.7, 1.4, 1H, HC(7')); 4.92 (d, J=5.9, 1H, HC(6)); 4.71 (ABX, J=17.6, 5.4, 2H, H$_2$C(5')); 4.00 (dq, J=7.3, 6.8, 1H, HC(4")); 3.60–3.52 (m, 3H, H$_2$C(3") and HC(4")); 3.34 (dd, J=6.8, 3.4, 1H, HC(4)); 2.03 (quint, J=6.9 1H, HC(5)); 1.62–1.56 (m, 2H, H$_2$C(1")); 1.50–1.46 (m, 2H, H$_2$C(2")); 1.20 (t, J=7.3, 3H, H$_3$C(5")); MS (ESI) 369 (M+Na); 299; 280; 217. HRMS (ESI) C$_{20}$H$_{26}$O$_5$—Na requires 369.1678; found 369.1577.

(4R,5S,6R)-4-Benzo[1,3]dioxol-5-yl-6-ethoxy-5-{2-[2-(2-hydroxy-ethoxy)-ethoxy]-ethyl}-5,6-dihydro-4H-pyran-2-carboxylic acid allyl ester

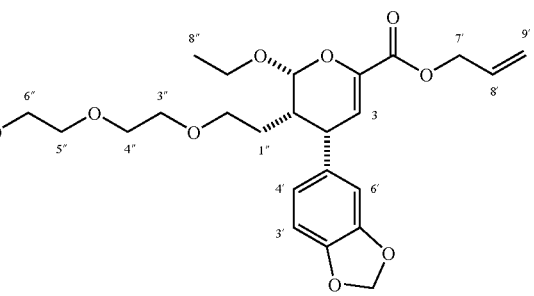

$^1$H NMR (600 MHz) 6.75–6.65 (m, 3H, HAr); 6.24 (d, J=3.9, 1H, HC(3)); 5.99–5.92 (m, 1H, HC(8')); 5.93 (d, J=1.5, 1H, HCO$_2$)); 5.91 (d, J=1.5, HCO$_2$); 5.35 (dd, J=17.1, 1.5, 1H, HC(9')); 5.25 (dd, J=10.7, 1.5, 1H, HC(9')); 5.19 (d, J=2.4, 1H, HC(6)); 4.77–4.66 (m, 2H, H$_2$C(7')); 3.93–3.90 (m, 1H, HC(7")); 3.78–3.30 (m, 12H, H$_2$CO; HC(7"); HC(4)); 1.19 (t, J=6.9, 3H, H$_3$C(8")); other signals obscured; MS (ESI) 487 (M+Na); 419; 417; 261; HRMS (ESI) C$_{24}$H$_{32}$O$_9$—Na 487.1944; found 487.1943.

(4R,5R,6R)-4-Benzo[1,3]dioxol-5-yl-6-ethoxy-5-{2-[2-(2-hydroxy-ethoxy)-ethoxy]-ethyl}5,6-dihydro-4H-pyran-2-carboxylic acid allyl ester

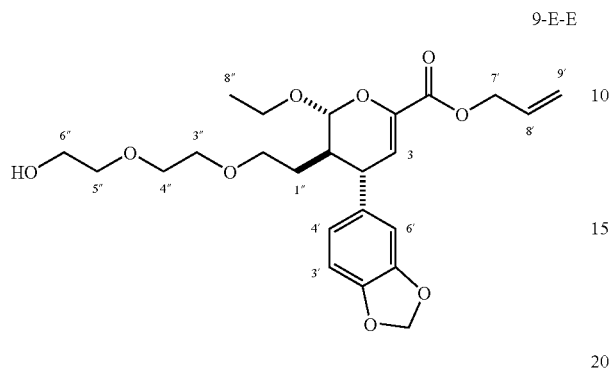

9-E-E $^1$H NMR (600 MHz) 6.75–6.66 (m, 3H, HAr); 6.11 (d, J=3.4, 1H, HC(3)); 5.97–5.92 (m, 1H, HC(8')); 5.93 (d, J=2.4, 2H, H$_2$CO$_2$)); 5.35 (dd, J=17.6, 1.5, 1H, HC(9')); 5.25 (d, J 10.3, 1H, HC(9')); 4.92 (d, J=5.9, 1H, HC(6)); 4.70 (ABX, J=13.6, 5.9, 2H, H$_2$C(7')); 3.96 (qd, J=7.3, 6.8, 1H, HC(7'')); 3.75–3.43 (m, 11H, HCO; HC(7')); 3.33 (dd, J=6.3, 3.4, 1H, HC(4)); 2.07, quint, J=5.9, 1H, HC(5)); 1.72–1.63 (m, 2H, H2C(1'')); 1.19 (t, J=6.8, 3H, H$_3$C(8'')); MS (ESI) 487 (M+Na); 419; 261; HRMS (ESI) C$_{24}$H$_{32}$O$_9$—Na requires 487.1944; found 487.1921.

(4R,6R)-4-Benzo[1,3]dioxol-5-yl-6-{2-[(2-hydroxy-ethyl)-(4-methoxy-benzenesulfonyl-amino]-ethoxy}-5,6-dihydro-4H-pyran-2-carboxylic acid allyl ester

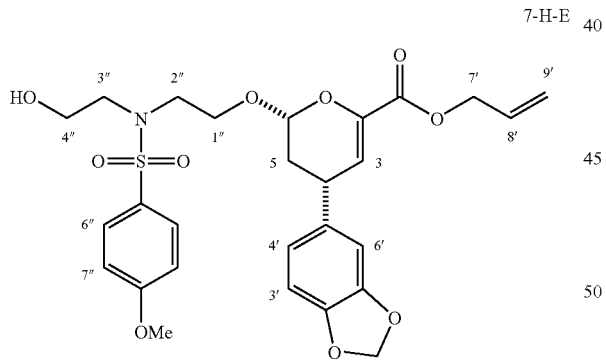

7-H-E $^1$H NMR (600 MHz) 7.76 (d, J=8.8, 2H, HAr); 6.97 (d, J=8.8, 2H, HAr); 6.74 (d, J=7.8, 1H, HAr)); 6.68–6.64 (m, 2H, HAr)); 6.13 (d, J=2.9, 1H, HC(3)); 6.00–5.90 (m, 1H, HC(8')); 5.93 (s, 2H, H$_2$CO$_2$)); 5.35 (d, J=17.1, 1.5, 1H, HC(9')); 5.26 (dd, J=10.7, 1.5, 1H, HC(9')); 5.10 (dd, J=8.3, 2.0, 1H, HC(6)); 4.77–4.65 (m, 2H, H$_2$C(7')); 4.14–4.10 (m, 1H); 3.92–3.84 (m, 1H, 3.86 (s, 3H, H$_3$CO); 3.71–3.68 (m, 2H); 3.64–3.62 (m, 1H, HC(4)); 3.48 (dt, J=15.1, 4.4, 1H); 3.36–3.22 (m, 2H); 3.08 (dt, J=14.6, 4.9, 1H); 2.26 (dd, J=12.7, 6.8, 1H, HC(5)); 1.86 (dt, J=13.2, 8.3, 1H, HC(5)); MS (ESI) 584 (M+Na); 287; 276. HRMS (ESI) C$_{27}$H$_{31}$NO$_{10}$S—Na requires 584.1566; found 584.1572.

(e) Heterodiene Testing:

(4S,6R)-6-{2-[(2-Hydroxy-ethyl)-(4-methoxy-benzenesulfonyl)-amino]-ethoxy}-4-isoproplyl-5,6-dihydro-4H-pyran-2-carboxylic acid allyl ester

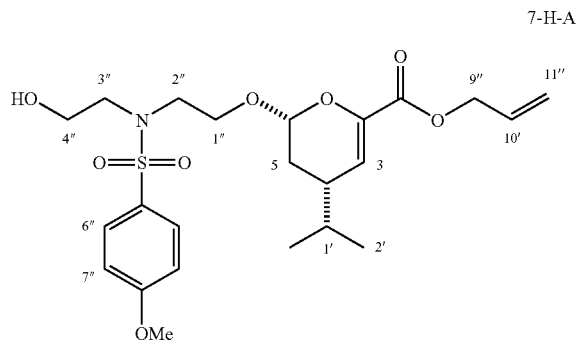

7-H-A $^1$H NMR (600 MHz) 7.78–7.77 (m, 2H, HAr); 7.00–6.96 (m, 2H, HAr); 6.04 (d, J=2.0, 1H, HC(3)); 5.87 (ddd, J=17.1, 10.7, 1.5, 1H, HC(10'')); 5.35 (dd, J=17.1, 1.5, 1H, HC(11 '')); 5.25 (dd, J=10.7, 1.5, 1H, HC(1'')); 4.97 (dd, J=9.3, 1.3, 1H, HC(6)); 4.72–4.64 (m, 2H, H$_2$C(9'')); 4.14–4.10 (m, 1H); 4.02–3.99 (m, 1H); 3.96–3.90 (m, 1H); 3.87 (s, 3H, H$_3$CO); 3.80–3.70 (m, 2H); 3.50–3.32 (m, 2H); 3.29–3.26 (m, 1H); 3.18–3.16 (m, 1H); 2.32-2.26 (m, 1H, HC(5)); 1.98–1.96 (m, 1H, HC(5)); 1.74–1.65 (m, 1H, HC(1')); 0.96 (d, J=7.1, 3 H, H$_3$C(2')); 0.94 (d, J=7.1, 3H, H$_3$C(1')); MS (ESI506 (M+Na); 484 (M+Na); 484 (M+1); 2.76; 258; HRMS (ESI) C$_{23}$H$_{33}$NO$_8$S—Na requires 506.1825; found 506.1847.

(4R,6R)-6-{2-[(2-Hydroxy-ethyl)-(4-methoxy-benzenesulfonyl)-amino]-ethoxy}-4-phenyl-5,6-dihydro-4H-pyran-2-carboxylic acid allyl ester

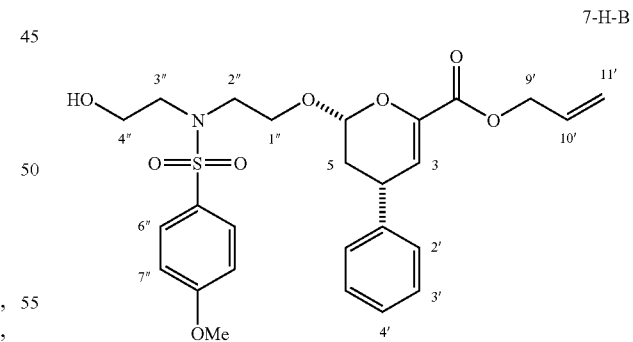

7-H-B $^1$H NMR (600 MHz) 7.76–7.70 (m, 2H, HAr); 7.31–7.19 (m, 5H, HAr); 7.00-6.96 (m, 2H, HAr); 6.20 (d, J=2.9, 1H, HC(3)); 5.93 (ddd, J=17.1, 10.7, 1.6, 1H, HC(10'')); 5.36 ()dd, J=17.1, 1.5, 1H, HC(11 '')); 5.26 (dd, J=10.7, 1.5, 1H, HC(1141 )); 5.14 (dd, J=7.8, 2.0, 1H, HC(6)); 4.77–4.68 (m, 2H, H$_2$C(9'')); 4.15–4.10 (m, 1H); 4.02–3.98 (m, 1H); 3.91-3.84 (m, 1H); 3.87 (s,. 3H, H$_3$CO); 3.74–3.70 (m, 1H); 3.65–3.60 (m, 1H); 3.50–3.40 (m, 2H); 3.29–3.22 (m, 2H); 3.08–3.00 (m, 1H); 2.31 (m, 1H, HC(5)); 1.93 (dt, J=14.0, 7.5, 1H, HC(5)); MS (ESI) 540 (M+Na); 518 (M+1); 276; 258; HRMS (ESI) C$_{26}$H$_{31}$N$_O$8S—Na requires 540.1668; found 540.1644.

(4R,6R)-4-(9H-Fluoren-2-yl)-6-{2-[(2-hydroxy-ethyl)-(4-methoxy-benzenesulfonyl-amino]-ethoxy}-5,6-dihydro-4H-pyran-2-carboxylic acid allyl ester

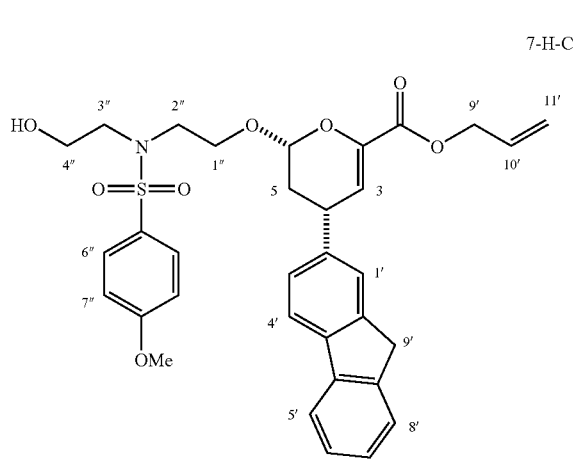

7-H-C $^{1}$H NMR (600 MHz) 7.77–7.70 (m); 7.55–7.53 (m); 7.38–7.20 (m); 7.70–6.94 (m); 6.24 (d, J=2.9, 1H, HC(3)); 5.96 (ddd, J=17.1, 10.7, 1.5, 1H, HC(10")); 5.36 (dd, J=17.1, 1.5, 1H, HC(11")); 5.26 (dd, J=10.7, 1.5, 1H, HC(11")); 5.17 (dd, J=7.8, 2.0, 1H, HC(6)); 4.77–4.68 (m, 2H, H$_2$C(9")); 4.16–4.11 (m, 1H); 3.95–3.90 (m, 1H); 3.88–3.82 (m, 1H); 3.83 (s, 3H, H$_3$CO); 3.82–3.80 (m, 1H, HC(4)); 3.64–3.62 (m, 1H); 3.51–3.46 (m, 1H); 3.30–3.22 (m, 2H); 3.06–3.00 (m, 1H); 2.36 (dd, J=12.7, 7.3, 1H, HC(5)); 1.98 (dt, J=13.6, 8.8, 1H, HC(5)); MS (ESI) 628 (M+Na); 606 (M+1); 536; 478; 276; HRMS (ESI) C$_{33}$H$_{35}$NO$_8$S—Na requires 628.1998; found 628.2008.

(4R,6R)-6-{2-[(2-Hydroxy-ethyl)-(4-methoxy-benzenesulfonyl)-amino]-ethoxy}-4-(4-methoxycarbo-nyl-phenyl)-5,6-dihydro-4H-pyran-2-carboxylic acid allyl ester

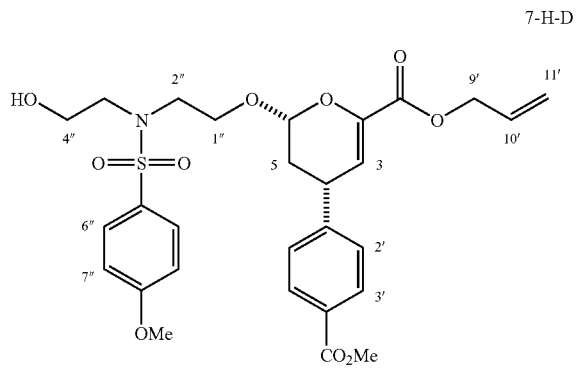

7-H-D $^{1}$H NMR (600 MHz) 7.98 (d, J=8.8, 2H, HC(3')); 7.76–7.72 (m, 2H, HAr); 7.28 (d, J=8.8, 2H, HC(2')); 6.99–6.95 (m, 2H, HAr); 6.19 (d, J=2.9, 1H, HC(3)); 5.86 (ddd, J=17.1, 10.7, 1.5, 1H, HC(10")); 5.36 (dd, J=17.1, 1.4, 1H, HC(11")); 5.26 (dd, J=10.7, 1.5, 1H, HC(11")); 5.17 (dd, J=7.8, 2.0, 1H, HC(6)); 4.77–4.66 (m, 2H, H$_2$C(9")); 4.14–4.08 (m, 1H); 3.93–3.85 (m, 2H); 3.91 (s, 3H, H$_3$CO$_2$C)); 3.86 (s, 3H, H$_3$CO); 3.79–3.76 (m, 1H, HC(4)); 3.62–3.60 (m, 1H); 3.46–3.42 (dt, J=15.1, 4.9, 1H); 3.26–3.19 (m, 2H); 3.01 (dt, J=10.2, 5.9, 1H); 2.36–2.30 (m, 1H, HC(5)); 1.96–1.92 (m, 1H, HC(5)); MS (ESI) 598 (M+Na); 576 (M+1); 276; HRMS (ESI) C$_{28}$H$_{33}$NO$_{10}$S—Na requires 598.1723; found 598.1702.

(4R,6R)-6-{2-[(2-Hydroxy-ethyl)-(4-methoxy-benzenesulfonyl)-amino]-ethoxy}-4-thiophen-3-yl-5,6-dihydro-4H-pyran-2-carboxylic acid allyl ester

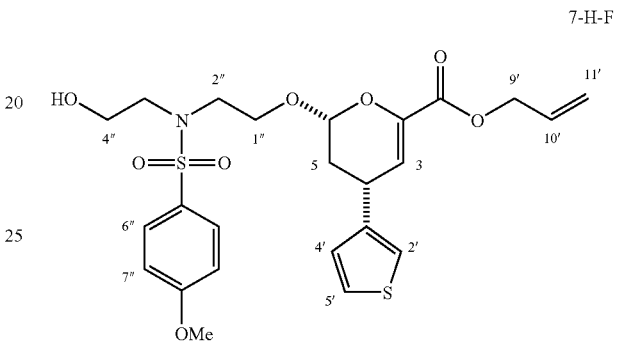

7-H-F $^{1}$H NMR (600 MHz) 7.77–7.74 (m, 2H, HAr); 7.74–7.72 (m, 1H, HAr); 7.29 (dd, J=4.9, 2.9, 1H, HAr); 7.05–6.95 (m, 3H, HAr); 6.21 (d, J=3.4, 1H, HC(3)); 5.86 (ddd, J=17.1, 10.7, 1.4, 1H, HC(10")); 5.36 (dd, J=17.1, 1.5, 1H, HC(11")); 5.26 (dd, J=10.7, 1.5, 1H, HC(11")); 5.15 (dd, J=7.8, 2.0, 1H, HC(6)); 4.75–4.64 (m, 2H, HC(9")); 4.12–4.08 (m, 1H); 4.02–3.98 (m, 1H); 3.92–3.80 (m, 2H); 3.86 (s, 3H, H$_3$CO); 3.74–3.70 (m, 1H); 3.68 (t, J=4.9, 1H); 3.50–3.40 (m, 1H); 3.32–3.22 (m, 1H); 3.07–3.02 (m, 1H); 2.34–2.30 (m, 1H, HC(5)); 2.00–1.95 (m,1H, HC(5)); MS (ESI) 546 (M+Na); 524 (M+1); 302; 276; 258; 249; HRMS (ESI) C$_{24}$H$_{29}$NO$_8$S$_2$ requires 546.1232; found 546.1230.

(4R,6R)-4-Benzofuran-3-yl-6-{2-[(2-hydroxy-ethyl)-(4-methoxy-benzenesulfony)amino]-ethoxy}-5,6-dihydro-4H-pyran-2-carboxylic acid allyl ester

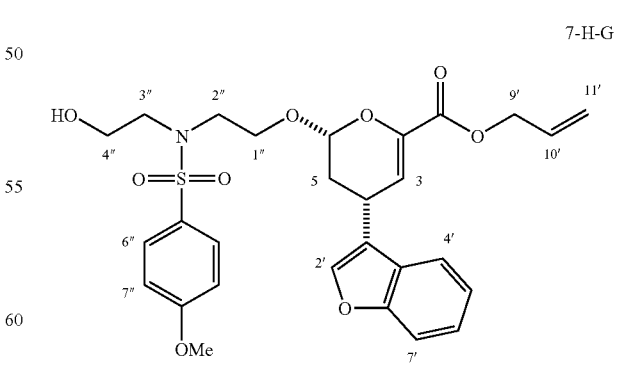

7-H-G $^{1}$H NMR (600 MHz) 7.74–7.70 (m, 2H, HAr); 7.48 (d, J=6.8, 1H, HAr); 7.42 (d, J=8.3, 1H, Hr); 7.26–7.18 (m, 2H, HAr); 7.00–6.97 (m, 2H, HAr); 6.47 (s, 1H, HC(2')); 6.34 (d, J=3.9, 1H, HC(3)); 5.97 (ddd, J=17.1, 10.7, 1.5, 1H, HC(10")); 5.38 (dd, J=17.1, 1.5, 1H, HC(11")); 5.24 (dd, J=10.1, 1.4, 1H, HC(11")); 5.19 (dd, J=6.3, 2.4, 1H, HC(6")); 4.78–4.68 (m, 2H, H₂C(9")); 4.05–4.00 (m, 1H); 3.90–3.80 (m, 1H); 3.86 (s, 3H, H₃CO); 3.74–3.70 (m, 1H); 3.50–3.40 (m, 2H); 3.29–3.24 (m, 1H); 3.20–3.16 (m, 1H); 3.13–3.07 (m, 1H); 2.98–2.90 (m, 1H); 2.37–2.25 (m, 2H, H₂C(5")); MS (ESI) 580 (M+Na); 558 (M+1); 258; HRMS (ESI) $C_{28}H_{31}NO_9S$—Na requires 580.1617; found 580.1595.

(4R,6R)-4-(1-Acetyl-1H-indol-3-yl)-6-{2-[(2-hydroxy-ethyl)-(4-methoxy-benzenesulfonyl-amino]-ethoxy}-5,6-dihydro-4H-pyran-2-carboxylic acid allyl ester

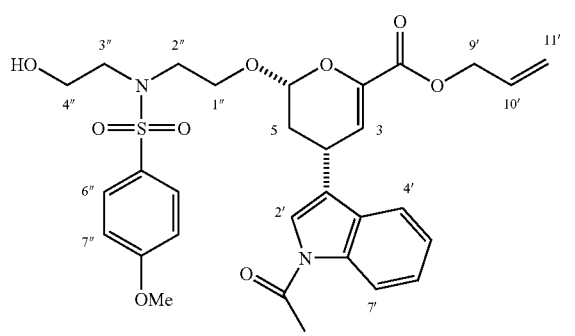

¹H NMR (600 MHz) 7.77–7.75 (m, 2H, HAr); 7.51–7.49 (m, 1H); 7.35–7.26 (m, 3H, HAr); 6.95–6.90 (m, 2H, HAr); 6.21 (d, J=2.8, 1H, HC(3)); 5.91 (ddd, J=17.1, 10.7, 1.4, 1H, HC(10")); 5.36 (dd, J=17.1, 1.5, 1H, HC(11")); 5.25 (dd, J=10.7, 1.5, 1H, HC(11")); 5.19 (dd, J=8.4, 1.3, 1H, HC(6)); 4.68–4.61 (m, 2H, H₂C(9")); 4.05-4.00 (m, 1H); 3.99–3.82 (m, 2H); 3.85 (s, 3H, H₃CO); 3.84–3.80 (m, 1H); 3.60–3.56 (m, 1H); 3.45–3.20 (m, 3H); 3.01 (dt, J=14.1, 5.1, 1H); 2.58 (s, 3H, H₃CC(O))); 2.38–2.33 (m, 1H, HC(5)); 2.06–2.00 (m, 1H, HC(5)); MS (ESI) 621 (M+Na); 599 (M+1); 276; HRMS (ESI) $C_{30}H_{34}N_2O_9S$—Na requires 621.1883; found 621.1860.

(4R,6R)-6-{2-[(2-Hydroxy-ethyl)-(4-methoxy-benzenesulfonyl)-amino]-ethoxy}-4-(4-oxo-4H-chromen-3-yl)-5,6-dihydro-4H-pyran-2-carboxylic acid allyl ester

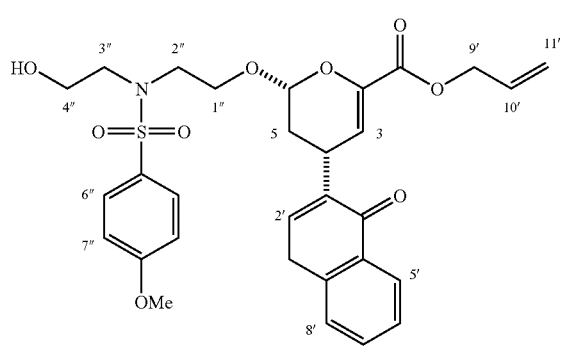

¹H NMR (600 MHz) 8.25 (d, J=7.8, 1.5, 1 HAr); 7.87 (s, 1H, HC(2')); 7.72 (d, J=9.3, 2H, HC(6")); 7.68–7.64 (m, 1H, HAr); 7.46–7.40 (m, 2H, HAr); 6.97 (d, J=9.3, 2H, HC(7")); 6.19 (d, J=3.9, 1H, HC(3)); 6.03 (ddd, J=17.1, 10.7, 1.5, 1H, HC(10")); 5.37 (dd, J=17.1, 1.5, 1H, HC(11")); 5.28 (dd, J=10.7, 1.4, 1H, HC(11")); 5.20 (dd, J=4.9, 2.4, 1H, HC(6)); 4.78–4.69 (m, 2H, HC(9")); 4.02–3.98 (m, 1H, HC(4)); 3.88-3.72 (m, 2H); 3.86 (s, 3H, H₃CO); 3.58 (t, J=4.8, 1H); 3.36 (dt, J=14.7, 4.9, 1H); 3.32–3.24 (m, 1H); 3.17 (dt, J=15.1, 4.9, 1H); 3.10–3.06 (m, 1H); 2.38–2.34 (m, 1H, HC(5)); 2.00–1.94 (m, 1H, HC(5)); MS (ESI) 608 (M+Na); 586 (M+1); 311; HRMS (ESI) $C_{29}H_{31}NO_{10}S$—Na requires 608.1566; found 608.1572.

(4R,6R)-4-(1,5-Dimethyl-3-oxo-2-phenyl-2,3-dihydro-1H-pyrazol-4-yl)-6-{2-[(2-hydroxy-ethyl)-(4-methoxy-benzenesulfonyl)-amino]-ethoxy}-5,6-dihydro-4H-pyran-2-carboxylic acid allyl ester

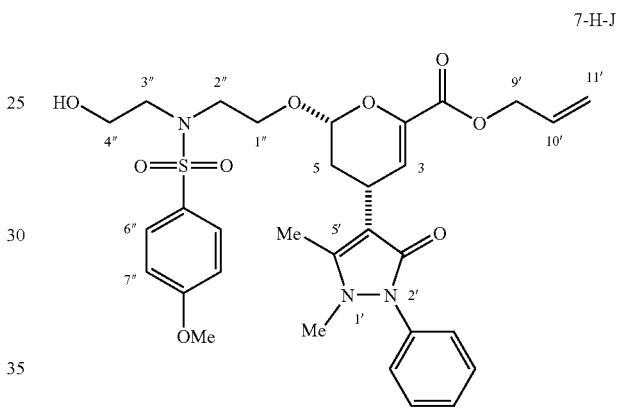

¹H NMR (600 MHz) 7.76 (m, 2H, HAr); 7.46–7.30 (m, 5H, HAr); 6.99–6.96 (m, 2H, HAr); 6.11 (d, J=2.9, 1H, HC(3); 5.96 (ddd, J=17.1, 10.7, 1.5, 1H, HC(10")); 5.35 (dd, J=17.1, 1.5, 1H, HC(11")); 5.26 (dd, J=10.7, 1.5, 1H, HC(11")); 5.11 (dd, J=8.3, 2.0, 1H, HC(6)); 4.77–4.65 (m, 2H, H₂C(9")); 4.04–3.99 (m, 1H); 3.90–3.85 (m, 1H); 3.86 (s, 3H, H₃CO); 3.72–3.70 (m, 2H); 3.44–3.40 (m, 2H); 3.33–3.20 (m, 3H); 3.06 (s, 3H, H₃CN); 2.30–2.22 (m, 1H, HC(5)); 2.22 (s, 3H, H₃CC); 2.02–1.96 (m, 1H, HC(5)); MS (ESI) 650 (M+Na); 628 (M+1); HRMS (ESI) $C_{31}H_{37}N_3O_9S$—Na requires 628.2329; found 628.2348.

(f) Amine Building Blocks:

[4-(2-Amino-phenylcarbamoyl)-benzyl]-carbamic acid tert-butyl ester

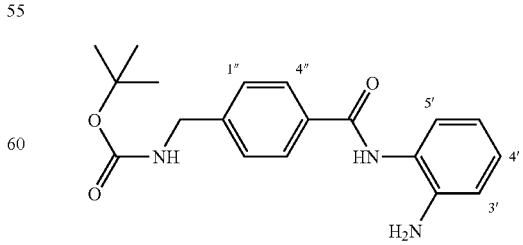

¹H NMR (500 MHz, dmso-d₆) 9.60 (s, 1H, ArNH); 7.91 (d, J=7.8, 2H, HC(3")); 7.48 (t, J=6.4, 1H, CH₂NH); 7.33 (d, J=6.8, 2H, HC(2")); 7.15 (d, J=7.8, 1H, HC(6')); 6.96 (t, J=7.8, 1H, HC(4')); 6.76 (d, J=7.8, 1H, HC(3')); 6.58 (t, J=7.3, 1H, HC(5')); 4.88 (s, 2H, NH2); 4.17 (d, J=6.4, 2H, H$_2$Car); 1.39 (s, 9H, H$_3$C); $^{13}$C NMR (100 MHz, dmso-d$_6$) 165.17; 155.85; 143.78; 143.16; 133.06; 127.83; 127.56; 126.95; 126.66; 126.48; 123.37; 116.28; 116.15; 77.94; 43.19; 28.26; MS (ESI) 342 (M+1); 286.

(g) Encoded Split-Pool Library Synthesis

Loading. A potion of the silyl functionalized resin 2 (1.43 meq/g, 2.10 g, 3.0 mmol) was divided into eight equal portions (262 mg, 0.375 mmol, 1.0 equiv), placed under argon in PD-10 tubes and suspended in 3 mL of 3% (vol/vol) TMSCl/CH$_2$Cl$_2$ (in PD-10 columns). The swollen beads were allowed to stand for 30 min, then filtered (under argon) and washed with 4×3 mL×2 min CH$_2$Cl$_2$. Then, a solution of TfOH (3% in CH2C12, 6.6 mL, 2.25 mmol, 6.0 equiv) was added and the resin was allowed to stand (with occasional gentle mixing) for 25 min. The resin was filtered (under argon) and washed with 4×3 mL×2 min CH$_2$Cl$_2$. After the final wash an additional 2 mL of CH$_2$Cl$_2$ was added to each pool, followed by 2,6-lutidine (350 uL, 3.0 mmol, 8.0 equiv) and the resin was allowed to stand (with occasional gentle mixing) for 15 minutes. At this point each of the vinyl ethers BB1A-H were added (0.75 mmol, 2.0 equiv) as solutions in 1 mL of CH$_2$Cl$_2$. The tubes were then allowed to stand for 2.5 h (with occasional gentle mixing) then the resin was filtered and washed with 4×3 mL×2 min CH$_2$Cl$_2$, then 1×5 mL×15 min THF, then 1×5 mL×15 min CH$_2$Cl$_2$ then the resin pools were dried, first by simple suction for 10 min, then under vacuum for 2 h and taken to the next step.

First Encoding Step. Each of the eight resin pools from above (0.375 mmol, 1 equiv) was placed in a dry 8 mL vial capped with a septum. To each vial was added the appropriate diazoketone tags (see Table 3 below) (0.0672 mmol total tag for each reaction), followed by CH$_2$Cl$_2$ (4.0 mL, 16.8 mM total tag concentration) was added to each vial and the vials were gently shaken on a vortexer for 1 h. Then, a solution of Rh$_2$(O$_2$CPh$_3$)$_4$ (4 mL, 2.5 mg/mL) in CH$_2$Cl$_2$ was added to each vial and the resulting mixture vortexed for an additional 4 h, then the resin was filtered and washed with 2×5 mL×15 min CH$_2$Cl$_2$, then 1×5 mL×5 min THF, then 1×5 mL×8 h THF, then 2×5 mL×10 min THF, then 3×5 mL×15 min CH$_2$CH$_2$. At this point the resin was pooled and rotated/washed in 1×15 mL×30 min THF then 3×15 mL×30 min CH$_2$Cl$_2$, and dried as above to give 2.12 g of tagged vinyl ether.

TABLE 3

Binary tagging scheme for first tagging step.

| BB1- | T2B (C4Cl3) | T4B (C6Cl3) | T1A (C3Cl5) | T2A (C4Cl5) |
|---|---|---|---|---|
| A | 29.7 mg | — | — | — |
| B | — | 31.8 mg | — | — |
| C | — | — | 33.5 mg | — |
| D | — | — | — | 34.5 mg |
| E | 14.9 mg | 15.9 mg | — | — |
| F | 14.9 mg | — | 16.7 mg | — |
| G | 14.9 mg | — | — | 17.2 mg |
| H | — | 15.9 mg | 16.7 mg | — |

Cycloaddition. The resin from above was divided into 20 equal portions (106 mg each, 0.15 mmol (theory), 1.0 equiv) and placed in dry 4 mL vials containing diene building blocks BB2A–J (2 vials per building block, 0.45 mmol, 3.0 equiv) and 10 mg of activated powdered 4A molecular sieves. The vials were capped with septa and placed under argon. THF (0.8 mL) was added to each vial, followed by a solution of appropriate catalyst solution (0.8 mL). (Catalyst solutions were prepared by mixing 1 equiv of each 2,2'-Isopropylidenebis[(4S)-4t-butyl-2-oxazoline] ligand (141 mg) and Cu(OTf)$_2$ (173 mg) with 4A molecular sieves (50 mg) in THF (12.8 mL) and stirred at rt temp to give a deep green mixture. An identical procedure was used for the (R)-enantiomer of catalyst). The resulting mixtures were vortexed gently for 20 h then filtered (powdered sieves pass through the filter, thus separating them from the resin beads) and washed with 4×5 mL×30 min THF, then 3×5 mL×15 min CH$_2$Cl$_2$ and dried as above to give 20 pools of partially encoded cycloadducts.

Second Encoding Step. Each of the 20 resin pools (0.15 mmol (theory), 1 equiv) was placed in a dry 8 mL vial capped with a septum. To each pool was added the appropriate combination of tags (0.027 mmol total tag, see table 4 below) followed by 1.6 mL of CH$_2$Cl$_2$ and the mixture vortexed gently for 1 h. Then, a solution of Rh$_2$(O$_2$CPh$_3$)$_4$ (1.6 mL, 2.5 mg/mL) in CH$_2$Cl$_2$ was added to each vial and the resulting mixture vortexed for an additional 14 h, then the resin was filtered and washed with 2×5 mL×15 min CH$_2$Cl$_2$, then 2×5 mL×15 min THF, then 1×5 mL×6 h THF, then 2×5 mL×15 min THF, then 3×5 mL×15 min CH$_2$Cl$_2$point the resin pools derived from the (R) were combined (likewise the pools from the (S) catalyst were combined) and the two pseudo-enantiomeric pools were independently mixed/washed with 2×15 mL×30 min THF and 3×15 mL×15 min CH$_2$Cl$_2$, then filtered and dried to give two pseudo-enantiomeric pools of resin, each containing roughly 1.43 g of fully encoded, resin bound cycloadducts. A portion of each pool (1/27) by weight was set aside at this point to provide samples of the initial cycloadducts in the final library collection.

TABLE 4

Binary tagging scheme for second tagging step.

| BB2- | catalyst | T3A (C5C15) | T4A (C6C15) | T5A (C7C15) | T6A (C8C15) | T7A (C9C15) |
|---|---|---|---|---|---|---|
| A | (S)-1 | 14.2 mg | — | — | — | — |
| B | (S)-1 | — | 14.5 mg | — | — | — |
| C | (S)-1 | — | — | 14.9 mg | — | — |
| D | (S)-1 | — | — | — | 15.3 mg | — |
| E | (S)-1 | — | — | — | — | 15.7 mg |
| F | (S)-1 | 7.1 mg | 7.3 mg | — | — | — |
| G | (S)-1 | 7.1 mg | — | 7.5 mg | — | — |

TABLE 4-continued

Binary tagging scheme for second tagging step.

| BB2- | catalyst | T3A (C5C15) | T4A (C6C15) | T5A (C7C15) | T6A (C8C15) | T7A (C9C15) |
|---|---|---|---|---|---|---|
| H | (S)-1 | 7.1 mg | — | — | 7.6 mg | — |
| I | (S)-1 | 7.1 mg | — | — | — | 7.9 mg |
| J | (S)-1 | — | 7.3 mg | 7.5 mg | — | — |
| A | (R)-1 | — | 7.3 mg | — | 7.6 mg | — |
| B | (R)-1 | — | 7.3 mg | — | — | 7.9 mg |
| C | (R)-1 | — | — | 7.5 mg | 7.6 mg | — |
| D | (R)-1 | — | — | 7.5 mg | — | 7.9 mg |
| E | (R)-1 | — | — | — | 7.6 mh | 7.9 mg |
| F | (R)-1 | 4.7 mg | 4.8 mg | 5.0 mg | — | — |
| G | (R)-1 | 4.7 mg | 4.8 mg | — | 5.1 mg | — |
| H | (R)-1 | 4.7 mg | 4.8 mg | — | — | 5.2 mg |
| I | (R)-1 | 4.7 mg | — | 5.0 mg | 5.1 mg | — |
| J | (R)-1 | 4.7 mg | — | 5.0 mg | — | 5.2 mg |

Deallylation. Each of the two resin pools from above (1.5 mmol (theory) 1.0 equiv) was treated identically. Tetrakis(triphenylphosphine)palladium (1.73 g, 1.5 mmol, 1.0 equiv) was dissolved in 26 mL of THF. The dry resin was then added to this solution followed by thiosalicylic acid (1.62 g, 10.5 mmol, 7 equiv) and the mixture was vortexed gently for 12 h, then the resin pools were filtered and each washed separately with 4×15 mL×1 h THF, then 2×15 mL×15 min DMF, then 1×15 mL×15 min THF, then 1×15 mL×15 min DMF, then 4×15 mL×15 min $CH_2Cl_2$ then dried to give two pools of resin each weighing roughly 1.34 g. A portion of each pool (1/26 by weight) was set aside at this point to provide samples of the cycloadduct carboxylic acids in the final library collection.

Amide Formation. Each of the two pools from above were split into 25 equal portions (0.056 mmol (theory), 1 equiv), then each set of 25 was treated identically. To each portion of resin in a 4 mL vial was added a stock solution of PyBop (193 mg/mL in $CH_2Cl_2$, 1.5 mL, 0.55 mmol, 10 equiv) followed by stock solutions of the amine building blocks (1.1 M in DMF, 500 uL, 0.56 mmol, 10 equiv). Then, diisopropylethylamine (100 uL, 0.56 mmol, 10 equiv) was added to each vial and the resulting mixtures were vortexed for 12 h. Each reaction mixture was then filtered and washed with 2×1 mL×30 min $CH_2Cl_2$, then 2×1 mL×30 min DMF, then 3×1 mL×30 min THF, then 3×1 mL×30 min $CH_2Cl_2$ then dried as above to give 50 spatially segregated pools of dihydropyrancarboxamides plus the four pools from above for both (R) and (S)-derived esters and acids. These samples were kept separate to allow for "spatial coding" of the amine building block, in addition to the chemical encoding of the first and second building blocks.

EXAMPLE 2

Solid Support Synthesis of Inventive Compounds—Decoding Methodology:

Discussion of Methodology

As described above and in Scheme 4, an encoded split-pool library of 4320 dihydropyrancarboxamides (12) was synthesized featuring an R- or S-bis(oxazoline)copper (II) triflate-catalyzed heterocycloaddition reaction as a diversity-generating step. The three sets of BBs used in te library synthesis are shown in FIG. 3. As discussed above, the library synthesis was based on three chemical steps: (1) loading of eight vinyl ethers onto the PS beads (4), (2) enantioselective cycloaddition with 10 β,c-unsaturated ketoesters, followed by allyl ester deprotection, and (3) PyBOP (benzotriazole-1-yl-oxy-tris-pyrrolidino-phosphonium hexafluorophosphate)-mediated coupling (See J. Coste, D. Lenguyen, B. Castro, PyBOP: a new peptide coupling reagent devoid of toxic byproduct, *Tetrahedron Lett.* 1990, 31:205–208) to 25 different amines to yield support-bound dihydropyrancarboxamides (11).

Scheme 4

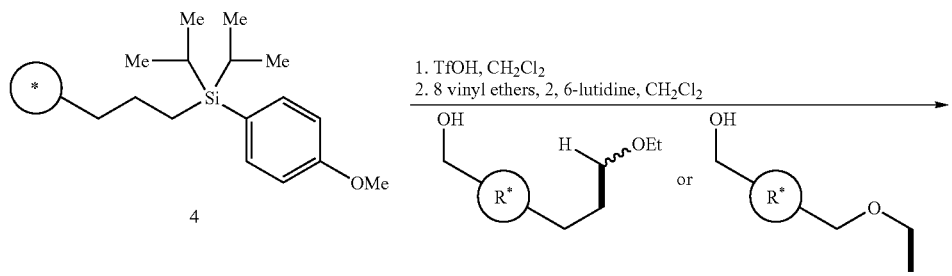

encircled R* = groups in Figure 3A 3. encoding step 1: tags-1,
   $Rh_2(O_2CC(Ph)_3)_4(5)$, $CH_2Cl_2$

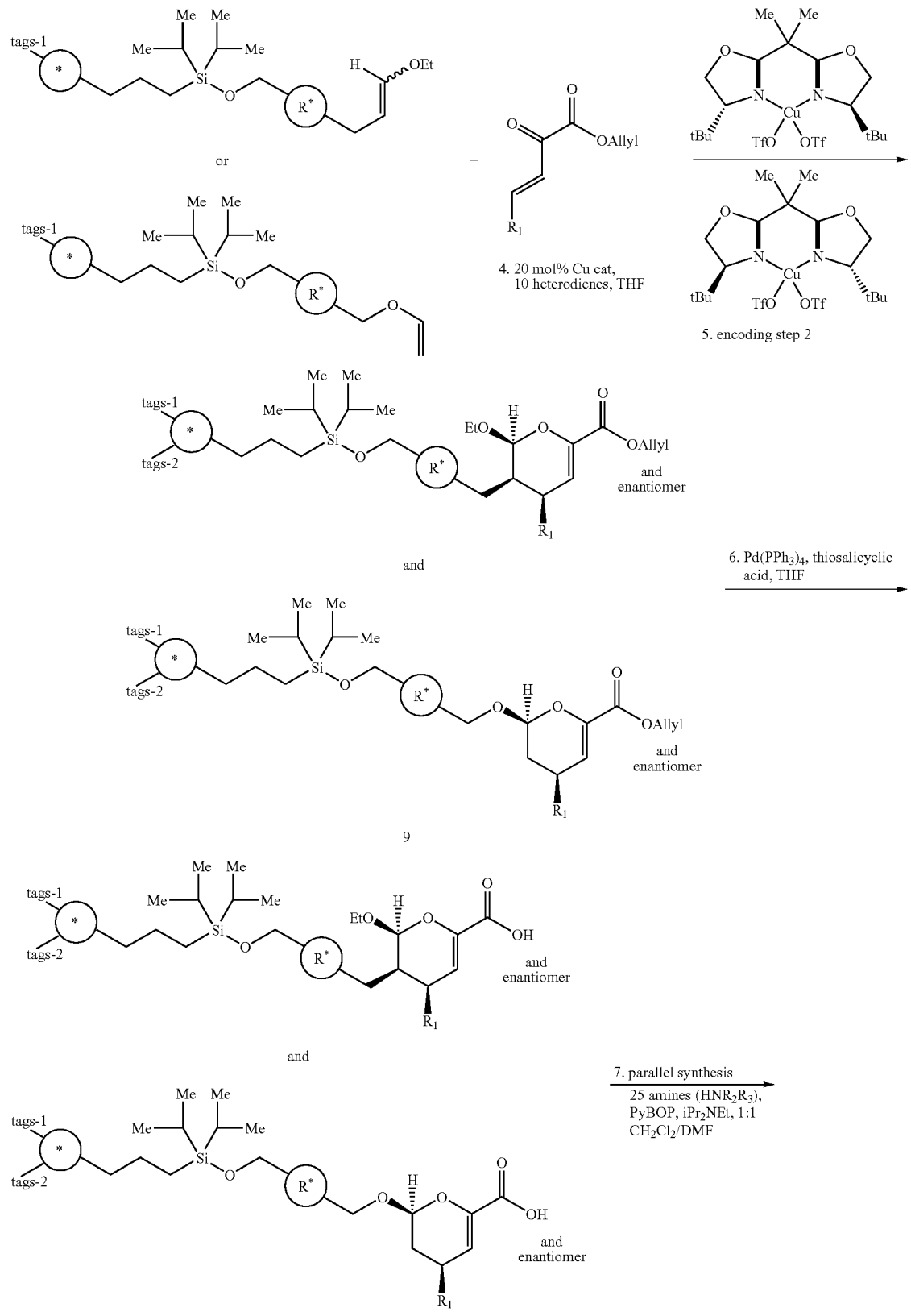

-continued

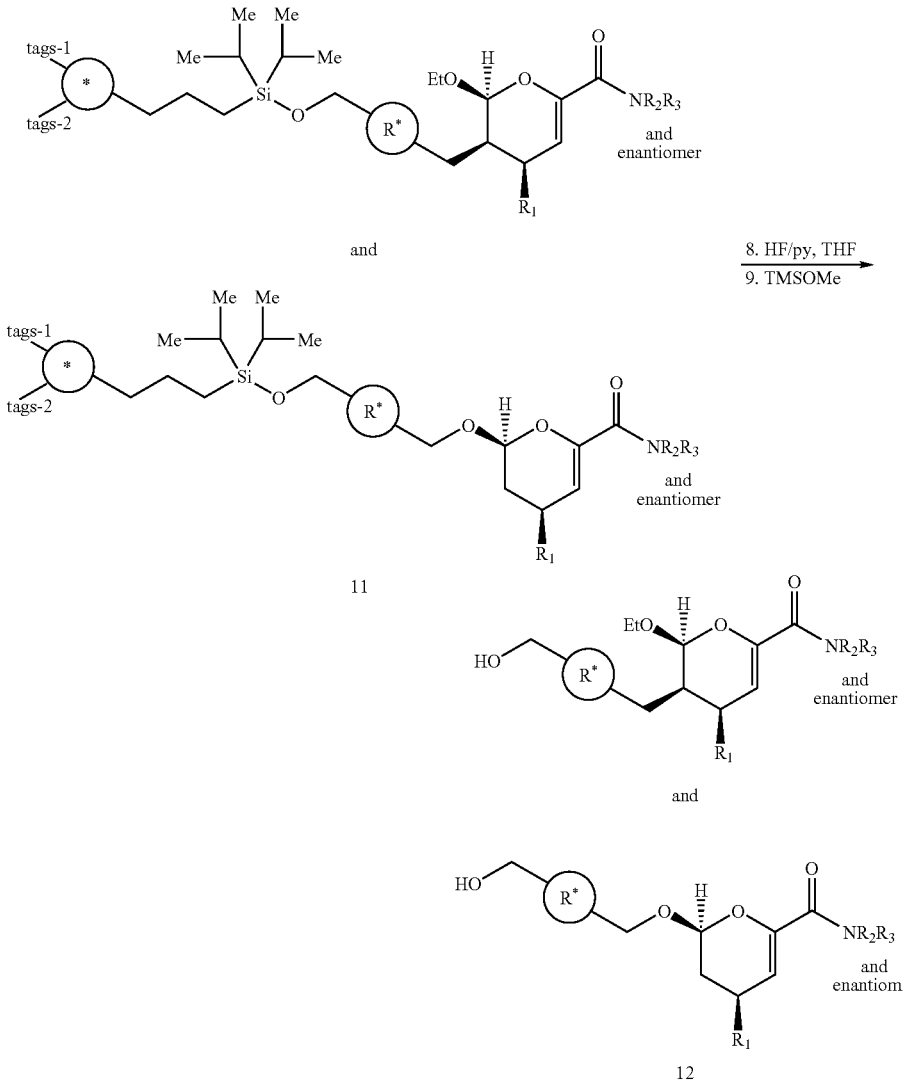

Figure 7:
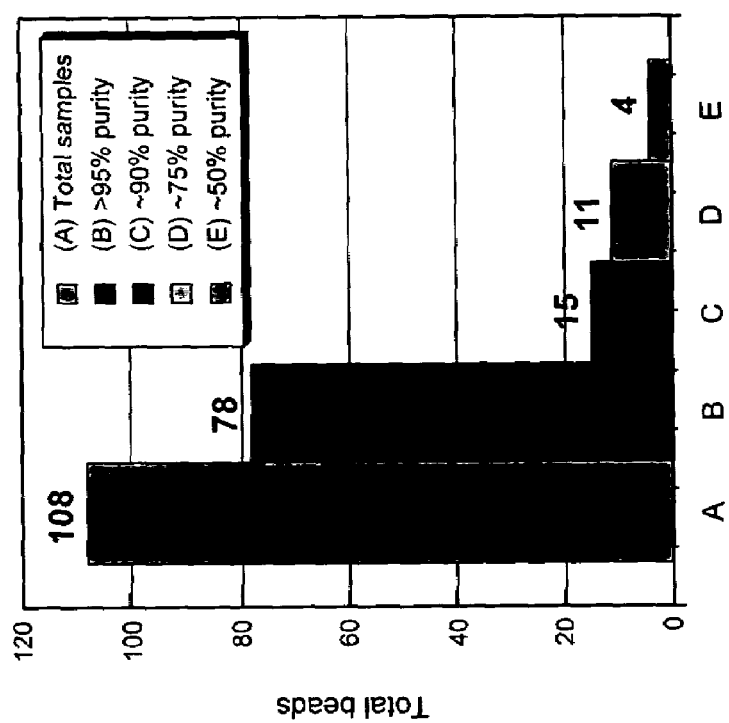
FIG. 7 depicts purity data determined by LC/MS for the 108 representative compounds cleaved from library 12, as described in Example 2 herein.
Figure 8A:
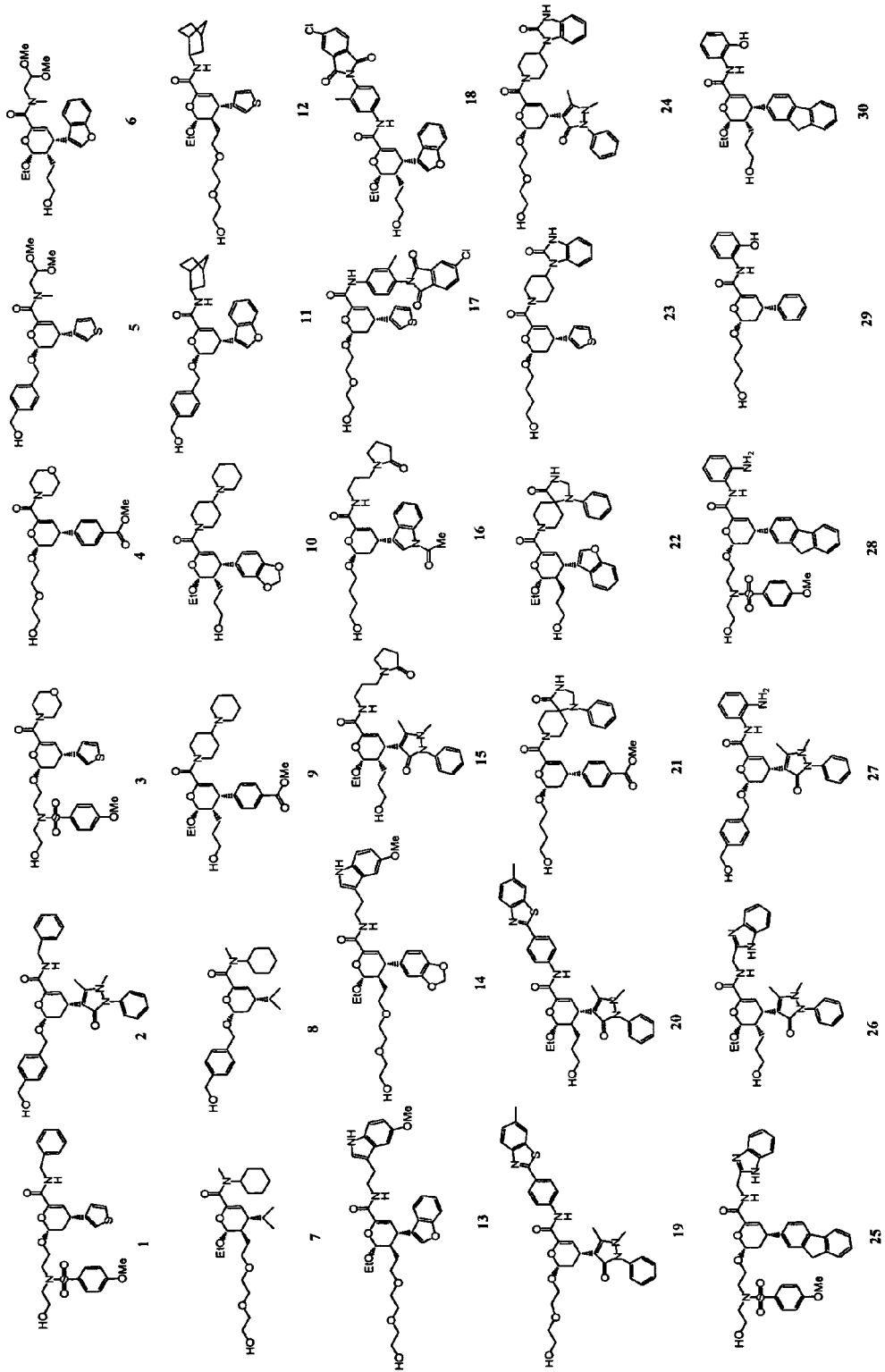
FIGS. 8A–8D depicts structures of the 54 compounds cleaved from beads chosen from batches of resin exposed to the S—Cu (II) catalyst in library 12, as described in Example 2 herein. Numbers in bold refer to bead number. Except for compound 105, all structures showed agreement between GC decoding and MS data.
Figure 8B:
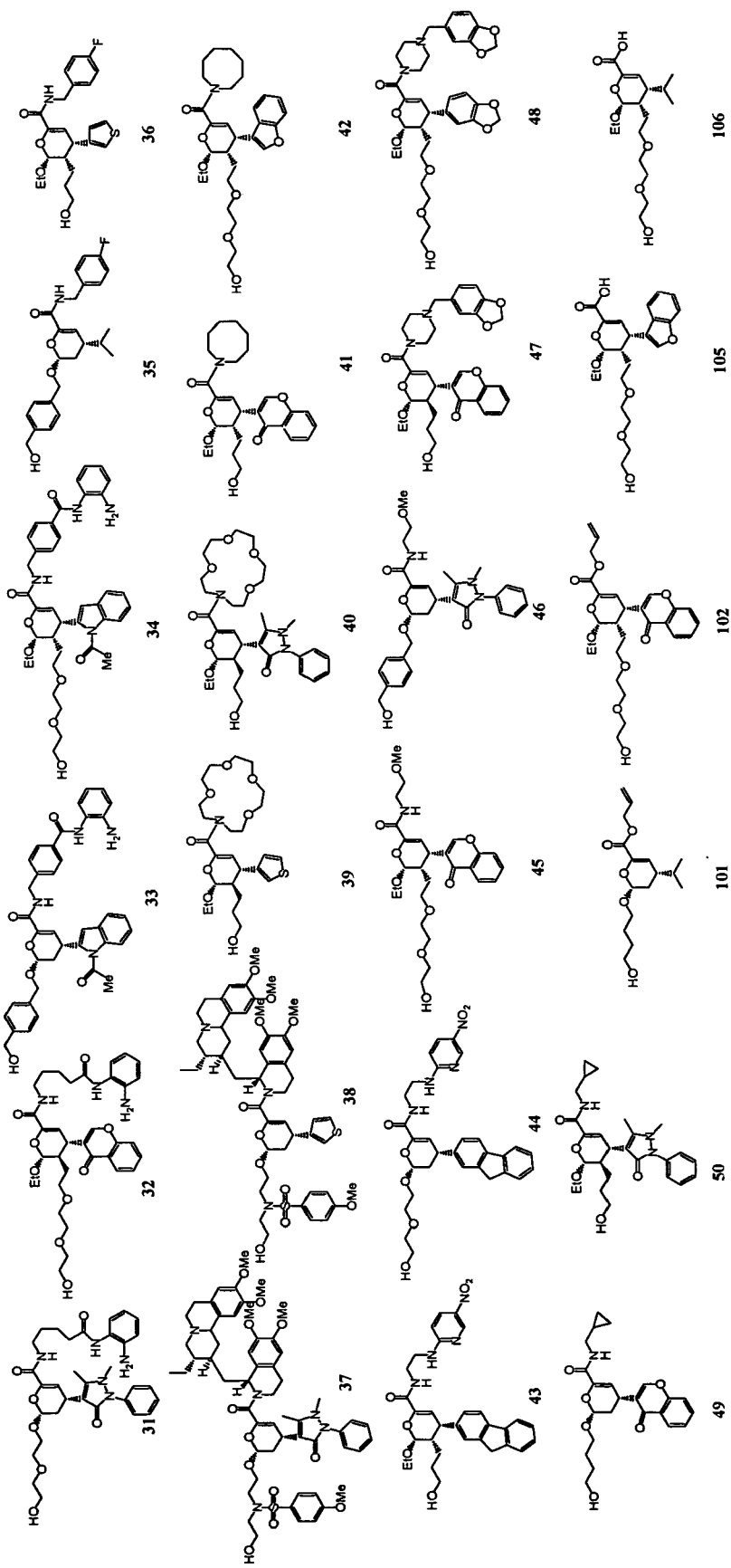
Figure 8C:
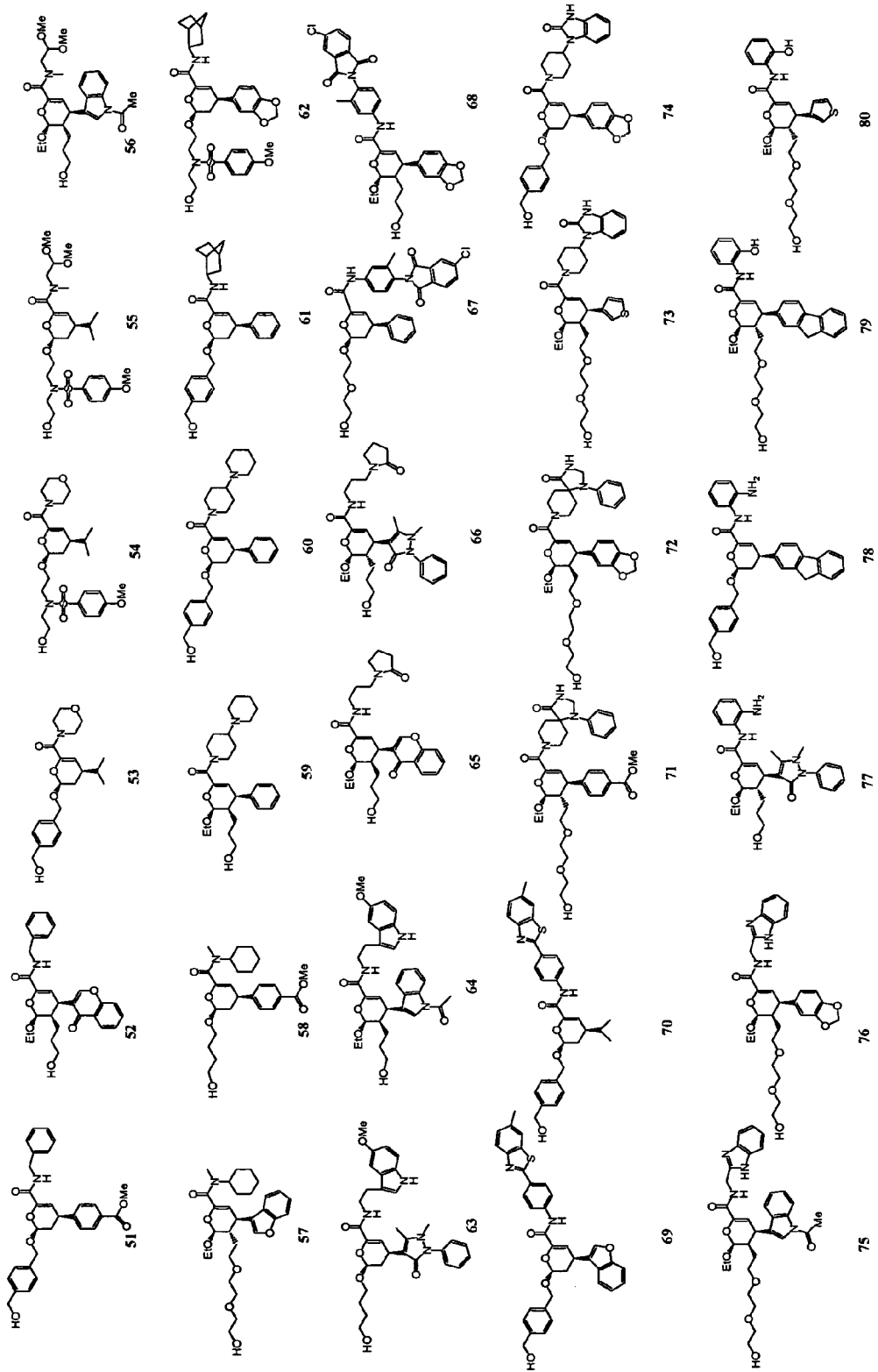
Figure 8D:
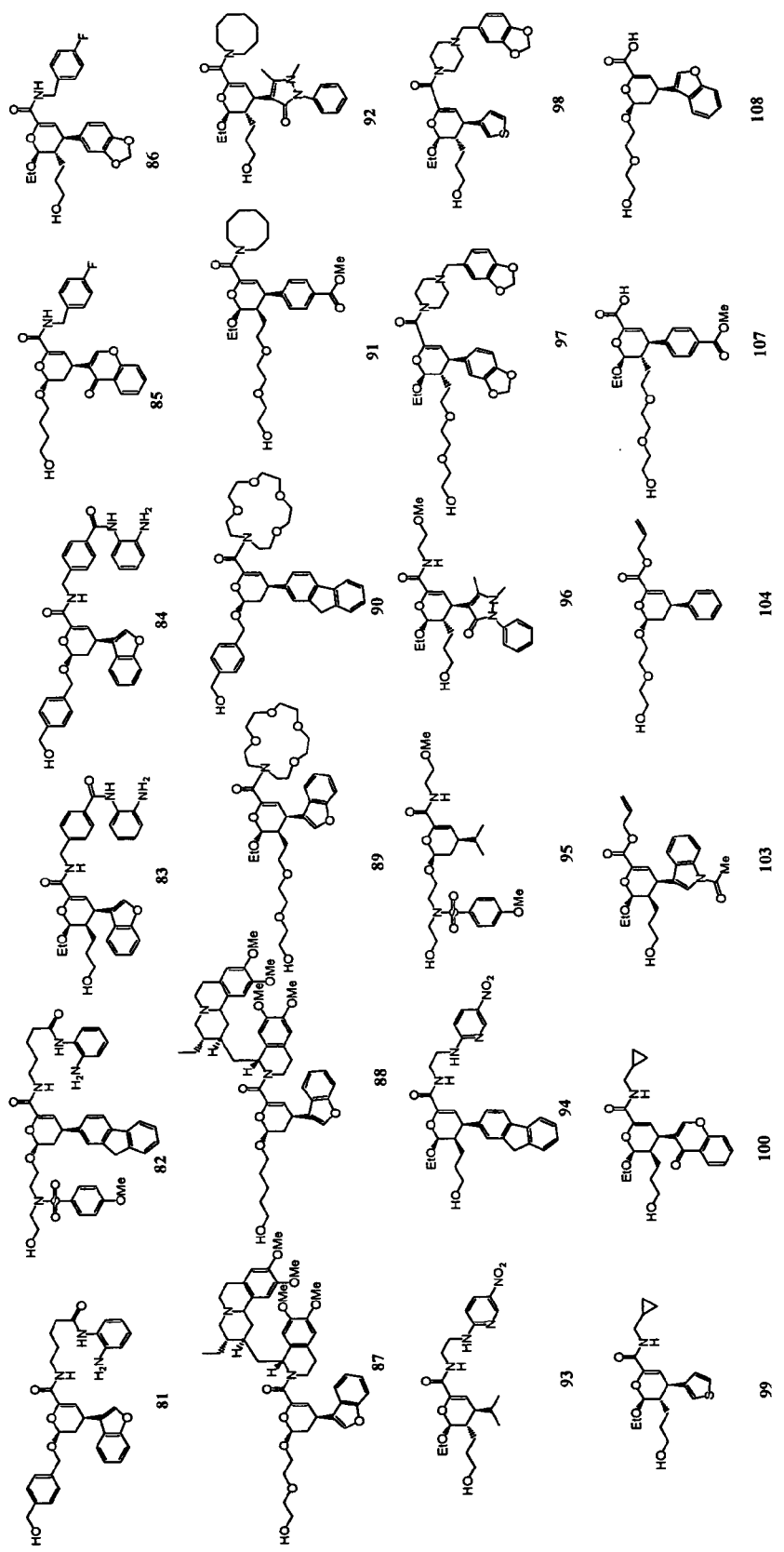

Reaction step and BB encoding were carried out twice in the library synthesis: first, after loading the eight vinyl ethers, and second, after the cycloaddition reaction with ten heterodienes. The tags and binary codes used for each BB are shown in Tables 5 and 6. In the cycloaddition reaction, one set of beads (10 portions) was treated with the (S)-Cu (II) catalyst, and the other ten portions were treated with the (R)-catalyst (Scheme 4). From this step onwards, these two groups of enantiomers were kept separate even though they were encoded for each enantiomer of the catalyst used. The subsequent reactions were carried out in parallel so that spatial decoding could be performed had the chemical encoding failed. The 25 final amide pools were kept separate to reduce the number of chemical encoding steps. This library synthesis resulted in 54 (27×2 enantiomers) separate portions of solid supports (11) containing, theoretically, three copies of 4320 stereochemically and structurally distinct compounds (12). Finally, as our macrobead handling 'best practices' were observed throughout the library synthesis, the majority of the library supports remained intact (>90%). In order to test the integrity of our optimized library encoding/decoding protocol, 108 macrobeads from the library (theoretically 2.5% of the total library compounds) were arrayed into tubes and treated with HF/py, followed by TMSOMe to release the compounds (12) from the beads. The residue isolated from each bead was dissolved in $CH_3CN$ and transferred to individual glass autosampler inserts to provide arrayed stock solutions of small molecules. A fraction of each of these stock solutions was subjected to LC/MS analysis, and the corresponding macrobeads were submitted to our optimized decoding protocol to compare the two results (FIG. 7).

TABLE 5

Binary codes for encoding BB1 of library 12

| Entry | Tag C4Cl3 | Tag C6Cl3 | Tag C3Cl5 | Tag C4Cl5 |
|---|---|---|---|---|
| BB1-A | 1 | 0 | 0 | 0 |
| BB1-B | 0 | 1 | 0 | 0 |
| BB1-C | 0 | 0 | 1 | 0 |
| BB1-D | 0 | 0 | 0 | 1 |
| BB1-E | 1 | 1 | 0 | 0 |
| BB1-F | 1 | 0 | 1 | 0 |
| BB1-G | 1 | 0 | 0 | 1 |
| BB1-H | 0 | 1 | 1 | 0 |

TABLE 6

Binary codes for encoding BB2 of library 12 in heterocycloadditions catalyzed by either R- or S-bis(oxazoline)copper (II) tri£ate

| Entry | Catalyst | Tag C5C15 | Tag C6C15 | Tag C7C15 | Tag C8C15 | Tag C9C15 |
|---|---|---|---|---|---|---|
| BB2-A | S | 1 | 0 | 0 | 0 | 0 |
| BB2-B |   | 0 | 1 | 0 | 0 | 0 |
| BB2-C |   | 0 | 0 | 1 | 0 | 0 |
| BB2-D |   | 0 | 0 | 0 | 1 | 0 |
| BB2-E |   | 0 | 0 | 0 | 0 | 1 |
| BB2-F |   | 1 | 1 | 0 | 0 | 0 |
| BB2-G |   | 1 | 0 | 1 | 0 | 0 |
| BB2-H |   | 1 | 0 | 0 | 1 | 0 |
| BB2-I |   | 1 | 0 | 0 | 0 | 1 |
| BB2-J |   | 0 | 1 | 1 | 0 | 0 |
| BB2-A | R | 0 | 1 | 0 | 1 | 0 |
| BB2-B |   | 0 | 1 | 0 | 0 | 1 |
| BB2-C |   | 0 | 0 | 1 | 1 | 0 |
| BB2-D |   | 0 | 0 | 1 | 0 | 1 |
| BB2-E |   | 0 | 0 | 0 | 1 | 1 |
| BB2-F |   | 1 | 1 | 1 | 0 | 0 |
| BB2-G |   | 1 | 1 | 0 | 1 | 0 |
| BB2-H |   | 1 | 1 | 0 | 0 | 1 |
| BB2-I |   | 1 | 0 | 1 | 1 | 0 |
| BB2-J |   | 1 | 0 | 1 | 0 | 1 |

Figure 9A:
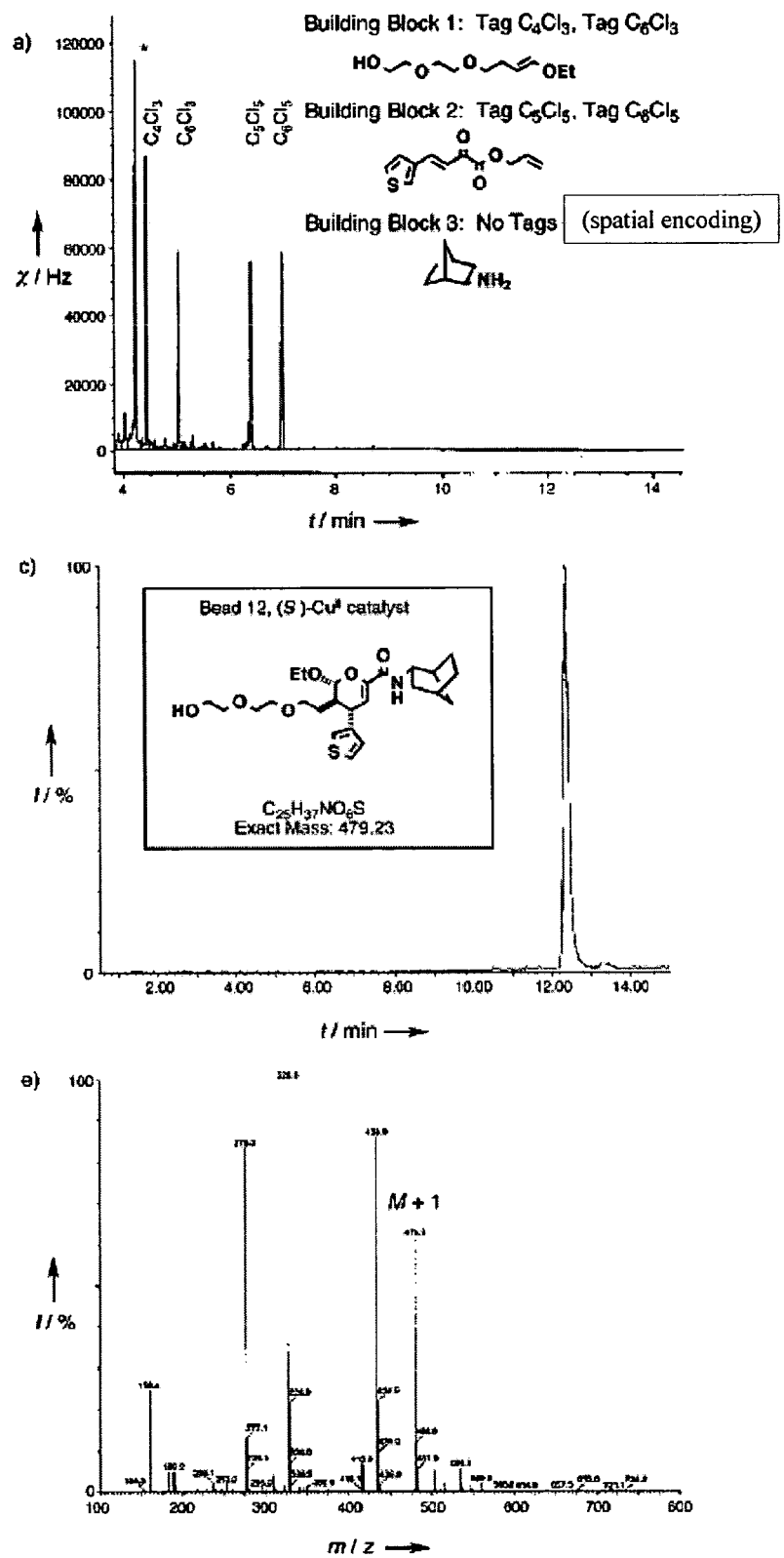
FIGS. 9A and 9B depict representative examples of GC (a, b), LC (c, d), and MS (e, f) spectra from bead and stock-solution decoding (samples 12 and 48, respectively), as described in Example 2 herein. The bead-decoding GC trace for sample 12 (a) decodes for a library compound with an exact mass identical to that obtained by MS (e) of the compound cleaved from that bead (APCI, observed mass=479.9 [M+1]). The stock-solution-decoding GC trace for sample 48 (b) decodes for a library compound with an exact mass identical to that obtained by MS (f) of the compound stock solution (APCI, observed mass=626.8 [M+1]). The single peaks in the LC spectra (c, d) correspond to these molecular ions. [The starred peak (*) in the GC traces (a, b) is an impurity frequently present with the electrophoric tags.]
Figure 9B:
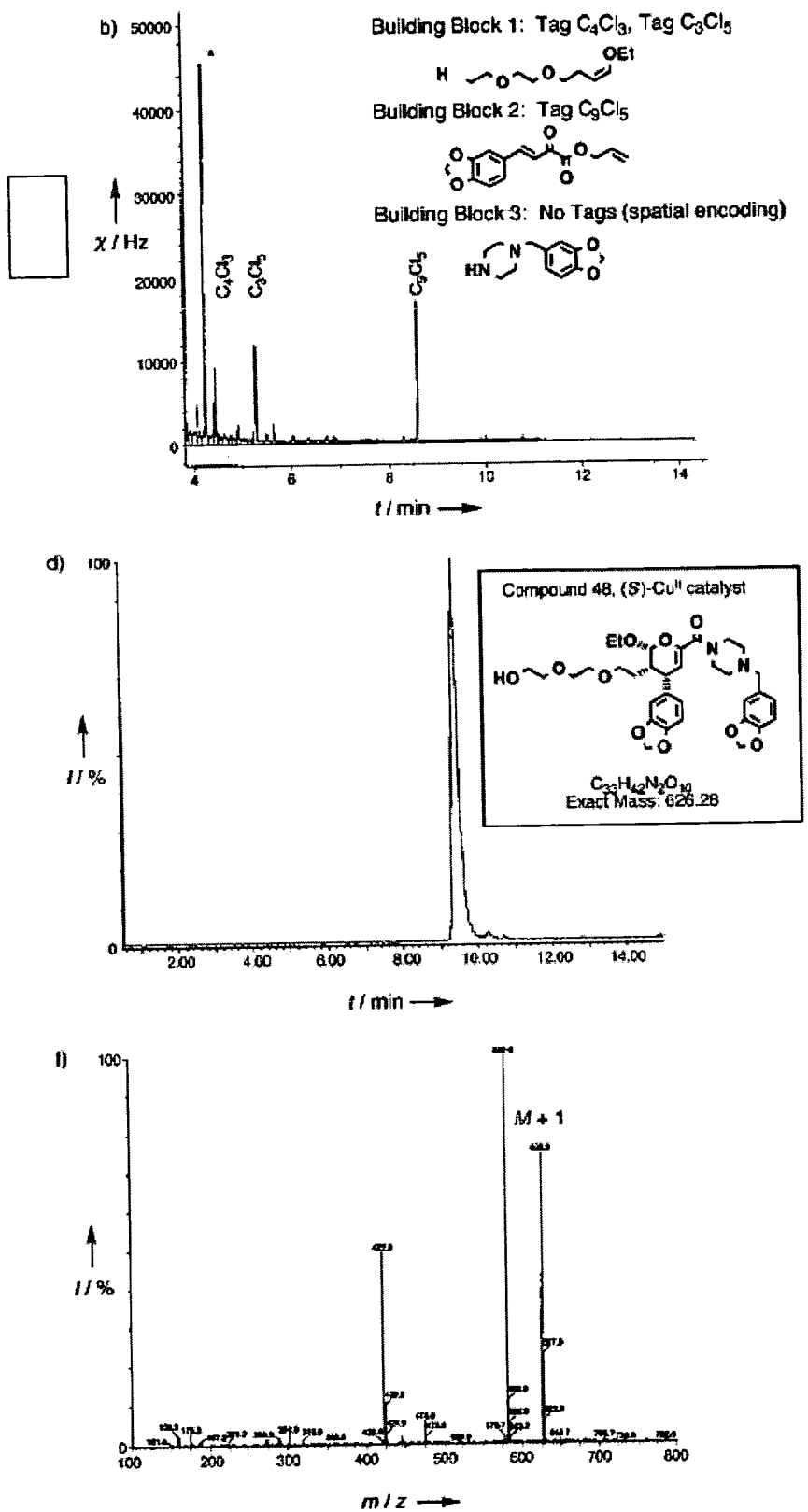

Decoding consisted of deriving the identities of BBs 1 and 2 by GC tag analysis, adding their combined molecular weight to that of the amine corresponding to the pool of supports from which the macrobead was taken, and comparing this composite mass to the mass observed experimentally by APCI/MS. The structural data obtained via GC decoding were in complete agreement with the MS data obtained from the compounds' stock solutions (FIGS. 6A–I) for 107 of the 108 samples. Seventy of the 108 macrobeads (65%) yielded GC traces that decoded for a compound with a molecular ion identical to that expected based on the MS data. Twenty-five macrobeads (23%) showed GC traces that decoded for a compound whose molecular ion corresponded to a fragment of the proposed structure. Direct stock solution decoding, using the optimized decoding protocol on a fraction (~5%) of the stock solutions generated from individual macrobeads, was carried out successfully to identify the structures of the 12 remaining samples (See H. E. Blackwell, L. Perez, S. L. Schreiber, "Decoding products of diversity pathways from stock solutions derived from single polymeric macrobeads", Angew. Chem. Int. Ed. 2001, 40:3421–3425). Structures of 25 representative compounds from the 108 beads decoded of library 12 are shown below (numbers in bold refer to bead number). All structures show agreement between their GC and MS decoding data. Representative GC, LC, and MS traces for a single macrobead are shown in FIGS. 9A–B. In addition, LC and MS traces for 25 inventive compounds (quality control compounds) are depicted in FIGS. 16 (16A–16D) and 17 (17A–17C).

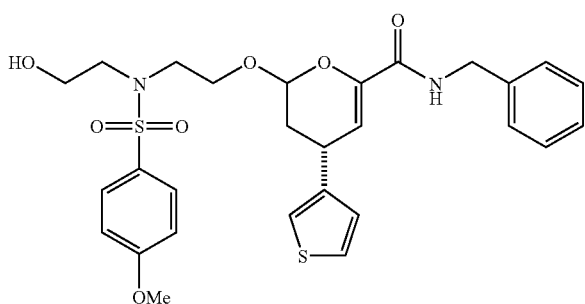

1

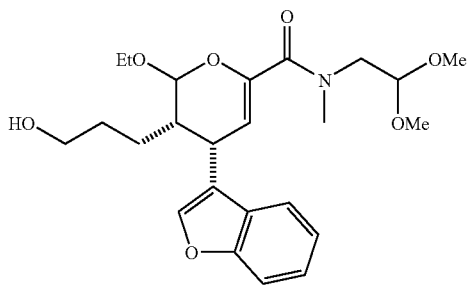

6

-continued
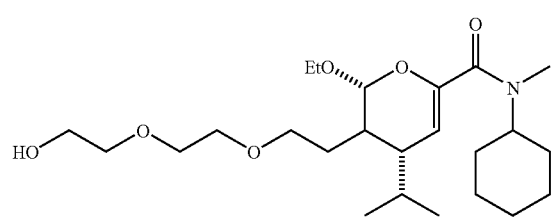
7
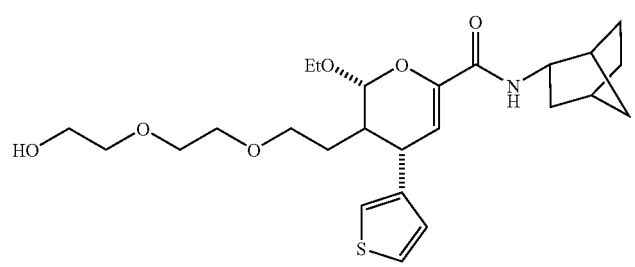
12
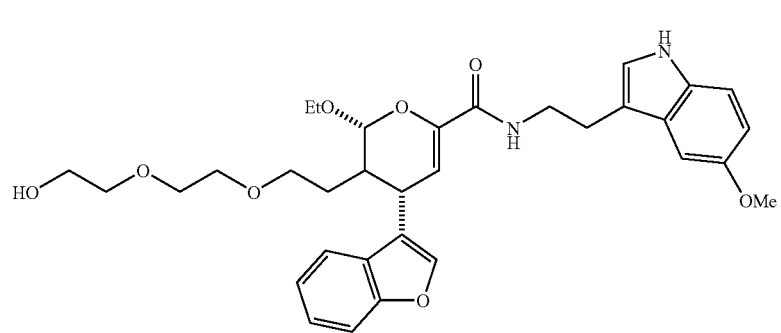
13
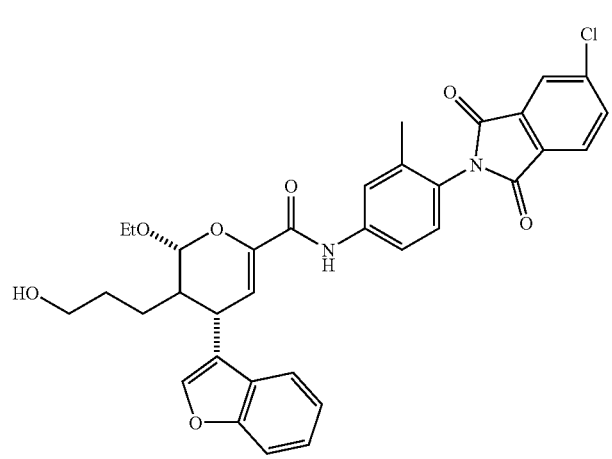
18

19
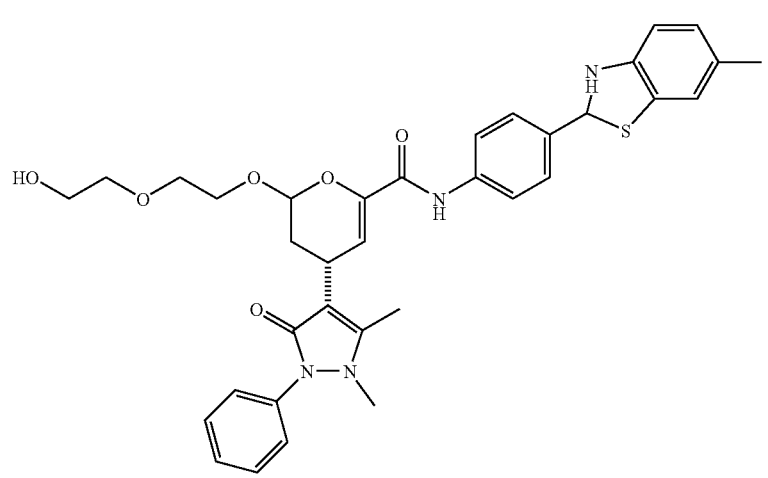
24
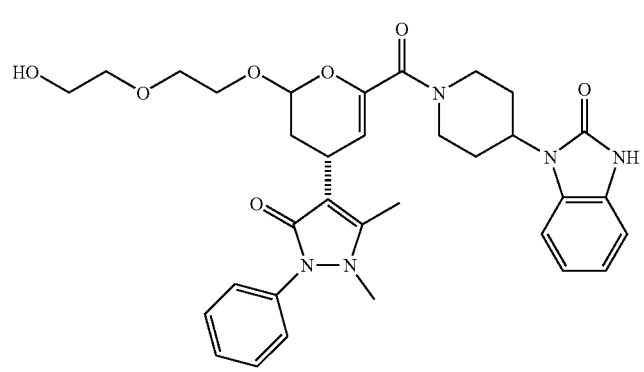
25
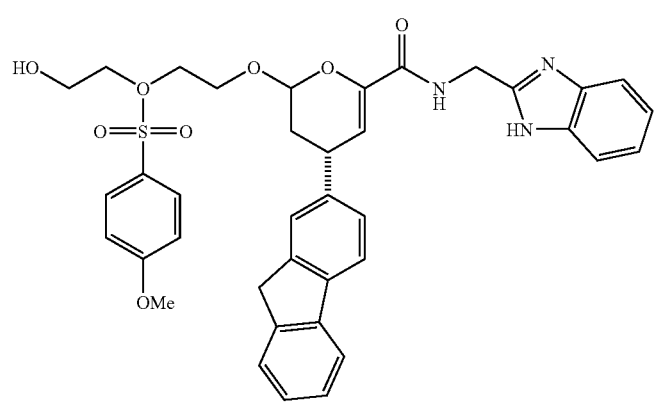
30
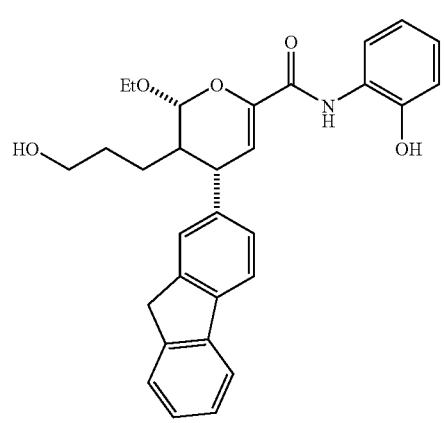

-continued
31
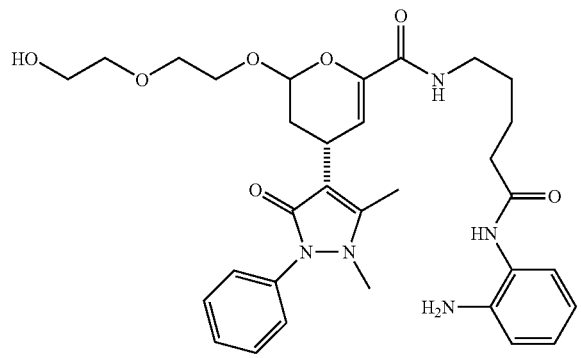
35
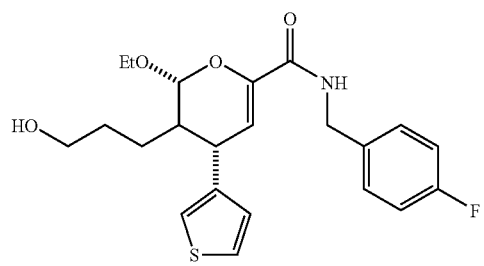
37
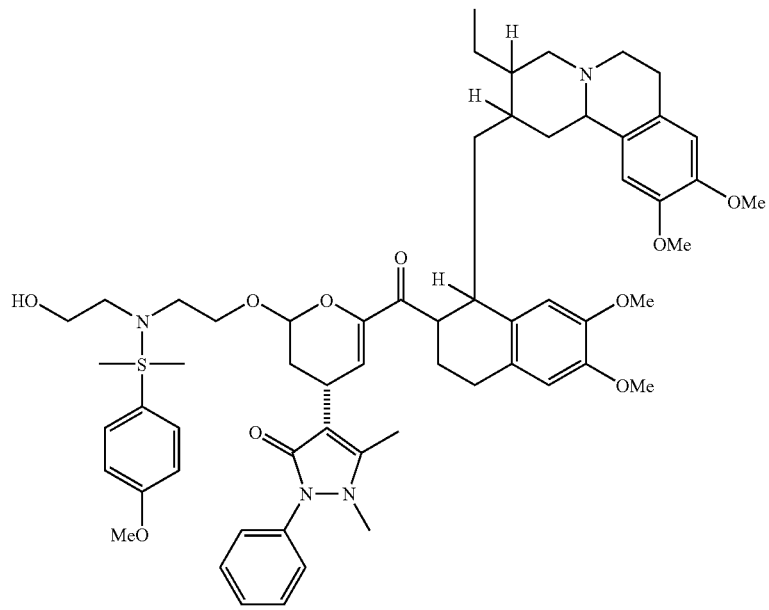
42
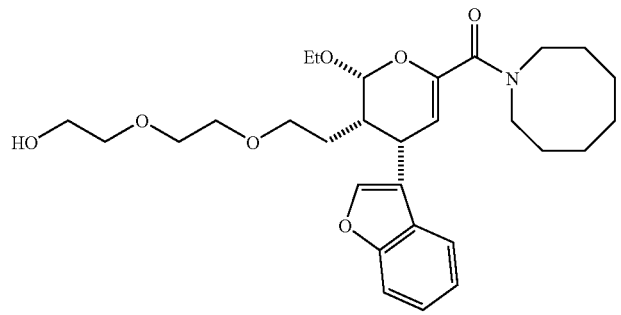

-continued
| | |
|---|---|
| 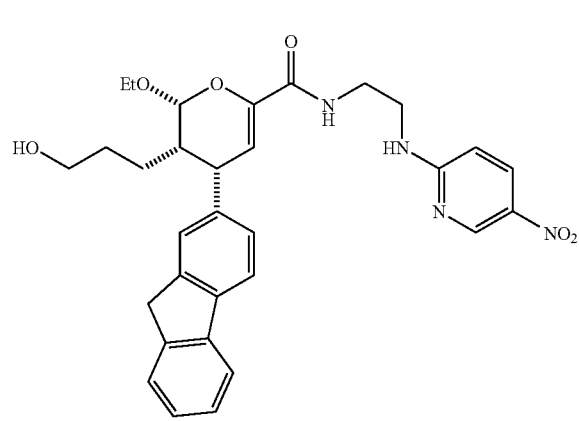 | 43 |
| 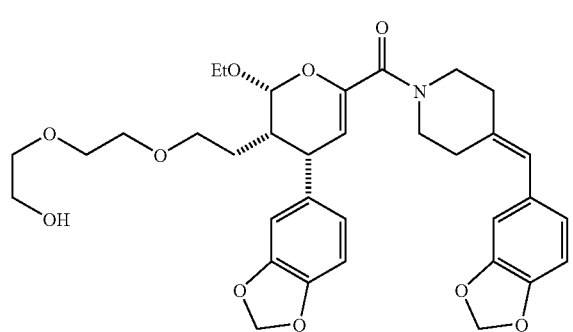 | 48 |
| 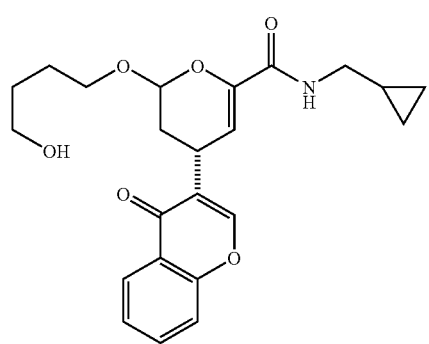 | 49 |
| 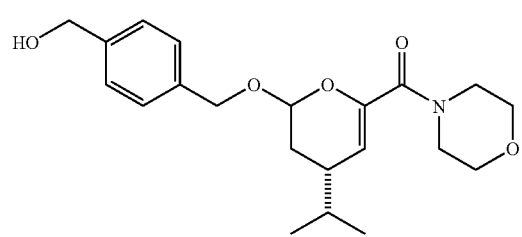 | 53 |
| 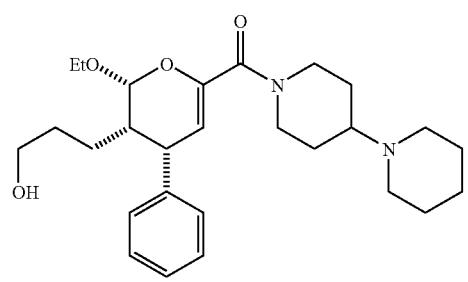 | 59 |

65
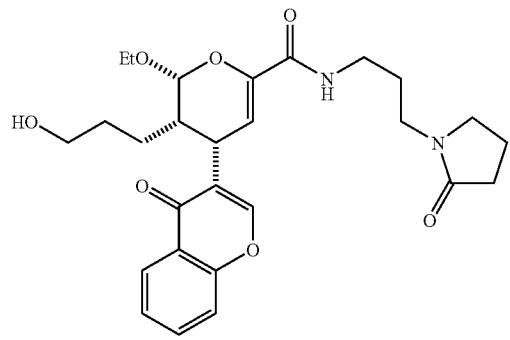
71
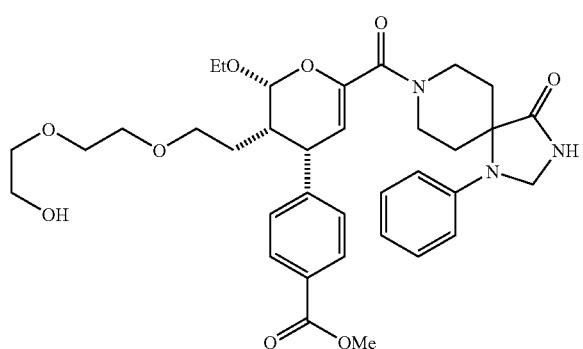
77
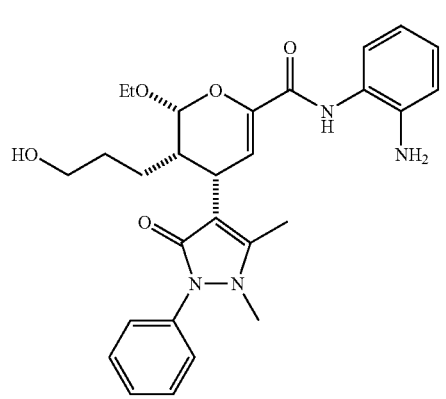
83
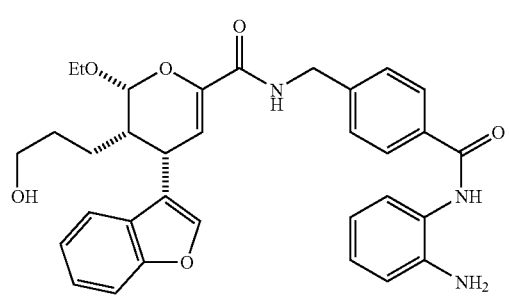

-continued

89

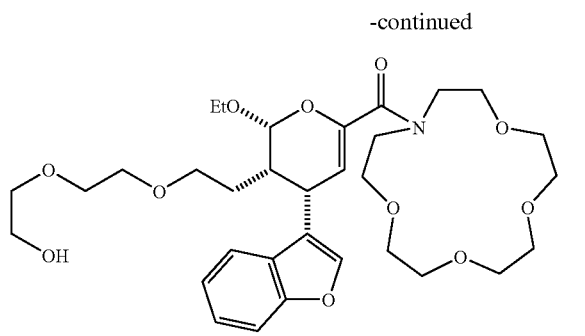

95

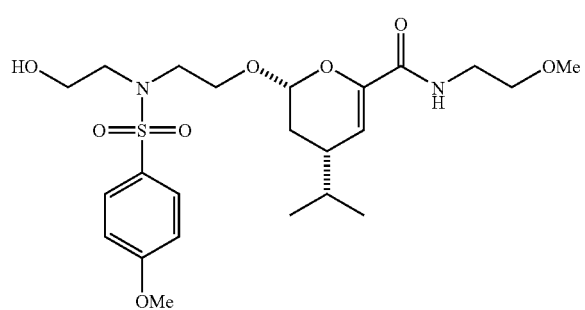

103

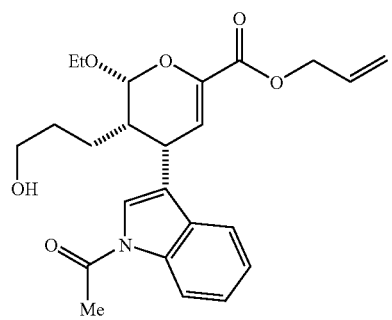

106

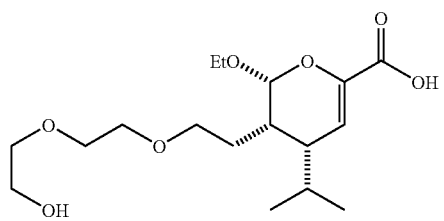

The successful synthesis and partial decoding of library 12 validate not only our binary encoding/decoding protocol, but also the entire synthesis platform as a reliable procedure for the generation of encoded split-pool libraries. The use of stock solution decoding further enables this platform as it simplifies the elucidation of structures of 'hits' from assays and lends itself to future automation.

Figure 10:
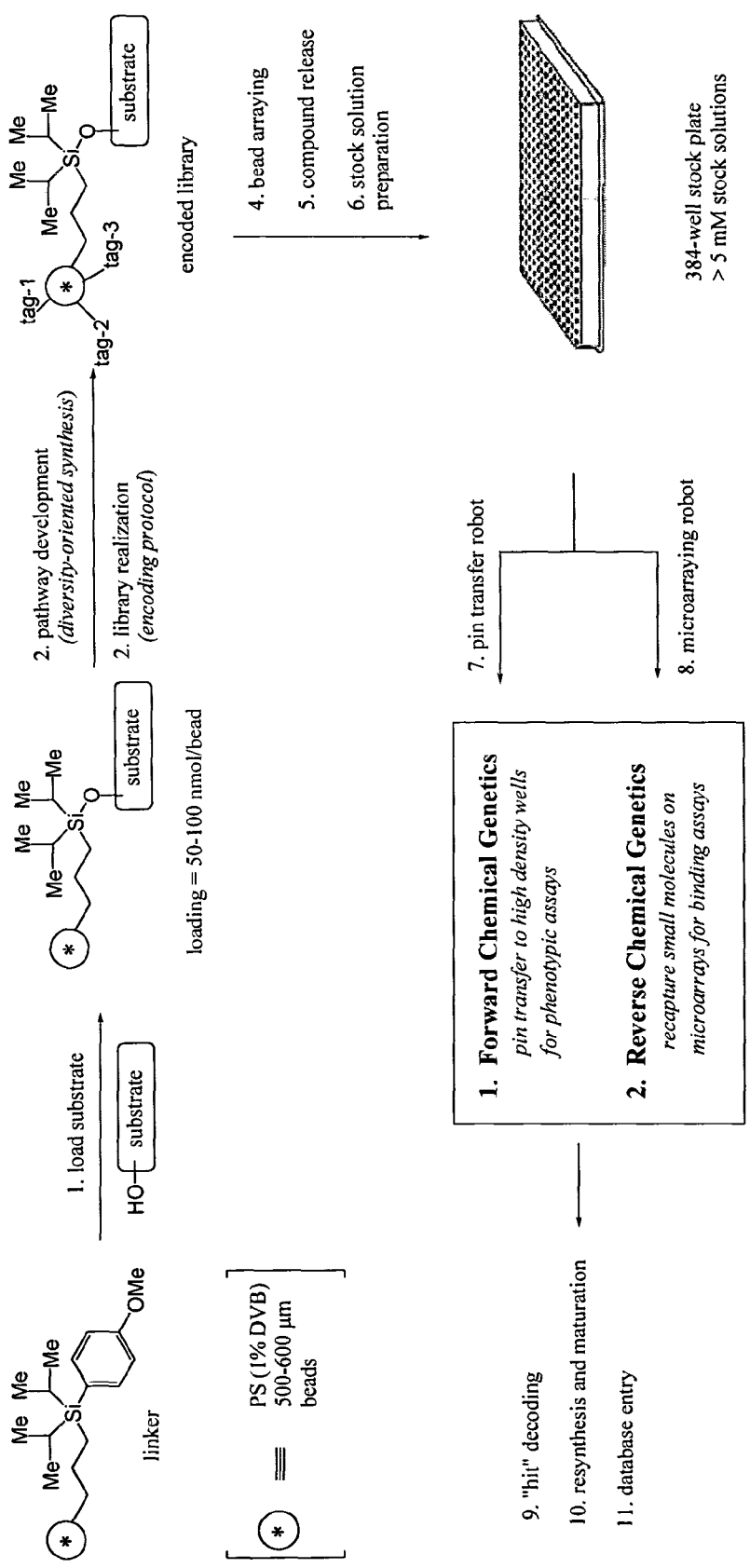
FIG. 10 outlines an exemplary embodiment of the invention: a 'one-bead, onestock solution' technology platform directed toward chemical genetics. DVB=divinylbenzene.

The successful synthesis of an encoded split-pool library (12) using this platform validates the approach. The synthesis platform uses commercially available reagents and straightforward synthetic procedures; therefore, we believe it could be readily established in other laboratories. This work lays the foundation for the second phase of platform development, where the members of libraries are distributed on a per bead basis into multiwell assay plates, submitted to automated cleavage, and resuspended to generate plates of pure, arrayed stock solutions, as described in Example 3 (See also P. A. Clemons, A. N. Koehler, B. K. Wagner, T. G. Sprigings, D. R. Spring, R. W. King, S. L. Schreiber, M. A. Foley, "A one-bead, onestock solution approach to chemical genetics, part 2", *Chem. Biol.* 2001, 8:1183–1195). The individual stock solutions originating from single macrobeads have been found to be sufficient for hundreds of phenotypic assays (forward chemical genetics) and thousands of protein-binding assays (reverse chemical genetics) before a need for re-synthesis (FIG. 10).

Experimental Section.

General Synthetic Methods

General Methods. Reagents were obtained from Aldrich Chemical Co., Acros, Novabiochem, or J. T. Baker and used without further purification. Reaction solvents (THF, Et$_2$O, DMF, toluene, and CH$_2$Cl$_2$) were obtained from J. T. Baker (HPLC grade) and purified by passage through two solvent columns prior to use. The CH$_2$Cl$_2$ and toluene purification systems were composed of one activated alumina (A-2) column and one supported copper redox catalyst (Q-5 reactant) column. The THF and Et$_2$O purification systems were composed of two activated alumina (A-2) columns, and the DMF purification system was composed of two activated molecular sieve columns. See: Pangborn, A. B.; Giardello, M. A.; Grubbs, R. H.; Rosen, R. K.; Timmers, F. J. *Organometallics* 1996, 15, 1518–1520. Diisopropylethylamine (DIPEA) and 2,6-lutidene were distilled from calcium hydride; MeOH was distilled from magnesium methoxide. Brominated polystyrene (Br—PS, 2 mequiv/g) was obtained from Polymer Labs (Product #:1462-9999, $18/g). Solution phase reactions were performed in oven- or flame-dried glassware under positive N$_2$ pressure.

Solid Phase Reactions. Small-scale solid phase reactions (5–10 mg resin) were performed in 500 μL polypropylene Eppendorf tubes with mixing provided by a Vortex Genie-2 vortexer fitted with a 60 microtube insert. Medium-scale solid phase reactions (20–500 mg resin) were performed in 2 mL fritted polypropylene Bio-Spin® chromatography columns (Bio-Rad) or 10 mL fritted polypropylene PD-10 columns (Pharmacia Biotech) with 360° rotation on a Barnstead-Thermolyne Labquake™ Shaker. Large-scale solid phase reactions (>500 mg resin) were performed in silanized 50 or 100 mL fritted glass tubes equipped for vacuum filtration and N$_2$ bubbling. The tubes were silanized by treatment with 20% dichlorodimethylsilane/CH$_2$Cl$_2$ for 15 min, MeOH for 15 min, followed by oven heating at 120 °C. for at least 2 h.

After small-scale reactions, resin samples were transferred to 2 mL BioSpin® columns. Resin samples in polypropylene columns were washed on a Vac-Man® Laboratory Vacuum Manifold (Promega) fitted with nylon 3-way stopcocks (Bio-Rad). Resin samples in glass tubes were washed in the tubes with alternating periods of N$_2$ bubbling and vacuum draining. The following standard wash procedure was used: 3×THF, 3×DMF, 3×THF, 3×CH$_2$Cl$_2$.

Resin samples were then transferred via spatula to 500 μL Ependorf tubes and suspended in Ar-degassed HPLC grade THF followed by pryidine and hydrogen fluoride-pyridine (Aldrich, HF(70%)/pyridine(30%)) in a ratio of 90:5:5. Samples were then sealed with parafilm and gently agitated on a vortexer for 30 min. Methoxy-trimethylsilane (TMSOMe) was added and the samples were sealed with Parafilm and placed on a vortexer for an additional 30 min. The supernatant fluid was removed, transferred to another Eppendorf tube, and concentrated in vacuo.

Purification and Analysis. Flash chromatography was performed on E. Merck 60 230–400 mesh silica gel. TLC was performed on 0.25 mm E. Merck silica gel 60 F$_{254}$ plates and visualized by UV (254 nm) and cerium ammonium molybdate. HPLC was performed on a Nest Group (Southborough, Mass.) Hypersil C18 100 Å 3 μM, 4.6 mm×6 cm column using a flow rate of 3 mL/min and a 4 min gradient of 0–99.9% CH$_3$CN in H$_2$O/0.1% TFA, constant 0.1% MeOH with diode array UV detection. IR spectra were recorded on a Nicolet 5PC FT-IR Spectrometer or a Bruker Vector 22 Spectrometer with peaks reported in cm$^{-1}$. NMR spectra were recorded on Varian Inova 500 MHz and 400 MHz instruments. Solid-phase NMR spectra were recorded on a Varian Inova 500 MHz equipped with a Nanoprobe (See (a) Fitch, W. L.; Detre, G.; Holmes, C. P.; Shoolery, J. N.; Keifer, P. A. *J. Org. Chem.* 1994, 59, 7955–7956. (b) Keifer, P. A.; Baltusis, L.; Rice, D. M.; Tymiak, A. A.; Shoolery, J. N. *J. Magn. Reson., Series A* 1996 119, 65–75). Chemical shifts are expressed in ppm relative to TMS (0.00 ppm) or residual solvents. Peak assignments were made based on homonuclear decoupling and/or two-dimensional DQF-COSY, TOCSY, and/or NOESY experiments. Mass spectra were obtained on JEOL AX-505H or SX-102A mass spectrometers by electron impact ionization (EI), chemical ionization (CI) with ammonia (NH$_3$), or fast atom bombardment ionization (FAB) with glycerol or 3-nitrobenzyl alcohol/sodium iodide (NBA/NaI) matrices. LC/MS data was obtained on a Micromass Platform LCZ mass spectrometer in atmospheric pressure chemical ionization (APCI) mode attached to a Waters 2690 HPLC system. LC/MS chromatography was performed on a Waters Symmetry C18 3.5 μM, 2.1 mm×50 mm column using a flow rate of 0.4 mL/min and a 10 min gradient of 15–100% CH$_3$CN in H$_2$O, constant 0.1% formic acid with 200–450 nm detection on Waters 996 photodiode array detector. GC/ECD data was obtained on a Hewlett Packard 6890 Gas Chromatograph fitted with a 7683 series injector and autosampler, split-splitless inlet, μ-ECD detector, and a J&W DB1 15 m×0.25 mm×0.25 μm column. (Gradient start temperature: 110° C.; hold 1 min, ramp 45° C./min to 250° C., hold 2 min, ramp 15° C./min to 325° C., hold 2 min. Flow rate: constant flow, 1 mL/min. Inlet is purged at 1 min with flow rate 60 mL/min, reduced to 20 mL/min at 2 min).

II. Allyl Silane Linker Synthesis

Diisopropyl(4-methoxyphenyl)silane. A solution of p-bromoanisole (28.6 mL, 228 mmol, 1.0 equiv.) in THF (550 mL) was chilled to −78° C. (CO$_2$(s), acetone) and treated with n-BuLi (91.2 mL, 228 mmol, 2.5 M in hexanes, 1 equiv.) via cannula over a 5 min period. After 5 min a white precipitate began to form. The mixture had stirred for 30 min at −78° C. when diisopropylchlorosilane (34.6 g, 228 mmol, 1.0 equiv.) was slowly added via syringe. After 1 h the ice bath was removed, and the solution was allowed to come to 23° C. with continued stirring overnight. The mixture was treated with saturated NH$_4$Cl (50 mL) and extracted with ether (3×500 mL). The combined organic extracts were washed with brine, dried over MgSO$_4$, filtered and concentrated in vacuo to yield a light yellow oil. Silica gel chromatography (gradient: 3–5% EtOAc/hexanes) yielded (47.7 g, 94%) of a colorless oil. This material could also be purified by distillation [BP=76–85° C. @ 275 mTorr (40 g, 63%)]. TLC R$_f$=0.61 (1:9 EtOAc/hexanes). IR(film): 2393, 1853, 1710, 1691, 1658, 1584, 1482, 1346. $^1$H NMR (500 MHz, CDCl$_3$): δ7.48 (d, 2H, J=8.10), 6.95(d, 2H, J=8.10), 3.97(s, 1H, Si—H), 3.85 (s, 3H), 1.39(q, 2H, J=3), 1.10(d, 6H, J=6.5), 1.03(d, 6H, J=7.5). $^{13}$C NMR (126 MHz, CDCl$_3$): δ137.13, 113.73, 113.62, 55.18, 18.95, 18.72, 11.08. Elemental analysis, Calcd.: C 70.21, H 9.97, Si 12.63. Found: C 70.43, H 9.83, Si 12.39.

Chloro(4-methoxyphenyl)diisopropylsilane. Diisopropyl (4methoxyphenyl)silane (47.7 g, 214 mmol, 1.0 equiv.), was taken up in CH$_2$Cl$_2$ (700 mL). The solution was cooled to 0° C. and trichloroisocyanuric acid (16.6 g, 71.3 mmol, 0.33 equiv.) was carefully added in three equal portions, making sure that each portion had at least 7 min to react before the next was added. (Caution! Adding trichloroisocyanuric acid too rapidly results in a rapid evolution of gas and concomitant expulsion of the reaction vessel contents). The mixture was stirred at 0° C. for 40 min, followed by warming to 23° C. with stirring. The solids were filtered under an inert atmosphere, and the filtrate was concentrated in vacuo to yield 54.8 g (98%) of a cloudy oil. The chlorosilane, which is unstable, was used immediately and without purification in the next step.

Allyl(4-methoxyphenyl)diisopropylsilane. To the crude chloro(4-methoxyphenyl)-diisopropylsilane (54.8 g, 214 mmol, 1.0 equiv.) was added THF (335 mL) via cannula under Ar. The solution was chilled to 0° C. and treated with allylmagnesium chloride (128 mL, 256 mmol, 2.0 M in THF, 1.2 equiv.). After 3 h at 0° C., the solution was allowed to warm to 23° C. with stirring overnight (16 h). The mixture was treated with saturated $NH_4Cl$ (50 mL), and the aqueous layer was extracted with ether (3×500 mL). The combined organic extracts were washed with brine, dried over $MgSO_4$, filtered, and concentrated in vacuo. The crude material was purified by silica flash chromatography (3–5% EtOAc/hexanes) to yield 52.86 g (94%) of a slightly cloudy, clear viscous oil. This reagent distills at 80° C. at 500 mTorr as a colorless oil. TLC $R_f$=0.40 (1:9 EtOAc/hexanes). IR(film): 2942, 2865, 1630, 1595, 1504, 1463, 1277. $^1$H NMR (500 MHz, $CDCl_3$): δ7.32 (d, 2H, J=6.84), 6.81(d, 2H, J=6.84), 5.82 (q, 1H, J=8.5, 8.5), 4.88 (d, 1H, J=17.05), 4.76 (d, 1H, J=9.77), 1.82 (d, 2H, J=7.32), 1.17 (q, 2H, J=7.3), 0.94 (d, 6H, J=7.3), 0.90 (d, 6H, J=7.3). $^{13}$C NMR (126 MHz, $CDCl_3$): δ160.51, 136.48, 135.70, 125.78, 113.78, 113.62, 55.09, 19.34, 18.22, 18.17, 17.68, 11.30. Elemental analysis, Calcd.: C 73.22, H 9.98, Si 10.70. Found: C 73.25, H 9.97, Si 10.77.

III. PS Resin Derivatization

Hydroboration of Allyl(4-methoxyphenyl)diisopropylsilane. Solid 9-BBN dimer (6.29 g, 53.0 mmol, 0.95 equiv.) was weighed out in a glove box and sealed under an Ar atmosphere. Freshly distilled THF (365 mL) and allyl(4-methoxyphenyl)diisopropylsilane (14.64 g, 55.8 mmol, 1.0 equiv.) were added via syringe, and the mixture was allowed to stir for 3 h at 23° C. The overall concentration of the allyl(4-methoxyphenyl)diisopropylsilane in THF was 0.16 M, which was the appropriate concentration for the subsequent Suzuki coupling. The yield of this reaction was assumed to be quantitative.

Suzuki Coupling. To the alkyl-borane containing THF solution above (53.0 mmol in 365 mL of THF, 1.74 equiv.) was added the solid Br—PS (15.25 g, 2 mequiv/g 30.5 mmol of Br, 1.0 equiv.) Care was taken to maintain an Ar blanket over the solution. Br—PS was allowed to swell for 45 min, and then treated with tetrakis(triphenylphosphine)palladium (0) (880 mg, 0.76 mmol, 0.025 equiv.) followed by aqueous NaOH solution (61 mmol, 30.5 mL of a 2M NaOH solution, 2.0 equiv.). The reaction was then heated to reflux with gentle stirring for 24 h. Pd(0) (880 mg, 0.76 mmol, 0.025 equiv.) was added, and the reaction was heated to reflux for another 12 h. The biphasic reaction mixture turned slightly green from its initial yellow color. The mixture was filtered, and the beads were washed repeatedly (see below). While it was unnecessary to agitate the beads during the wash cycle, it was critical to allow the beads sufficient time to absorb the washing solvent. Wash procedure: THF (2×100 mL×45 min), 3:1 THF/1 M NaCN (1×100 mL×1 h or until all dark color is gone), 3:1 THF/$H_2O$ (2×100 mL×45 min), 3:1 THF/IPA (2×100 mL×45 min), THF (2×100 mL×45 min), $CH_2Cl_2$ (2×100 mL×45 min). The beads were air-dried overnight, then placed on a lyophilizer for 24 h, producing an almost colorless, opaque resin. $^1$H NMR (500 MHz, nanoprobe, $CD_2Cl_2$ gel phase): δ7.34 (m, 4H), 6.82 (m, 4H), 3.69 (s, 3H), 1.76 (m, 2H), 1.22 (m, 2H), 1.16 (m, 2H), 0.97 (m, 2H), 0.91 (m, 12H) [For a discussion of the effect of resin linker length on gel-phase NMR spectral linewidths, see: Keifer, P. A. *J. Org. Chem*. 1996, 61, 1558–1559]. Elemental analysis: Found C 83.54, H 8.28, Si 4.35, Br<0.02, Cl 0.247.

Determination of Bead Loading by Elemental Analysis. 2.0 mmol p-bromopolystyrene beads, quantitatively loaded with the silicon linker above, contain 41 mg Si/g resin or 4.1% Si. Assuming quantitative loading, the mass of 1 g resin would increase to 1.37 g; therefore, the linker loading is calculated as 1.45 mequiv/mol. Thus, the resin loading is estimated from two elemental analyses parameters, % Si and % Br. The % Br<0.02 by weight indicates qualitative disappearance of Br (note that halogens can be confused by elemental analysis, hence it is necessary to perform separate Br and Cl analysis), while percent Si indicates the loading level. Percent Si typically ranges from 3.79 to 4.05%. The procedure used to calculate percent Si can overestimate the actual amount of Si by 0.2–0.3% as these numbers are calculated by weighing ash resultant from sample digestion with acid and residue combustion, which leaves some elements unresolved from Si. 4.35% Si is equivalent to 43.5 mg Si/g resin, or 1.54 mequiv Si/g. The actual loading used in subsequent calculations was 1.45 mequiv/g, the theoretical maximum. There were 9,350 beads/g of 500–600 copolymerized p-bromopolystyrene beads with 2.0 mmol Br/g loading level. We assumed quantitative conversion, justified by disappearance of bromine and appearance of appropriate amount of silicon. Thus, the number of polystyrene beads in one gram of resin was then scaled with a 37% mass increase, or about 6,800 beads/g.

Figure 4:
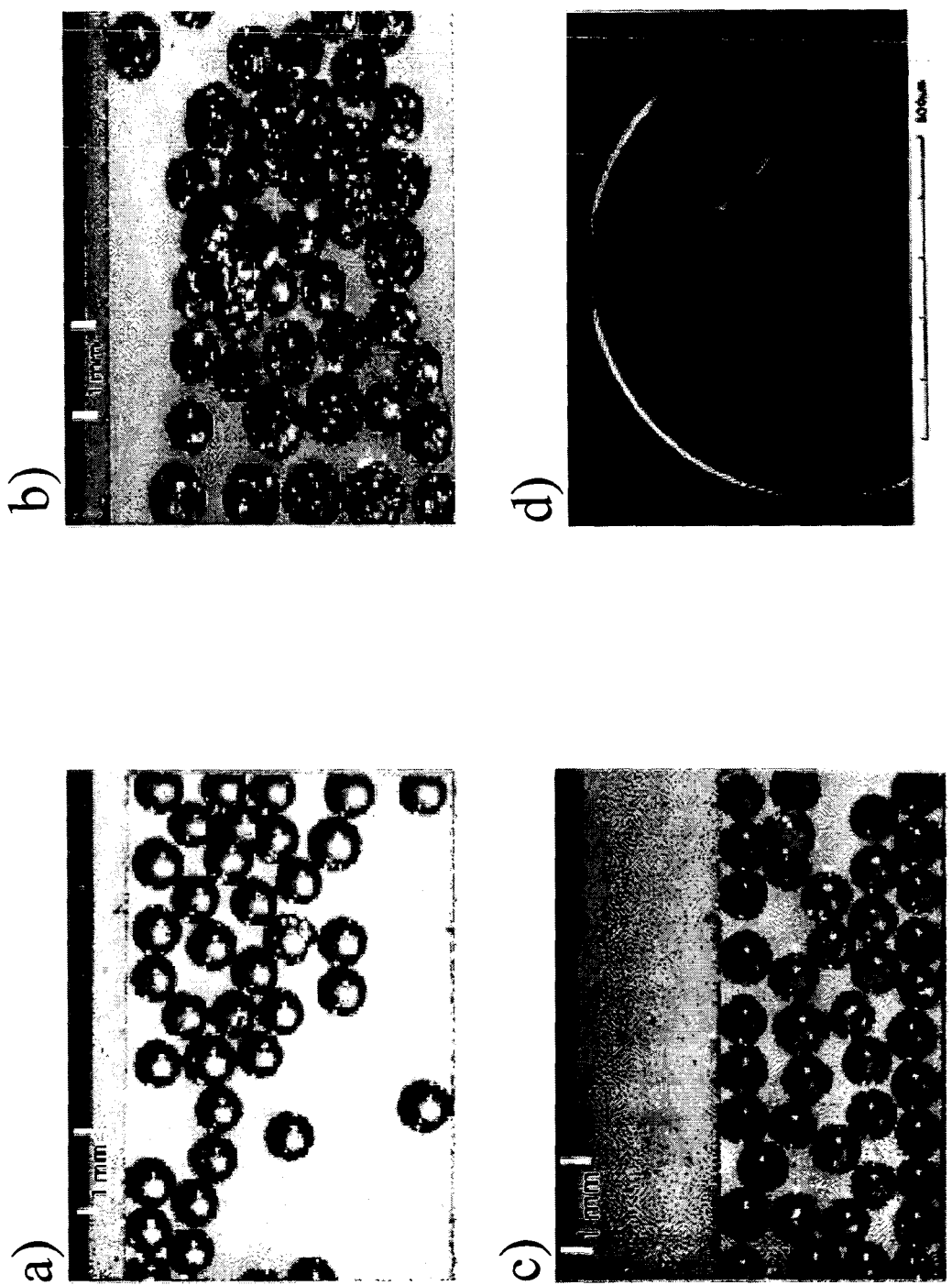
FIG. 4 depicts four bright-field microscopy images of silicon-functionalized polystyrene resins that have been subjected to different washing and drying experiments as described in the text: (a) an image of "reference beads"; (b) an image of "gentle conditions"; (c) an image of "best practice" beads; (d) a magnified image of a typical broken bead found in the "damaged beads".
Figure 5:
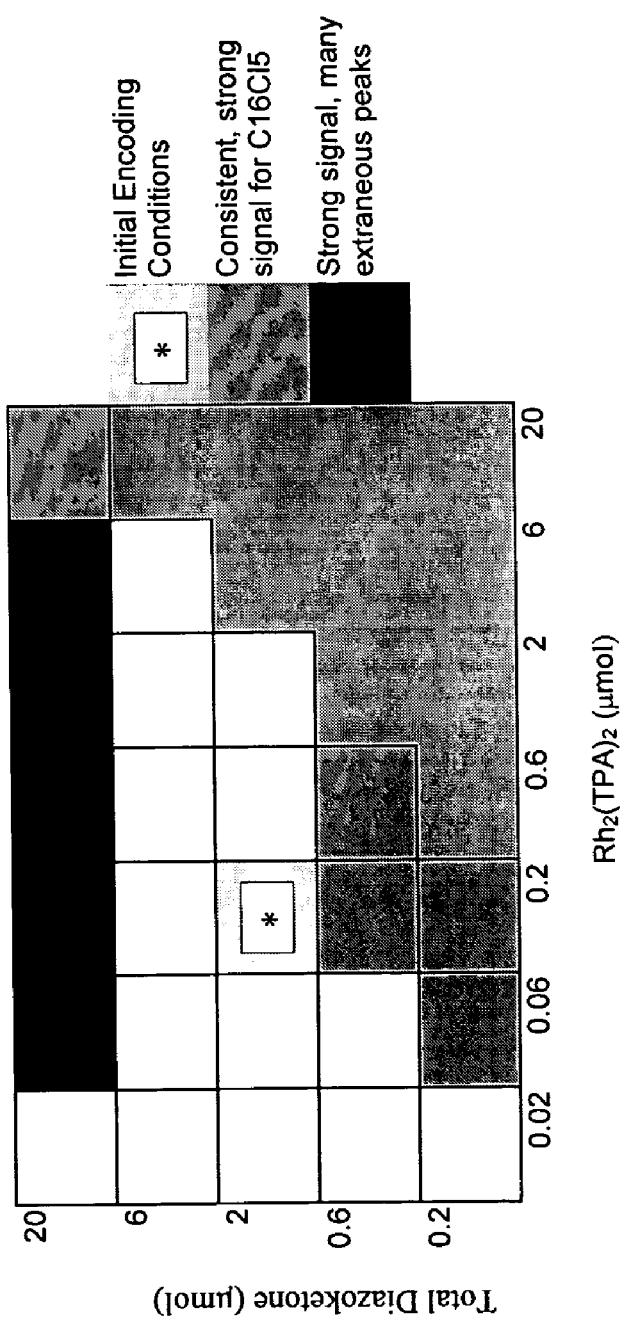
FIG. 5 depicts a graphical representation of the optimization of diazoketone tag and rhodium catalyst 5 concentration in encoding reactions.
Figure 6:
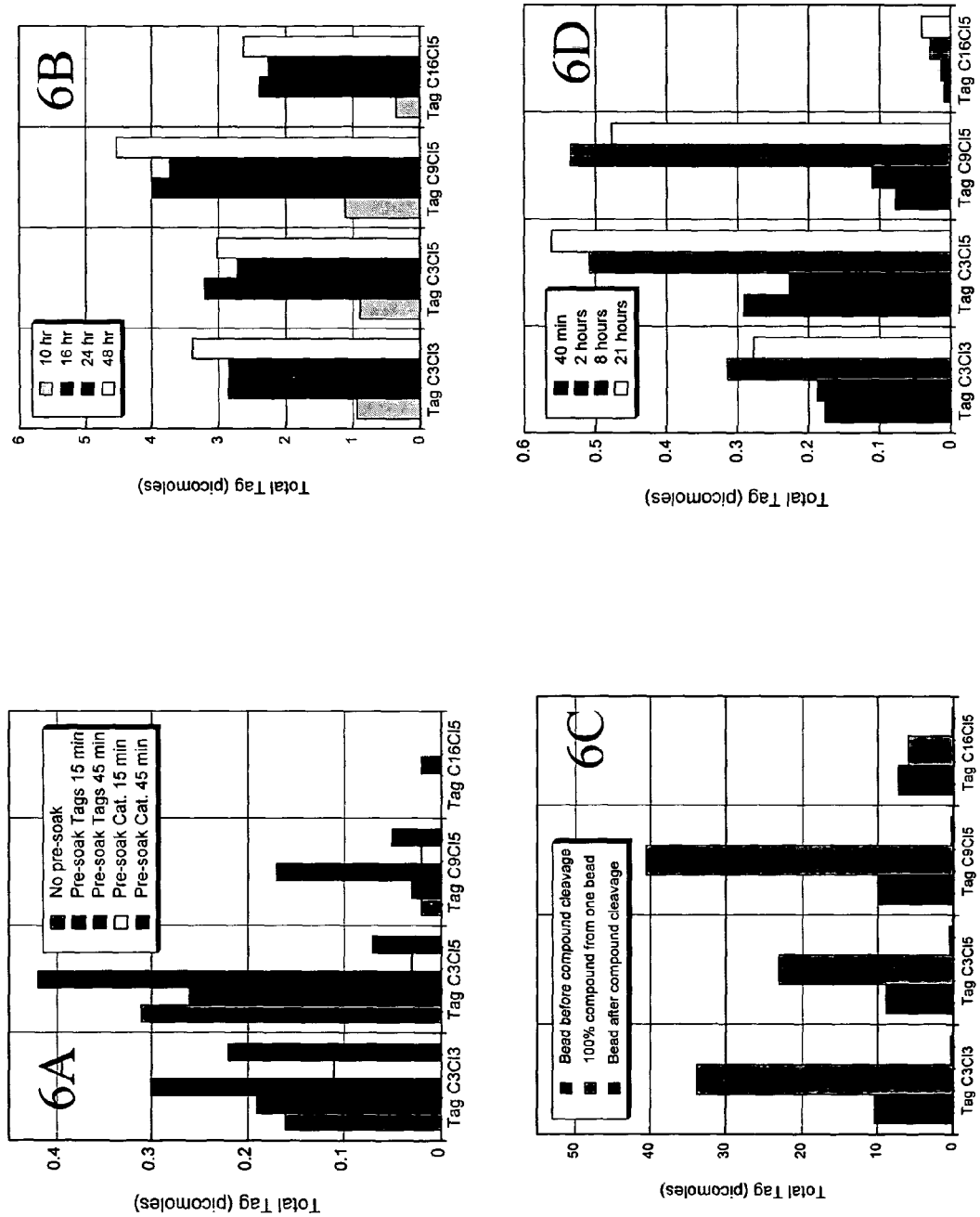
FIG. 6A depicts a graph of quantitative GC data for encoding test resin 6 with Tags C3C13, C3C15, C9C15, and C16C15 with various tag pre-soaking times. Encoding conditions: 2 h reaction time after addition of Tags or catalyst 5, 25° C. Decoding conditions: 0.25 M CAN (1:1 THF/$H_2O$), 2 h, 25° C., 1 min sonication, 1 µL N,O-bis(trimethylsilyl)aceteamide (BSA). Each data point is an average of 10 identical experiments with individual beads.
FIG. 6B depicts a graph of quantitative GC data for a time course experiment for encoding test resin 6 with Tags C3C13, C3C15, C9C15, and C16C15. Encoding conditions: pre-soak with Tags 45 min prior to addition of catalyst 5, quench reactions by the addition of 5 µL heptylamine. Decoding conditions: 0.24 M CAN (5:1 THF/$H_2O$), 21 h, 37° C., 1 min sonication, 1 µL 1:1 BSA/decane. Each data point is an average of 10 identical experiments with individual beads.
FIG. 6C depicts a graph of quantitative GC data for the decoding one bead of test resin 6 before compound cleavage, after compound cleavage, or from 100% of the cleaved compound. Encoding conditions: 45 min tag pre-soak prior to addition of catalyst 5, 2 h, 25° C. Decoding conditions: 0.25 M CAN (1:1 THF/$H_2O$), 2 h, 25° C., 1 min sonication, 1 µL BSA. Each data point is an average of 10 identical experiments with individual beads.
FIG. 6D depicts a graph of quantitative GC data for a time course experiment for decoding test resin 7. Decoding conditions: 0.25 M CAN (1:1 THF/$H_2O$), 25° C., 1 min sonication, 1 µL 1:1 BSA:decane. Each data point is an average of 10 identical experiments with individual beads.
FIG. 6E depicts a graph of quantitative GC data for decoding test resin 7 at various temperatures. Reactions stored at room temperature, placed in a 37° C. incubator, or placed in a 60° C. oven. Decoding conditions: 0.25 M CAN (1:1 THF/$H_2O$), 2 h, 1 min sonication, 1 µL 1:1 BSA:decane. Each data point is an average of 10 identical experiments with individual beads.
FIG. 6F depicts a graph of quantitative GC data for the decoding of test resin 7 with varying CAN solution concentrations and solvent compositions. Decoding conditions: 21 h, 37° C., 1 min sonication, 1 µL 1:1 BSA:decane. Each data point is an average of 10 identical experiments with individual beads.
FIG. 6G depicts a graph of quantitative GC data for subjection of decoding test resin 7 to various time periods of sonication after CAN cleavage. Decoding conditions: 0.25 M CAN (1:1 THF/$H_2O$), 2 h, 25° C., 1 µL 1:1 BSA:decane. Each data point is an average of 10 identical experiments with individual beads.
FIG. 6H depicts a graph of quantitative GC data for subjection of Tag alcohols cleaved from decoding test resin 7 to various amounts of BSA/decane solutions prior to GC analyses. Decoding conditions: 0.24 M CAN (5:1 THF/$H_2O$), 21 h, 37° C., 1 min sonication. Each data point is an average of 10 identical experiments with individual beads.
FIG. 6I depicts a graph of quantitative GC data for the decoding of test resin 7 using either our optimized decoding protocol for 500–600 µm polystyrene beads or the decoding protocol reported by the Pharmacopeia Company for 90 µm TentaGel (See Dolle, R. E.; Guo, J.; O'Brien, L.; Jin, Y.; Piznik, M.; Bowman, K. J.; Li, W.; Ehan, W. I.; Carvallaro, C.; Roughton, A. L.; Zhao, Q.; Reader, J. C.; Orlowski, M.; Jacob-Samuel, B.; Carroll, C. D. *J. Comb. Chem.* 2000, 2, 716–731). Each data point is an average of 10 identical experiments with individual beads.
Figure 6:
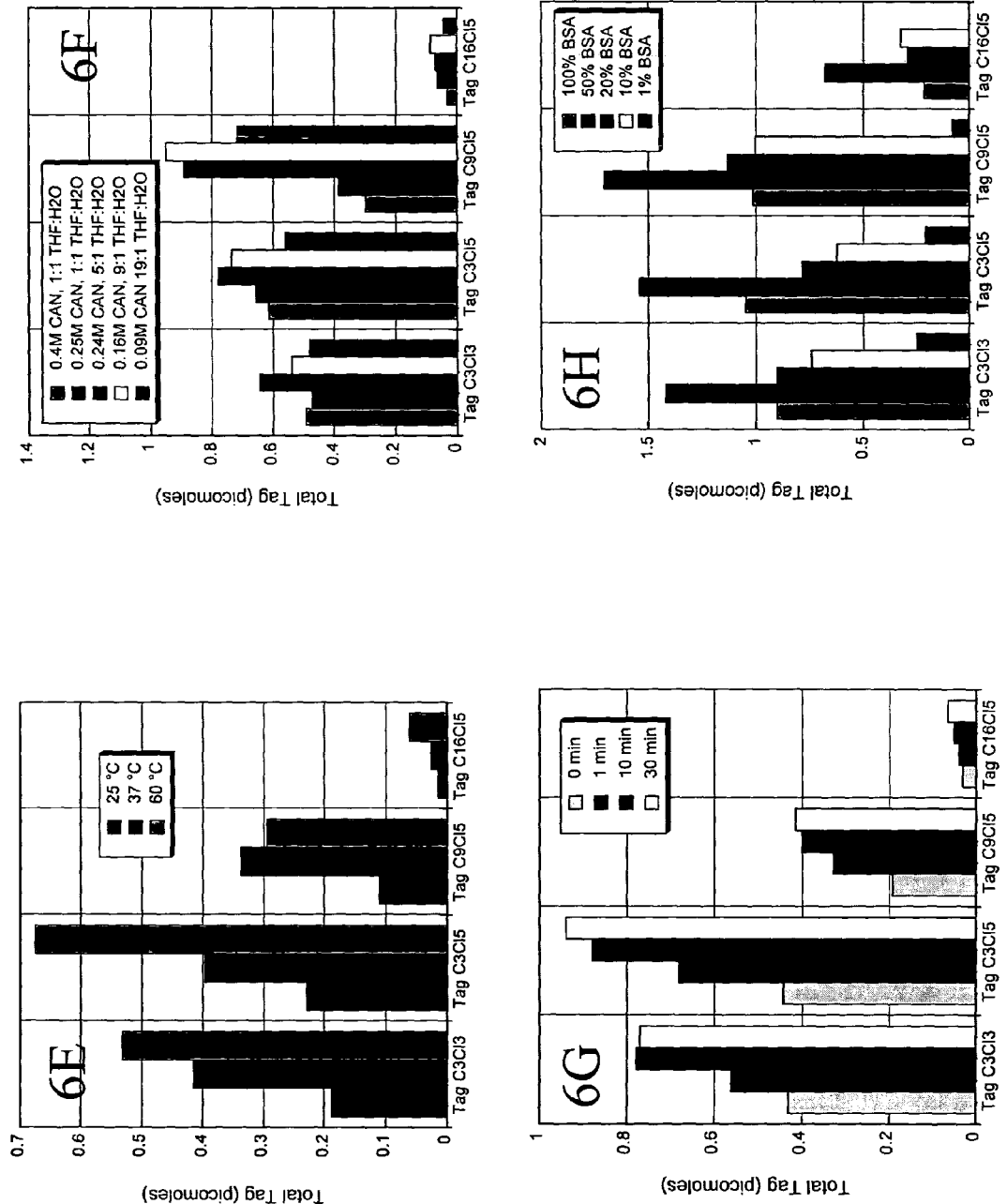
Figure 6:
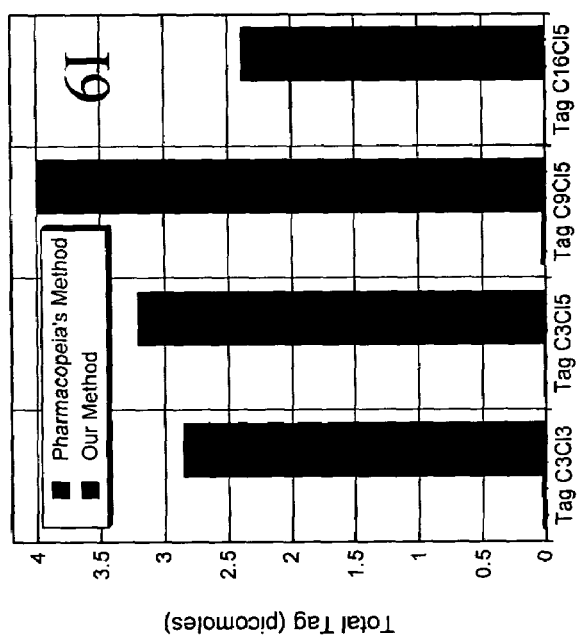

IV Bead Stability Studies (FIG. 4)

While the use of sequences of tandem organic reactions can efficiently generate complex molecules in diversity-oriented syntheses [S. L. Schreiber, Target-oriented and diversity-oriented organic synthesis in drug discovery, *Science* 287 (2000) 1964–1969], we have observed that successive organic transformations, coupled with rigorous bead washing between reactions, can damage the PS macrobeads. The exemplary technology platform used for the present study (FIG. 10), however, implies that we isolate one physically intact bead per well prior to compound cleavage for several reasons. First, fragments of beads yield weaker compound stock solutions after bead arraying, cleavage, and resuspension. Second, the possibility of isolating more than one fragment per well allows for stock solution contamination and the concomitant incorrect decoding of that well. To avoid these problems, we have developed a set of standard practices for bead handling during library synthesis and encoding that dramatically minimize the possibility of bead breakage.

In general, we have found that the less we handle the solid supports physically, either by submission to chemical reactions, washing, or drying, the less bead breakage we observe. This reinforces the importance of an effective planning algorithm for diversity-oriented syntheses. Short reaction sequences yielding complex and diverse compounds not only ensure that positives can be re-synthesized readily, but also promote the integrity of the beads. In order to quantify bead integrity, we used population size distribution measurements (obtained by light obscuration) to monitor the shift of the average particle size in a sample of beads (data not shown). We first observed that the PS macrobeads were fragile when swollen in organic solvents. Since the use of solvents and drying are required in library synthesis, we assessed several solvent, drying, and agitation conditions. Even though certain chemical transformations appear to cause more bead breakage than others, we did not include dijerent chemical reactions as experimental variables in our studies because we did not want to limit the types of chemistry utilized in library synthesis.

As evidence that even the most simple and gentle handling induces damage, supports swollen in dichloro-methane ($CH_2Cl_2$) and drained seven times, followed by overnight air drying resulted in a shift to a smaller average size distribution. As an example of extreme damage, beads were subjected to swelling in tetrahydrofuran (THF) (45 min), followed by treatment with methanol (MeOH) (45-min) and 360° rotation. The beads were then rapidly dried via lyophilization, and the whole process was repeated seven times. These supports show even more extensive damage and a greater degree of bead fragmentation. The 'best practices' we extrapolated from these experiments include light agitation from a wrist-action shaker, followed by blowing $N_2$ over the resin (30 min), and final drying under high vacuum conditions from any organic solvent. While a shift in average size still exists, these conditions minimize fragmentation and are suitable for library syntheses, as judged by our ability to array one intact bead per well after library synthesis (see FIG. 4) [See S. M. Stemson, J. B. Louca, J. C. Wong, S. L. Schreiber, Split-pool synthesis of 1,3-dioxanes leading to arrayed stock solutions of single compounds sufficient for multiple phenotypic and protein-binding assays, *J. Am. Chem. Soc.* 123 (2001) 1740–1747; and P. A. Clemons, A. N. Koehler, B. K. Wagner, T. G. Sprigings, D. R. Spring, R. W. King, S. L. Schreiber, M. A. Foley, A one-bead, one-stock solution approach to chemical genetics, part 2, *Chem. Biol.* 8 (2001) 1183–1195].

V Library Encoding and Decoding Protocols

Representative Bead Encoding Procedure. Place 20 dry beads (approximately 3 mg resin) in a 700 µL Eppendorf tube. Prepare a fresh 8.4 mM (in each tag) solution in dry $CH_2Cl_2$ in an oven-dried, Teflon capped glass vial. (NOTE: The tag concentration can be cut by one-half to one-fifth, and the tags will still be readable by GC (the late tags will be weak). This might be necessary for large library syntheses where a large quantity of tag is required, or if more than 4 tags are used in each tagging step. Use the same volume of tag solution as described below.) Add 50 µL of the tag solution to the Eppendorf tube. Set the tube to shake for 45 min at room temperature on a tabletop orbital shaker. Prepare a 4.4 mg/mL solution of the catalyst, rhodium triphenylacetate ($Rh_2(O_2CC(Ph)_3)_4$), in dry $CH_2Cl_2$ under Ar in an oven-dried, Teflon capped glass vial. (NOTE: The catalyst concentration can be cut by one-half to one-fifth and the tags will still be readable by GC (the late tags will be weak). Use the same volume of catalyst solution as described below.) Add 50 µL of the catalyst solution to the resin and keep the Eppendorf in agitation for 16 h (overnight) at room temperature. Wash the resin in a 1 mL BioRad tube 2×15 min $CH_2Cl_2$, 16 h (overnight) THF, 2×15 min THF, and 2×15 min $CH_2Cl_2$. Dry the resin under house vacuum for ca. 15 min before proceeding to compound cleavage. Compound Cleavage: Place the beads into a 700 µL Eppendorf tube. Add 100 µL of freshly-prepared 5% (HF/py)/THF solution (v/v). Set the tube to shake for 90 min at room temperature on a tabletop Eppendorf shaker. Quench HF by adding 200 µL TMSOMe to the tube. Set the tube to shake for 30 min at room temperature on a tabletop Eppendorf shaker. Collect the filtrate (if desired) and wash the resin: 3×5 min $CH_2Cl_2$, 3×5 min THF, and 3×5 min $CH_2Cl_2$. Dry under house vacuum for at least 1 h before decoding.

Representative Bead Decoding Procedure. Place one bead into an autosampler glass sample insert with the aid of tweezers. A 0.24 M solution of CAN in 5:1 THF/$H_2O$ is prepared (132 mg CAN/0.83 mL dry, degassed THF +0.17 mL doubly-distilled $H_2O$) in an oven-dried vial. This solution should be prepared immediately before use. Add 5 µL of the CAN solution to the glass autosampler insert. Add 8 µL of dry decane to the glass insert and then centrifuge the insert in a Micro-Centrifuge to separate the two layers. Place the insert in an autosampler vial and cap tightly. Seal with Parafilm, and heat the glass insert at 37° C. for 21 h (in a standard laboratory incubator). Allow the sample to cool to room temperature, and remove the glass insert from the autosampler vial. Sonicate the insert for 1–10 min. Centrifuge the insert again in the Micro-Centrifuge. Use a 200 µL Pipetman equipped with a gel-loading tip to remove the top decane layer and transfer it to a new GC autosampler glass insert. (After heating overnight, the CAN layer will be colorless, so caution must be used to not contaminate the decane layer with CAN in transfer.) Prepare a 1:1 BSA/decane solution in an oven-dried vial. This solution should be prepared immediately before use. Add 1.0 µL of this BSA solution to the decane layer in the GC insert. Spin down the insert in the Microfuge for 30–40 sec to ensure efficient mixing of the BSA solution with the sample. Place the insert in an autosampler vial, cap tightly, and store at 0° C. until GC analysis.

TABLE 5

Binary decoding data from GC and LC/MS analysis of 108 beads from dihydropyrancarboxamide library 12. (BB = building block). GC and MS data for bead #105 could not be correlated.

| Bead # | Tag 2B | Tag 4B | Tag 1A | Tag 2A | Tag3 A | Tag 4A | Tag 5A | Tag 6A | Tag 7A | BB1 | BB2 | BB3 | Expected mass | Observed mass |
|---|---|---|---|---|---|---|---|---|---|---|---|---|---|---|
| 1  | 0 | 1 | 1 | 0 | 1 | 1 | 0 | 0 | 0 | H | F | A | 572 | M + H |
| 2  | 1 | 0 | 0 | 1 | 0 | 1 | 1 | 0 | 0 | G | J | A | 539 | M + H |
| 3  | 1 | 1 | 0 | 1 | 1 | 0 | 0 | 0 | 0 | H | F | B | 552 | M + H |
| 4  | 1 | 1 | 0 | 0 | 0 | 0 | 0 | 1 | 0 | B | D | B | 435 | M + H |
| 5  | 1 | 0 | 0 | 1 | 1 | 1 | 0 | 0 | 0 | G | F | C | 447 | M + H |
| 6  | 0 | 0 | 0 | 1 | 1 | 0 | 1 | 0 | 0 | D | G | C | 447 | M + H |
| 7  | 1 | 1 | 0 | 0 | 1 | 0 | 0 | 0 | 0 | E | A | D | 441 | M + H |
| 8  | 1 | 0 | 0 | 1 | 1 | 0 | 0 | 0 | 0 | G | A | D | 401 | M + H |
| 9  | 0 | 0 | 0 | 1 | 0 | 0 | 0 | 1 | 0 | D | D | E | 514 | M + H |
| 10 | 0 | 1 | 0 | 0 | 0 | 0 | 0 | 0 | 1 | C | E | E | 500 | M + H |
| 11 | 1 | 0 | 0 | 1 | 1 | 0 | 1 | 0 | 0 | G | G | F | 473 | M + H |
| 12 | 1 | 1 | 0 | 0 | 1 | 1 | 0 | 0 | 0 | E | F | F | 479 | M + H |
| 13 | 1 | 1 | 0 | 0 | 1 | 0 | 1 | 0 | 0 | E | G | G | 592 | M + H |
| 14 | 1 | 1 | 0 | 0 | 0 | 0 | 0 | 0 | 1 | E | E | G | 596 | M + H |
| 15 | 0 | 0 | 0 | 1 | 0 | 1 | 1 | 0 | 0 | D | J | H | 540 | M − EtOH |
| 16 | 1 | 0 | 0 | 0 | 1 | 0 | 0 | 1 | 0 | A | H | H | 497 | M + H |
| 17 | 0 | 1 | 0 | 0 | 1 | 1 | 0 | 0 | 0 | B | F | I | 582 | M + H |
| 18 | 0 | 0 | 0 | 1 | 1 | 0 | 1 | 0 | 0 | D | G | I | 614 | M − BB1_D |
| 19 | 0 | 1 | 0 | 0 | 0 | 1 | 1 | 0 | 0 | B | J | J | 640 | M + H |
| 20 | 0 | 0 | 1 | 0 | 0 | 1 | 1 | 0 | 0 | C | J | J | 638 | M + H |

TABLE 5-continued

Binary decoding data from GC and LC/MS analysis of 108 beads from dihydropyrancarboxamide library 12. (BB = building block). GC and MS data for bead #105 could not be correlated.

| Bead # | Tag 2B | Tag 4B | Tag 1A | Tag 2A | Tag3 A | Tag 4A | Tag 5A | Tag 6A | Tag 7A | BB1 | BB2 | BB3 | Expected mass | Observed mass |
|---|---|---|---|---|---|---|---|---|---|---|---|---|---|---|
| 21 | 1 | 0 | 0 | 0 | 0 | 0 | 0 | 1 | 0 | A | D | K | 563 | M + H |
| 22 | 0 | 0 | 1 | 0 | 1 | 0 | 1 | 0 | 0 | C | G | K | 559 | M − EtOH |
| 23 | 1 | 0 | 0 | 0 | 1 | 1 | 0 | 0 | 0 | A | F | L | 497 | M + H |
| 24 | 0 | 1 | 0 | 0 | 0 | 1 | 1 | 0 | 0 | B | J | L | 617 | M + H |
| 25 | 0 | 1 | 1 | 0 | 0 | 0 | 1 | 0 | 0 | H | C | M | 694 | M + H |
| 26 | 0 | 0 | 0 | 1 | 0 | 1 | 1 | 0 | 0 | D | J | M | 545 | M + H |
| 27 | 1 | 0 | 0 | 1 | 0 | 1 | 1 | 0 | 0 | G | J | N | 540 | M + H |
| 28 | 0 | 1 | 1 | 0 | 0 | 0 | 1 | 0 | 0 | H | C | N | 655 | M + H |
| 29 | 1 | 0 | 0 | 0 | 0 | 1 | 0 | 0 | 0 | A | B | O | 383 | M + H |
| 30 | 0 | 0 | 0 | 1 | 0 | 0 | 1 | 0 | 0 | D | C | O | 485 | M − BB1_D |
| 31 | 0 | 1 | 0 | 0 | 0 | 1 | 1 | 0 | 0 | B | J | P | 607 | M + MeOH − H$_2$O |
| 32 | 1 | 1 | 0 | 0 | 1 | 0 | 0 | 0 | 1 | E | I | P | 637 | M + MeOH − H$_2$O |
| 33 | 1 | 0 | 0 | 1 | 1 | 0 | 0 | 1 | 0 | G | H | Q | 644 | M + H |
| 34 | 1 | 0 | 1 | 0 | 1 | 0 | 0 | 0 | 1 | F | H | Q | 684 | M + H |
| 35 | 1 | 0 | 0 | 1 | 1 | 0 | 0 | 0 | 0 | G | A | R | 413 | M + H |
| 36 | 0 | 0 | 0 | 1 | 1 | 1 | 0 | 0 | 0 | D | F | R | 419 | M − EtOH |
| 37 | 0 | 1 | 1 | 0 | 0 | 1 | 1 | 0 | 0 | H | J | S | 1049 | M + H |
| 38 | 0 | 1 | 0 | 0 | 1 | 0 | 0 | 0 | 0 | H | F | S | 945 | M + H |
| 39 | 0 | 0 | 1 | 0 | 1 | 1 | 0 | 0 | 0 | C | F | T | 513 | M + H |
| 40 | 0 | 0 | 1 | 0 | 0 | 1 | 1 | 0 | 0 | C | J | T | 617 | M + H |
| 41 | 0 | 0 | 0 | 1 | 1 | 0 | 0 | 0 | 1 | D | I | U | 469 | M − EtOH |
| 42 | 1 | 0 | 1 | 0 | 1 | 0 | 1 | 0 | 0 | F | G | U | 515 | M − C$_4$O$_2$H$_8$ |
| 43 | 0 | 0 | 0 | 1 | 0 | 0 | 1 | 0 | 0 | D | C | V | 558 | M − EtOH |
| 44 | 0 | 1 | 0 | 0 | 0 | 0 | 1 | 0 | 0 | B | C | V | 560 | M + H |
| 45 | 1 | 0 | 1 | 0 | 1 | 0 | 0 | 0 | 1 | F | I | W | 505 | M − C$_4$O$_2$H$_8$ |
| 46 | 1 | 0 | 0 | 0 | 1 | 1 | 0 | 0 | 0 | G | J | W | 507 | M + H |
| 47 | 0 | 0 | 1 | 0 | 1 | 0 | 0 | 0 | 1 | C | I | X | 576 | M − EtOH |
| 48 | 1 | 0 | 1 | 0 | 0 | 0 | 0 | 0 | 1 | F | E | X | 626 | M + H |
| 49 | 1 | 0 | 0 | 0 | 1 | 0 | 0 | 0 | 1 | A | I | Y | 413 | M + H |
| 50 | 0 | 0 | 1 | 0 | 0 | 1 | 1 | 0 | 0 | C | J | Y | 469 | M + H |
| 51 | 1 | 0 | 0 | 1 | 0 | 0 | 1 | 0 | 1 | G | D | A | 487 | M + H |
| 52 | 0 | 0 | 0 | 1 | 1 | 0 | 1 | 1 | 0 | D | I | A | 463 | M − EtOH |
| 53 | 1 | 0 | 0 | 1 | 0 | 1 | 0 | 1 | 0 | G | A | B | 375 | M − H$_2$O |
| 54 | 0 | 1 | 1 | 0 | 0 | 1 | 0 | 1 | 0 | H | A | B | 512 | M + H |
| 55 | 0 | 0 | 1 | 0 | 0 | 1 | 0 | 1 | 0 | H | A | C | 544 | M − MeOH |
| 56 | 0 | 0 | 0 | 1 | 1 | 1 | 0 | 0 | 1 | D | H | C | 488 | M + H |
| 57 | 0 | 0 | 1 | 0 | 1 | 1 | 0 | 1 | 0 | F | G | D | 515 | M − EtOH |
| 58 | 1 | 0 | 0 | 0 | 0 | 0 | 1 | 0 | 1 | A | D | D | 445 | M + H |
| 59 | 0 | 0 | 0 | 1 | 0 | 1 | 0 | 0 | 1 | D | B | E | 456 | M + H |
| 60 | 1 | 0 | 0 | 1 | 0 | 1 | 0 | 0 | 1 | G | B | E | 490 | M + H |
| 61 | 1 | 0 | 0 | 1 | 0 | 1 | 0 | 0 | 1 | G | B | F | 433 | M + H |
| 62 | 0 | 1 | 0 | 0 | 0 | 0 | 0 | 1 | 1 | H | E | F | 614 | M + H |
| 63 | 1 | 0 | 0 | 0 | 1 | 0 | 1 | 0 | 1 | A | J | G | 574 | M + H |
| 64 | 0 | 0 | 0 | 1 | 1 | 1 | 0 | 0 | 1 | D | H | G | 559 | M + H |
| 65 | 0 | 0 | 0 | 1 | 1 | 0 | 1 | 1 | 0 | D | I | H | 498 | M − EtOH |
| 66 | 0 | 0 | 1 | 0 | 1 | 0 | 0 | 0 | 1 | C | J | H | 540 | M + H |
| 67 | 0 | 1 | 0 | 0 | 0 | 1 | 0 | 0 | 1 | B | B | I | 576 | M + H |
| 68 | 0 | 1 | 1 | 0 | 0 | 0 | 0 | 1 | 1 | D | E | I | 618 | M + H |
| 69 | 1 | 0 | 0 | 1 | 1 | 1 | 0 | 1 | 0 | G | G | J | 602 | M + H |
| 70 | 1 | 0 | 0 | 1 | 0 | 1 | 0 | 1 | 0 | G | A | J | 528 | M + H |
| 71 | 1 | 1 | 0 | 0 | 0 | 0 | 1 | 0 | 1 | E | D | K | 651 | M + H |
| 72 | 1 | 0 | 1 | 0 | 0 | 0 | 1 | 1 | 1 | F | E | K | 637 | M + H |
| 73 | 1 | 0 | 1 | 0 | 1 | 1 | 1 | 0 | 0 | F | F | L | 585 | M + H |
| 74 | 1 | 0 | 0 | 1 | 0 | 0 | 0 | 1 | 1 | G | E | L | 583 | M + H |
| 75 | 1 | 0 | 1 | 0 | 1 | 1 | 0 | 0 | 1 | F | H | M | 590 | M + H |
| 76 | 1 | 0 | 1 | 0 | 0 | 0 | 0 | 1 | 1 | F | E | M | 553 | M − C$_4$O$_2$H$_8$ |
| 77 | 0 | 0 | 1 | 0 | 1 | 0 | 0 | 0 | 1 | C | J | N | 506 | M + H |
| 78 | 1 | 0 | 0 | 1 | 0 | 0 | 1 | 1 | 0 | G | C | N | 518 | M + H |
| 79 | 1 | 0 | 0 | 0 | 0 | 0 | 0 | 1 | 1 | E | C | O | 559 | M + H |
| 80 | 1 | 1 | 0 | 0 | 1 | 1 | 1 | 0 | 0 | E | F | O | 477 | M + H |
| 81 | 1 | 0 | 0 | 1 | 1 | 1 | 0 | 1 | 0 | G | G | P | 569 | M + MeOH − H$_2$O |
| 82 | 0 | 1 | 1 | 0 | 0 | 0 | 1 | 1 | 0 | H | C | P | 754 | M + H |
| 83 | 0 | 0 | 0 | 1 | 1 | 0 | 0 | 1 | 0 | D | G | Q | 569 | M − EtOH |
| 84 | 1 | 0 | 0 | 1 | 1 | 1 | 0 | 1 | 0 | G | G | Q | 603 | M − H$_2$O |
| 85 | 1 | 0 | 0 | 0 | 1 | 0 | 1 | 0 | 1 | A | I | R | 467 | M + H |
| 86 | 0 | 0 | 1 | 0 | 0 | 0 | 0 | 1 | 1 | C | E | R | 457 | M − EtOH |
| 87 | 0 | 1 | 0 | 0 | 0 | 0 | 1 | 1 | 0 | B | G | S | 810 | M + H |
| 88 | 1 | 0 | 0 | 0 | 1 | 1 | 1 | 0 | 0 | A | G | S | 794 | M + H |
| 89 | 1 | 0 | 1 | 0 | 1 | 0 | 1 | 0 | 0 | F | G | T | 621 | M − C$_4$O$_2$H$_8$ |
| 90 | 1 | 0 | 0 | 1 | 0 | 0 | 1 | 1 | 0 | G | C | T | 629 | M + H |
| 91 | 1 | 0 | 1 | 0 | 0 | 0 | 1 | 0 | 1 | F | D | U | 533 | M − C$_4$O$_2$H$_8$ |
| 92 | 0 | 0 | 1 | 0 | 1 | 0 | 1 | 0 | 1 | C | J | U | 511 | M + H |

TABLE 5-continued

Binary decoding data from GC and LC/MS analysis of 108 beads from dihydropyrancarboxamide library 12. (BB = building block). GC and MS data for bead #105 could not be correlated.

| Bead # | Tag 2B | Tag 4B | Tag 1A | Tag 2A | Tag3 A | Tag 4A | Tag 5A | Tag 6A | Tag 7A | BB1 | BB2 | BB3 | Expected mass | Observed mass |
|---|---|---|---|---|---|---|---|---|---|---|---|---|---|---|
| 93 | 0 | 0 | 1 | 0 | 0 | 1 | 0 | 1 | 0 | C | A | V | 436 | M − EtOH |
| 94 | 0 | 0 | 0 | 1 | 0 | 0 | 1 | 1 | 0 | D | C | V | 558 | M + H |
| 95 | 0 | 1 | 1 | 0 | 0 | 1 | 0 | 1 | 0 | H | A | W | 500 | M + H |
| 96 | 0 | 0 | 1 | 0 | 1 | 0 | 1 | 0 | 1 | C | J | W | 473 | M + H |
| 97 | 1 | 1 | 0 | 0 | 0 | 0 | 0 | 1 | 1 | E | E | X | 626 | M + H |
| 98 | 0 | 0 | 1 | 0 | 1 | 1 | 1 | 0 | 0 | C | F | X | 514 | M + H |
| 99 | 0 | 0 | 1 | 0 | 1 | 1 | 1 | 0 | 0 | C | F | Y | 365 | M + H |
| 100 | 0 | 0 | 0 | 1 | 1 | 0 | 1 | 1 | 0 | D | I | Y | 427 | M − EtOH |
| 101 | 1 | 0 | 0 | 0 | 1 | 0 | 0 | 0 | 0 | A | A | | 298 | M + Na |
| 102 | 1 | 0 | 1 | 0 | 1 | 0 | 0 | 0 | 1 | F | I | | 488 | M − EtOH |
| 103 | 0 | 0 | 0 | 1 | 1 | 1 | 0 | 0 | 1 | D | H | | 427 | M − EtOH |
| 104 | 0 | 1 | 0 | 0 | 0 | 1 | 0 | 0 | 1 | B | B | | 348 | M + H |
| 105 | 1 | 0 | 1 | 0 | 1 | 0 | 1 | 0 | 0 | F | G | | 420 | M − $C_4O_2H_8$ |
| 106 | 1 | 0 | 1 | 0 | 1 | 0 | 0 | 0 | 0 | F | A | | 346 | M + Na |
| 107 | 1 | 1 | 0 | 0 | 0 | 0 | 1 | 0 | 1 | E | D | | 438 | M − EtOH |
| 108 | 0 | 1 | 0 | 0 | 1 | 1 | 0 | 1 | 0 | B | G | | 348 | M + H |

EXAMPLE 3

Biological Testing

1. Discussion of Methodology

Cell and Protein Based Screens

Figure 11:
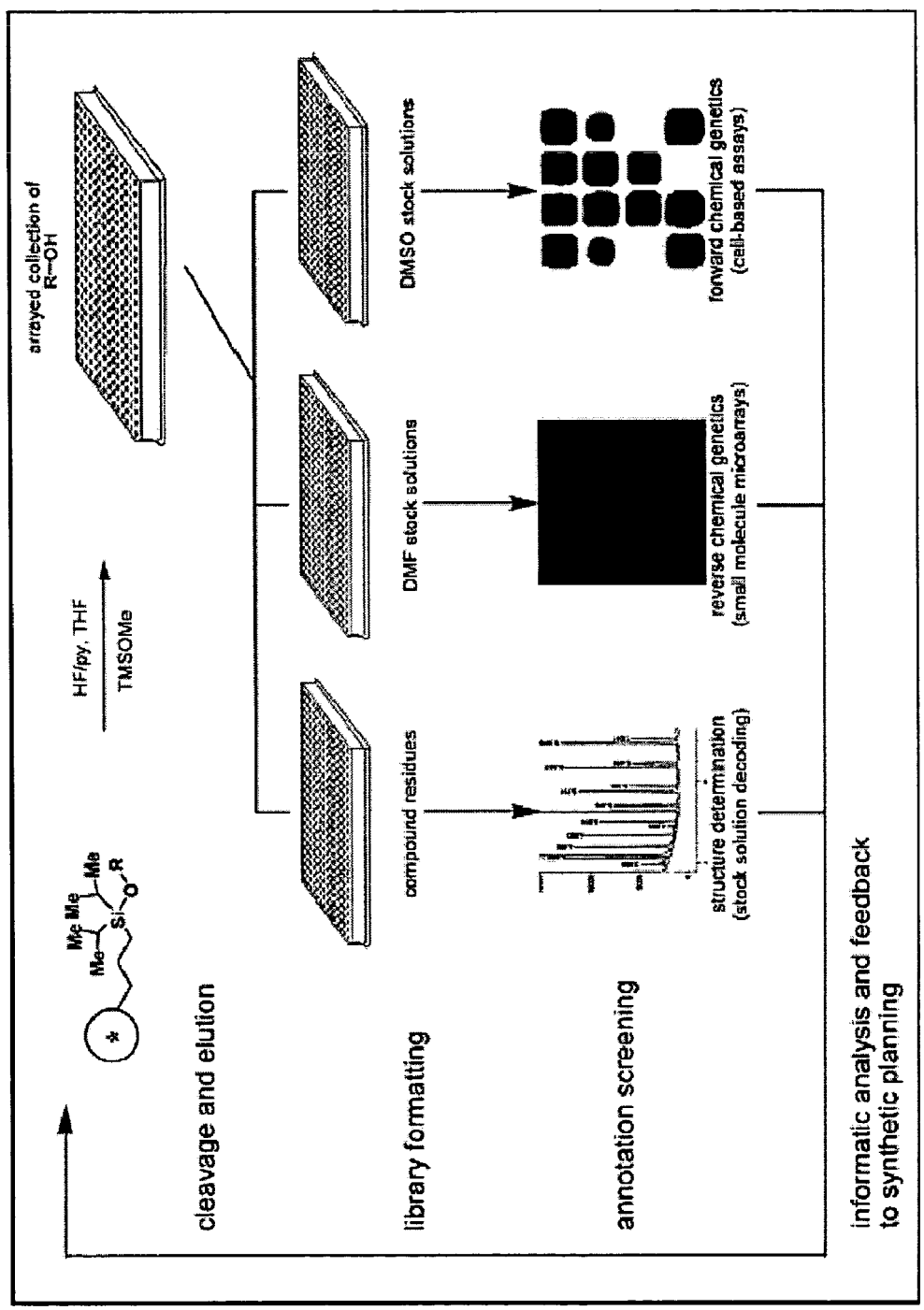
FIG. 11 depicts an overview of exemplary library formatting and annotation screening.
Figure 12:
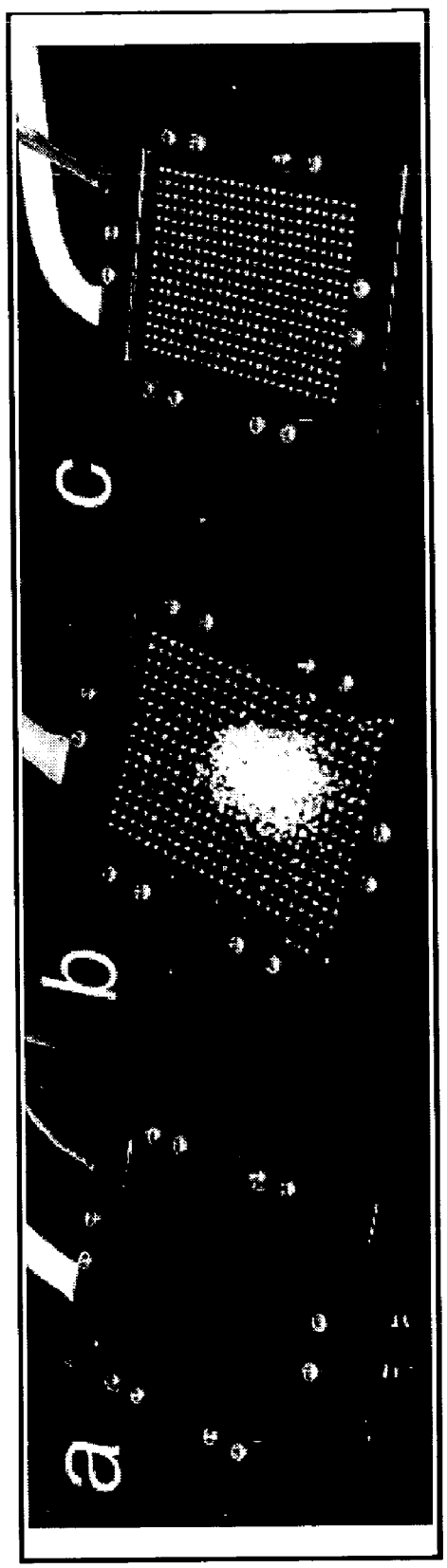
FIG. 12 depicts a bead arrayer. The bead arrayer is (a) attached to standard nitrogen and vacuum lines. Vacuum is applied and beads are (b) decanted onto the platform for entrainment by 384 depressions. Excess beads are recovered, leaving (c) a regular array of 384 beads with identical spacing to a standard 384-well microtiter plate.

It will be appreciated that the small molecule compounds of the present invention may be screened in any of a variety of biological assays. For example, cell-based assays may be employed (see FIG. 11). Such cell-based assays generally involve contacting a cell with a compound and detecting any of a number of events, such as binding of the compound to the cell, initiation of a biochemical pathway or physiological change in the cell, changes in cell morphology, initiation or blockage of the cell cycle etc.

Figure 23:
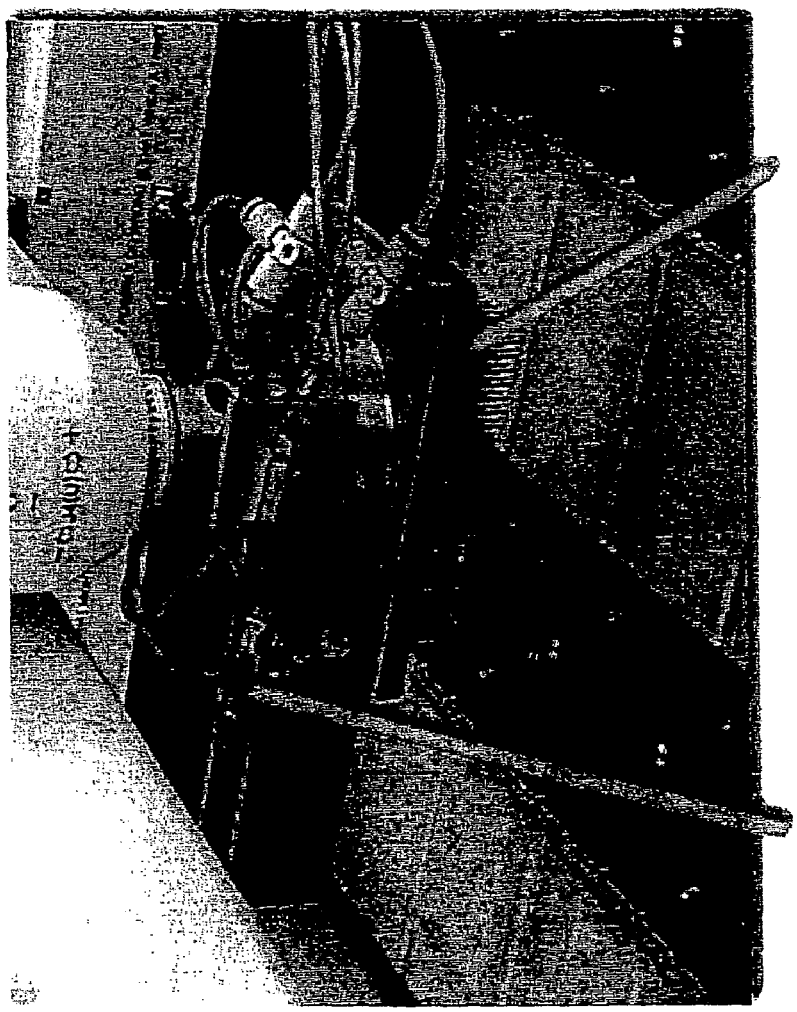
FIG. 23 depicts a robotic 384 pin arrayer.

In but one example, once synthesized, the compounds may be arrayed in 384-well plates by a robotic 384 pin arrayer, as shown in FIG. 23, and assayed for their ability to bind to a particular cell type present in the well. Detection can be carried out, for example, by detecting a tag that is attached to the small molecule. Alternatively, the small molecule may be detected by using a second molecule that has a tag, the second molecule specifically binding the small molecule, e.g., a tagged antibody specific to the small molecule.

Alternatively or additionally, inventive compounds may be studied in such assays. In such assays, the compounds are bound to a solid support and then contacted with a protein of interest. The presence or absence of binding between the compound and the protein is then detected. In certain cases, the protein itself is tagged with a molecule that can be detected, e.g., with a fluorescent molecule. Alternatively, the protein is detected by utilizing any immunoassay, such as the ELISA.

Figure 24:
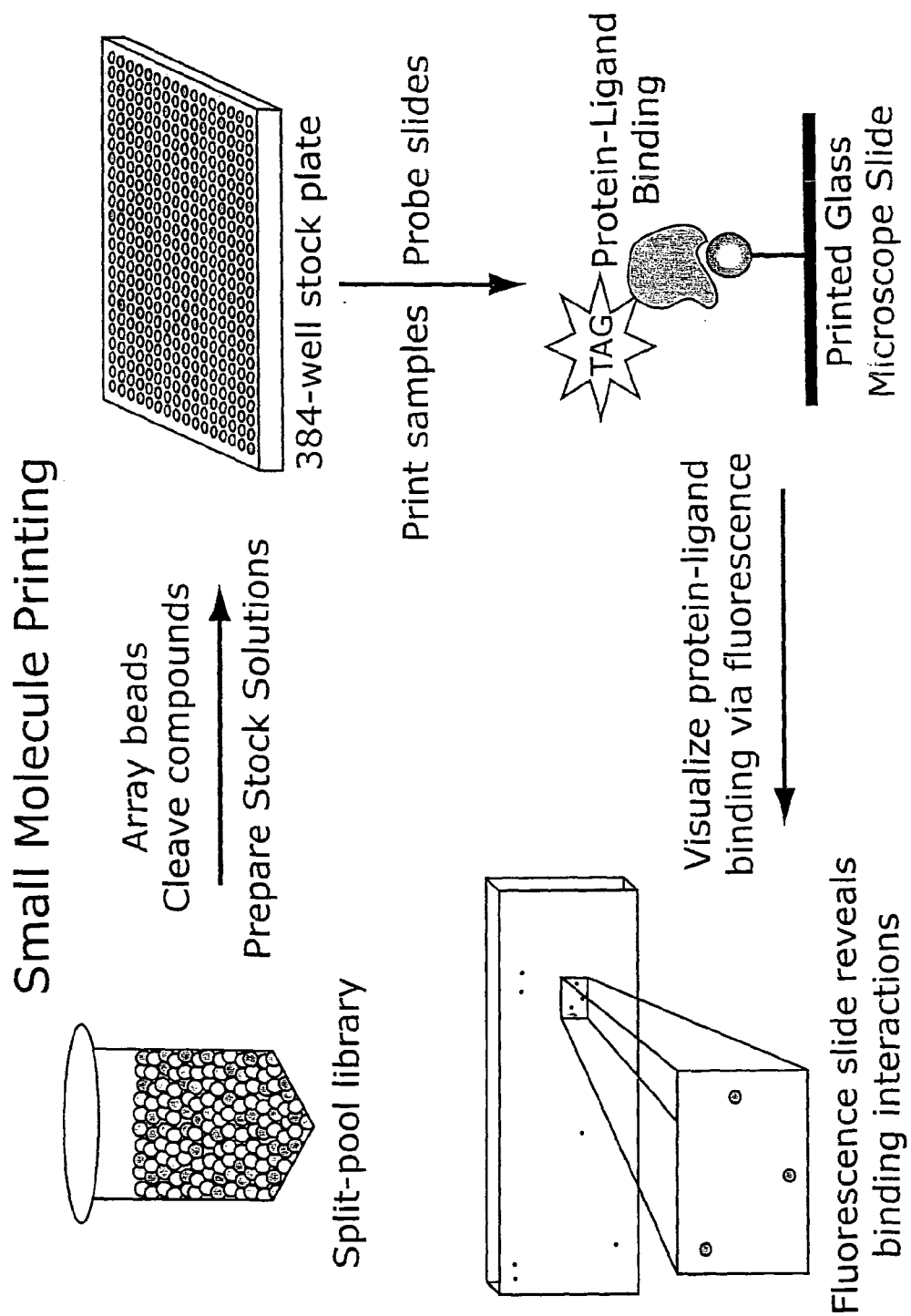
FIG. 24 depicts small molecule printing.
Figure 25:
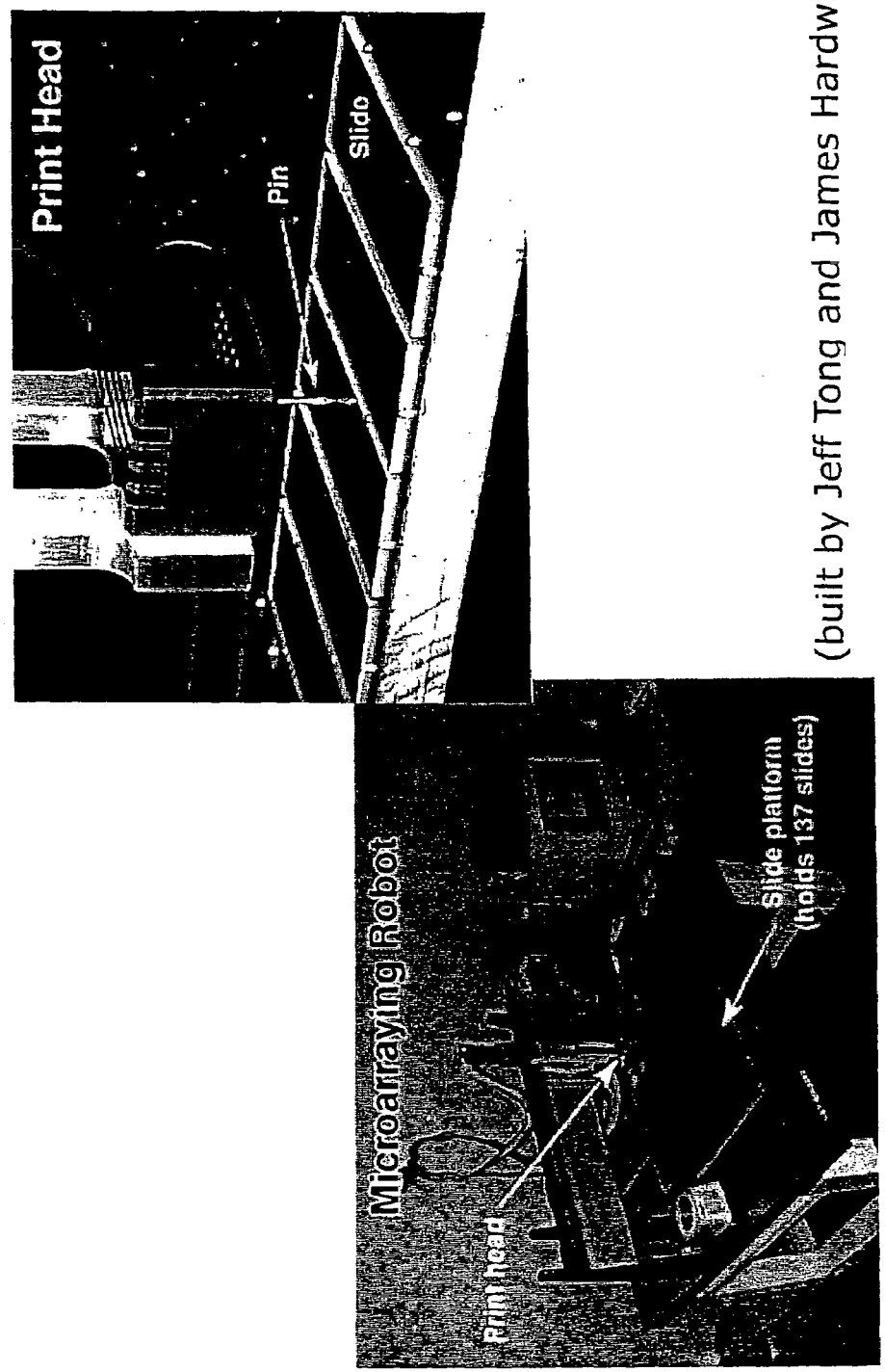
FIG. 25 depicts a small molecule microarraying robot.

For example, a process known as small molecule printing (see, for example, U.S. Ser. No. 09/567,910, filed May 10, 2000, the entire contents of which are hereby incorporated by reference), may be utilized to screen proteins that interact with the library compounds. First, a split pool library is arrayed onto beads. The compounds are then cleaved from the beads and prepared in a standard stock solution, such as DMSO. The compounds are then arrayed onto a 384-well stock plate. Next, the compounds are printed onto glass slides, e.g., a glass microscope slides, and the slides are probed with a tagged ligand, e.g., a tagged protein of interest. Binding between a compound and the ligand is then detected by any available means appropriate to the tag being utilized, e.g., via fluorescence. (See FIGS. 24 and 25).

It will be appreciated that any of the general assay methods described above, as well as other assays known in the art, may identify dihydropyrancarboxamide-like molecules having certain biological properties. Described below are assays that examples of assays that were used to screen the inventive library of compounds, and that helped identify library members that exhibited certain biological activity (e.g., BdrU incorporation, Genistein suppressor activity and Eg5 inhibition).

As discussed above, in certain embodiments, the inventive library is prepared by three diversity-generating steps, the first two of which were encoded with chloroaromatic tags, as described in Example 2 above. As the final diversity-generating step was not chemically encoded, the library was prepared as 54 separate portions of dry resin (9) totaling three theoretical copies of 4320 stereochemically and structurally distinct compounds (10) (see Scheme 4).

Cleavage and Elution of a Diversity Set of Dihydropyrancarboxamides

A robotic cleavage and elution protocol ws used to deliver actual library members from the inventive library into chemical genetic assays. As described in Scheme 5, an encoded, split-pool library of 4320 dihydropyrancarboxamides (10) (an exemplary synthesis of which is described herein. See also, R. A. Stavenger, S. L. Schreiber, Asymmetric catalysis in diversity-oriented organic synthesis: enantioselective synthesis of 4320 encoded and spatially segregated dihydropyrancarboxamides, *Angew. Chem. Int. Ed*. 2001, 40:3417–3421).

Scheme 5

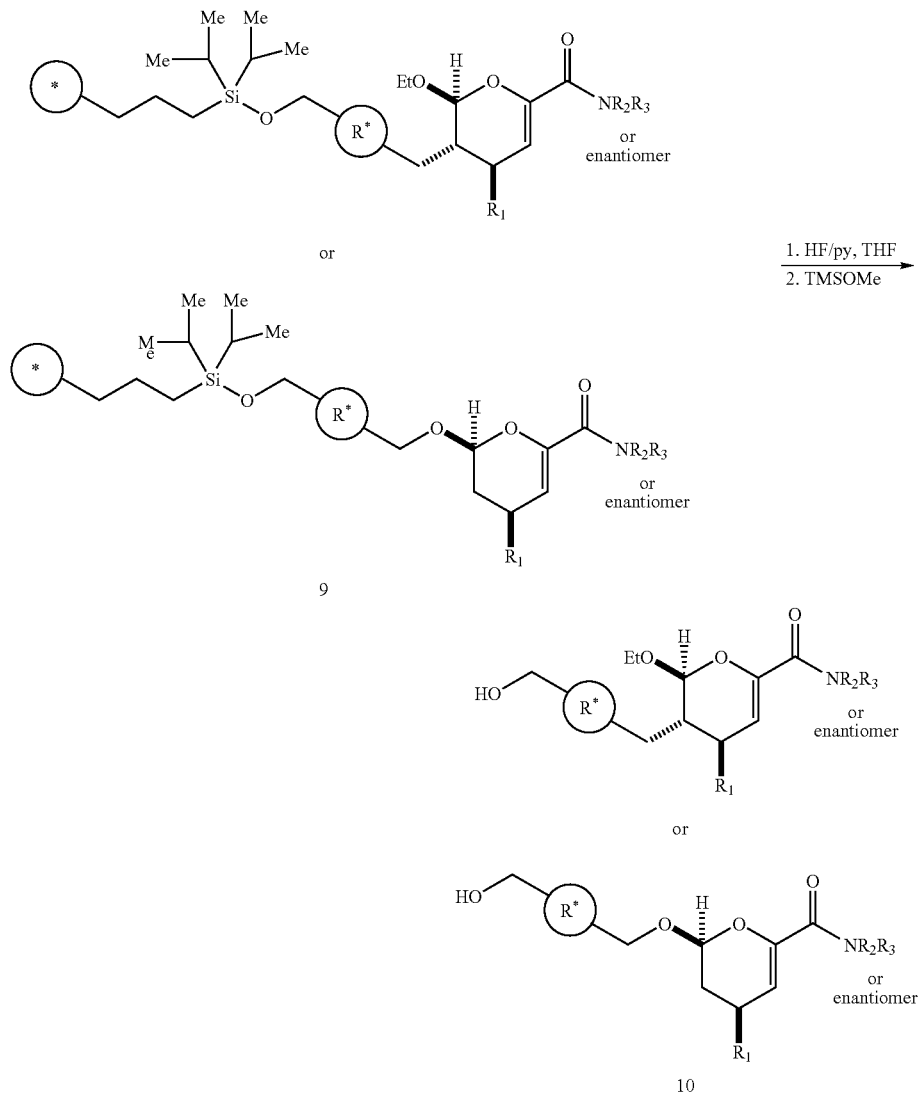

Briefly, as discussed above, in one embodiment, a method for preparing this library comprises three diversity-generating steps, the first two of which were encoded with chloroaromatic tags as described in H. E. Blackwell, L. Pérez, R. A. Stavenger, J. A. Tallarico, E. Cope-Eatough, S. L. Schreiber, M. A. Foley, "A one-bead, one-stock solution approach to chemical genetics, part 1", Chem. Biol. 2001, 8:1167–1182. As the final diversity-generating step was not chemically encoded, we acquired this library as 54 separate portions of dry resin (9) totaling three theoretical copies of 4320 stereochemically and structurally distinct compounds (10). We first exposed 324 individual beads, six from each of the 54 separate portions of 9, to our manual 'best practices' cleavage and elution conditions (Scheme 5) in a single microtiter plate. In this case, compounds were eluted directly into DMF to prepare a diversity plate of stock solutions (plate 0) amenable to small molecule printing. Glass microscope slides were activated for covalent attachment of alcohols, and compounds (10) from the 320 stock solutions were printed according to a method described in U.S. patent application Ser. No. 09/567,910 (see also, P. J. Hergenrother, K. M. Depew, S. L. Schreiber, Small molecule microarrays: covalent attachment and screening of alcohol-containing small molecules on glass slides, J. Am. Chem. Soc. 122 (2000) 7849–7850).

To test the availability of 10 to a protein-binding assay, we probed the small molecule microarray with purified Cy5-labeled (His)6-FKBP12 (See G. MacBeath, A. N. Koehler, S. L. Schreiber, Printing small molecules as microarrays and detecting protein-ligand interactions en masse, J. Am. Chem. Soc. 121 (1999) 7967–7968). As a positive control for protein-ligand interaction, AP1497 was included on the slide by adding it in DMF solution to an empty well of the stock plate (See, for example, D. A. Holt, J. I. Luengo, D. S. Yamashita, H.-J. Oh, A. L. Konialian, H.-K. Yen, L. W. Rozamus, M. Brandt, M. J. Bossard, M. A. Levy, D. S. Eggleston, J. Liang, L. W. Schultz, T. J. Stout, J. Clardy, Design, synthesis, and kinetic evaluation of high-a§nity FKBP ligands and the X-ray crystal structures of their complexes with FKBP12, J. Am. Chem. Soc. 115 (1993)

Figure 13:
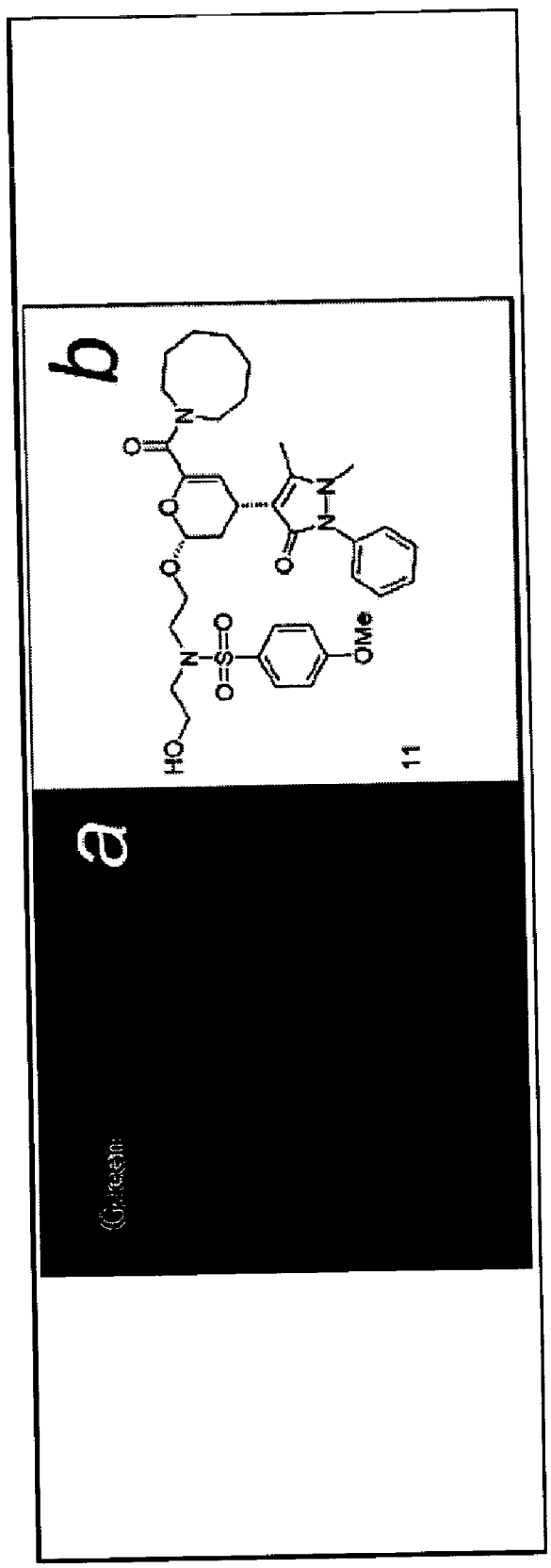
FIG. 13 depicts a representative reverse chemical genetic assay, as described in Example 3 herein. A small molecule microarray containing members of 10 was probed with purified Cy5-labeled (His)6-FKBP12. a: Fluorescence intensity at duplicate spots (false-colored red) containing a 'hit' is shown compared to a rhodamine control spot (false-colored green). b: The structure of the 'hit' (11) was determined by bead decoding and confirmed by LC/MS.

9925–9938; and J. F. Amara, T. Clackson, V. M. Rivera, T. Guo, T. Keenan, S. Natesan, R. Pollock, W. Yang, N. L. Courage, D. A. Holt, M. Gilman, A versatile synthetic dimerizer for the regulation of protein-protein interactions, *Proc. Natl. Acad. Sci. USA* 94 (1997) 10618–10623). Following incubation, the slide was washed and scanned for the presence of a Cy5 fluorescence signal (See G. MacBeath, A. N. Koehler, S. L. Schreiber, Printing small molecules as microarrays and detecting protein-ligand interactions en masse, *J. Am. Chem. Soc.* 121 (1999) 7967–7968), which appeared both at the AP1497 control spots (data not shown) and at spots corresponding to a member of 10 (FIG. 13(a)). The bead corresponding to the novel FKBP12-binding entity was subjected to the optimized bead decoding protocol described in Example 2 herein. Using this procedure, we were able unambiguously to determine the structure(FIG. 13(b)) of this 'hit' (11) in a protein-binding assay, as was subsequently confirmed by tandem liquid chromatography/ mass spectroscopy (LC/MS).

Formatting and Assaying of Representative Dihydropyrancarboxamides

To apply the robotic process to a fraction of resin 9, we arrayed 128 beads from each of three separate portions of 9 into a single 384-well microtiter plate. These beads were subjected to robotic cleavage and $CH_3CN$ elution as described earlier to prepare a 'mother plate' (plate 1) containing 384 members of 10. Subsequently, the 'mother plate' was mapped into six 'daughter plates' by volumetric transfer using the syringe-array robot. 'Daughter plates' were prepared for cell-based assays [1,2] (50% of stock solution), HPLC analysis (25%), LC/MS analysis (10%), small molecule printing [3,4] (2×5%), and stock solution decoding (5%) [(1) T. U. Mayer, T. M. Kapoor, S. J. Haggarty, R. W. King, S. L. Schreiber, T. J. Mitchison, Small molecule inhibitor of mitotic spindle bipolarity identified in a phenotype-based screen, Science 286 (1999) 971–974; (2) B. R. Stockwell, S. J. Haggarty, S. L. Schreiber, High-throughput screening of small molecules in miniaturized mammalian cell-based assays involving post-translational modifications, *Chem. Biol.* 6 (1999) 71–83; (3) G. MacBeath, A. N. Koehler, S. L. Schreiber, Printing small molecules as microarrays and detecting protein-ligand interactions en masse, *J. Am. Chem. Soc.* 121 (1999) 7967–7968; and (4) P. J. Hergenrother, K. M. Depew, S. L. Schreiber, Small molecule microarrays: covalent attachment and screening of alcohol-containing small molecules on glass slides, *J. Am. Chem. Soc.* 122 (2000) 7849–7850]. In each case, the $CH_3CN$ solution was evaporated following volumetric transfer so that each copy could be resuspended in the solvent most appropriate to its use. In particular, DMSO was used to resuspend the 'daughter plate' for cell-based assays and DMF was used to resuspend the 'daughter plate' for small molecule printing. The plate containing the beads was also stored, but due to the success of stock solution decoding [H. E. Blackwell, L. Perez, S. L. Schreiber, Decoding products of diversity pathways from stock solutions derived from single polymeric macrobeads, Angew. Chem. Int. Ed. 40 (2001) 3421–3425], and the difficulties associated with maintaining positional integrity within plates of beads, formatting a 'daughter plate' explicitly destined for structure determination has become the standard in our library realization process.

Figure 14:
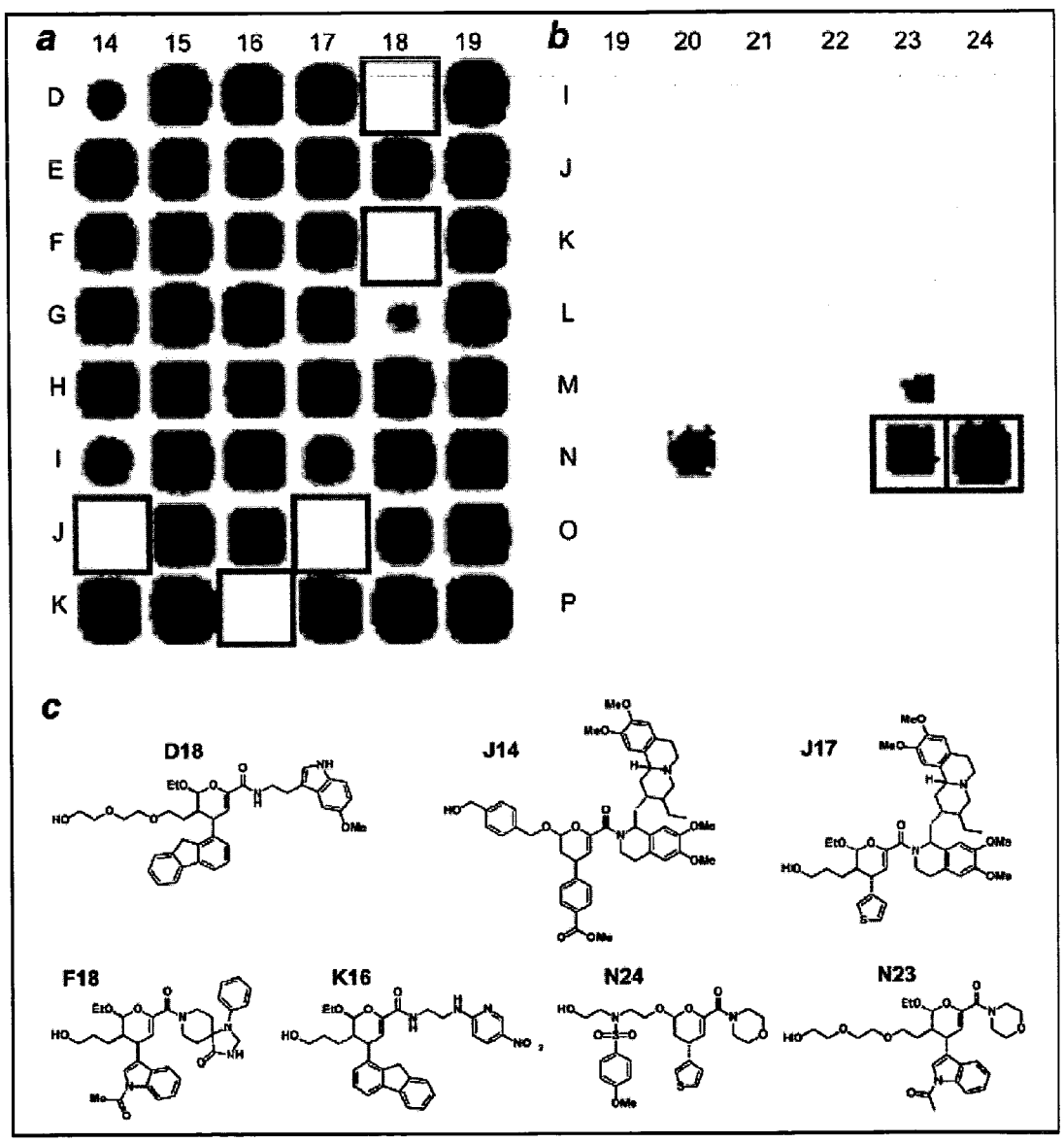
FIG. 14 depicts representative forward chemical genetic assays as described in Example 3 herein. Human A549 cells were exposed in duplicate to stock solutions of 10. 'Hits' (gray boxes) are those wells that scored in both replicates of a given experiment. Data from 48 representative wells are shown as multiplicative overlays of cytoblot results from (a) a BrdU incorporation assay, and (b) a genistein suppressor screen. c: Structures of representative 'hits'. Beads or stock solutions corresponding to 'hits' in cytoblot assays were exposed to the optimized decoding protocol described in the preceding paper in this issue. Compounds are labeled by well position in the assay plates.

Both plates of stock solutions (10) were used in phenotypic assays. In particular, we exposed living human A549 lung carcinoma cells to 708 (324+384) stock solutions under two different assay conditions. These experiments were performed with a hand-held pin-transfer tool, though our complete technology platform includes a pin-transfer robot capable of mapping into multiple microtiter plates. In certain embodiments, cultured cells exposed to 5-bromodeoxyuridine (BrdU) will incorporate this base analog into their DNA when actively dividing, and this incorporation can be detected by cytoblot assay using antibodies directed against BrdU (B. R. Stockwell, S. J. Haggarty, S. L. Schreiber, High-throughput screening of small molecules in miniaturized mammalian cell-based assays involving post-translational modifications, *Chem. Biol.* 6 (1999) 71–83). First, to determine if any stock solution of 10 inhibits BrdU incorporation, we transferred ~100 nl of each stock solution into individual assay wells containing A549 cells actively growing in the presence of 1% fetal bovine serum. Second, we exposed A549 cells to ~100 nl of each stock solution, and simultaneously challenged the cells with 100 μM genistein, a broad-spectrum protein tyrosine kinase inhibitor (T. Akiyama, J. Ishida, S. Nakagawa, H. Ogawara, S. Watanabe, N. Itoh, M. Shibuya, Y. Fukami, Genistein, a specific inhibitor of tyrosine-speciec protein kinases, *J. Biol. Chem.* 262 (1987) 5592–5595). Under the latter conditions, BrdU incorporation, again judged by cytoblot assay, is impaired (For a discussion of the cytoblot assay technology, see U.S. patent application Ser. No. 09/361,576; and B. R. Stockwell, S. J. Haggarty, S. L. Schreiber, High-throughput screening of small molecules in miniaturized mammalian cell-based assays involving post-translational modifications, *Chem. Biol.* 6 (1999) 71–83). Thus, 'hits' in the former assay are detected as a loss of signal in a high-signal array (FIG. 14(a)), while 'hits' in the latter assay are detected as a gain of signal in a lowsignal array (FIG. 14(b)). The latter assay is referred to as a genistein suppressor screen, as we are seeking a member of 10 that can suppress the ability of genistein to inhibit BrdU incorporation.

For each of these assays, aliquots from each of the two plates (10) were exposed to cells in duplicate to ensure the fidelity of the results. Compounds were scored as 'hits' only if they scored strongly in both replicates of a given experiment. From plate 0, 11 compounds scored as inhibitors of BrdU incorporation, while 10 compounds scored as suppressors of the action of genistein. From plate 1, 12 compounds scored as inhibitors of BrdU incorporation, while nine compounds scored as suppressors of the action of genistein. It is interesting that roughly the same number of first-pass 'hits' were identified on each plate, despite the difference in diversity between the two collections. This finding may reflect the fact that assay results were tabulated by visual scoring of photographic film, but is not limited to such detection methods. Conversely, in the case of an FKBP12-binding assay using microarrayed compounds, plate 1 produced no 'hits' (data not shown).

To ensure that we can obtain exact structural information on the 'hits' found in these experiments, we performed either bead decoding [H. E. Blackwell, L. Perez, R. A. Stavenger, J. A. Tallarico, E. Cope-Eatough, S. L. Schreiber, M. A. Foley, A one-bead, one-stock solution approach to chemical genetics, part 1, *Chem. Biol.* 8 (2001) 1167–1182] or stock solution decoding [H. E. Blackwell, L. Perez, S. L. Schreiber, Decoding products of diversity pathways from stock solutions derived from single polymeric macrobeads, *Angew. Chem. Int. Ed.* 40 (2001) 3421–3425] on all 42 compounds scoring as positive in either assay. Decoding results were compared with LC/MS results for each sample to verify that a compound of the correct mass was present. In all but nine cases, LC traces revealed a single clean peak, and for each of the 42 'hits', a parent ion or fragment matching the proposed structure was observed by MS. Thus, we were able to decode and confirm the structure (FIG. 14(c)) of each 'hit' detected in either the BrdU or the genistein suppressor cytoblot assay.

Figure 15:
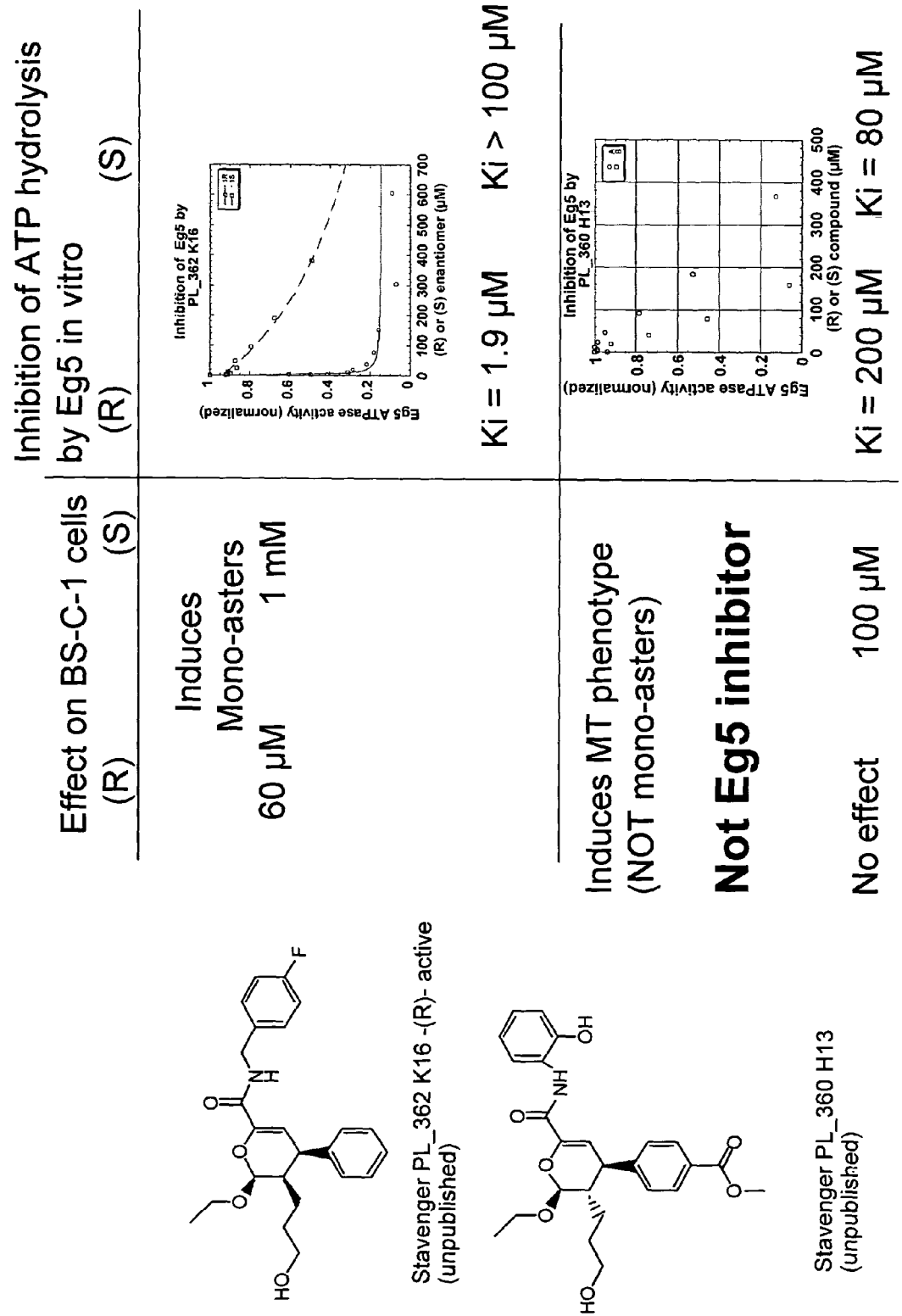
FIG. 15 depicts an exemplary inventive compound identified in an Eg5 inhibitor assay, as described in Example 3 herein.
Figure 16A:
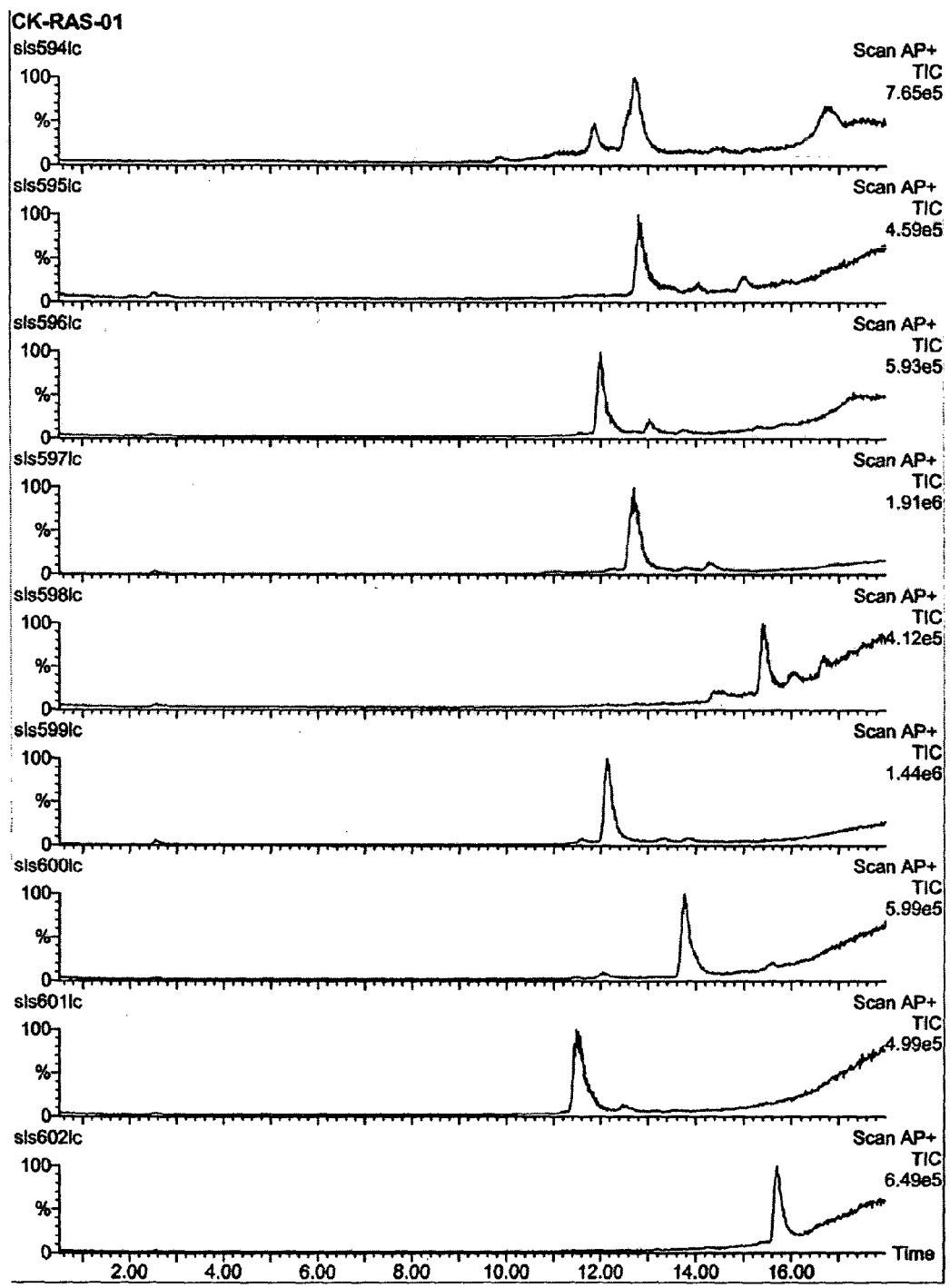
FIGS. 16A–16D depict LC traces from 25 inventive livrary members (e.g., quality control compounds).
Figure 16B:
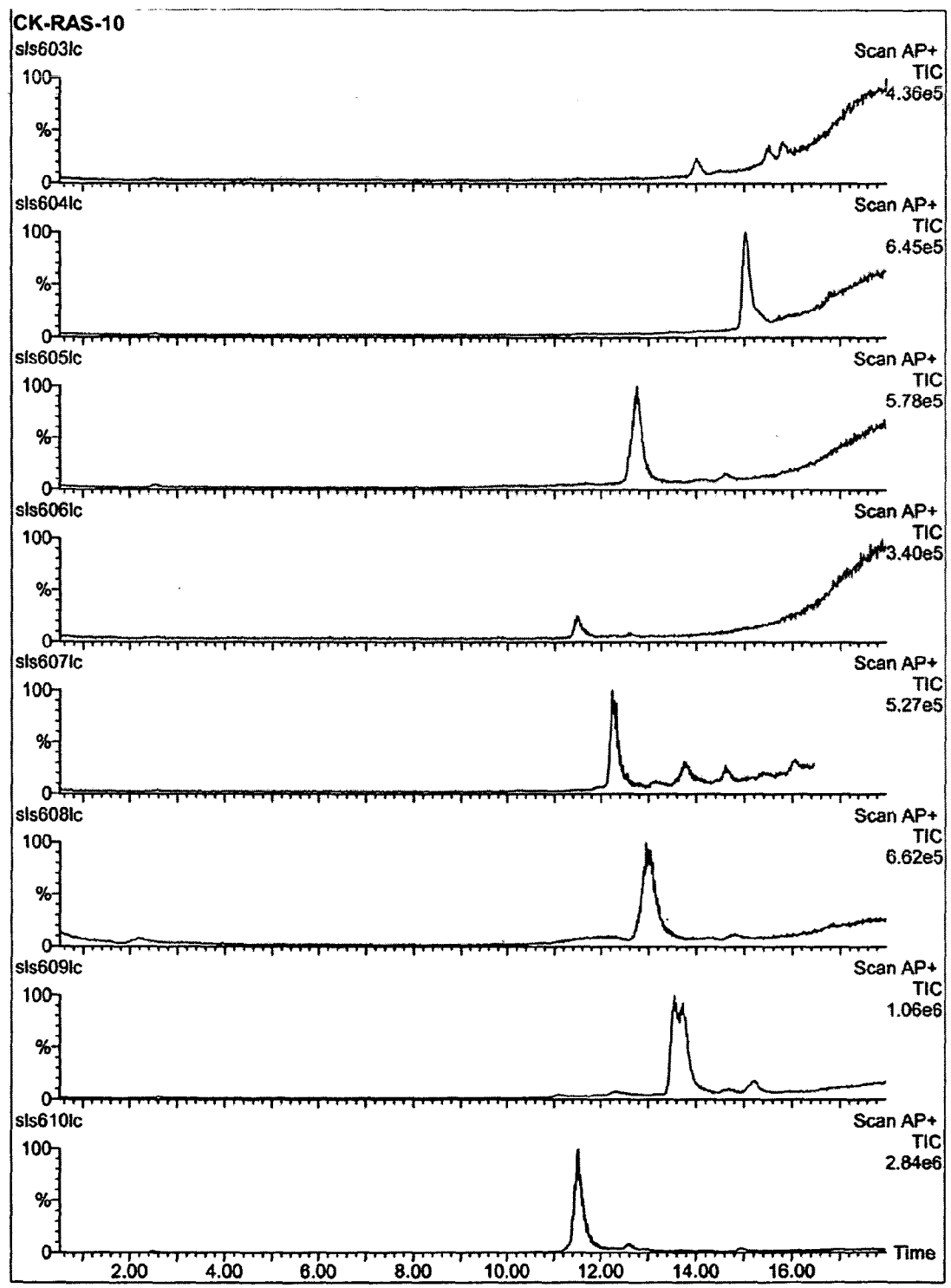
Figure 16C:
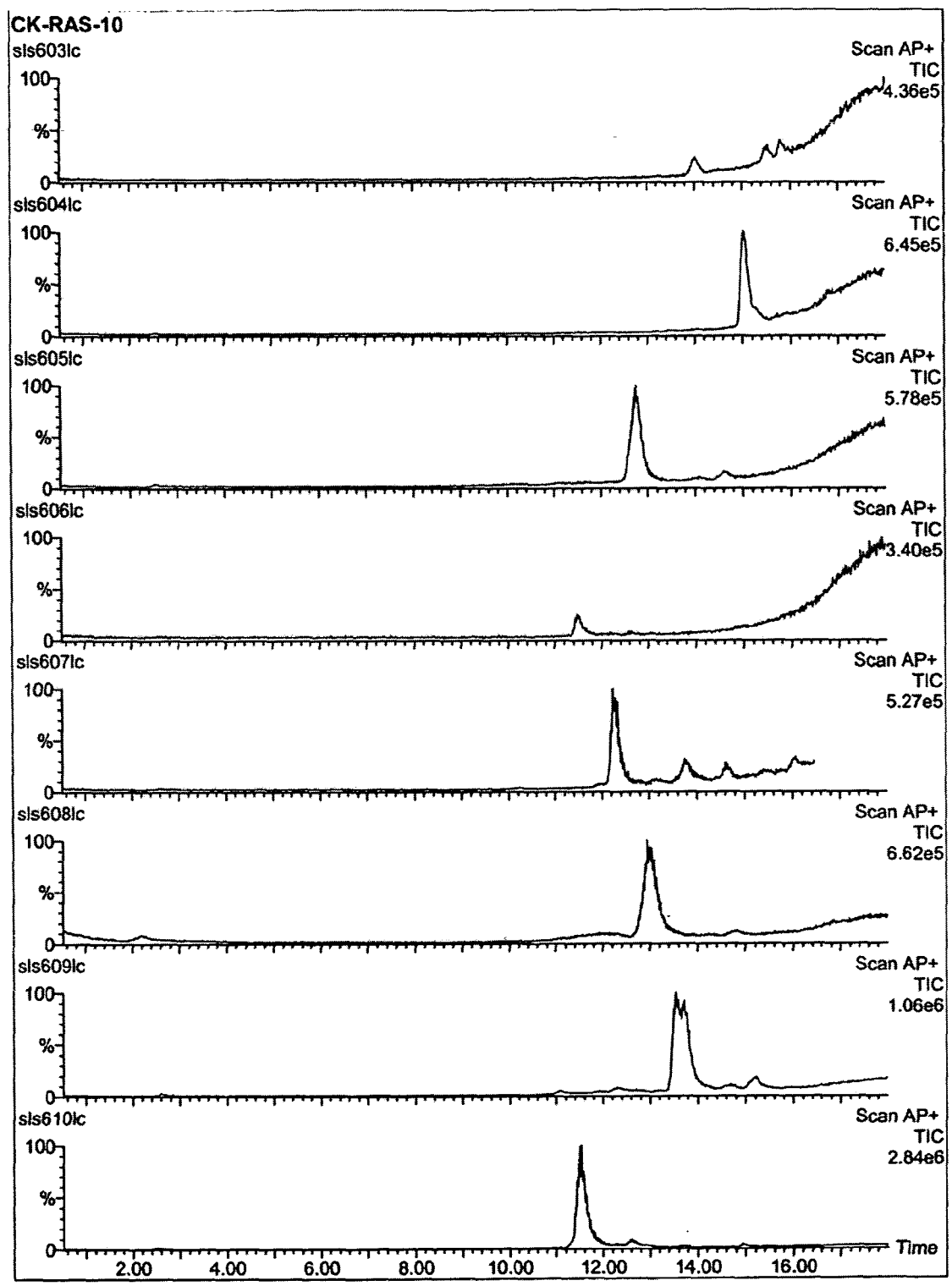
Figure 16D:
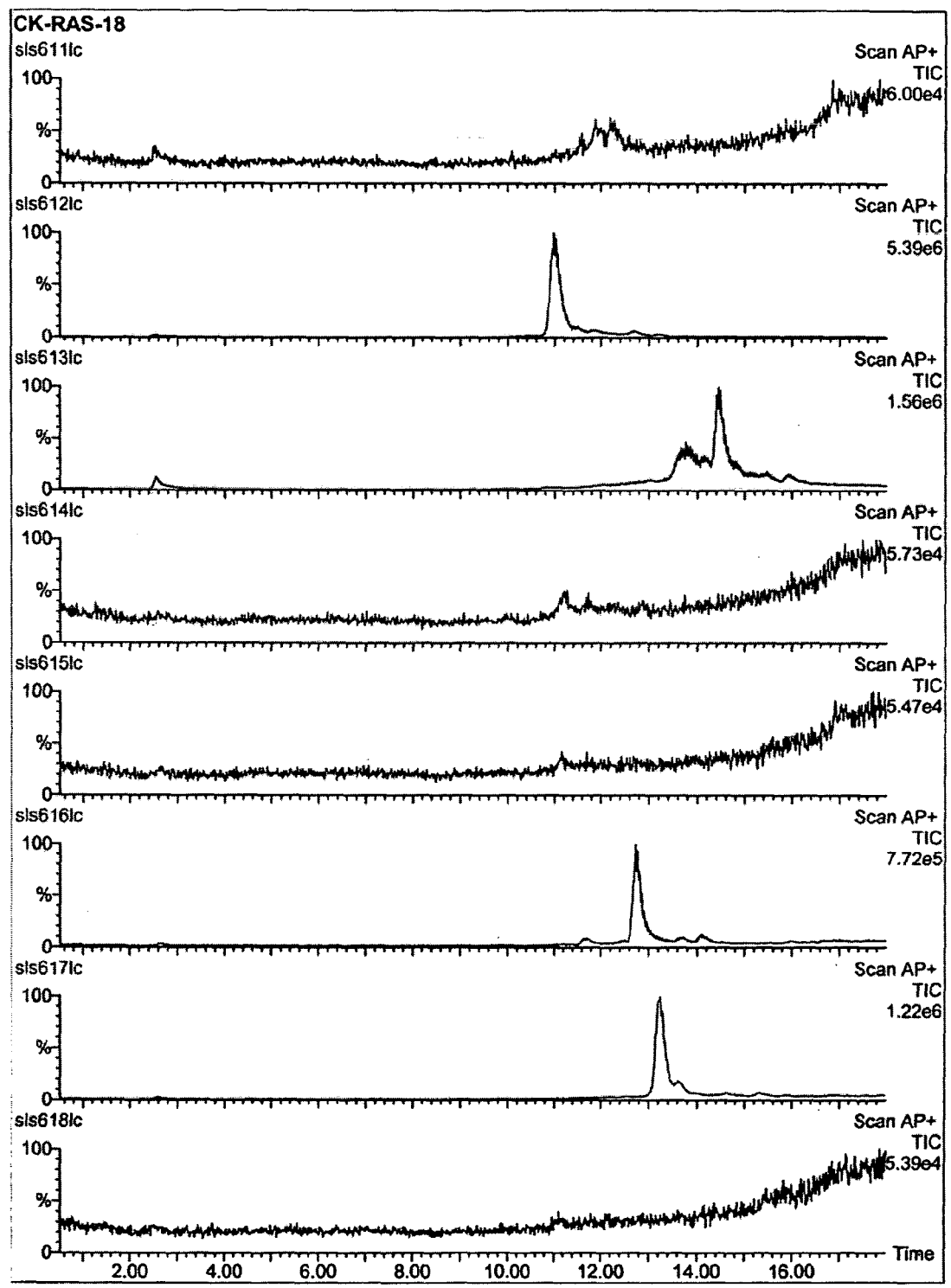
Figure 17A:
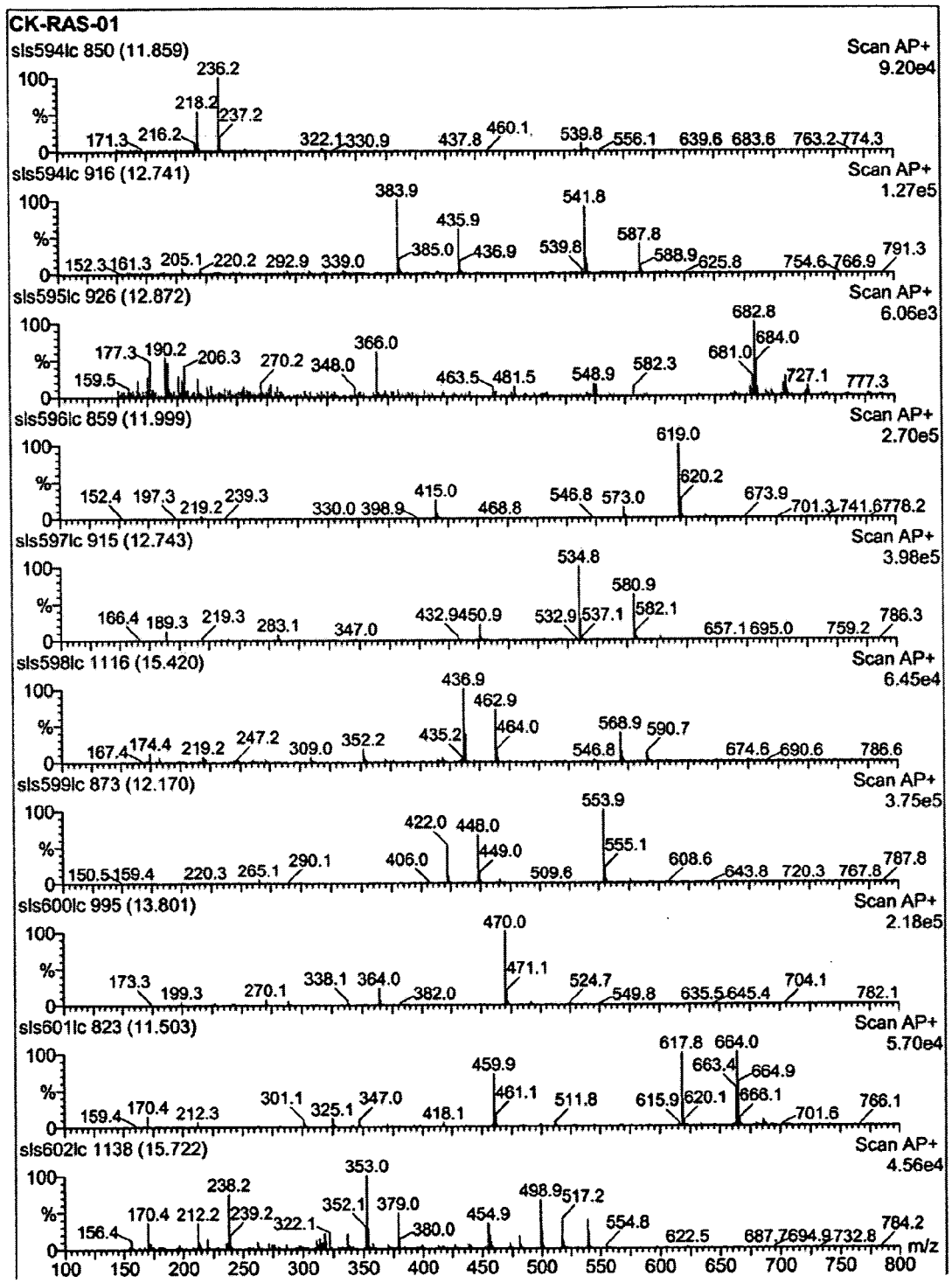
FIGS. 17A–17C depict MS traces corresponding to the LC traces of FIGS. 16A–16D.
Figure 17B:
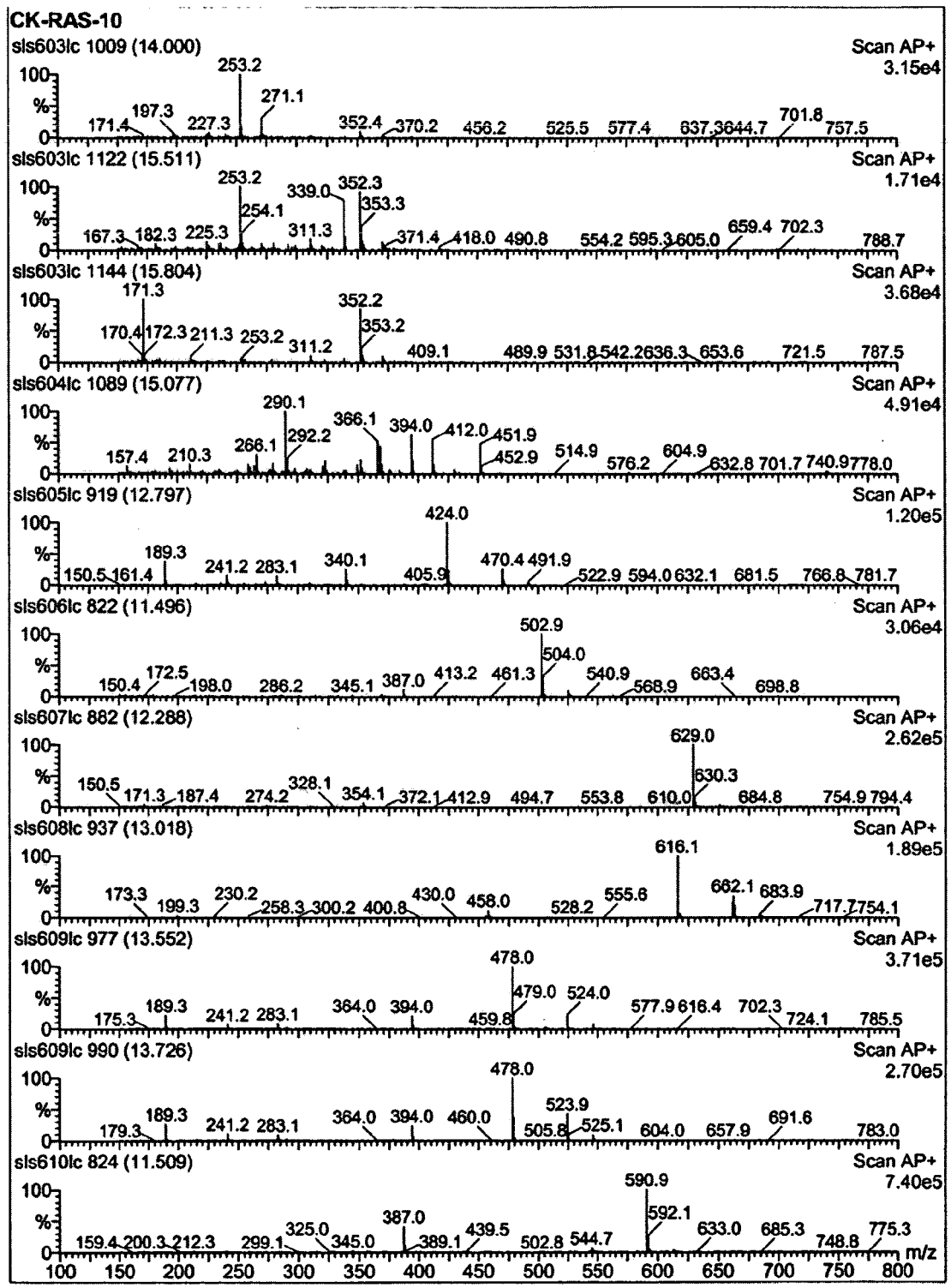
Figure 17C:
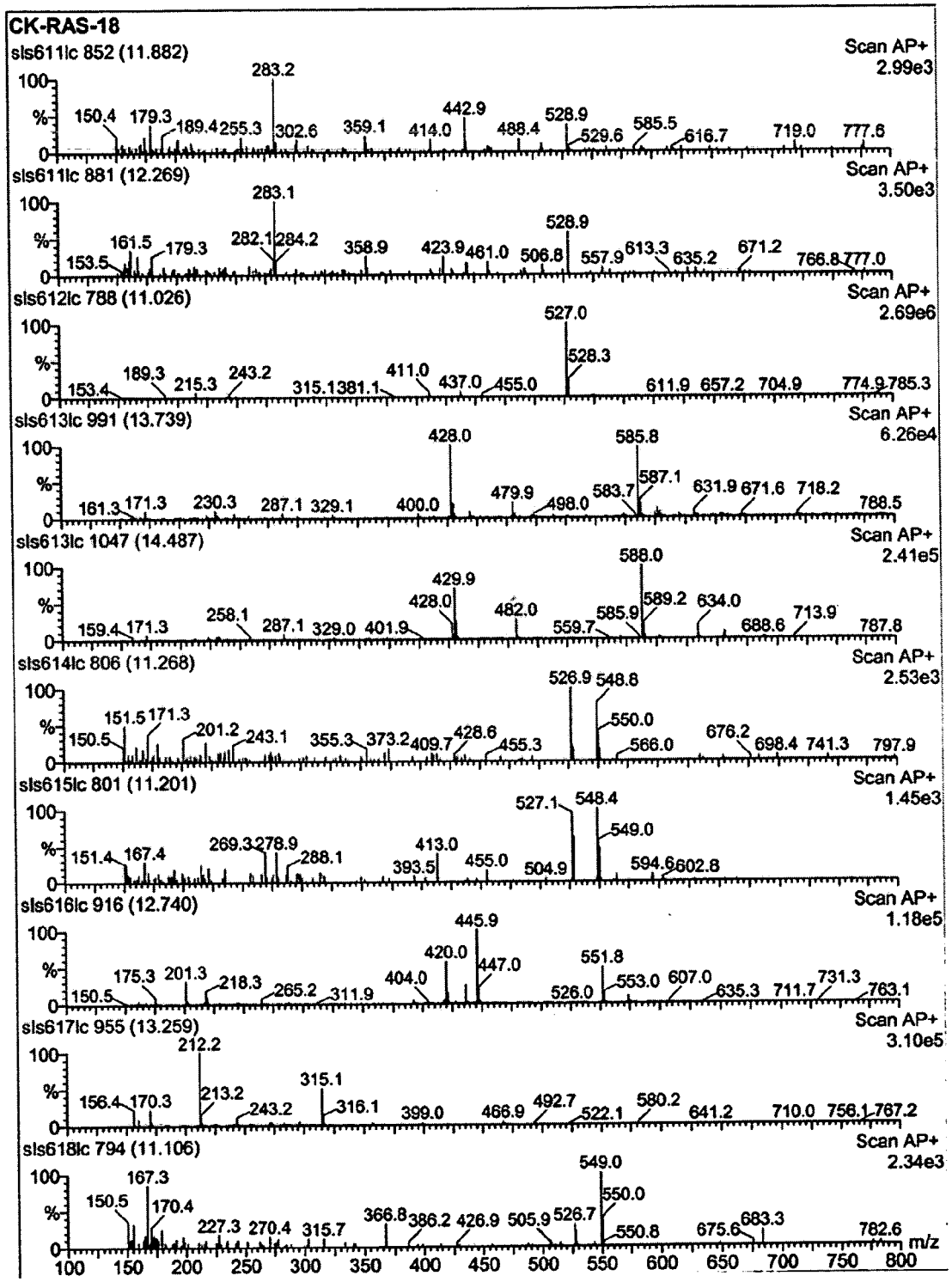
Figure 18A:
FIG. 18A depicts the array from "plate 0" probed with FKBP-Cy5.
Figure 18C:
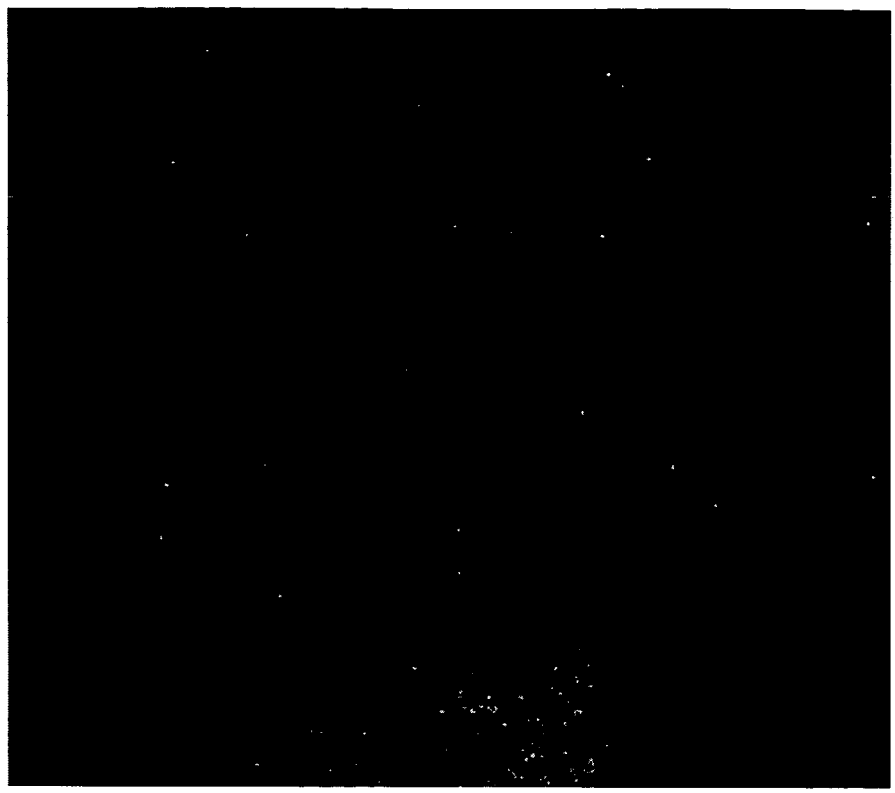
FIGS. 18B and 18C depict the array from "Plate 1" probed with FKBP-GST (red channel only).
Figure 18B:
Figure 18E:
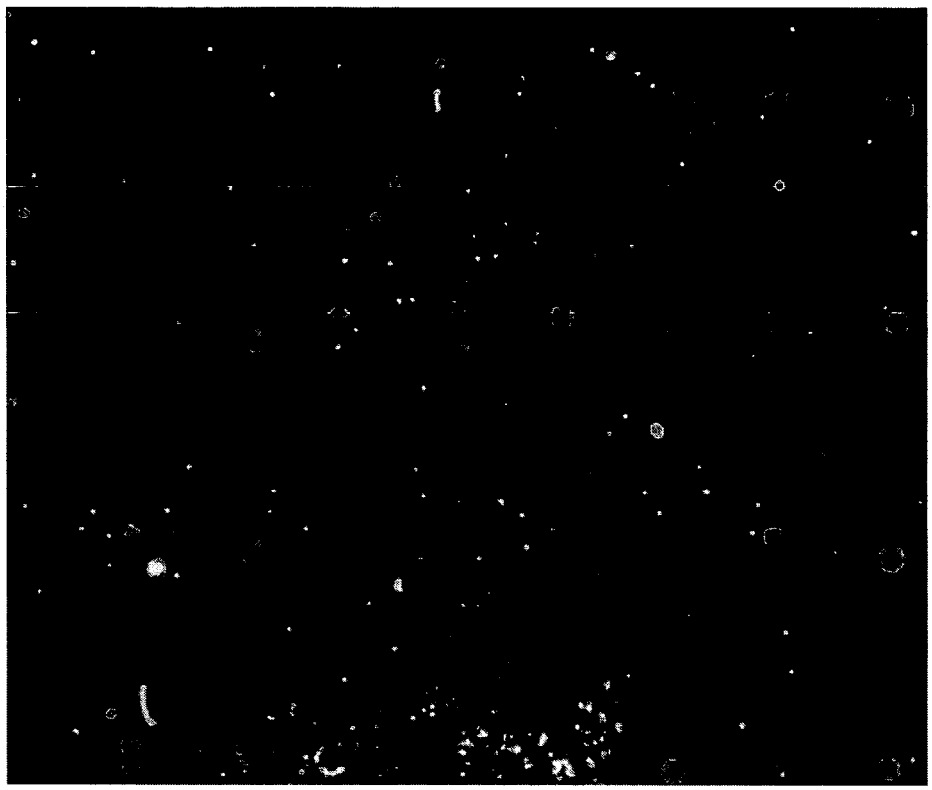
FIGS. 18D and 18E depict the array from "Plate 1" probed with FKBP-GST (red and green channels).
Figure 18D:
Figure 19A:
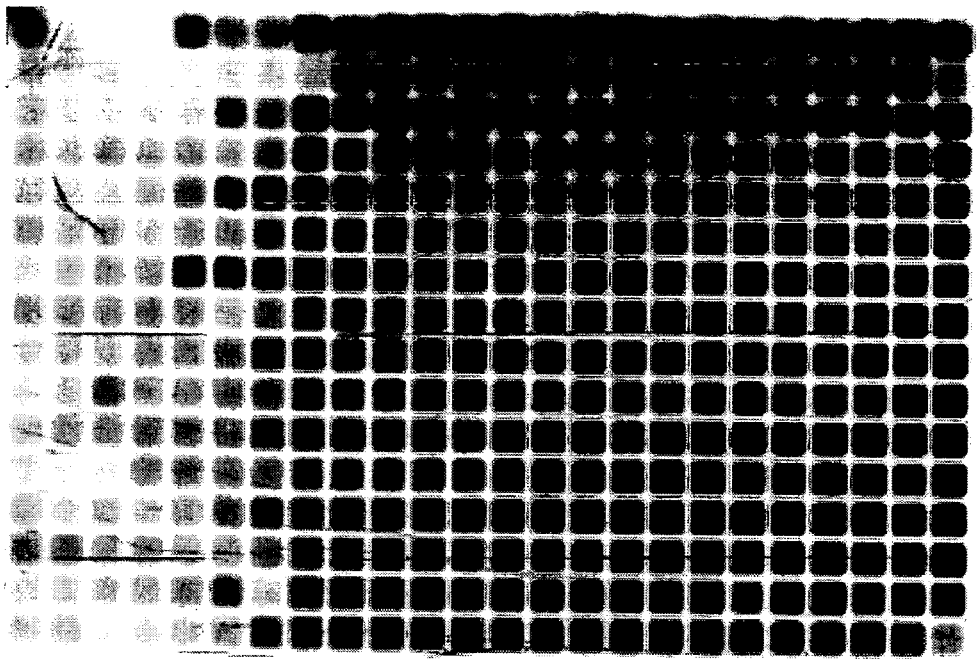
FIGS. 19A and 19B depict replicate assays of "Plate 0" by the BrdU cytoblot assay.
Figure 19B:
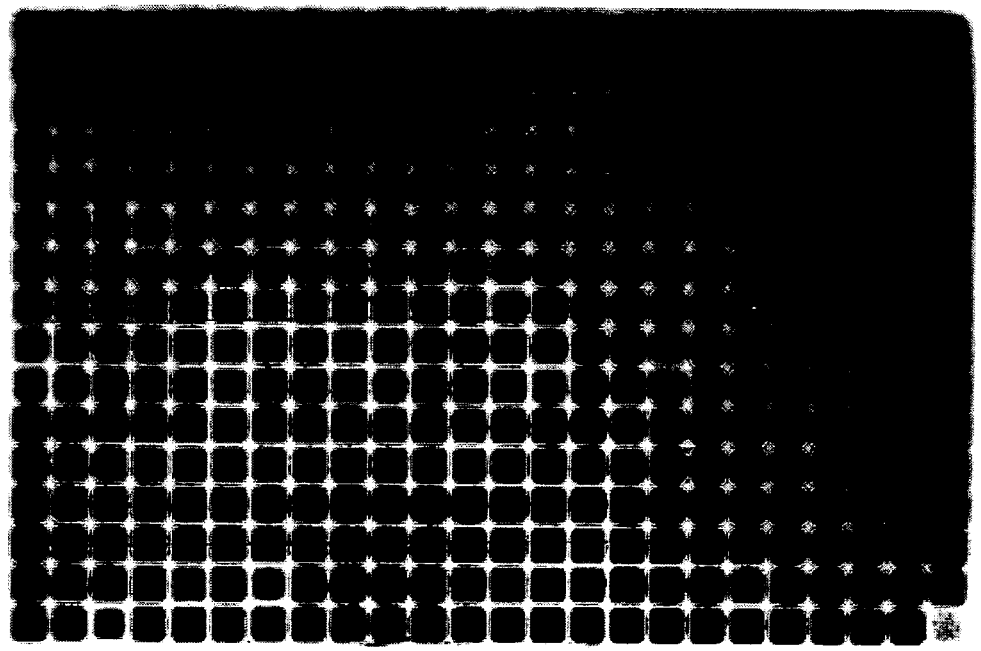
Figure 19C:
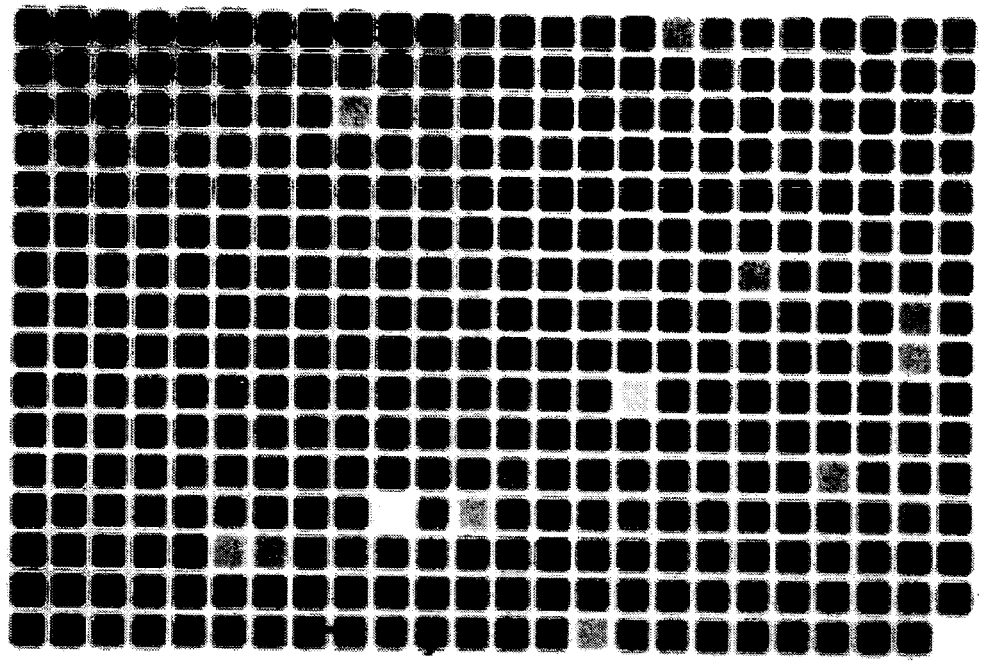
FIGS. 19C and 19D depict replicate assays of "Plate 1" by the BrdU cytoblot assay.
Figure 19D:
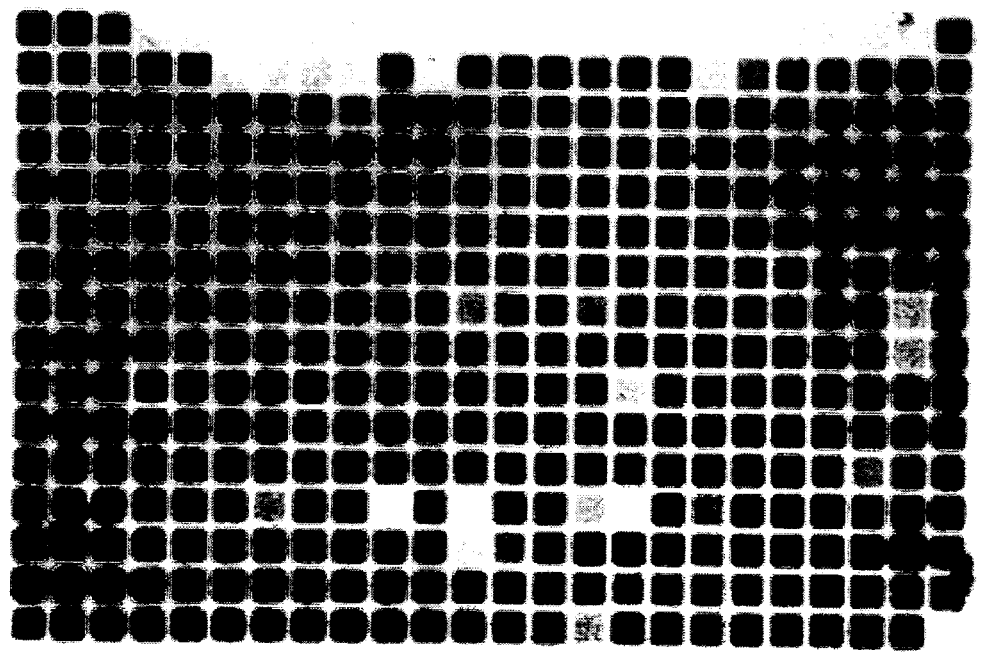
Figure 19E:
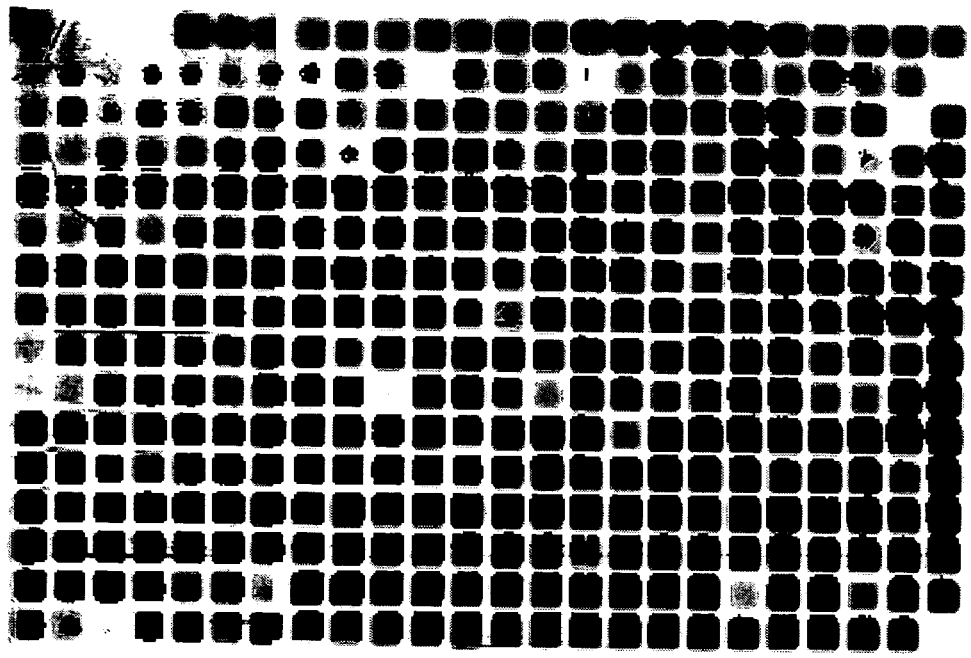
FIGS. 19E and 19F depict multiplicative overlays of the replicate "Plate 0" and "Plate 1" assays depicted in FIGS. 19A–B and FIGS. 19C–D, respectively.
Figure 19F:
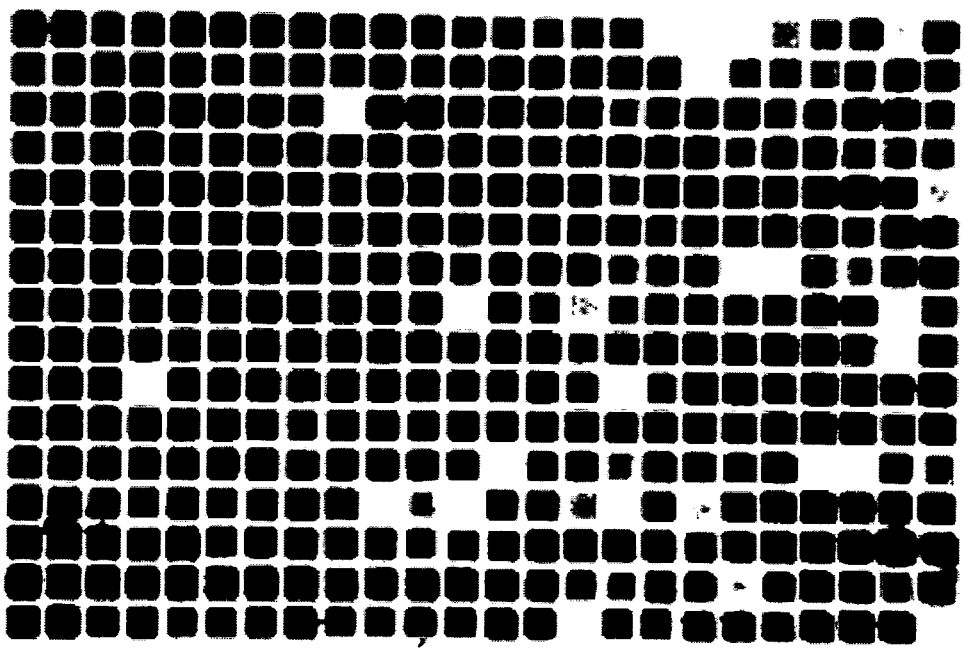
Figure 20A:
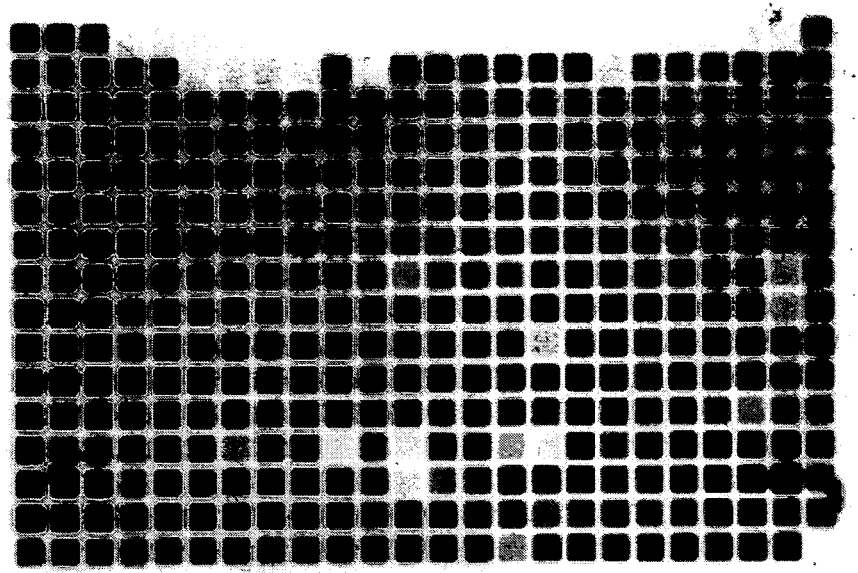
FIGS. 20A and 20B represent duplicate assays of "Plate 1".
Figure 20B:
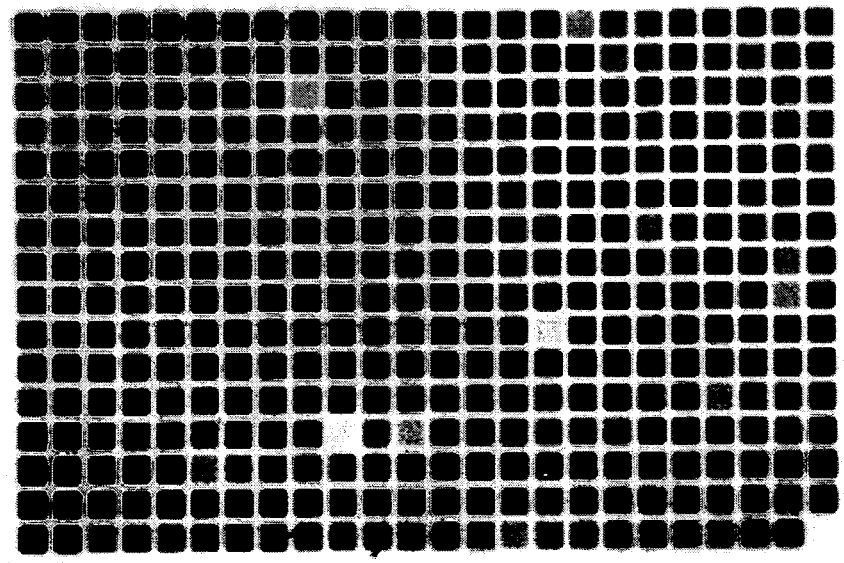
Figure 21A:
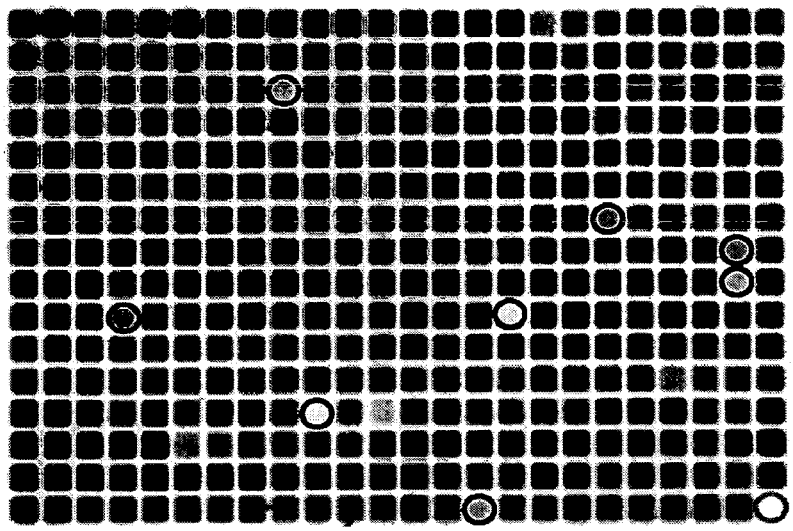
FIG. 21A depicts a 384-well-plate from a BrdU incorporation inhibition assay, identifying wells containing compounds inhibiting BrdU incorporation in cells.
Figure 21B:
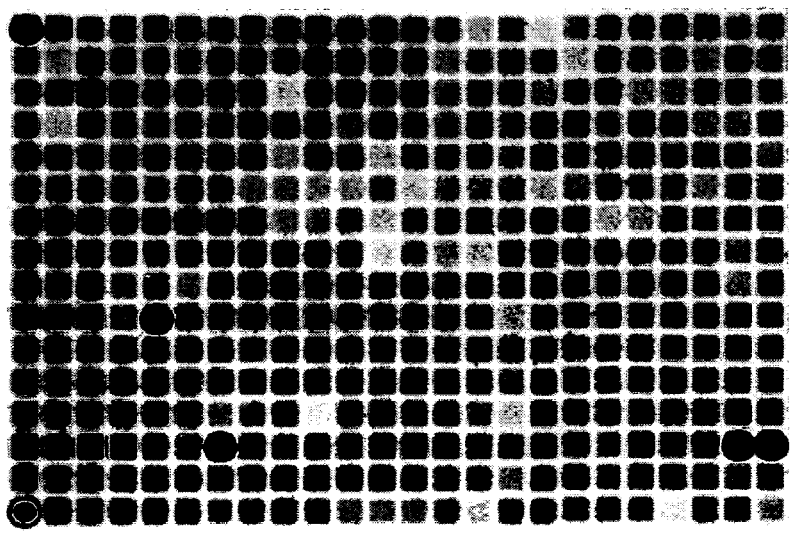
FIG. 21B depicts a 384-well-plate from a Genistein suppression assay, identifying wells containing compounds than can suppress the ability of genistein to inhibit BrdU incorporation.
Figure 22:
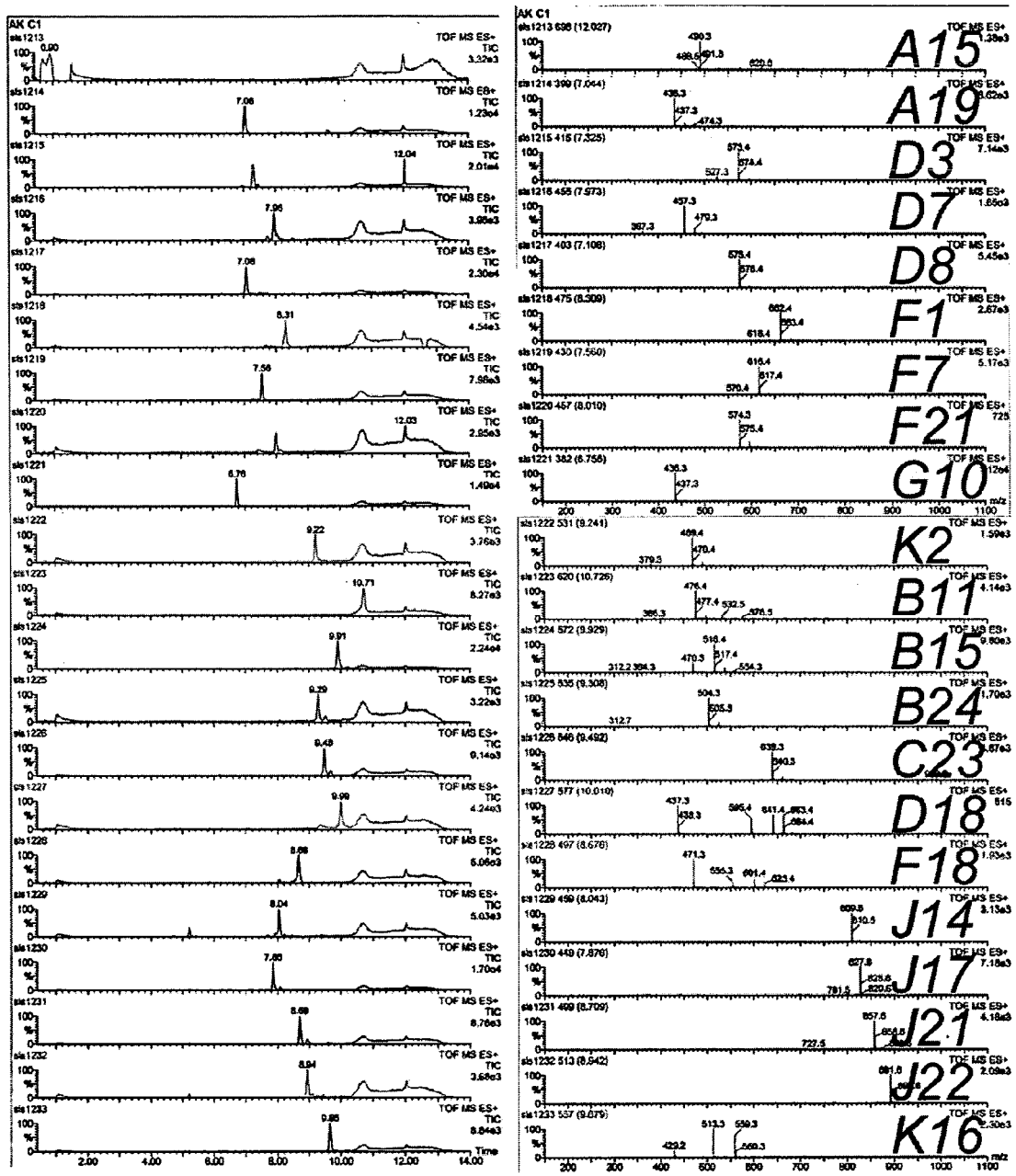
FIG. 22 depicts an example of LC and MS results from "hits" generated from cytoblot assay of exemplary inventive compounds.

The library was also screened for Eg5 inhibitory activity. The following library member was found to inhibit Eg5 (FIG. 15):

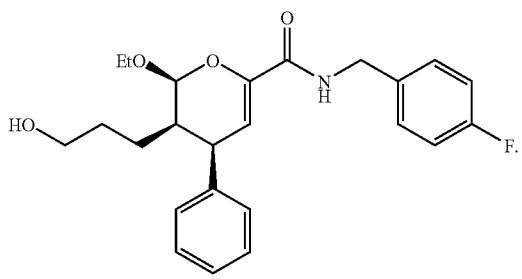

From a statistical perspective, the library of dihydropyrancarboxamides (9) was fully encoded, either chemically using chloroaromatic tags (first two diversity-generating steps), or positionally by inclusion into one of 54 pools of resin (third diversity-generating step). Our collection of decoded 'hits' was analyzed to assign statistical significance to a process of 'codon' selection, by a given assay, of particular encoded events (or combinations of encoded events) during the chemical history of the library. The formal details of this analytical process will be reported once applied to the entire collection of 4320 dihydropyrancarboxamides (9). One immediate consequence is that a consensus set of structures corresponding to a particular assay activity need not be limited to individual structures that scored as 'hits' in the assay. For example, if two codons corresponding to building blocks from two different diversity-generating steps were each strongly selected by a given assay, one might predict that a compound incorporating both moieties would yield higher potency in that assay. In the absence of additional information, we would predict such a consensus structure even if the exact compound in question was not present in the initial screen. Alternatively, if the assay in question selected against this particular combination of codons, we would uncover this 'forbidden' combination, even if each codon alone was frequently observed among structures scoring as 'hits'. Traditionally, structure-activity relationships are determined by processes ranging from an intuitive viewing of 'hit' structures to a comparison of 'hits' on the basis of existing quantitative molecular descriptors (each based on some arbitrary metric). Our analysis introduces a novel approach, whereby we require no structural information in advance of defining significant biological activity. Rather, we allow the biological system under study to dictate the requirements for its activity. Such analysis illustrates the power of annotation screens to inform chemistry, through the technology platform, in ways that can in£uence planning steps in future diversity-oriented syntheses.

CONCLUSION

A technology platform aimed at advancing chemical genetics was applied to the identification of novel dihydropyrancarboxamides with certain biological activities. The platform encompasses an optimized procedure for compound cleavage and elution from large PS beads, a novel bead arraying method, and robotic implementation of library formatting, the process by which small molecules from diversity-oriented syntheses are made accessible to chemical genetic assays. We validated this approach by successfully synthesizing, encoding, and formatting a split-pool library of dihydropyrancarboxamides (9). It is important to note that optimization of the library formatting process occurred independently of the development of chemistry required to synthesize the library. Rather, optimization of the formatting process used generic model compounds to establish parameters, while formatting the split-pool library used the output of the optimization as a general, or 'best practices', method for library realization.

By exposing each member of a diversity-oriented synthesis to multiple phenotypic and proteomic assays, we can annotate each compound in the collection in a way that is complementary to other methods of small molecule characterization, such as MS and NMR. Statistical analysis of the biological performance of an encoded collection of small molecules allows us to inform further synthetic efforts (e.g. scaled synthesis of subset libraries based on primary screening data) in ways not necessarily available by traditional structure^activity analyses. Annotation screening is a term we use to describe the generation of multiple datasets by comprehensive screening of such libraries over a range of biological outcomes. The analysis of data resulting from annotation screening comprises both the challenge and the promise of chemical genetic research.

2. Experimental

Materials and Methods

Model Resin Preparation

2-Naphthaleneethanol (6), K-methyl-2-naphthalenemethanol (7), and 2-naphthol (8) were obtained commercially (Sigma-Aldrich) and dried azeotropically prior to the loading reaction. Resin 1 was a generous gift of Max Narovlyansky and Dr. John A. Tallarico, and contains ~200 nmol Si/bead calculated based on elemental analysis, assuming that 550 μm is the average bead size in a population of beads pre-sized at 500–600 Wm. Loading reactions were performed in fritted polypropylene PD-10 columns (Amersham Pharmacia Biotech) and agitated by rocking on a Labquake™ (Barnstead Thermolyne) shaker.

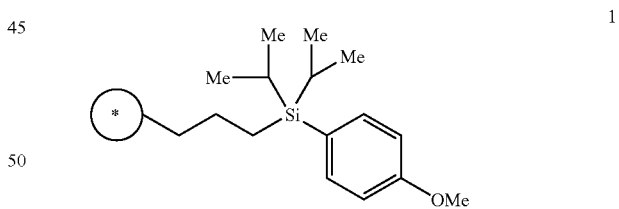

Resin samples were washed on a Vac-Man® vacuum manifold (Promega) fitted with nylon stopcocks (Bio-Rad). HPLC-grade reaction solvents (J. T. Baker) were purified by passage through two solvent columns prior to use. $Et_3N$ and 2,6-lutidene were distilled over calcium hydride. In loading reactions, bromostyrene-copolymerized beads were added to a PD-10 (Amersham Pharmacia Biotech) column, which was capped with a septum and plastic stopcock and flushed with Ar. After swelling with $CH_2Cl_2$ (10 ml), a 2.5% (v/v) solution of TMSCl in $CH_2Cl_2$ was added. The beads were suspended for 15 min and filtered with Ar pressure. The beads were washed with $CH_2Cl_2$ (3×2 min), then suspended in a solution of TfOH (6 eq.) in $CH_2Cl_2$ for 15 min, during which time Ar was bubbled gently through the reaction via a syringe. Next, the beads were rinsed with $CH_2Cl_2$ (3×2 min) under Ar and suspended in $CH_2Cl_2$. Freshly distilled 2,6-lutidine (8 eq.) and model alcohol 6, 7, or 8 (3 eq.) were successively added. The tube was capped and sealed to stand for 18 h at ambient temperature, after which the beads were filtered and rinsed with $CH_2Cl_2$ (4×3 min) and dried under house vacuum.

Cleavage and Quenching

Commercially available HF/py (Sigma-Aldrich) is approximately a 7:3 mixture of HF and pyridine, which was buffered with additional pyridine in THF solution. In manual experiments, beads were transferred individually by forceps to wells of 384-well microtiter plates (Genetix). Cleavage and quenching reagents, as well as elution solvents, were added by a P20 single-channel pipettor (Gilson). Data from 19F NMR experiments were obtained at 470.169 MHz on a Varian (Varian, Inc., http://www.varianinc.com/) AS500 (nt=128). To avoid etching of the NMR tube by HF/py solutions, samples were placed in a PTFE-FEP NMR tube liner (Wilmad-LabGlass).

HPLC Quantitation

HPLC analysis was carried out using a ThermoSeparation Products (Thermo-Finnigan) instrument with a PC1000 system controller and associated software. All samples were run on a Hypersil C18 mini-pharmaceutical column (The Nest Group) using a flow rate of 3 ml/min, an 80 s gradient of 0–99.9% $CH_3CN$ in water/0.1% trifluoroacetic acid/0.1% methanol, and diode array detection. Single peaks at 224 nm absorbance were characteristic of compounds 6 (rt=1.54 min), 7 (rt=1.54 min), and 8 (rt=1.49 min). To establish boundary conditions for detection of cleaved compounds by HPLC, standard curves were determined using pure samples of 6–8. Mock cleavage reactions (no HF present, but otherwise treated as described in the text) were carried out on resins 3–5 to determine the experimental noise for our HPLC detection method.

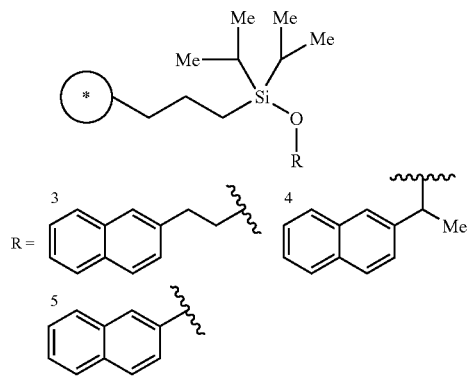

Robotic Implementation

Before bead arraying, 384-well plates (Genetix) were pre-wetted using a Multidrop 384 (Thermo-Labsystems) to dispense solvent. HF/py solutions were delivered using an Ivek multiplex controller module with linear actuator pump module (Ivek Corporation, http://www.ivek.com/) coupled to an ADM-661 automatic dispensing system with TruPath 300 controller module (Creative Automation, http://www.creativedispensing.com/), and fully contained within a Captair ductless fume hood with recirculating air filtration system (Captair LabX, http://www.erlab-dfs.com/). Automated plate handling was carried out by Twister Universal microplate handlers (Zymark Corporation, http://www.zymark.com/). Evaporation of quenched reaction mixtures was done using a GeneVac HT4 Atlas evaporator with VC3000D vapor condenser (GeneVac Technologies, http://www.genevac.co.uk/). Elution of compounds from beads into 100 μl/well 'mother plates' (Marsh), as well as formatting of 50 μl/well 'daughter plates' (Genetix), was done with a Hydra Microdispenser 384 (Robbins Scienticc Corporation, http://www.robsci.com/).

Small Molecule Microarrays

Small molecules were printed as described in P. J. Hergenrother, K. M. Depew, S. L. Schreiber, Small molecule microarrays: covalent attachment and screening of alcohol-containing small molecules on glass slides, *J. Am. Chem. Soc.* 122 (2000) 7849–7850, either with a microarray robot built as described by Dr. Pat O. Brown (http://cmgm.stanford.edu/pbrown/mguide/), or with an Omni-Grid™ multi-axis robot (GeneMachines, http://www.genemachines.com/). Briefly, slides were activated for covalent attachment of alcohols as described previously. Standard microscope slides (VWR, 48300–036) were cleaned in piranha solution (70:30 v/v solution of concentrated $H_2SO_4$ and 30% $H_2O_2$) for 16 hours at room temperature. The slides were washed extensively in dd$H_2O$ and kept in water until use. To convert to a silyl chloride surface, the slides were removed from water and dried by centrifugation. The slides were then immersed in a solution of dry THF containing 1% $SOCl_2$ and 0.1% DMF. The slides were incubated in this activating solution for 4 hours at room temperature. The slides were then removed, washed briefly in THF, and then placed onto the encased microarrayer platform under argon. Small molecules were printed as described previously. Printing was carried out using a microarraying robot, constructed in this laboratory by Dr. James Hardwick and Dr. Jeff Tong according to directions provided by Dr. Pat Brown (http://cmgm.stanford.edu/pbrown/mguide/). The microarrayer typically withdraws 250 nL from a 384-well (or 96-well) plate and repetitively delivers 1 nL to defined locations on a series of activated slides. The pins were washed for 8 seconds in acetone and dried under vacuum for 8 seconds in between each sample. The arrayer was instructed to print the samples described here approximately 500 μm apart. Following printing, the slides were allowed to stand at ambient temperature for 12 hours. The slides were then washed for 2 hours in DMF, 1 hour in THF, and 1 hour in ethanol. Slides were dried by centrifugation and were at room temperature under vacuum until use.

(His)6-FKBP12 was purified to homogeneity as described in G. MacBeath, A. N. Koehler, S. L. Schreiber, Printing small molecules as microarrays and detecting protein-ligand interactions en masse, *J. Am. Chem. Soc.* 121 (1999) 7967–7968. Cy5-labeled protein was prepared using FluoroLink™ monofunctional reactive dye (Amersham Pharmacia Biotech) according to the manufacturer's protocol. Fluorescence detection of binding events was monitored using an ArrayWoRx biochip reader (Applied Precision, http://www.api.com/).

N-terminal His-tagged FKBP12 was expressed using the T5 expression plasmid pQE-30-FKBP12 (3757 bp) in M15 [pREP4] (Qiagen) purified to homogeneity as described previously. A starter culture was prepared by inoculating 5 mL LB medium supplemented with 100 μg/mL sodium ampicillin and 50 μg/mL kanamycin from a single colony and grown for 16 hours at 37° C. The cells were subcultured into 500 mL of the same medium at an initial $OD_{600}$ of 0.1. The culture was grown at 37° C. up to an $OD_{600}$ of 0.8. The culture was cooled to room temperature and isopropyl 1-thio-β-D-galactopyranoside (IPTG) was added to a final concentration of 1 mM. After a 16 hour induction at 30° C., the cells were harvested and frozen at −80° C. for 24 hours. The cell pellet was resuspended in 20 mL of PBS buffer supplemented with 10% (v/v) glycerol and a protease inhibitor cocktail mini-tablet (Boerhinger Mannheim). Cells were lysed by addition of 1 mg lysozyme per gram of wet cell pellet. The suspension was incubated on ice for 1 hour and followed by a 4 minute incubation at 37° C. with gentle mixing. The lysate was then kept on ice for 10 minutes. The lysate was clarified by centrifugation (28,000 g, 30 minutes, 4° C.) and loaded onto a column packed with 5 mL of Ni—NTA (Qiagen) that had been equilibrated in PBS. The column was washed with 50 mL of PBS buffer containing 10 mM imidazole. Protein bound to the column was eluted with PBS buffer containing 250 mM imidazole. The sample was dialyzed against PBS at 4° C. Cy5-labeled (His)6-FKBP12 was prepared using FluoroLink™ monofunctional reactive dye (Amersham Pharmacia Biotech) according to the manufacturer's protocol. Slides were blocked for 1 hour by incubation with PBST (PBS buffer containing 0.1% Tween-20) containing 3% BSA. After a brief rinse with PBST, fluorescently labeled protein was added a concentration of 1 µg/mL in PBST supplemented with 1% BSA. Slides were incubated with labeled protein for 30 minutes at room temperature. Slides were then washed in PBST for 3 minutes three times and dried by centrifugation. Slides were then scanned using an ArrayWoRx slide scanner (Applied Precision) at a resolution of 5 µm per pixel. The following filter sets were employed: Cy5 excitation/emission (1 second exposure) and Cy3 excitation/emission (1 second exposure).

Cell-based Assays

Transfer of stock solutions of 10 into assay plates (Nunc) was done using a VP386 384-pin MultiBlot™ replicator (VpP Scientific, http://www.vp-scientific.com/). Cell culture methods and the BrdU assay protocol were carried out as described in B. R. Stockwell, S. J. Haggarty, S. L. Schreiber, High-throughput screening of small molecules in miniaturized mammalian cell-based assays involving post-translational modifications, Chem. Biol., 6:71–83, 1999. Detection of assay results was carried out using X-oMAT AR film (Kodak), and multiplicative overlays of digitally scanned replicate films were prepared using Photoshop 5.0 (Adobe Systems). The Multidrop 384 liquid dispenser (Labsystems) was used for all liquid additions, and a 24-channel wand (V&P Scientific) attached to a house vacuum source was used for all liquid aspirations. Two thousand A549 cells were seeded per well of a 384-well plate (Nalge Nunc, white, tissue culture treated) in Dulbecco's modified Eagle medium (DMEM) supplemented with 10% fetal bovine serum (FBS). Immediately upon seeding, 50 nL compound from the RAS combinatorial library was pin-transferred, one compound per well, from a 5-mM stock solution in DMSO to a final concentration of 5 µM. After 24 hours at 37° C. with 5% $CO_2$, 10 µL of a 10× stock of bromodeoxyuridine (BrdU) in DMEM+10% FBS was added, for a final concentration of 10 µM BrdU. The cells were incubated for 4 hours at 37° C. with 5% $CO_2$, cooled on ice for 15 minutes, and fixed in 50 µL 70% ethanol/30% phosphate buffered saline (PBS). All subsequent steps were performed at 4° C. Cells were washed with 90 µL cold PBS, incubated in 25 µL 2 M HCl/0.5% Tween-20 in ddH20 for 20 minutes at room temperature, and incubated instantly in 90 µL 10% 2 M NaOH/90% Hanks Buffered Salt Solution (HBSS; Gibco BRL). Cells were washed twice with 90 µL HBSS and blocked with 75 µL PBSTB (PBS, 0.1% Tween-20, 3% bovine serum albumin). Subsequently, 20 µL antibody solution, consisting of 0.5 µg/mL mouse anti-BrdU (Pharmingen), diluted 1:1000 in PBSTB, and anti-mouse IgG conjugated to horseradish peroxidase (HRP; Amersham), diluted 1:2000 in PBSTB, was added to each well. After overnight incubation at 4° C., wells were washed twice in 90 µL PBS and detected with 20 µL HRP substrate solution (ECL detection; Amersham). Film (X-OMAT AR; Kodak) was placed on top of the plates in a darkroom and developed after one to five minutes with a Kodak M35A X-OMAT processor.

Eg5 Inhibition

Cloning and Expression of Eg5 Constructs

Coding regions for the expression of C-terminally $His_6$-tagged constructs of human Eg5 were generated by polymerase chain reaction using a pBluescript template containing full length human Eg5 [23] and the following primers: a common N-terminal primer 5'-GCAACGATTAATATG-GCGTCGCAGCCAAATTCGTCTGCGAAG and specific C-teminal primers; 5'-GCAACGCTCGAGTCAGT GATGATGGTGGTGATGCTGATTCACTTCAGGCTTA TTCAATAT (hEg5–367H), 5'-GCAACGCTCG AGTCAGTGATGATGGTGGTGATGCATGACTCTAAA ATTTTCTTCAGAAAT (hEg5–405H), 5'-GCAACGCTC-GAGTCAGTGATGATGGTGGTGATGTGTAACCCTATT CAGCTCCTCCTCAACAGC (hEg5–437H). The PCR products were ligated into a pRSETa backbone. Eg5 protein constructs were expressed and purified as described previously [Woehike, G., Ruby, A. K., Hart, C. L., Ly, B., Hom-Booher, N. and Vale, R. D. (1997) Microtubule interaction site of the kinesin motor. Cell. 90, 207–216]. The Eg5 containing fractions from Superose 6 sizing chromatography were pooled, supplemented with sucrose to 10% (w/v) as a cryo-protectant, flash frozen in liquid nitrogen, and stored at −80° C. The concentration of Eg5 was measured using the Edelhoch [Pace, C. N., Vajdos, F., Fee, L., Grimsley, G. and Gray, T. (1995) How to measure and predict the molar absorption coefficient of a protein. Protein Science. 4(11), 2411–2423] as well as Bradford techniques.

Stead-state Eg5 ATPase Assay

We measured the ATPase activity of Eg5 in vitro using an assay that couples the hydrolysis of ATP to the oxidation of NADH [Woehike, G., Ruby, A. K., Hart, C. L., Ly, B., Hom-Booher, N. and Vale, R. D. (1997) Microtubule interaction site of the kinesin motor. Cell. 90, 207–216]. In the assay, the concentration of ATP remains constant however, the decrease in NADH fluorescence is a convenient measure of the amount of ATP turned over. Our typical reaction buffer contained 25 mM Potassium Chloride, 25 mM Potassium PIPES (6.90), 2 mM Magnesium Chloride, 1 mM Potassium Phosphoenol Pyruvate, 200 µM di-Potassium NADH, 1 mM Dithiothreitol, 10 µM Taxol, 9 U/ml Lactate Dehydrogenase, 1 U/ml Pyruvate Kinase and taxol-stabilized microtubules as needed. To measure the ATPase activity in a reaction, the assay buffer was supplemented with 1 mM $MgCl_2$:ATP (1:1), 1 µM microtubules and 40 nM Eg5-367H. Time-points for NADH fluorescence were measured in 384 well black plates (NalgeneNUNC) by a Wallac Victor$^2$ 1420 multilabel counter, umbelliferone filter set (excitation: 355 nm, emission: 420 nm), and the steady-state rate of fluorescence decay was calculated using a linear fit by Microsoft Excel. The coupling activity of the enzyme system was 100-fold greater than the Eg5 ATPase activity used in our experiments. To calculate $IC_{50}$ values for enantiomerically pure monastrol in the presence or absence of microtubules, we fit enzyme velocity as a function of monastrol concentration to the equation: $V = V_{residual} + (V_{ihibited} \times IC_{50})/(IC_{50} + [monastrol])$. Enzyme velocities were fit as a function of microtubule or ATP concentrations at particular monastrol concentration to the equation: $V=([\text{substrate}] \times V_{max})/([\text{substrate}]+K_m)$.

Cell Culture Methods

BS-C-1 cells were cultured on glass coverslips as described previously [Cramer L P, Mitchison T J, Theriot J A. (1994) Actin-dependent motile forces and cell motility. Curr. Opin. Cell. Biol. 6(1), 82–6]. AB9 Zebrafish cells [Hukreide N A, Joly L, Tsang M, et. al. (1999) Radiation hybrid mapping of the zebrafish genome. Proc. Natl. Acad. Sci. 96, 9745–9750] were grown in DMEM at 28° C. in a 5% $CO_2$ atmosphere on polylysine coated coverslips. Cells were grown to 50% confluence, rinsed with warm PBS, and incubated an additional 6 hours in growth medium supplemented with 20 mM Potassium HEPES and compound at a final DMSO concentration of 0.2%. Cells were fixed with 1% formaldehyde in 1× Tris Buffered Saline containing 0.1% Triton X-100 as detergent. Cells were so-stained with Alexa-488-conjugated goat anti-mouse antibodies, DM-1A, a mouse antibody against α-tubulin (Sigma), and Hoechst dye. We counted mono-astral, mitotic, and interphase cells by visual inspection to calculate the percentage of monastral cells at each drug concentration.

What is claimed is:

1. A compound having the structure:

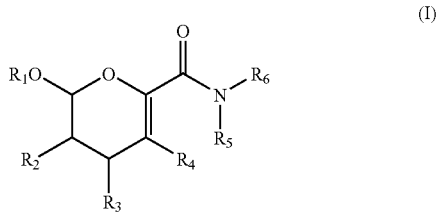

(I)

or pharmaceutically acceptable salt, ester, or salt of such ester;

wherein $R_1$, $R_2$ and $R_4$ are each independently hydrogen or an aliphatic, heteroaliphatic, aryl, heteroaryl, alkylaryl or alkylheteroaryl moiety;

$R_3$ is an aryl moiety having one of the following structures:

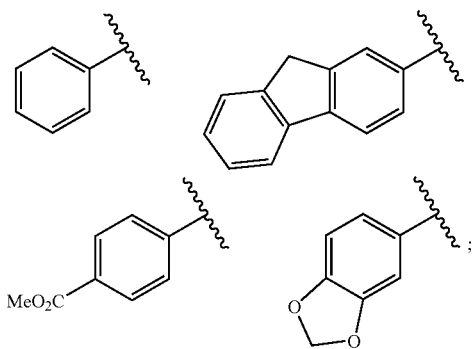

$R_5$ and $R_6$ are each independently hydrogen or an aliphatic, heteroaliphatic, aryl, heteroaryl, alkylaryl, or alkylheteroaryl moiety, and wherein $R_5$ and $R_6$, taken together, may form a cyclic aliphatic, heteroaliphatic, aliphatic(aryl), heteroaliphatic(aryl), aliphatic(heteroaryl) or heteroaliphatic(heteroaryl) moiety, or an aryl or heteroaryl moiety;

wherein each of the foregoing aliphatic and heteroaliphatic moieties may be substituted or unsubstituted, cyclic or acyclic, saturated or unsaturated or linear or branched; and each of the foregoing aryl, heteroaryl, alkylaryl or alkylheteroaryl moieties may be substituted or unsubstituted.

2. The compound of claim 1, wherein the compound has the structure (II):

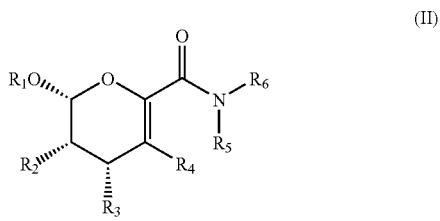

(II)

or pharmaceutically acceptable salt, ester, or salt of such ester;

wherein $R_1$, $R_2$ and $R_4$ are each independently hydrogen or an aliphatic, heteroaliphatic, aryl, heteroaryl, alkylaryl or alkylheteroaryl moiety;

$R_3$ is an aryl moiety having one of the following structures:

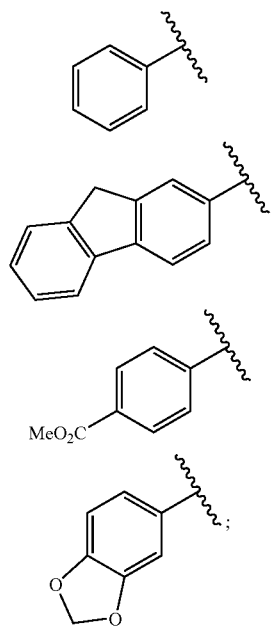

$R_5$ and $R_6$ are each independently hydrogen or an aliphatic, heteroaliphatic, aryl, heteroaryl, alkylaryl, or alkylheteroaryl moiety, and wherein $R_5$ and $R_6$, taken together, may form a cyclic aliphatic, heteroaliphatic, aliphatic(aryl), heteroaliphatic(aryl), aliphatic(heteroaryl) or heteroaliphatic(heteroaryl) moiety, or an aryl or heteroaryl moiety;

wherein each of the foregoing aliphatic and heteroaliphatic moieties may be substituted or unsubstituted, cyclic or acyclic, saturated or unsaturated or linear or branched; and each of the foregoing aryl, heteroaryl, alkylaryl or alkylheteroaryl moieties may be substituted or unsubstituted.

3. The compound of claim 1, wherein $R^1$ is hydrogen or an alkyl, heteroalkyl, aryl or heteroaryl moiety substituted with Z, wherein Z is hydrogen, —$(CH_2)_qOR^Z$, —$(CH_2)_q SR^Z$, —$(CH_2)_qN(R^Z)_2$, —(C=O)$R^Z$, —(C=O)N$(R^Z)_2$, or an aliphatic, heteroaliphatic, aryl, heteroaryl, -(aliphatic)aryl, -(aliphatic)heteroaryl, -(heteroaliphatic)aryl, or -(heteroaliphatic)heteroaryl moiety, wherein q is 0–4, and wherein each occurrence of $R^Z$ is independently hydrogen, a protecting group, a solid support unit, or an aliphatic, heteroaliphatic, aryl, heteroaryl, -(aliphatic)aryl, -(aliphatic)heteroaryl, -(heteroaliphatic)aryl, or -(heteroaliphatic)heteroaryl moiety; wherein each of the foregoing alkyl or heteroalkyl moieties may be substituted or unsubstituted, linear or branched, cyclic or acyclic, saturated or unsaturated; and wherein each of the foregoing aryl, heteroaryl, -(alkyl)aryl, -(alkyl)heteroaryl, -(heteroalkyl)aryl, or -(heteroalkyl)heteroaryl moieties may be substituted or unsubstituted.

4. The compound of claim 3, wherein $R^1$ is hydrogen, lower alkyl, a substituted or unsubstituted phenyl or -(lower alkyl)phenyl moiety, —$(CH_2)_nOR^Z$, —$[(CH_2)_nO]_mR^Z$, —$(CH_2)_n$—Ar—$(CH_2)_mOR^Z$; wherein n and m are each independently integers from 1–6, Ar represents a substituted or unsubstituted aryl or heteroaryl moiety, and $R^Z$ is independently hydrogen, a protecting group, a solid support unit, or an aliphatic, heteroaliphatic, aryl, heteroaryl, -(aliphatic)aryl, -(aliphatic)heteroaryl, -(heteroaliphatic)aryl, or -(heteroaliphatic)heteroaryl moiety; wherein each of the foregoing alkyl or heteroalkyl moieties may be substituted or unsubstituted, linear or branched, cyclic or acyclic, saturated or unsaturated; and wherein each of the foregoing aryl, heteroaryl, -(alkyl)aryl, -(alkyl)heteroaryl, -(heteroalkyl)aryl, or -(heteroalkyl)heteroaryl moieties may be substituted or unsubstituted.

5. The compound of claim 4, wherein $R^1$ is hydrogen, ethyl, or has one of the structures:

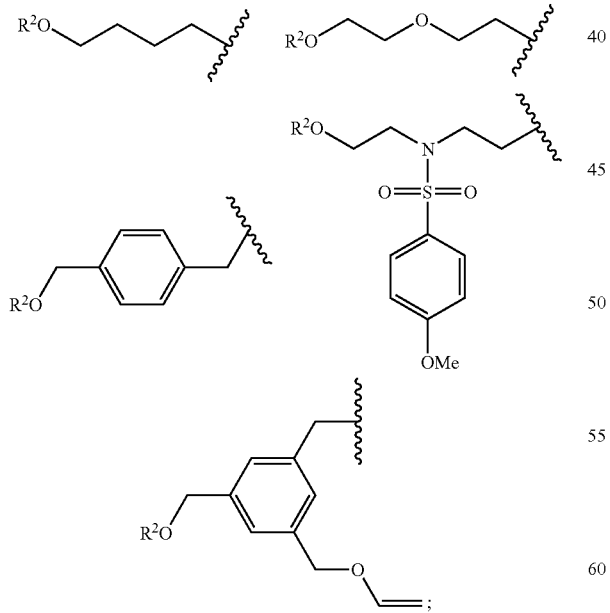

$R^z$ is as defined in claim 4.

6. The compound of claim 1, wherein $R^2$ is hydrogen or an alkyl, heteroalkyl, aryl or heteroaryl moiety substituted with Z, wherein Z is hydrogen, —$(CH_2)_qOR^Z$, —$(CH_2)_q SR^Z$, —$(CH_2)_qN(R^Z)_2$, —(C=O)$R^Z$, —(C=O)N$(R^Z)_2$, or an aliphatic, heteroaliphatic, aryl, heteroaryl, -(aliphatic)aryl, -(aliphatic)heteroaryl, -(heteroaliphatic)aryl, or -(heteroaliphatic)heteroaryl moiety, wherein q is 0–4, and wherein each occurrence of $R^Z$ is independently hydrogen, a protecting group, a solid support unit, or an aliphatic, heteroaliphatic, aryl, heteroaryl, -(aliphatic)aryl, -(aliphatic)heteroaryl, -(heteroaliphatic)aryl, or -heteroaliphatic)heteroaryl moiety; wherein each of the foregoing alkyl or heteroalkyl moieties may be substituted or unsubstituted, linear or branched, cyclic or acyclic, saturated or unsaturated; and wherein each of the foregoing aryl, heteroaryl, -(alkyl)aryl, -(alkyl)heteroaryl, -(heteroalkyl)aryl, or -(heteroalkyl)heteroaryl moieties may be substituted or unsubstituted.

7. The compound of claim 6, wherein $R^2$ is hydrogen, lower alkyl, a substituted or unsubstituted phenyl or -(lower alkyl)phenyl moiety, —$(CH_2)_nOR^Z$, —$[(CH_2)_nO]_mR^Z$, —$(CH_2)_n$—Ar—$(CH_2)_mOR^Z$; wherein n and m are each independently integers from 1–6, Ar represents a substituted or unsubstituted aryl or heteroaryl moiety, and $R^Z$ is independently hydrogen, a protecting group, a solid support unit, or an aliphatic, heteroaliphatic, aryl, heteroaryl, -(aliphatic)aryl, -(aliphatic)heteroaryl, -(heteroaliphatic)aryl, or -(heteroaliphatic)heteroaryl moiety; wherein each of the foregoing alkyl or heteroalkyl moieties may be substituted or unsubstituted, linear or branched, cyclic or acyclic, saturated or unsaturated; and wherein each of the foregoing aryl, heteroaryl, -(alkyl)aryl, -(alkyl)heteroaryl, -(heteroalkyl)aryl, or -(heteroalkyl)heteroaryl moieties may be substituted or unsubstituted.

8. The compound of claim 6, wherein $R^2$ is hydrogen or has one of the structures:

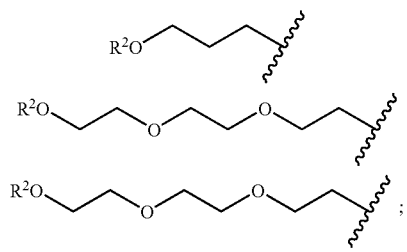

wherein $R^z$ is as defined in claim 6.

9. The compound of claim 1, wherein $R^4$ is hydrogen or an alkyl, heteroalkyl, aryl, heteroaryl, -(alkyl)aryl, -(alkyl)heteroaryl, -(heteroalkyl)aryl, or -heteroalkyl)heteroaryl moiety; wherein each of the foregoing alkyl or heteroalkyl moieties may be substituted or unsubstituted, linear or branched, cyclic or acyclic, saturated or unsaturated; and wherein each of the foregoing aryl, heteroaryl, -(alkyl)aryl, -(alkyl)heteroaryl, -(heteroalkyl)aryl, or -heteroalkyl)heteroaryl moieties may be substituted or unsubstituted.

10. The compound of claim 9, wherein $R^4$ is hydrogen alkyl or heteroalkyl.

11. The compound of claim 1, wherein $R^5$ and $R^6$ are each independently hydrogen or an alkyl, heteroalkyl, aryl, heteroaryl, -(alkyl)aryl, -(alkyl)heteroaryl, -(heteroalkyl)aryl, or -(heteroalkyl)heteroaryl moiety; or wherein $R^5$ and $R^6$, taken together, form a substituted or unsubstituted, saturated or unsaturated cyclic moiety comprising 5–12 carbon atoms, 0–5 oxygen atoms, 0–5 sulfur atoms and 1–5 nitrogen atoms; and wherein each of the foregoing alkyl or heteroalkyl moieties may be substituted or unsubstituted, linear or branched, cyclic or acyclic, saturated or unsaturated; and wherein each of the foregoing aryl, heteroaryl, -(alkyl)aryl, -(alkyl)heteroaryl, -(heteroalkyl)aryl, or -heteroalkyl)heteroaryl moieties may be substituted or unsubstituted.
12. The compound of claim 1, wherein —NR$^5$R$^6$ is one of the following the structures:
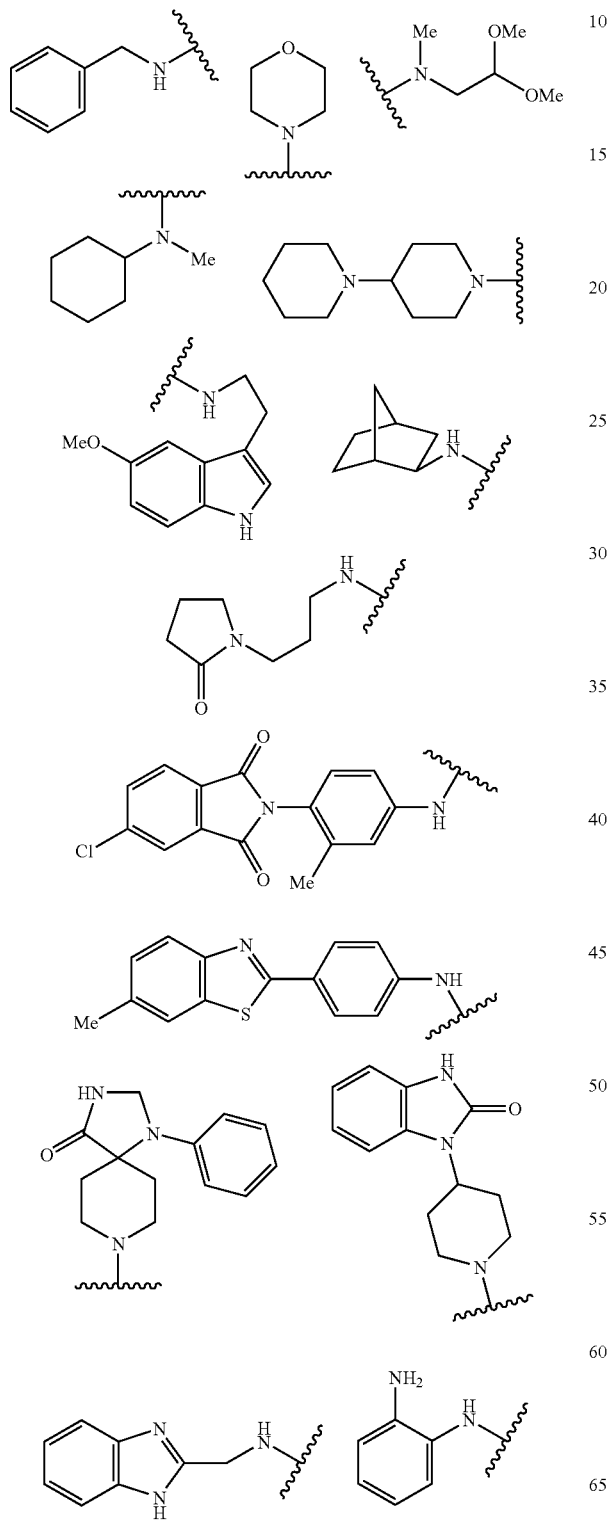
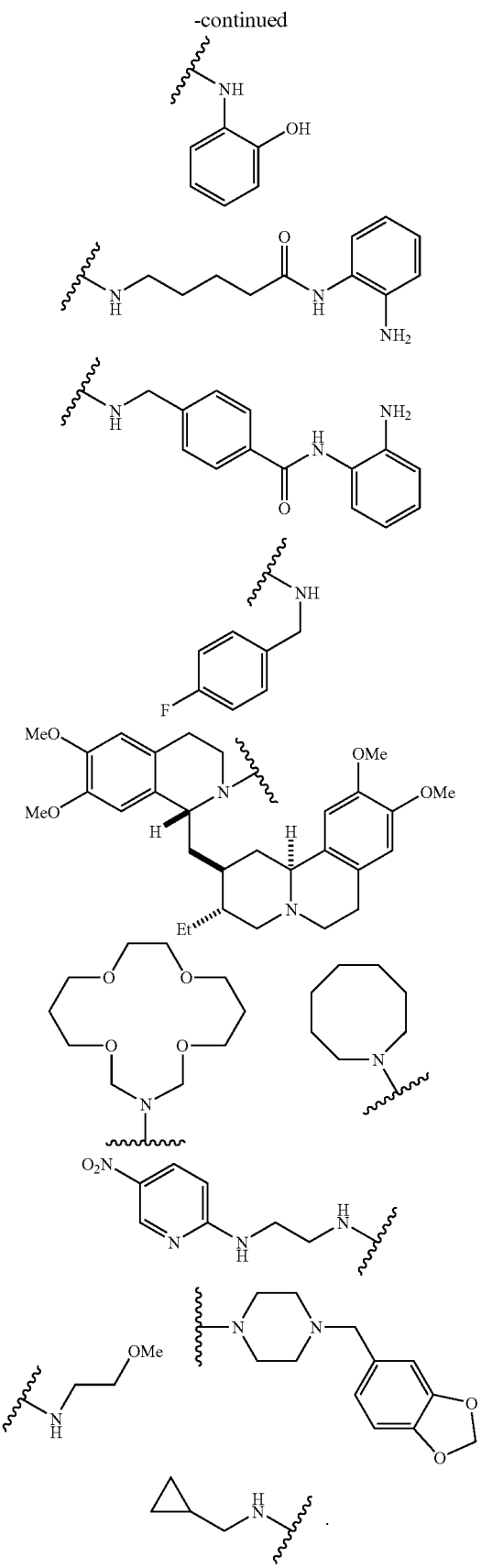

13. The compound of claim 1 having the structure:

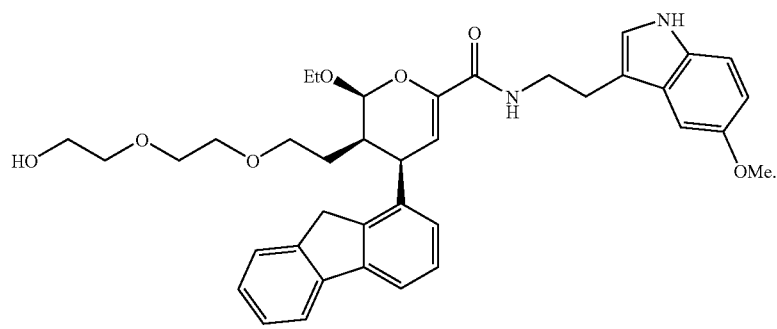

14. The compound of claim 1 having the structure:

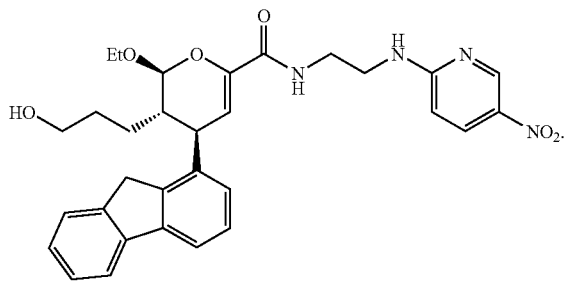

15. The compound of claim 1 having the structure:

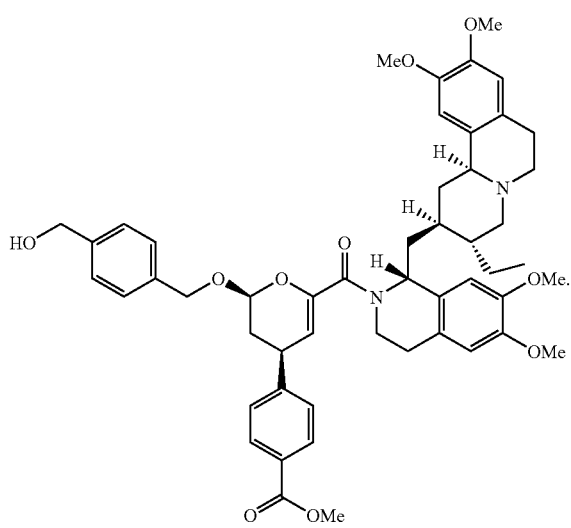

16. The compound of claim 1 having the structure:

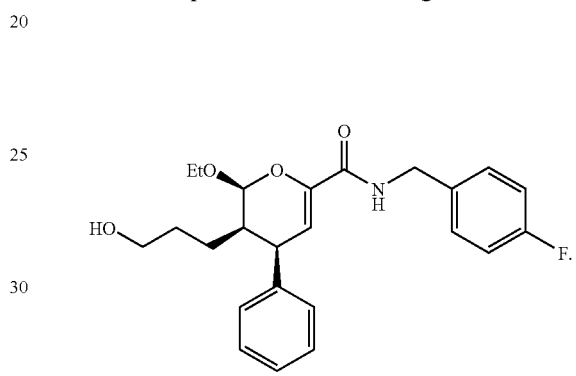

17. A library of compounds comprising a plurality of library members, wherein at least two library members are a compound of claim 1 or 2.

18. The library of claim 17, wherein the library comprises at least 100 compounds.

19. The library of claim 17, wherein the library comprises at least 1,000 compounds.

20. The library of claim 17, wherein the library comprises at least 2,000 compounds.

21. The library of claim 17, wherein the library comprises at least 10,000 compounds.

22. A pharmaceutical composition comprising:
  a compound of any one of claims 1, 2, 5, 8, 12, 13–15 and 16 and
  a pharmaceutically acceptable carrier.

* * * * *